(12) United States Patent
Park et al.

(10) Patent No.: US 10,381,577 B2
(45) Date of Patent: Aug. 13, 2019

(54) HETERO-CYCLIC COMPOUND AND ORGANIC LIGHT EMITTING DEVICE USING THE SAME

(71) Applicant: HEESUNG MATERIAL LTD., Yongin, Gyeonggi-do (KR)

(72) Inventors: Geon-Yu Park, Osan-si (KR); Han-Kook Oh, Osan-si (KR); Yun-Ji Lee, Osan-si (KR); Jae-Yeol Ma, Yongin-si (KR); Dong-Jun Kim, Yongin-si (KR); Jin-Seok Choi, Suwon-si (KR); Dae-Hyuk Choi, Yongin-si (KR); Joo-Dong Lee, Seongnam-si (KR)

(73) Assignee: HEESUNG MATERIAL LTD., Yongin (KR)

( * ) Notice: Subject to any disclaimer, the term of this patent is extended or adjusted under 35 U.S.C. 154(b) by 204 days.

(21) Appl. No.: 15/321,397

(22) PCT Filed: Jul. 27, 2016

(86) PCT No.: PCT/KR2016/008189
§ 371 (c)(1),
(2) Date: Dec. 22, 2016

(87) PCT Pub. No.: WO2017/018795
PCT Pub. Date: Feb. 2, 2017

(65) Prior Publication Data
US 2017/0213988 A1  Jul. 27, 2017

(30) Foreign Application Priority Data

Jul. 27, 2015 (KR) .................. 10-2015-0106063
May 11, 2016 (KR) .................. 10-2016-0057665
May 13, 2016 (KR) .................. 10-2016-0059084

(51) Int. Cl.
*H01L 51/50* (2006.01)
*H01L 51/00* (2006.01)
(Continued)

(52) U.S. Cl.
CPC ........ *H01L 51/0074* (2013.01); *C07D 209/82* (2013.01); *C07D 333/76* (2013.01);
(Continued)

(58) Field of Classification Search
CPC .. C07D 409/14; C07D 209/86; C07D 495/04; C07D 491/04; C07D 487/04;
(Continued)

(56) References Cited

U.S. PATENT DOCUMENTS 4,356,429 A    10/1982  Tang
2011/0006670 A1  1/2011  Katakura et al.
(Continued)

FOREIGN PATENT DOCUMENTS

EP    3243820 A1    11/2017
JP    2009-267255 A    11/2009
(Continued)

OTHER PUBLICATIONS

Bin, J.K. et al, "New sulfur-containing host materials for blue phosphorescent organic light-emitting diodes," J. Mater. Chem., 2012, vol. 22, pp. 21720-21726.
(Continued)

*Primary Examiner* — Gregory D Clark
(74) *Attorney, Agent, or Firm* — Birch, Stewart, Kolasch & Birch, LLP

(57) ABSTRACT

The present application provides a hetero-cyclic compound which may significantly improve the lifetime, efficiency, electrochemical stability, and thermal stability of an organic light emitting device, and an organic light emitting device in
(Continued)

which the hetero-cyclic compound is contained in an organic compound layer.

17 Claims, 28 Drawing Sheets

(51) Int. Cl.
| | |
|---|---|
| C07D 409/14 | (2006.01) |
| C07D 487/04 | (2006.01) |
| C07D 491/04 | (2006.01) |
| C07D 495/04 | (2006.01) |
| C09K 11/02 | (2006.01) |
| C09K 11/06 | (2006.01) |
| C07D 333/76 | (2006.01) |
| C07D 209/82 | (2006.01) |

(52) U.S. Cl.
CPC ......... *C07D 409/14* (2013.01); *C07D 487/04* (2013.01); *C07D 491/04* (2013.01); *C07D 495/04* (2013.01); *C09K 11/025* (2013.01); *C09K 11/06* (2013.01); *H01L 51/00* (2013.01); *H01L 51/0067* (2013.01); *H01L 51/0071* (2013.01); *H01L 51/0072* (2013.01); *H01L 51/50* (2013.01); *C09K 2211/1007* (2013.01); *C09K 2211/1044* (2013.01); *C09K 2211/1059* (2013.01); *C09K 2211/1092* (2013.01); *H01L 51/0081* (2013.01); *H01L 51/0085* (2013.01); *H01L 51/5016* (2013.01); *H01L 2251/552* (2013.01)

(58) Field of Classification Search
CPC ........... H01L 2251/552; H01L 51/0074; H01L 51/0072; H01L 51/0071; H01L 51/0067; H01L 51/5016; H01L 51/5012; C09K 2211/1092; C09K 2211/1059; C09K 2211/1044; C09K 2211/1007; C09K 11/06; C09K 11/025; C07C 333/76
See application file for complete search history.

(56) References Cited

U.S. PATENT DOCUMENTS

| | | | |
|---|---|---|---|
| 2011/0260138 A1* | 10/2011 | Xia | C07D 405/14 257/40 |
| 2015/0014649 A1 | 1/2015 | Ma et al. | |
| 2015/0179958 A1* | 6/2015 | Otsu | H01L 51/0085 257/40 |
| 2015/0322337 A1 | 11/2015 | Hattori et al. | |
| 2016/0072078 A1 | 3/2016 | Lee et al. | |
| 2017/0331052 A1 | 11/2017 | Park et al. | |
| 2018/0037546 A1* | 2/2018 | Sugino | C07D 405/14 |

FOREIGN PATENT DOCUMENTS

| | | |
|---|---|---|
| JP | 2012-222268 A | 11/2012 |
| JP | 2013-16717 A | 1/2013 |
| JP | 2014-017494 A | 1/2014 |
| JP | 2016-51901 A | 4/2016 |
| JP | 2016-149473 A | 8/2016 |
| KP | 10-2014-0122929 A | 10/2014 |
| KR | 10-2011-0112098 A | 10/2011 |
| KR | 10-2013-0100236 A | 9/2013 |
| WO | WO 2011/004639 A1 | 1/2011 |
| WO | WO 2011/126224 A1 | 10/2011 |
| WO | WO 2013/168534 A1 | 11/2013 |
| WO | WO 2014/091958 A1 | 6/2014 |

OTHER PUBLICATIONS

Office Action issued in Korean Patent Application No. 10-2016-0057665, dated Oct. 5, 2016.
Office Action issued in Korean Patent Application No. 10-2016-0059084, dated Aug. 8, 2016.
Extended European Search Report for European Application No. 16830828.6, dated Jan. 17, 2019.

* cited by examiner

[Figure 1]
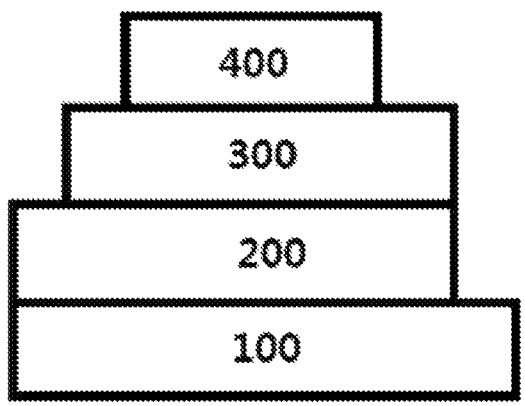
[Figure 2]
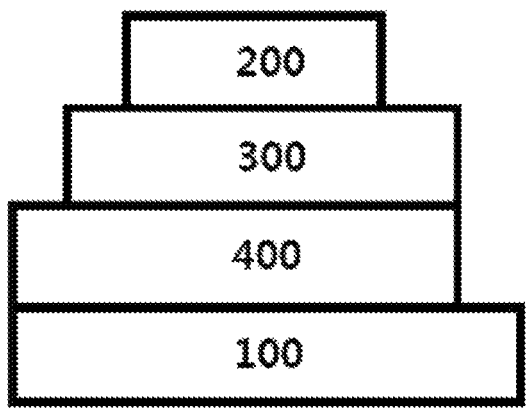

[Figure 3]
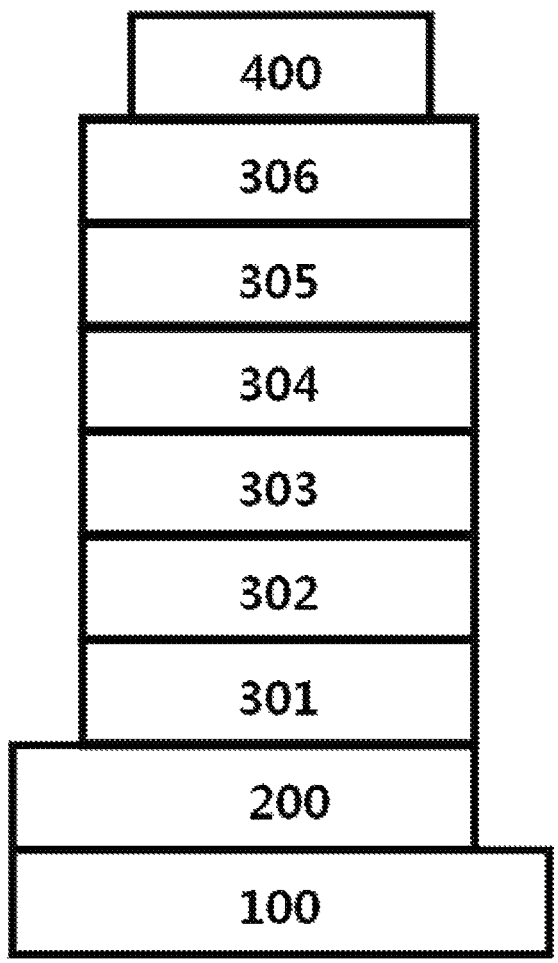

[Figure 4]
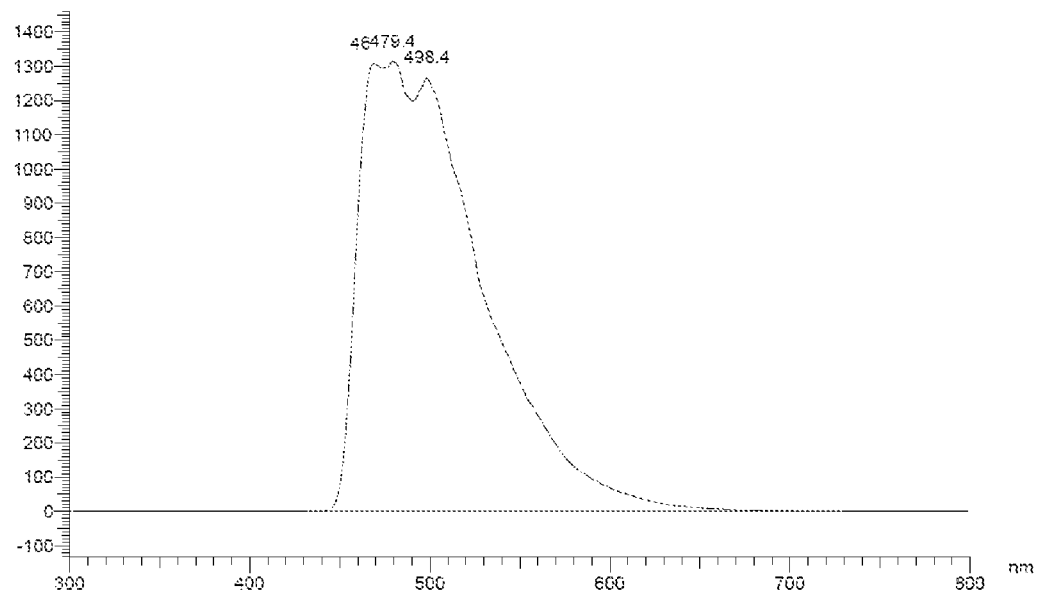
[Figure 5]
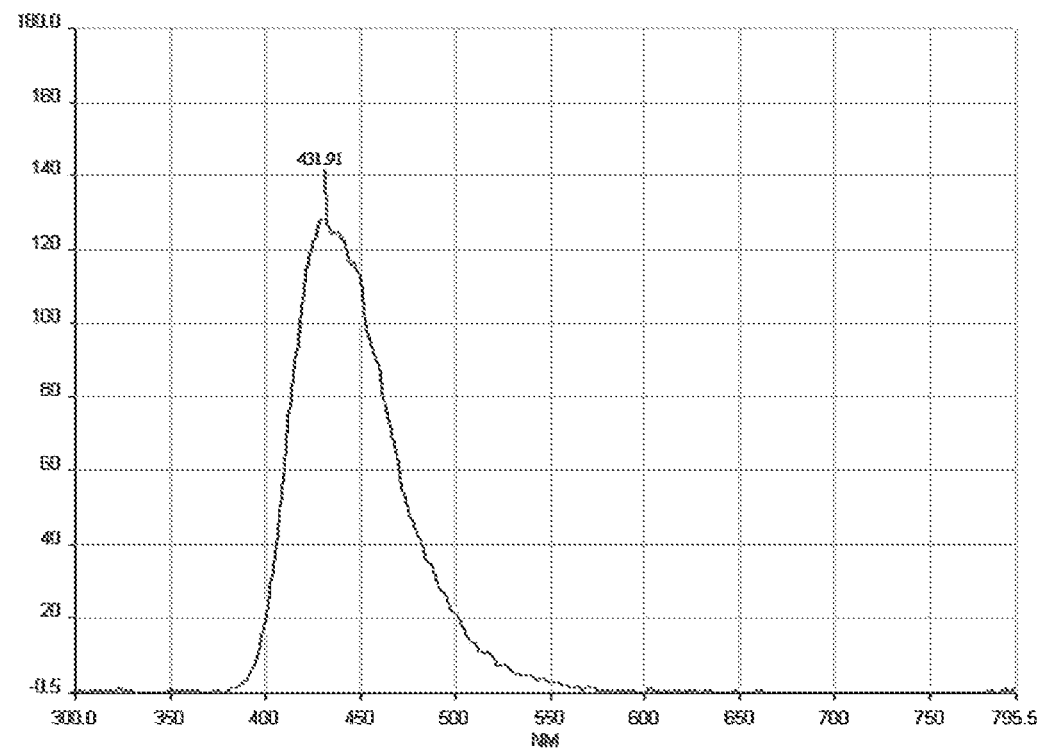

[Figure 6]
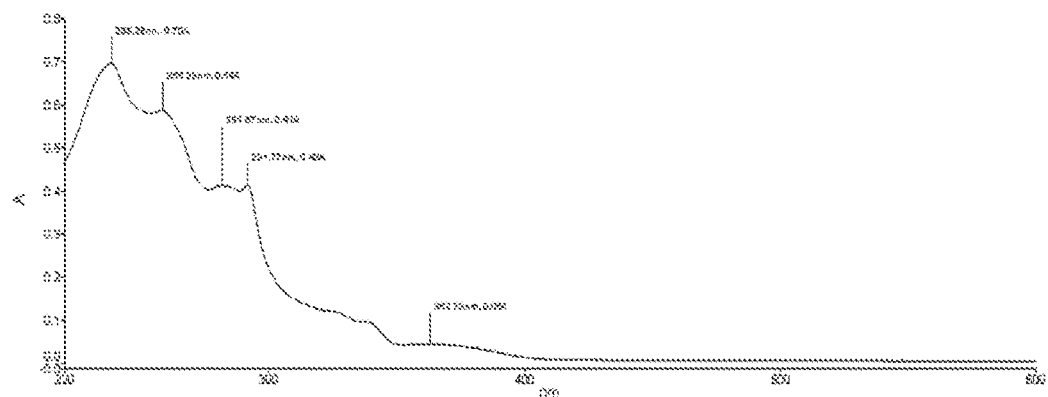
[Figure 7]
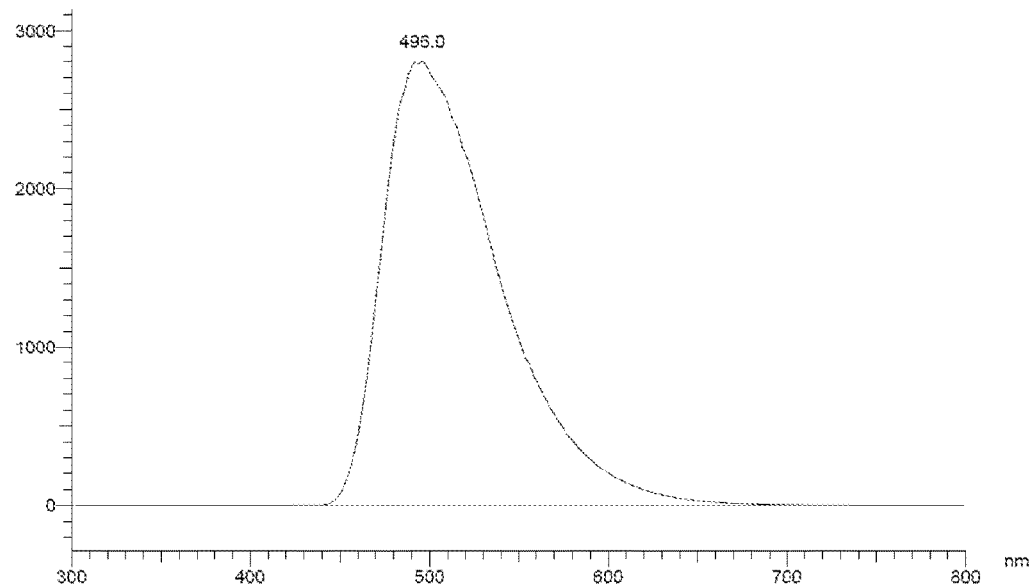

[Figure 8]
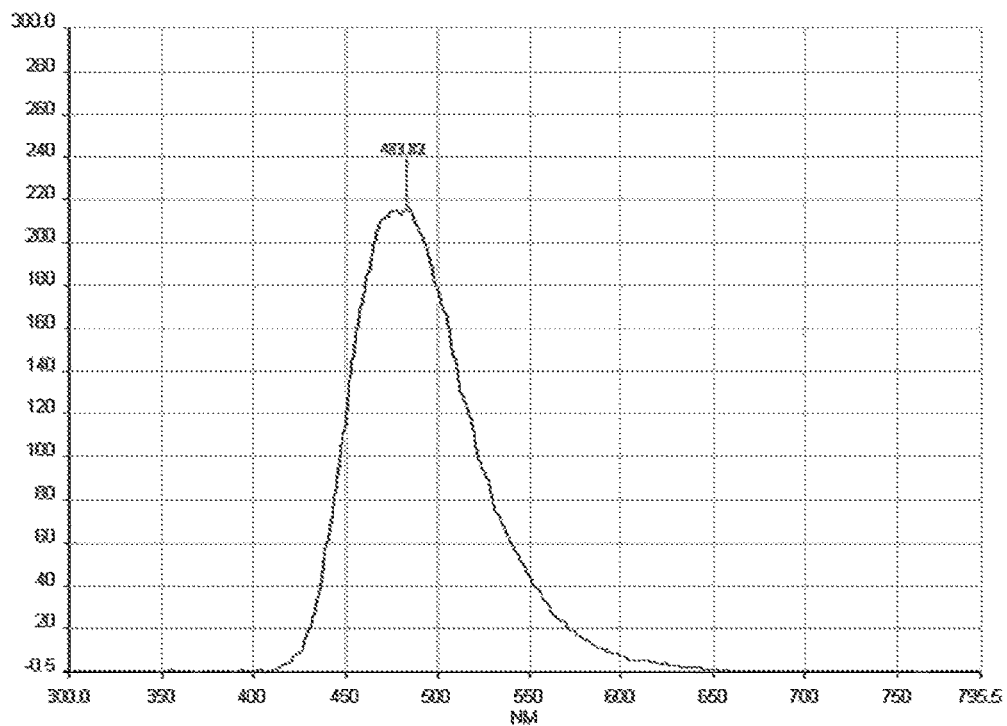
[Figure 9]
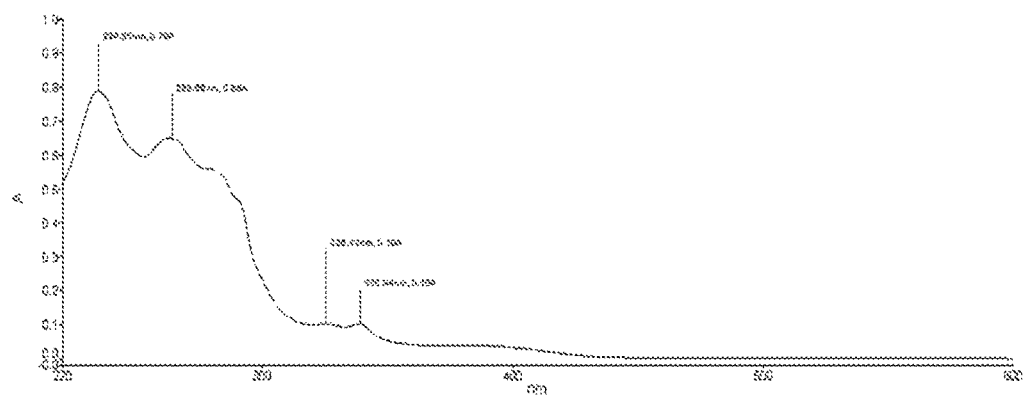

[Figure 10]
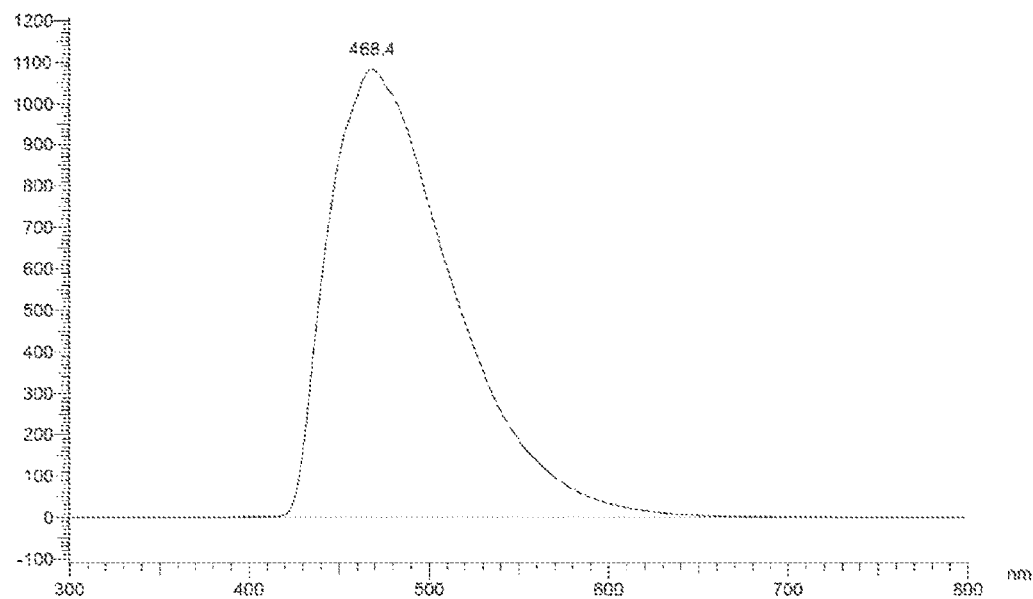
[Figure 11]
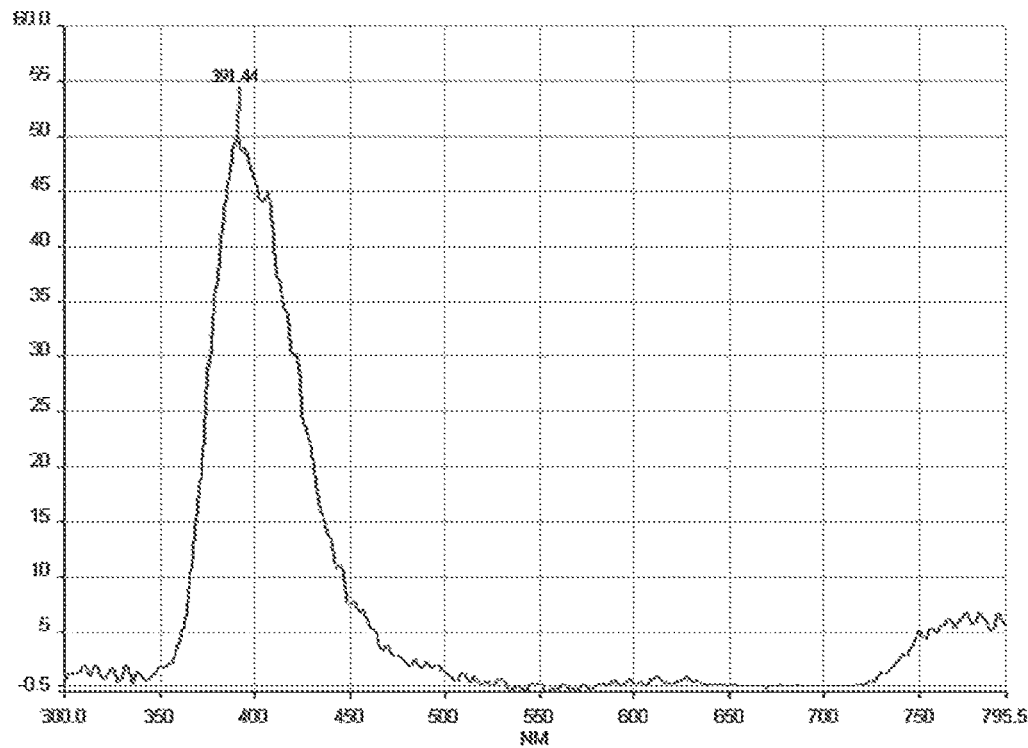

[Figure 12]
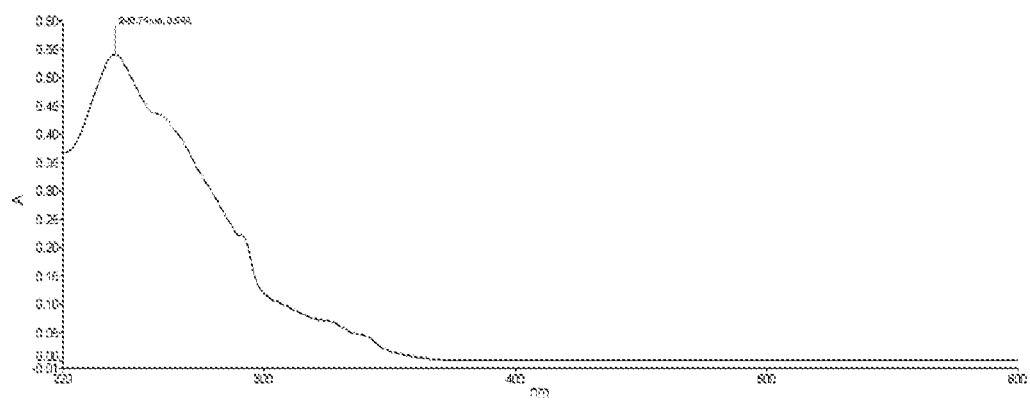
[Figure 13]
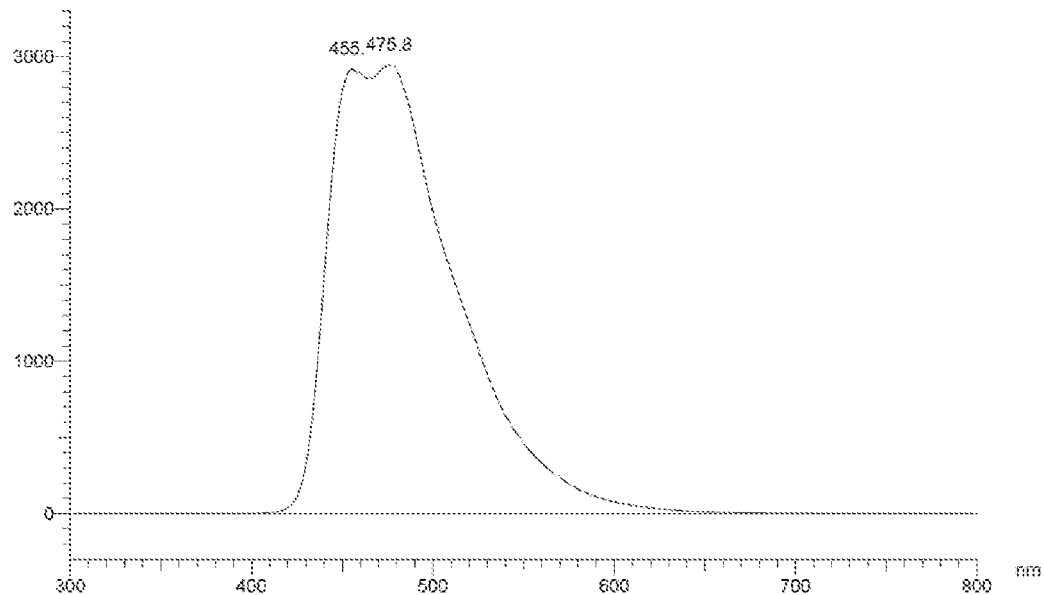

[Figure 14]
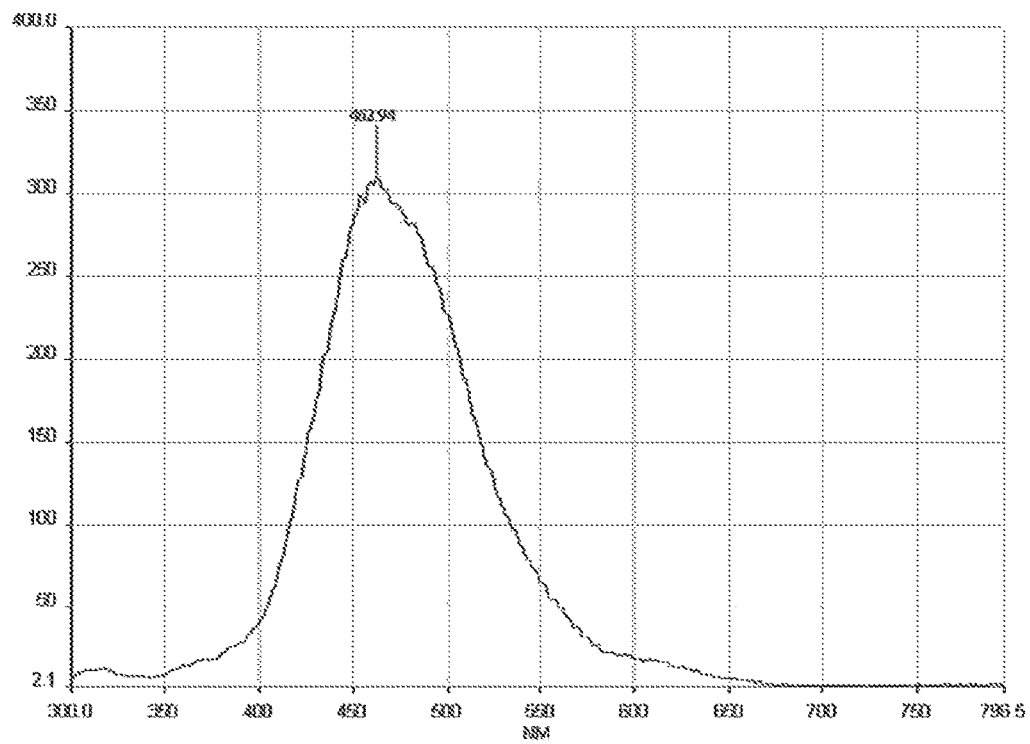
[Figure 15]
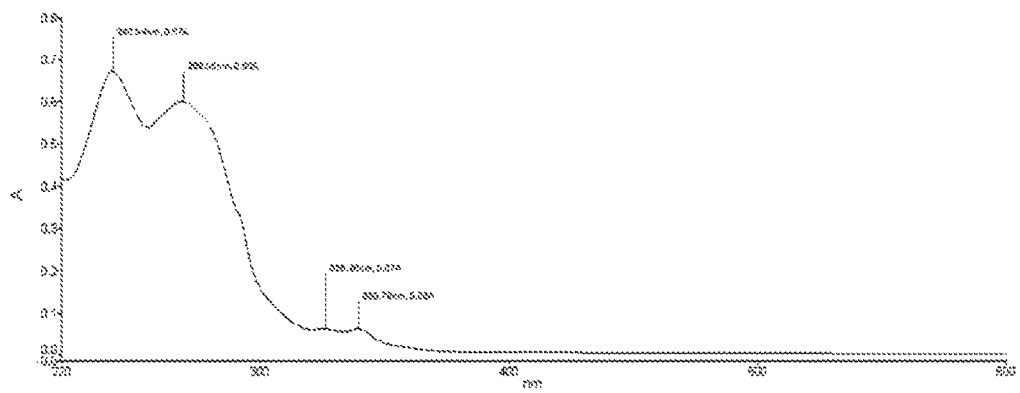

[Figure 16]
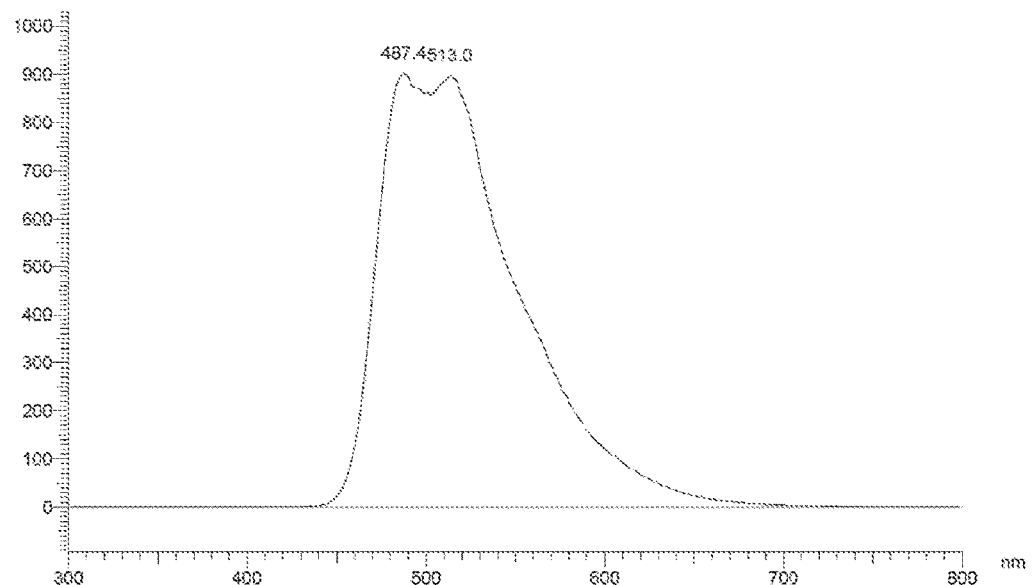
[Figure 17]
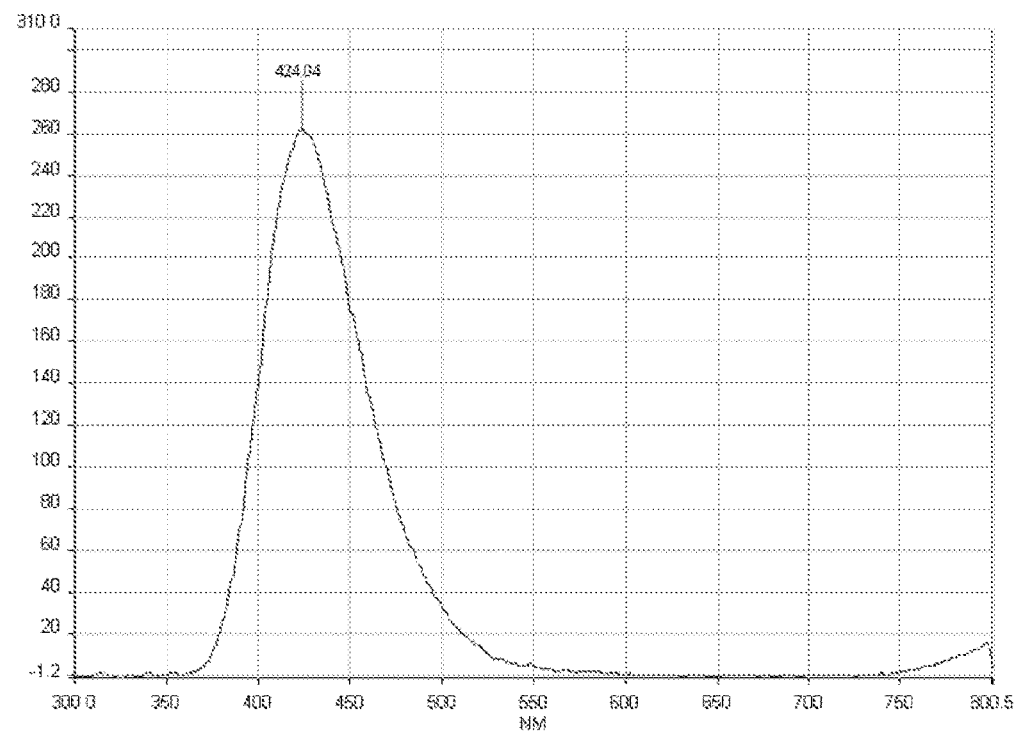

[Figure 18]
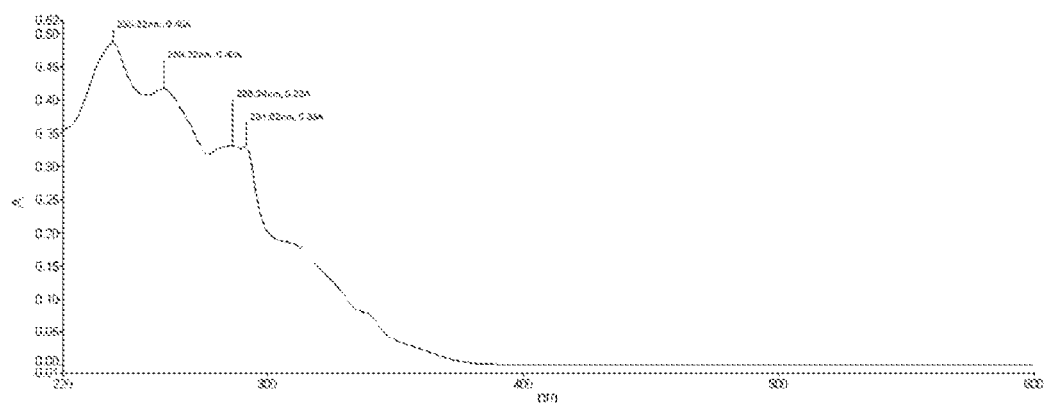
[Figure 19]
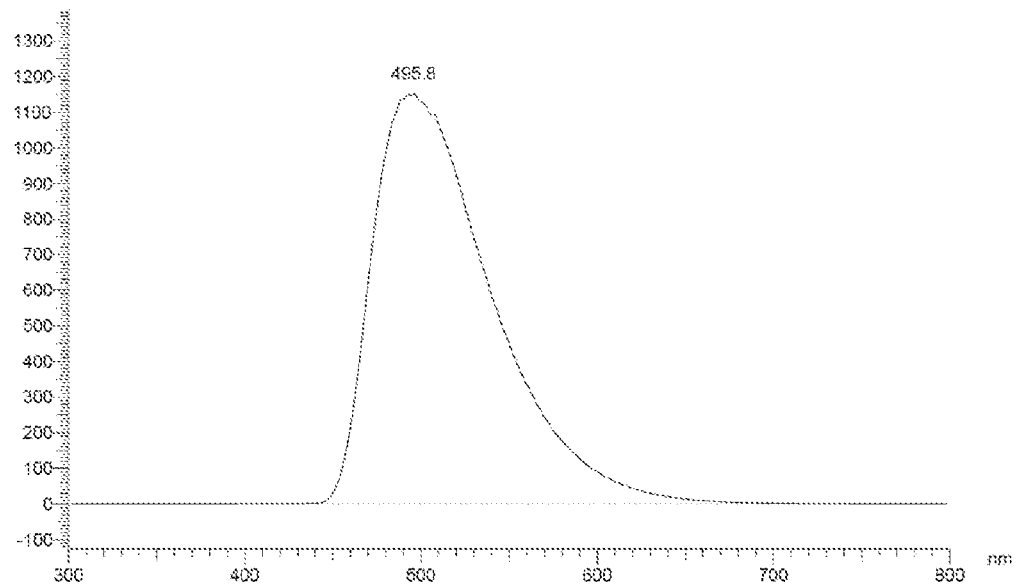

[Figure 20]
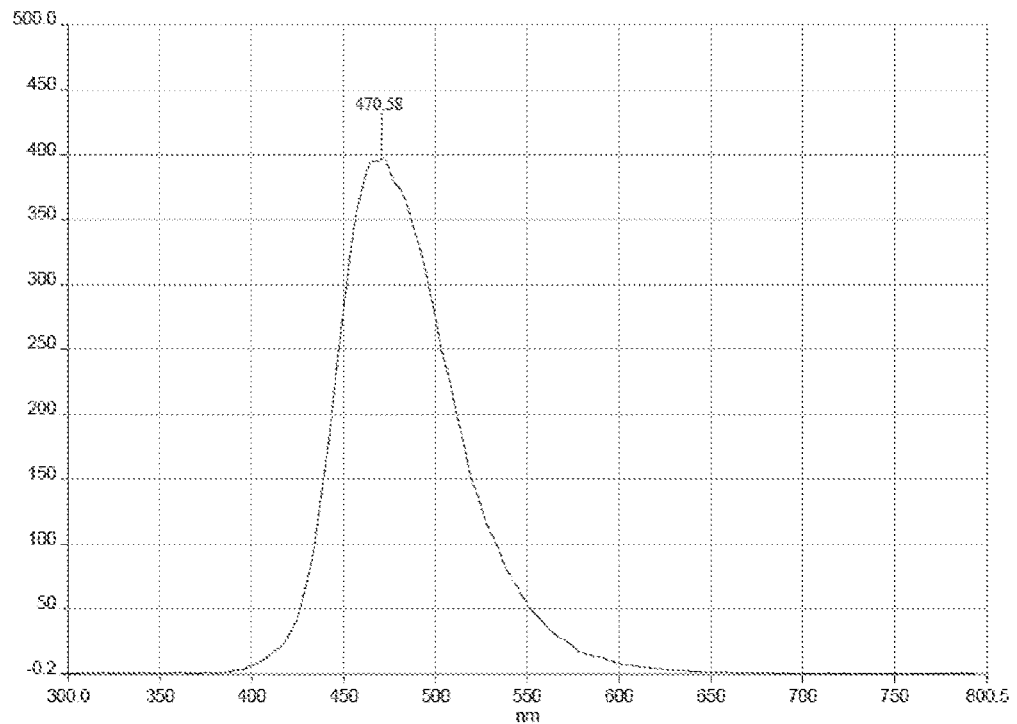
[Figure 21]
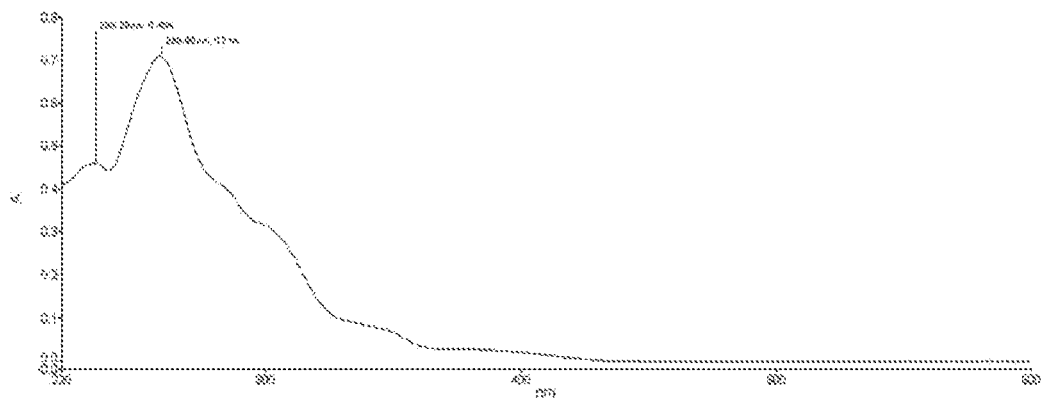

[Figure 22]
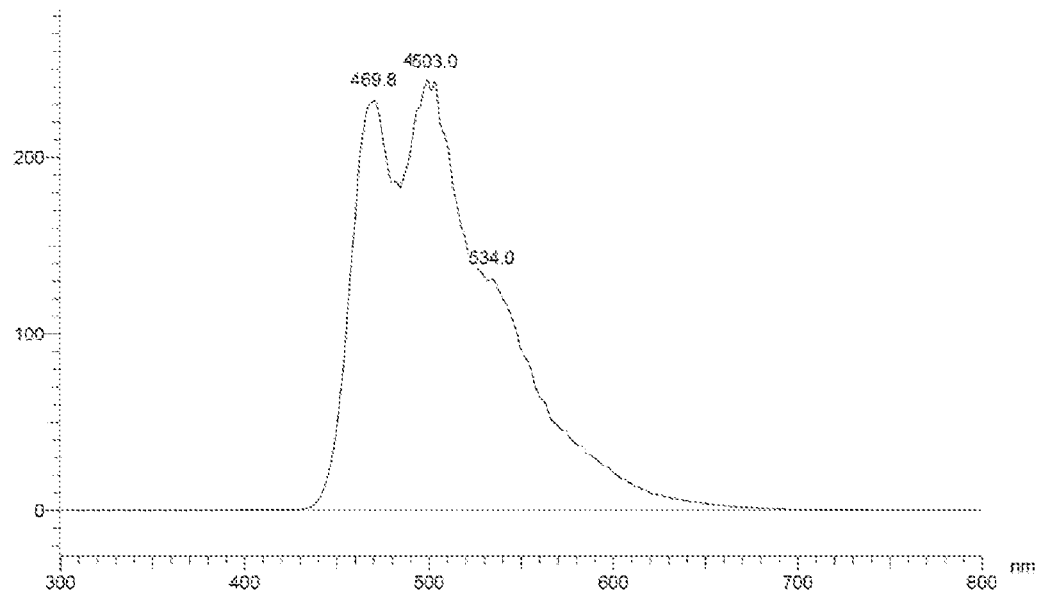
[Figure 23]
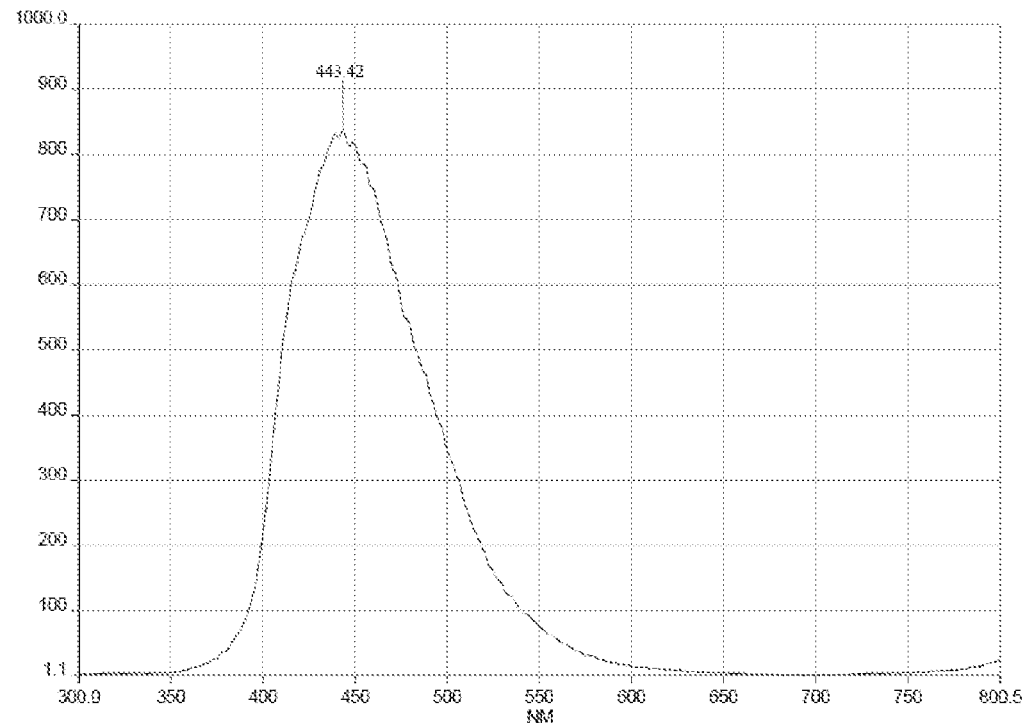

[Figure 24]
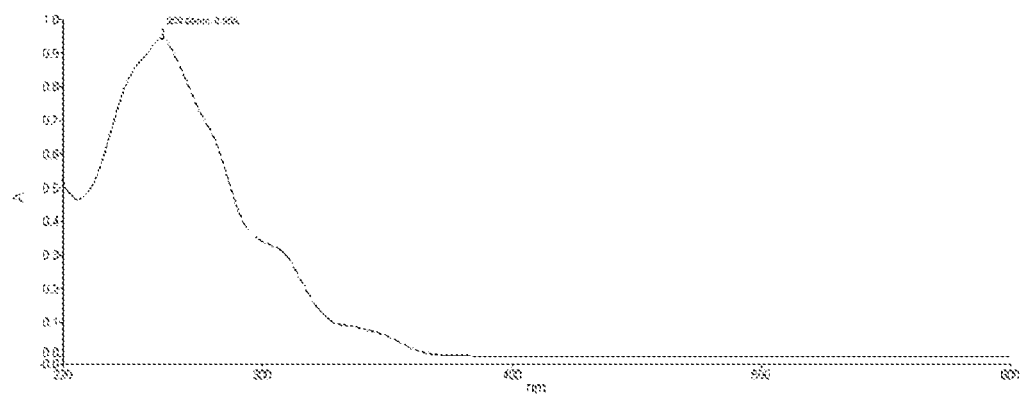
[Figure 25]
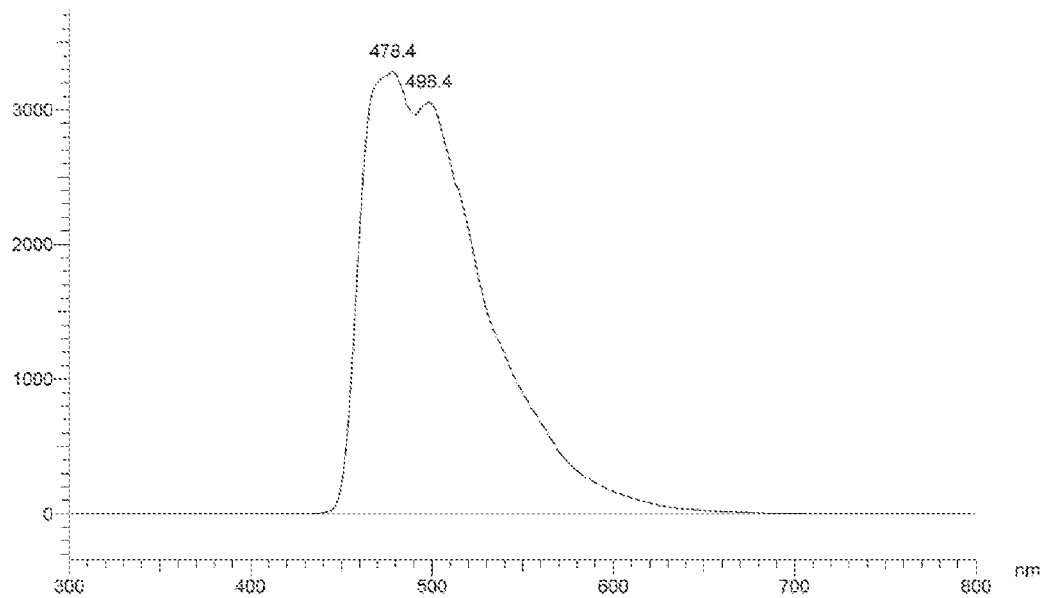

[Figure 26]
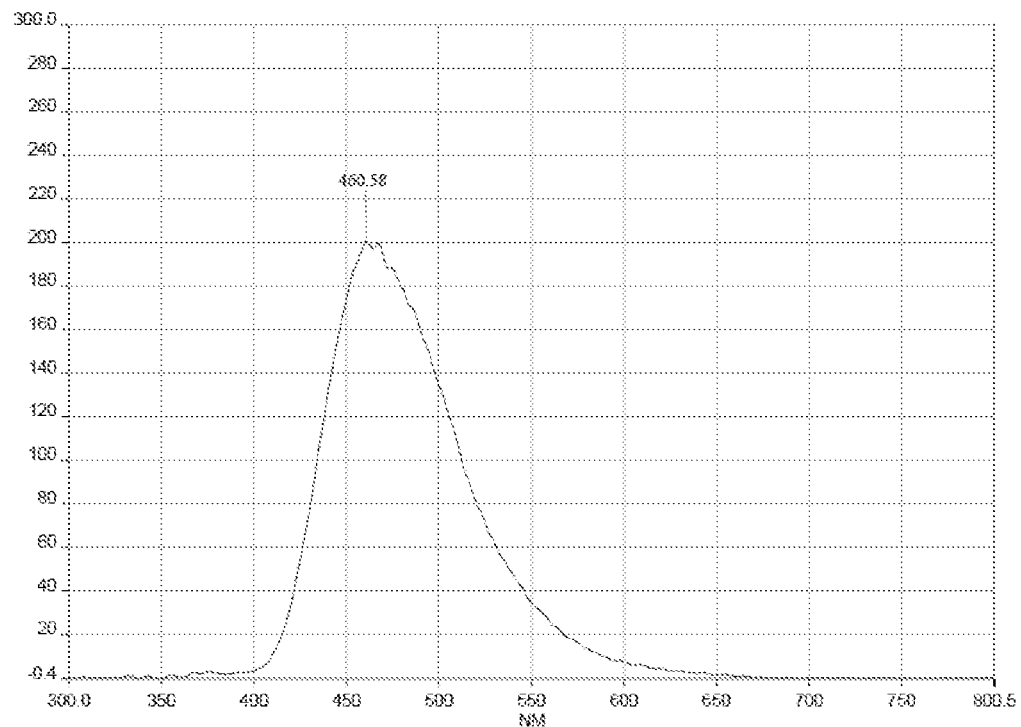
[Figure 27]
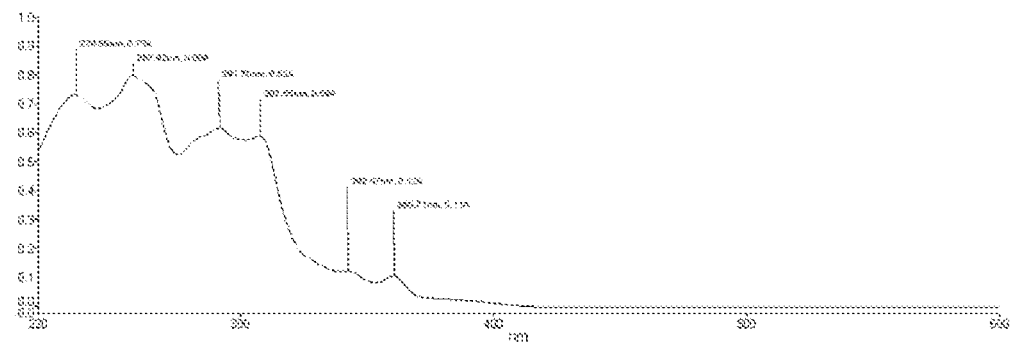

[Figure 28]
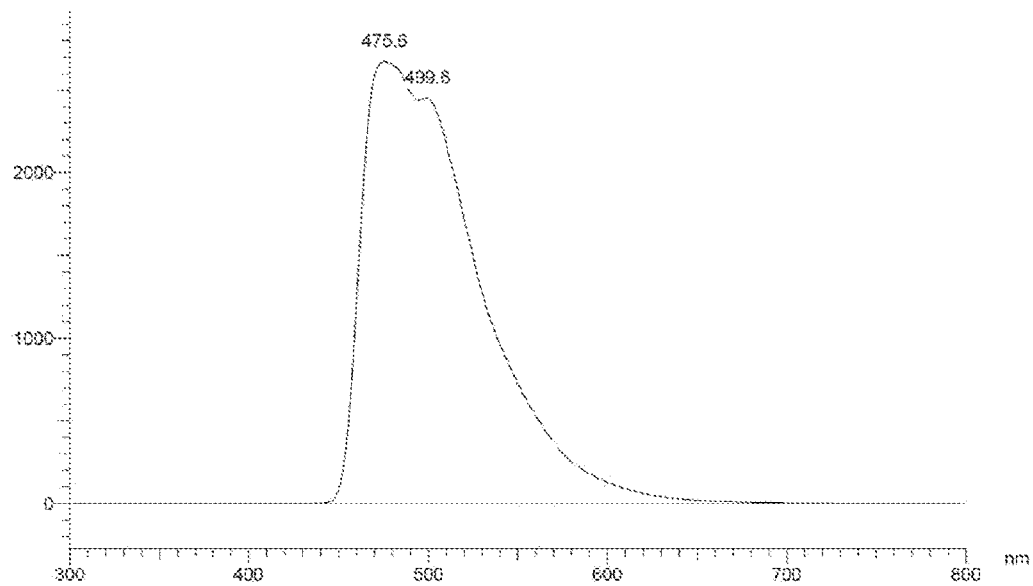
[Figure 29]
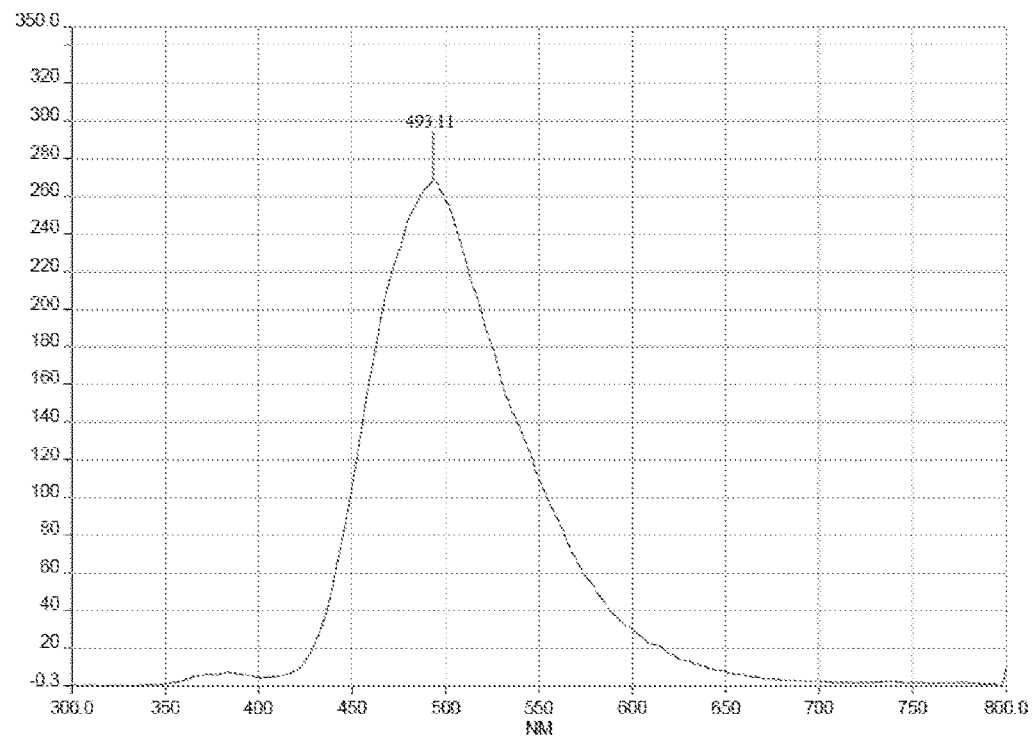

[Figure 30]
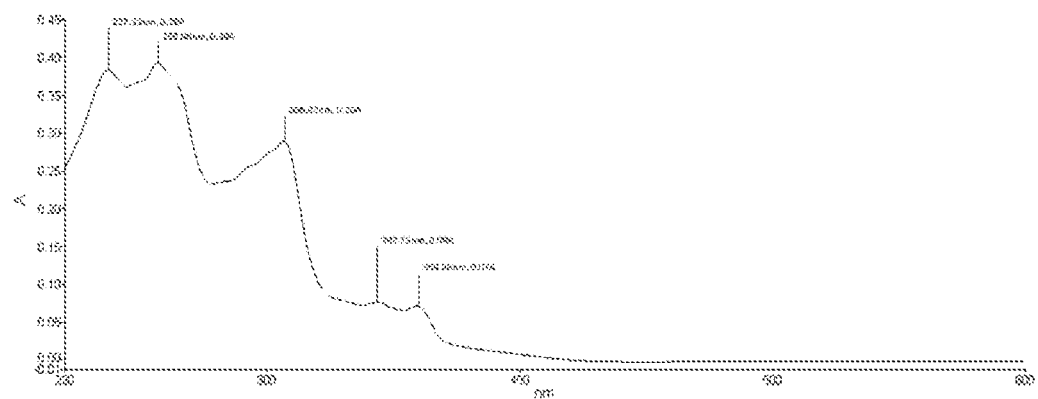
[Figure 31]
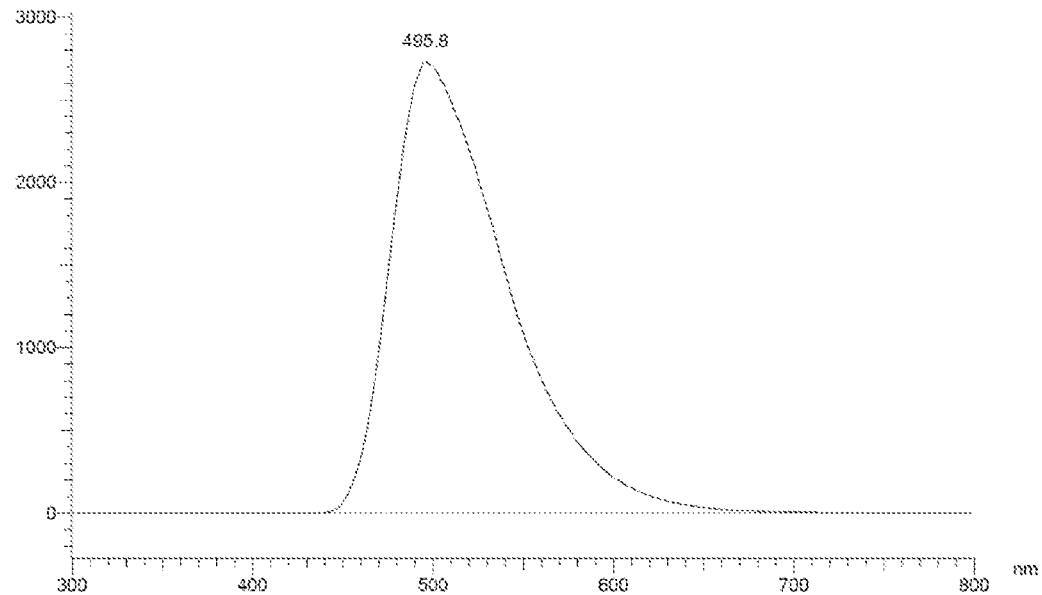

[Figure 32]
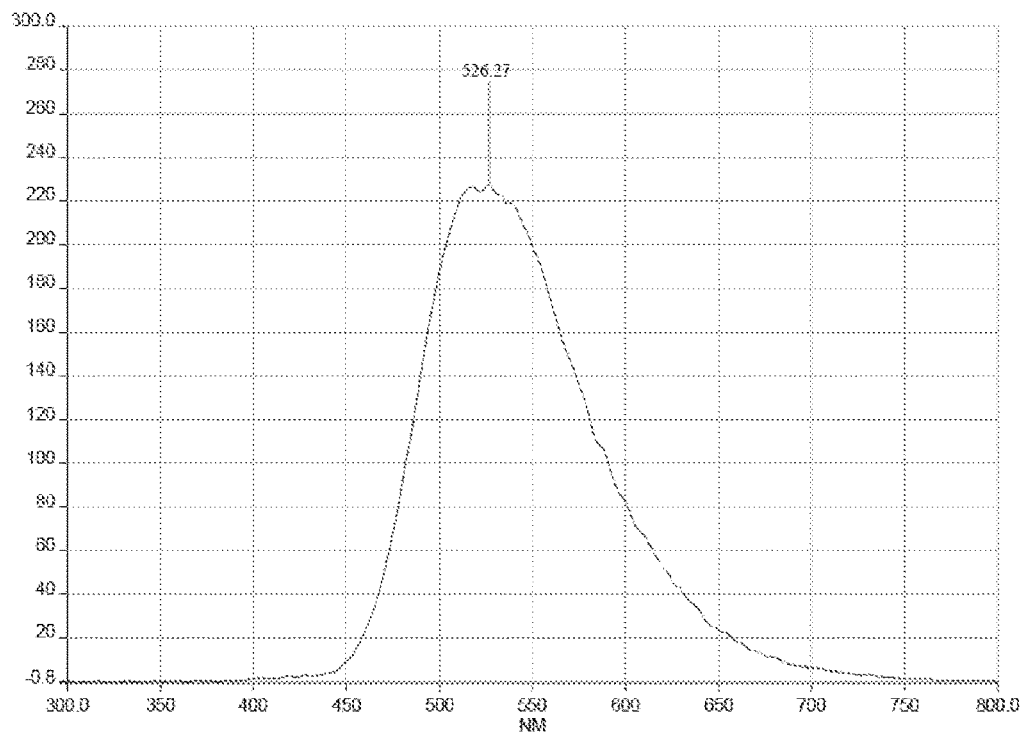
[Figure 33]
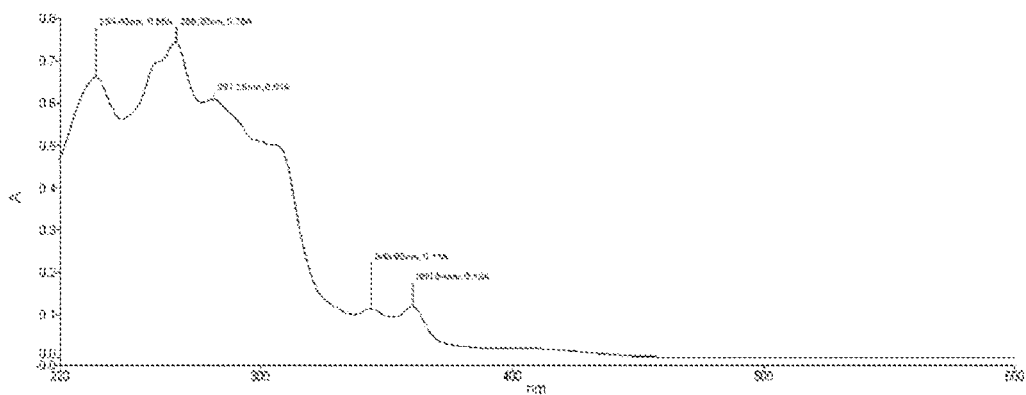

[Figure 34]
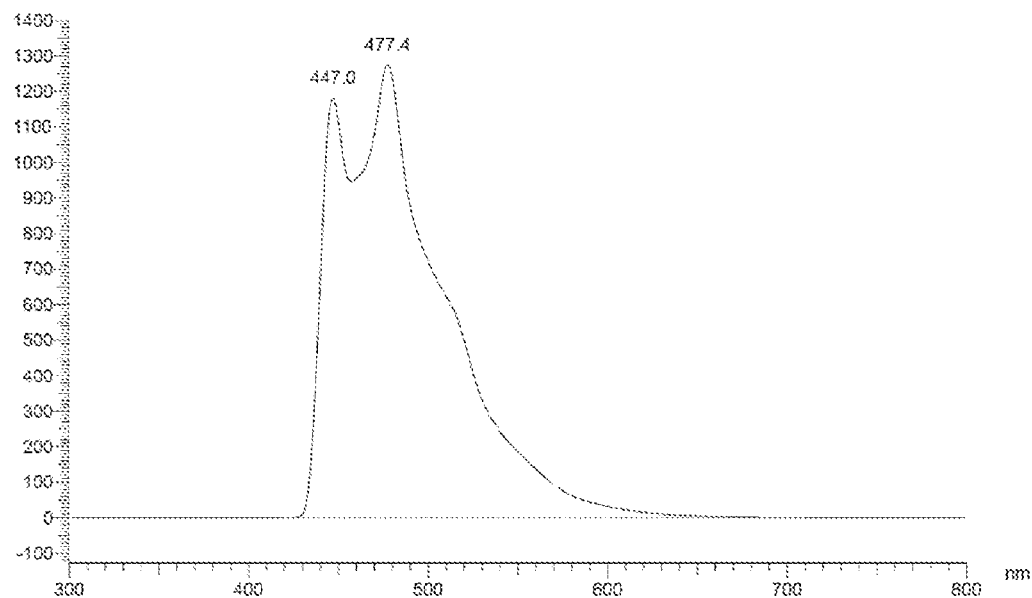
[Figure 35]
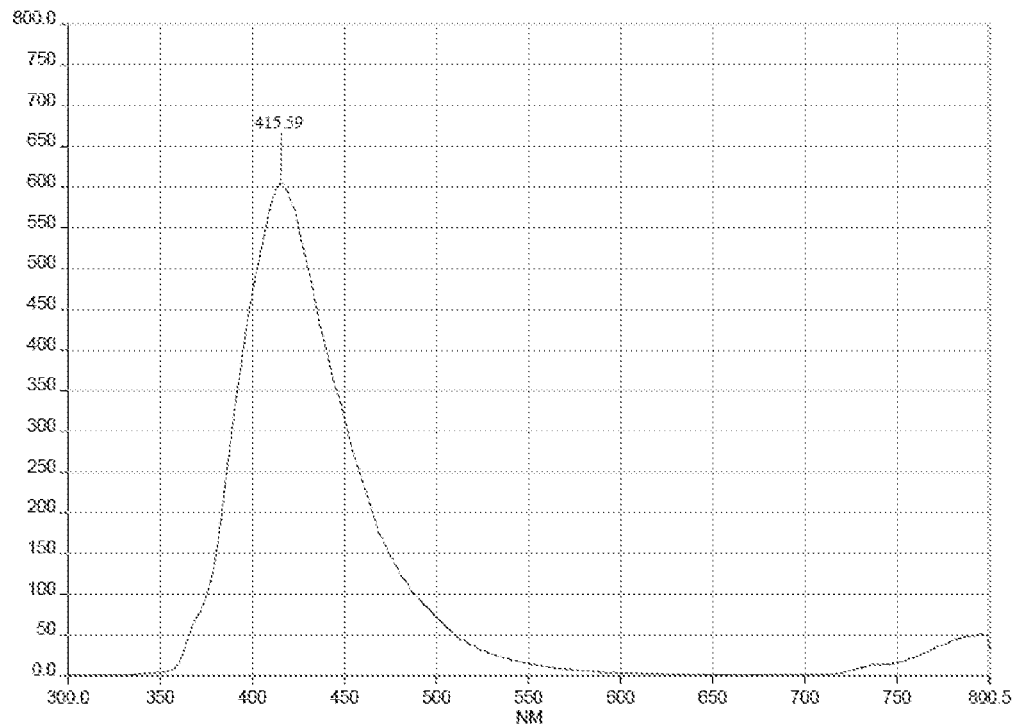

[Figure 36]
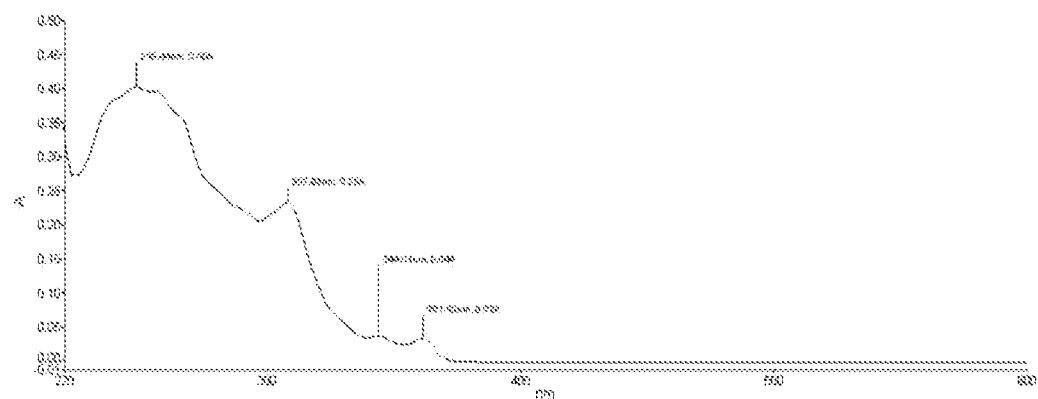
[Figure 37]
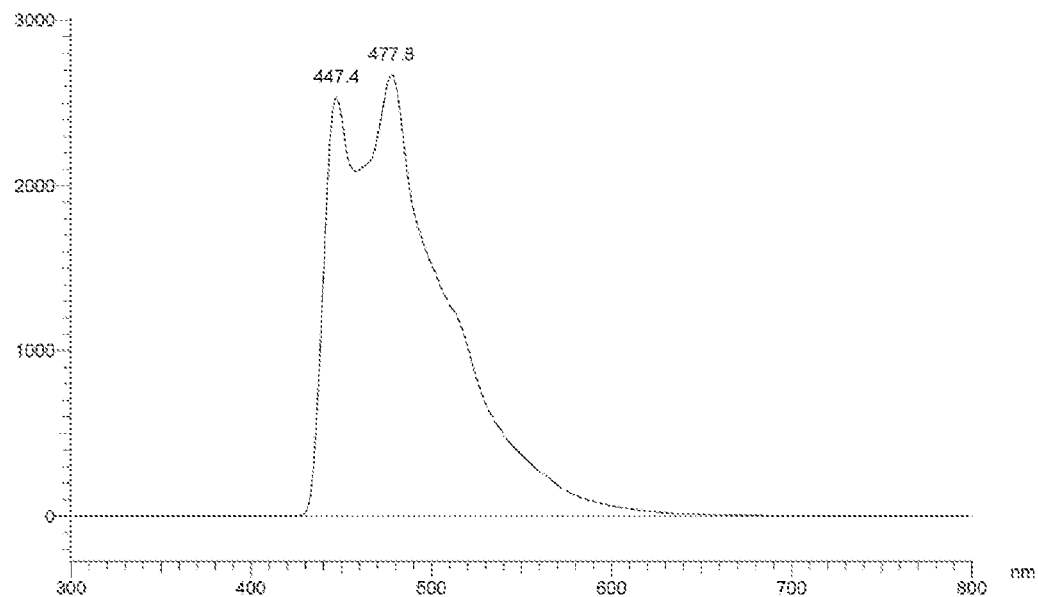

[Figure 38]
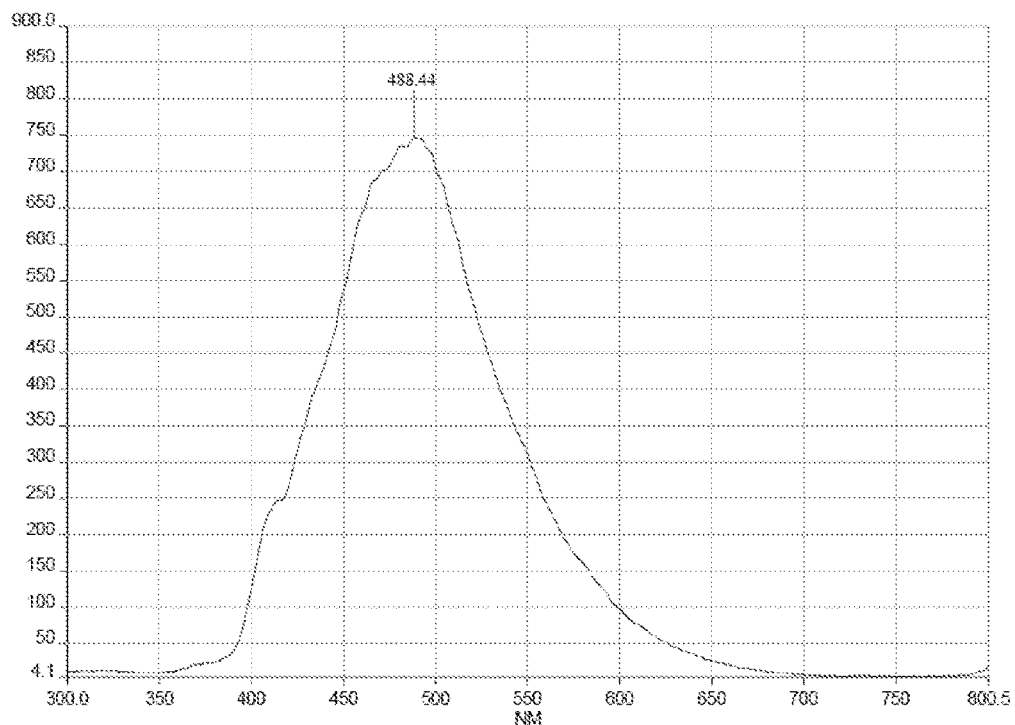
[Figure 39]
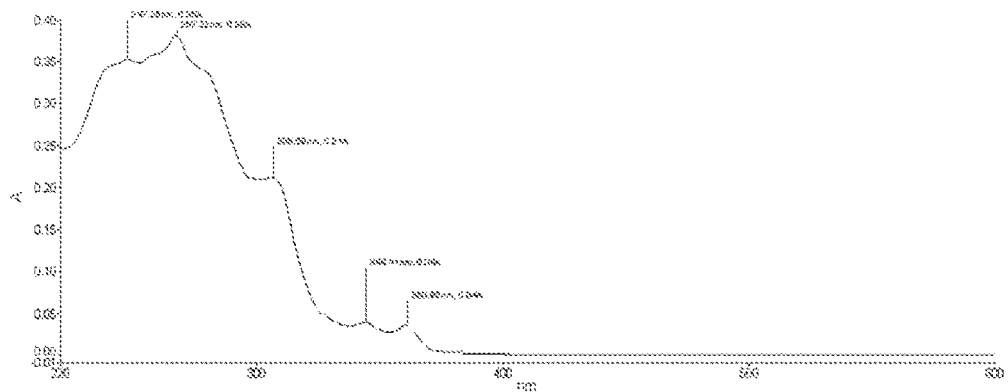

[Figure 40]
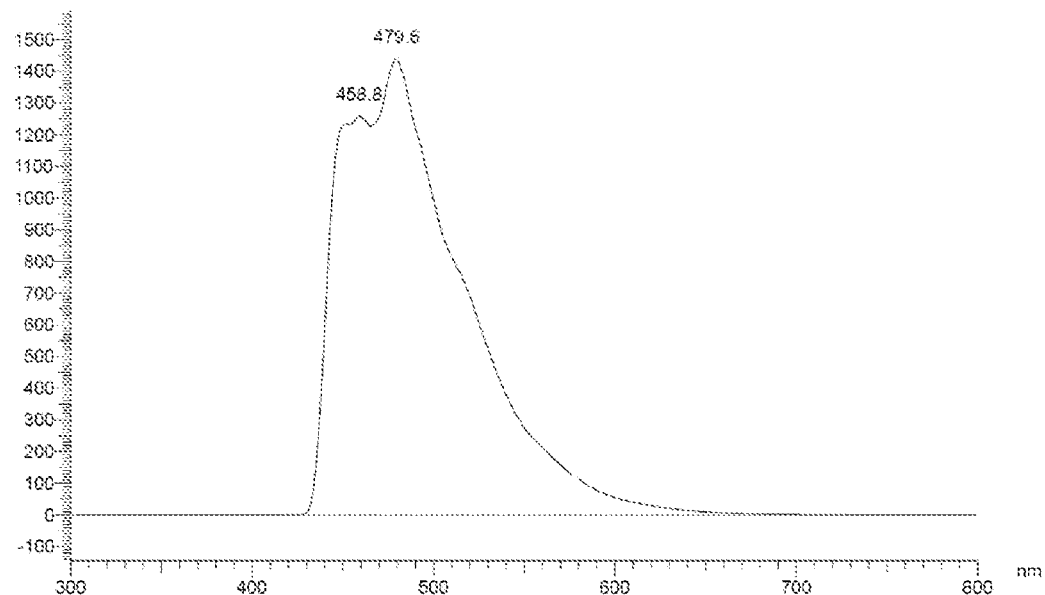
[Figure 41]
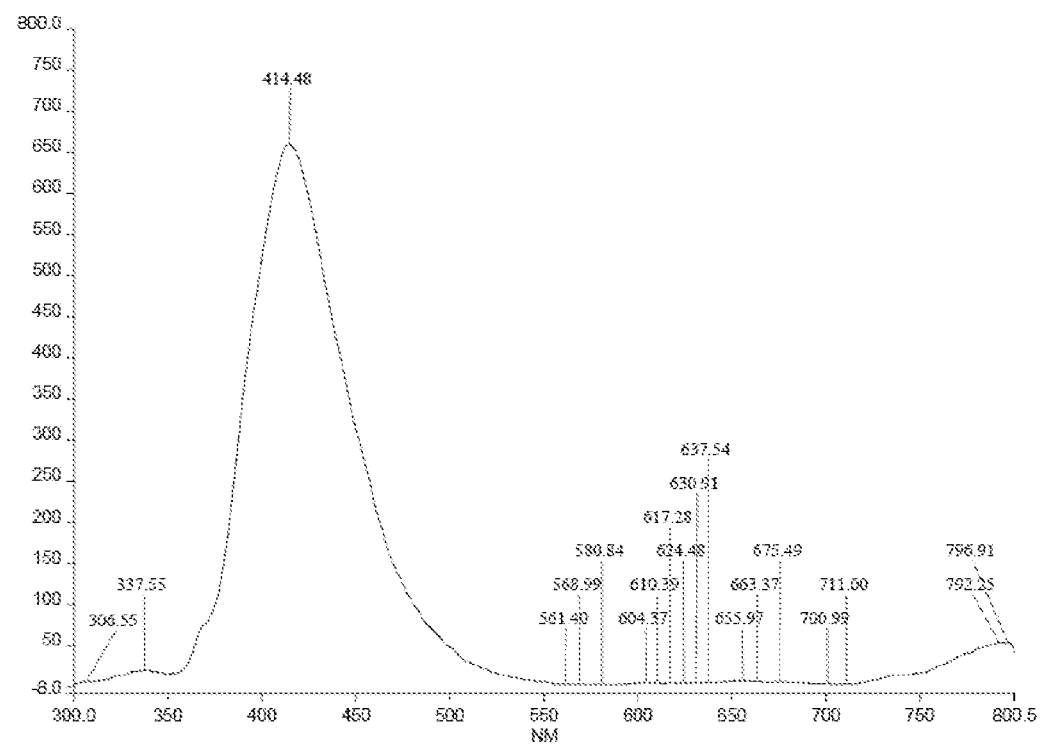

[Figure 42]
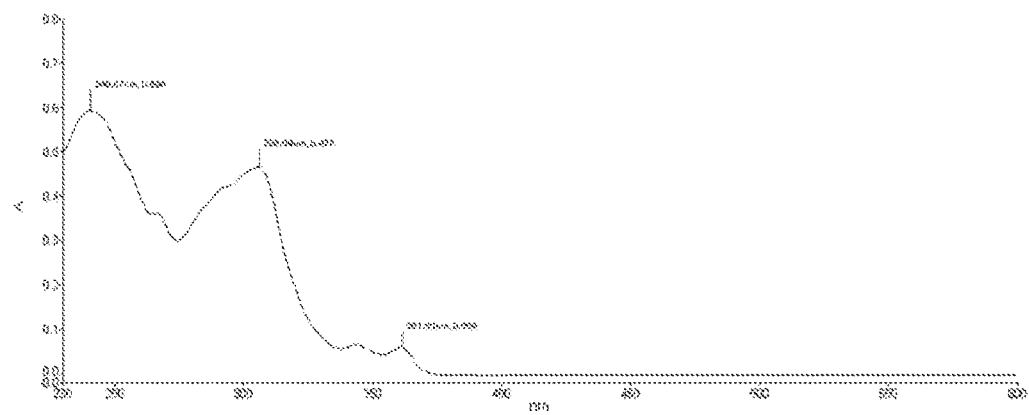
[Figure 43]
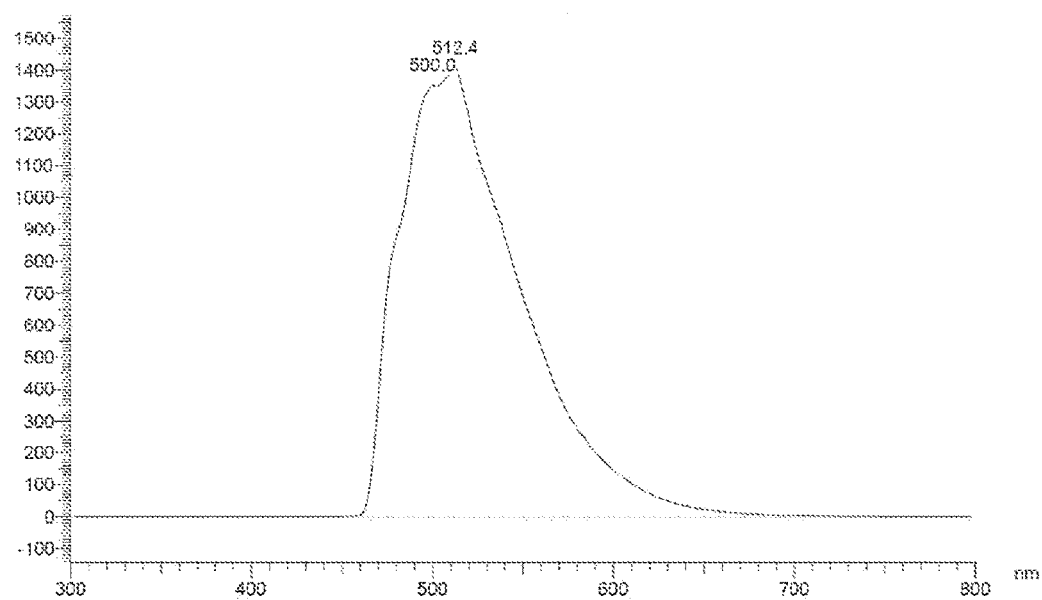

[Figure 44]
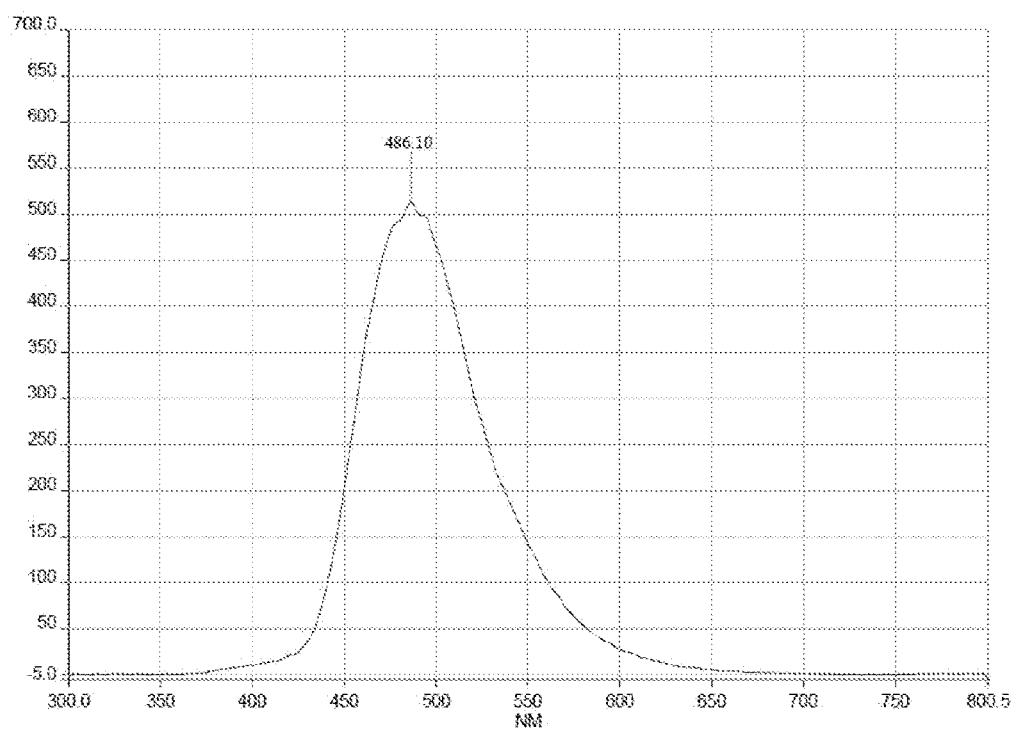
[Figure 45]
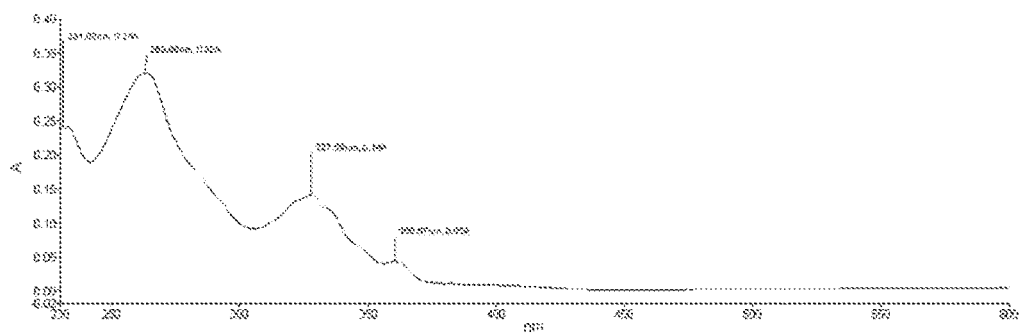

[Figure 46]
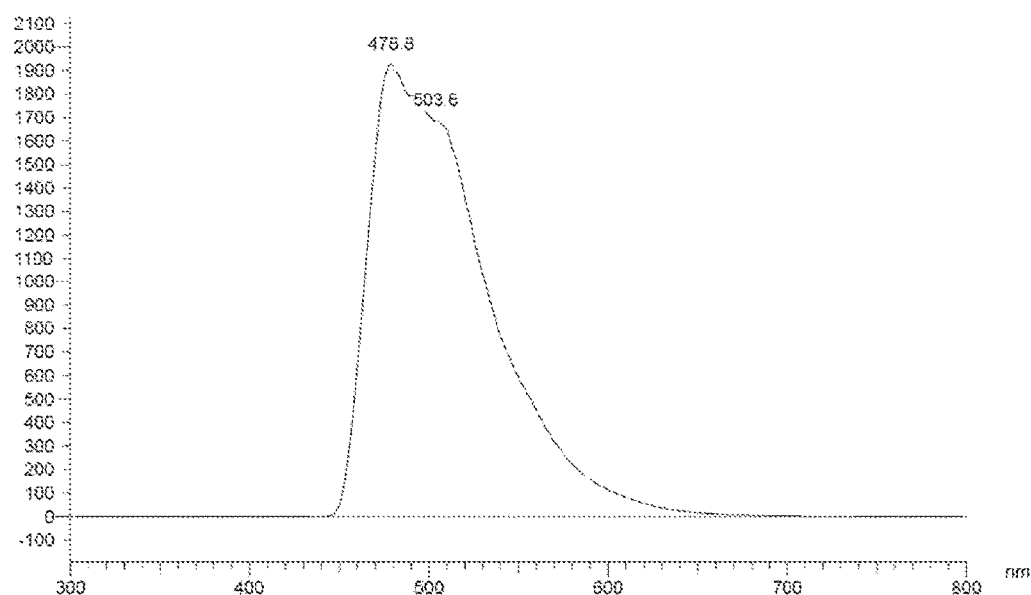
[Figure 47]
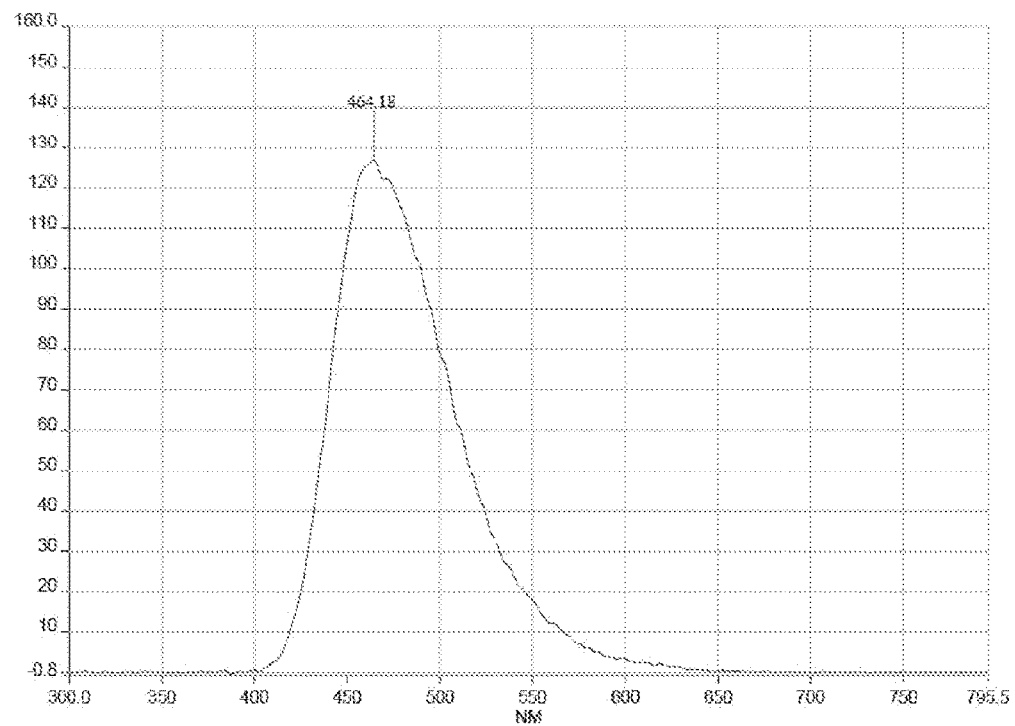

[Figure 48]
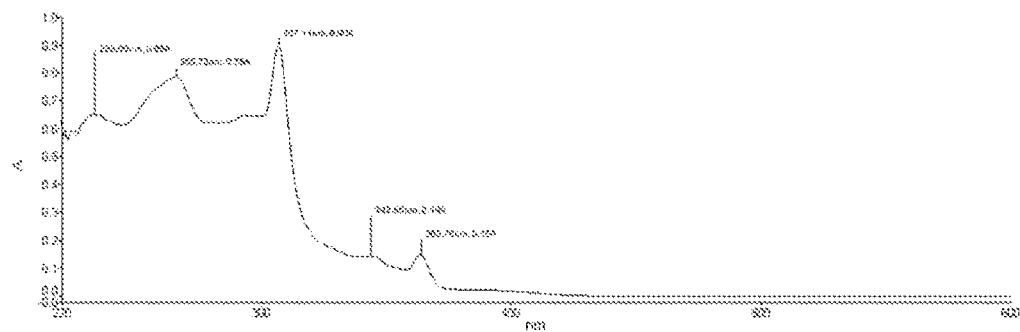
[Figure 49]
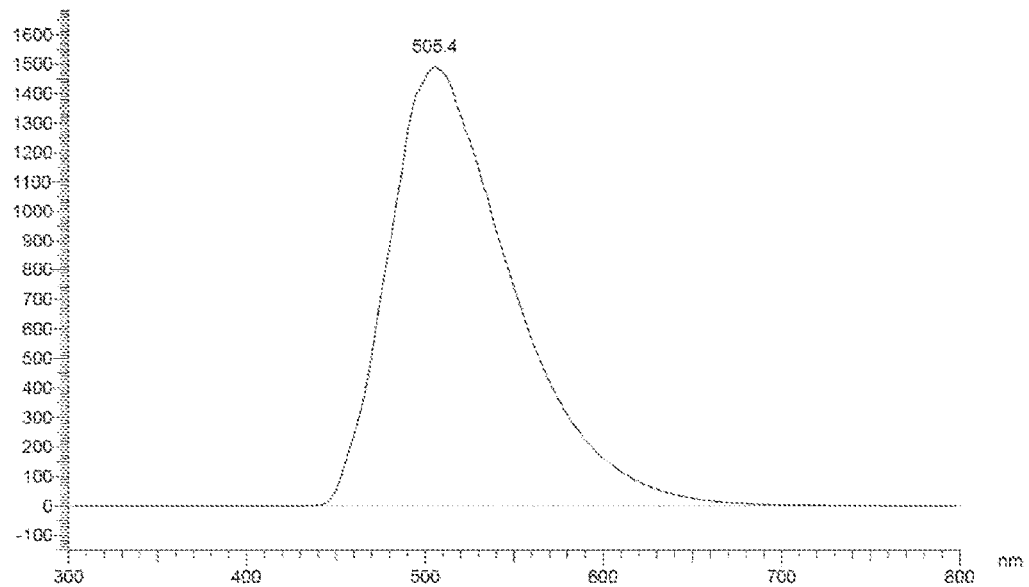

[Figure 50]
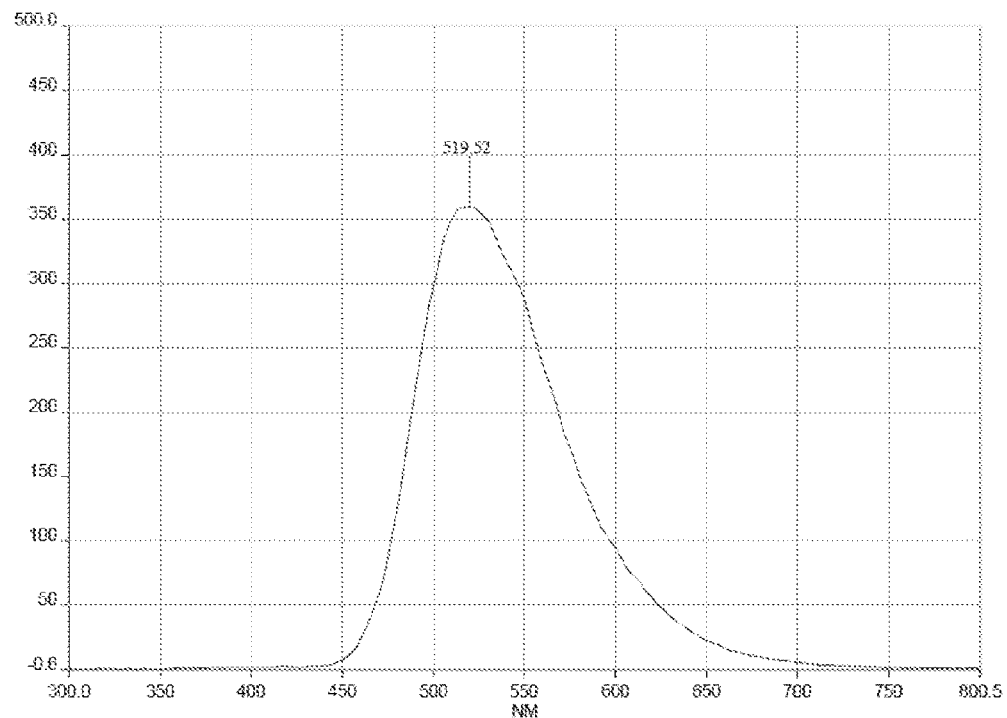
[Figure 51]
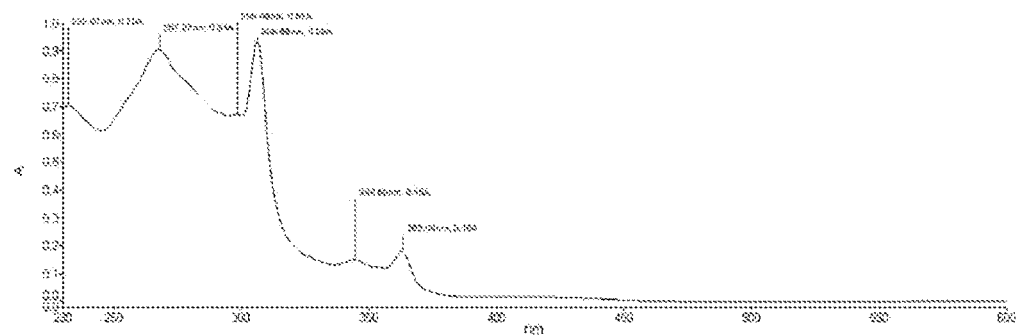

[Figure 52]
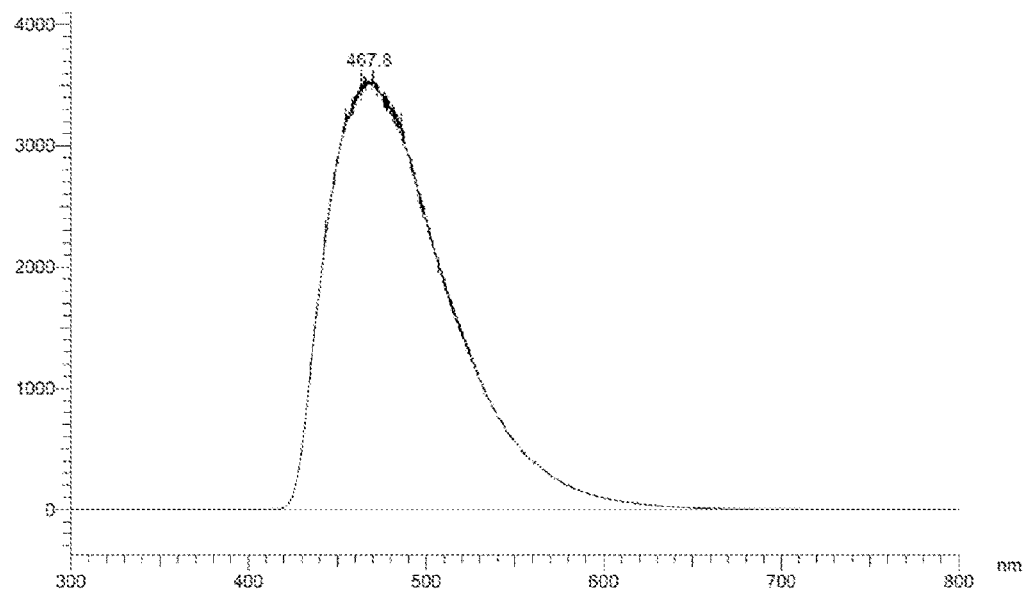
[Figure 53]
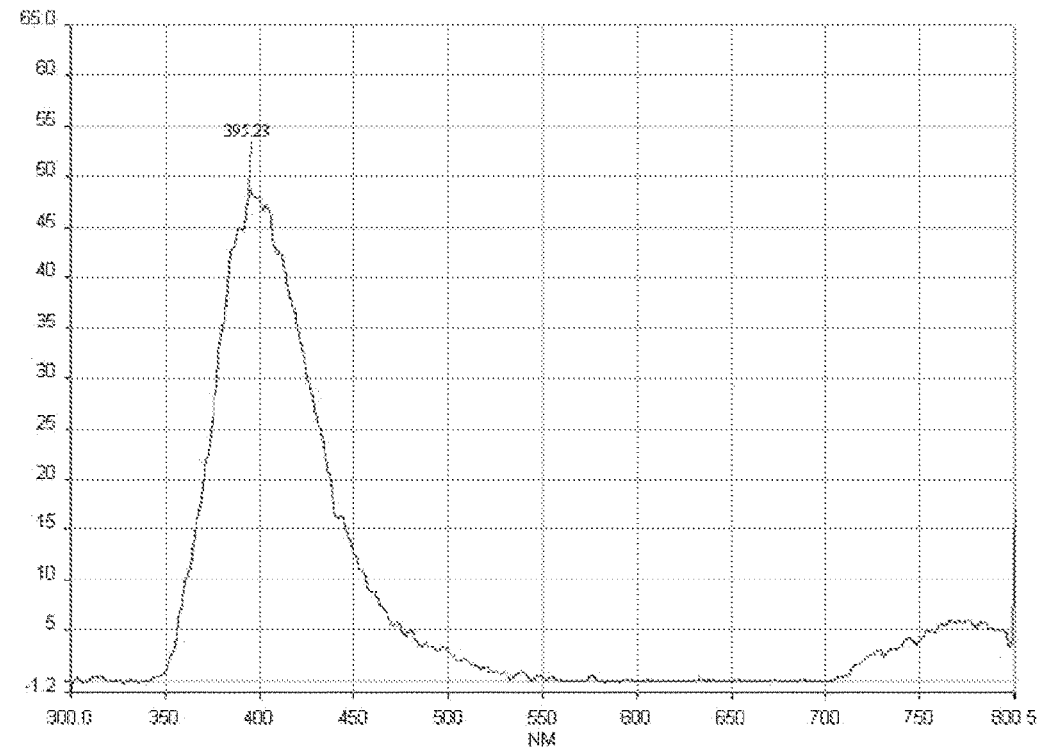

[Figure 54]
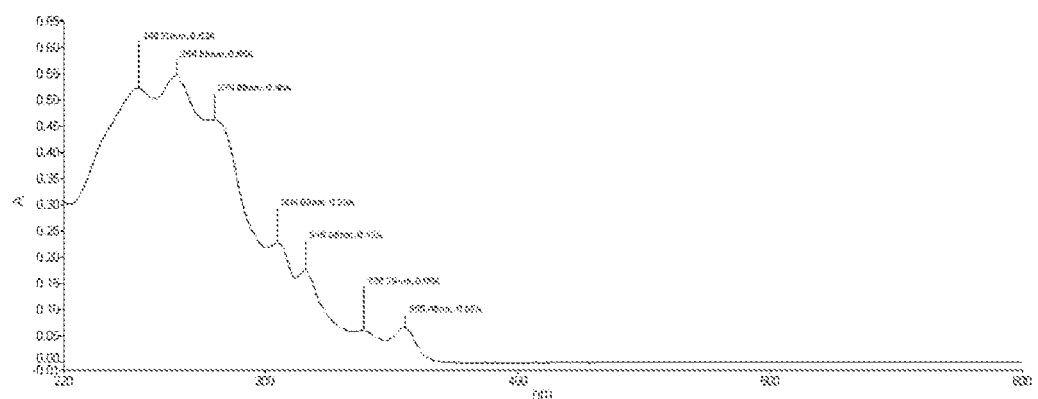

HETERO-CYCLIC COMPOUND AND ORGANIC LIGHT EMITTING DEVICE USING THE SAME

TECHNICAL FIELD

This application claims priority to and the benefit of Korean Patent Application Nos. 10-2015-0106063, 10-2016-0057665, and 10-2016-0059084 filed in the Korean Intellectual Property Office on Jul. 27, 2015, May 11, 2016, and May 13, 2016, respectively, the entire contents of which are incorporated herein by reference.

The present application relates to a hetero-cyclic compound and an organic light emitting device using the same.

BACKGROUND ART

An electroluminescence device is a kind of self-emitting type display device, and has an advantage in that the viewing angle is wide, the contrast is excellent, and the response speed is fast.

An organic light emitting device has a structure in which an organic thin film is disposed between two electrodes. When a voltage is applied to an organic light emitting device having the structure, electrons and holes injected from the two electrodes combine with each other in an organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may perform a function such as hole injection, hole transport, electron blocking, hole blocking, electron transport or electron injection.

In order to improve the performance, lifetime, or efficiency of the organic light emitting device, there is a continuous need for developing a material for an organic thin film.

DISCLOSURE

Technical Problem

It is necessary to perform studies on an organic light emitting device including a compound having a chemical structure, which may satisfy conditions required for a material which is available for the organic light emitting device, for example, appropriate energy levels, electrochemical stability, thermal stability, and the like, and may perform various functions required for the organic light emitting device according to the substituent.

Technical Solution

An exemplary embodiment of the present application provides a hetero-cyclic compound represented by the following Chemical Formula 1:

[Chemical Formula 1]

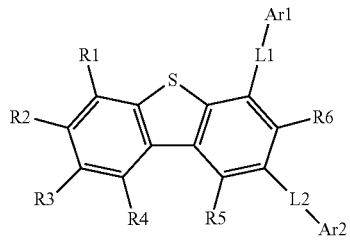

In Chemical Formula 1,

L1 and L2 are the same as or different from each other, and each independently a direct bond or a substituted or unsubstituted $C_6$ to $C_{60}$ arylene group, Ar1 is a substituted or unsubstituted $C_2$ to $C_{60}$ heteroaryl group including at least one N.

Ar2 is represented by any one of the following Chemical Formulae 3 and 4,

[Chemical Formula 3]

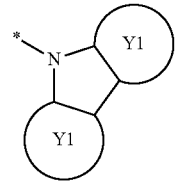

[Chemical Formula 4]

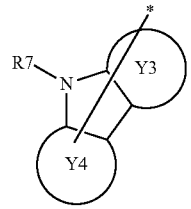

in Chemical Formulae 3 and 4,

Y1 to Y4 are the same as or different from each other, and each independently a substituted or unsubstituted $C_6$ to $C_{60}$ aromatic hydrocarbon ring; or a substituted or unsubstituted $C_2$ to $C_{60}$ aromatic hetero ring, R1 to R7 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R''; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups combine with each other to form a substituted or unsubstituted aliphatic or aromatic hydrocarbon ring, and R, R', and R'' are the same as or different from each other, and are each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

Further, another exemplary embodiment of the present application provides an organic light emitting device including a positive electrode, a negative electrode, and one or more organic material layers provided between the positive electrode and the negative electrode, in which one or more layers of the organic material layers include the hetero-cyclic compound represented by Chemical Formula 1.

In addition, still another exemplary embodiment of the present application provides a composition for an organic material layer of an organic light emitting device, which includes both the hetero-cyclic compound represented by Chemical Formula 1 and a compound represented by the following Chemical Formula 2.

[Chemical Formula 2]

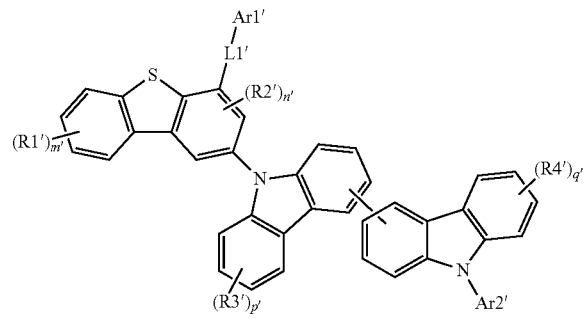

In Chemical Formula 2,

R1' to R4' are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups combine with each other to form a substituted or unsubstituted aliphatic or aromatic hydrocarbon ring, L1' is a direct bond or a substituted or unsubstituted $C_6$ to $C_{60}$ arylene group, Ar1' is a substituted or unsubstituted $C_6$ to $C_{60}$ aryl group; or a substituted or unsubstituted $C_2$ to $C_{60}$ heteroaryl group including at least one of S and O, Ar2' is a substituted or unsubstituted $C_6$ to $C_{60}$ aryl group; or a substituted or unsubstituted $C_2$ to $C_{60}$ heteroaryl group, R, R', and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, m', p' and q' are each independently an integer of 0 to 4, and n' is an integer of 0 to 2.

Advantageous Effects

A hetero-cyclic compound according to an exemplary embodiment of the present application may be used as a material for an organic material layer of an organic light emitting device. The hetero-cyclic compound may be used as a material for a hole injection layer, a hole transport layer, a light emitting layer, an electron transport layer, an electron injection layer, a charge generation layer, and the like in an organic light emitting device. In particular, the hetero-cyclic compound represented by Chemical Formula 1 may be used as a material for an electron transport layer, a hole transport layer, or a light emitting layer of the organic light emitting device. In addition, when the hetero-cyclic compound represented by Chemical Formula 1 is used for the organic light emitting device, the driving voltage of the device may be lowered, the light efficiency of the device may be improved, and the lifetime characteristics of the device may be improved by the thermal stability of the compound.

Furthermore, the hetero-cyclic compound represented by Chemical Formula 1 and the compound represented by chemical Formula 2 may be used simultaneously as a material for a light emitting layer of an organic light emitting device. In addition, when the hetero-cyclic compound represented by Chemical Formula 1 and the hetero-cyclic compound represented by Chemical Formula 2 are simultaneously used for the organic light emitting device, the driving voltage of the device may be lowered, the light efficiency of the device may be improved, and the lifetime characteristics of the device may be improved by the thermal stability of the compound.

DESCRIPTION OF DRAWINGS

FIGS. 1 to 3 each are views schematically illustrating a stacking structure of an organic light emitting device according to an exemplary embodiment of the present application.

FIG. 4 illustrates a measurement graph of LTPL of Compound 1-2 at a wavelength of 363 nm.

FIG. 5 illustrates a measurement graph of PL of Compound 1-2 at a wavelength of 238 nm.

FIG. 6 illustrates a UV absorption spectrum of Compound 1-2.

FIG. 7 illustrates a measurement graph of LTPL of Compound 1-11 at a wavelength of 339 nm.

FIG. 8 illustrates a measurement graph of PL of Compound 1-11 at a wavelength of 234 nm.

FIG. 9 illustrates a UV absorption spectrum of Compound 1-11.

FIG. 10 illustrates a measurement graph of LTPL of Compound 1-23 at a wavelength of 241 nm.

FIG. 11 illustrates a measurement graph of PL of Compound 1-23 at a wavelength of 241 nm.

FIG. 12 illustrates a UV absorption spectrum of Compound 1-23.

FIG. 13 illustrates a measurement graph of LTPL of Compound 1-27 at a wavelength of 340 nm.

FIG. 14 illustrates a measurement graph of PL of Compound 1-27 at a wavelength of 241 nm.

FIG. 15 illustrates a UV absorption spectrum of Compound 1-27.

FIG. 16 illustrates a measurement graph of LTPL of Compound 1-33 at a wavelength of 291 nm.

FIG. 17 illustrates a measurement graph of PL of Compound 1-33 at a wavelength of 239 nm.

FIG. 18 illustrates a UV absorption spectrum of Compound 1-33.

FIG. 19 illustrates a measurement graph of LTPL of Compound 1-39 at a wavelength of 259 nm.

FIG. 20 illustrates a measurement graph of PL of Compound 1-39 at a wavelength of 259 nm.

FIG. 21 illustrates a UV absorption spectrum of Compound 1-39.

FIG. 22 illustrates a measurement graph of LTPL of Compound 1-41 at a wavelength of 260 nm.

FIG. 23 illustrates a measurement graph of PL of Compound 1-41 at a wavelength of 260 nm.

FIG. 24 illustrates a UV absorption spectrum of Compound 1-41.

FIG. 25 illustrates a measurement graph of LTPL of Compound 1-65 at a wavelength of 361 nm.

FIG. 26 illustrates a measurement graph of PL of Compound 1-65 at a wavelength of 235 nm.

FIG. 27 illustrates a UV absorption spectrum of Compound 1-65.

FIG. 28 illustrates a measurement graph of LTPL of Compound 1-66 at a wavelength of 360 nm.

FIG. 29 illustrates a measurement graph of PL of Compound 1-66 at a wavelength of 307 nm.

FIG. 30 illustrates a UV absorption spectrum of Compound 1-66.

FIG. 31 illustrates a measurement graph of LTPL of Compound 1-67 at a wavelength of 361 nm.

FIG. 32 illustrates a measurement graph of PL of Compound 1-67 at a wavelength of 266 nm.

FIG. 33 illustrates a UV absorption spectrum of Compound 1-67.

FIG. 34 illustrates a measurement graph of LTPL of Compound 1-69 at a wavelength of 344 nm.

FIG. 35 illustrates a measurement graph of PL of Compound 1-69 at a wavelength of 308 nm.

FIG. 36 illustrates a UV absorption spectrum of Compound 1-69.

FIG. 37 illustrates a measurement graph of LTPL of Compound 1-70 at a wavelength of 344 nm.

FIG. 38 illustrates a measurement graph of PL of Compound 1-70 at a wavelength of 267 nm.

FIG. 39 illustrates a UV absorption spectrum of Compound 1-70.

FIG. 40 illustrates a measurement graph of LTPL of Compound 1-71 at a wavelength of 344 nm.

FIG. 41 illustrates a measurement graph of PL of Compound 1-71 at a wavelength of 241 nm.

FIG. 42 illustrates a UV absorption spectrum of Compound 1-71.

FIG. 43 illustrates a measurement graph of LTPL of Compound 1-78 at a wavelength of 361 nm.

FIG. 44 illustrates a measurement graph of PL of Compound 1-78 at a wavelength of 263 nm.

FIG. 45 illustrates a UV absorption spectrum of Compound 1-78.

FIG. 46 illustrates a measurement graph of LTPL of Compound 1-82 at a wavelength of 344 nm.

FIG. 47 illustrates a measurement graph of PL of Compound 1-82 at a wavelength of 307 nm.

FIG. 48 illustrates a UV absorption spectrum of Compound 1-82.

FIG. 49 illustrates a measurement graph of LTPL of Compound 1-84 at a wavelength of 363 nm.

FIG. 50 illustrates a measurement graph of PL of Compound 1-84 at a wavelength of 298 nm.

FIG. 51 illustrates a UV absorption spectrum of Compound 1-84.

FIG. 52 illustrates a measurement graph of LTPL of Compound 1-99 at a wavelength of 355 nm.

FIG. 53 illustrates a measurement graph of PL of Compound 1-99 at a wavelength of 355 nm.

FIG. 54 illustrates a UV absorption spectrum of Compound 1-99.

EXPLANATION OF REFERENCE NUMERALS AND SYMBOLS

100: Substrate
200: Positive electrode
300: Organic material layer
301: Hole injection layer
302: Hole transport layer
303: Light emitting layer
304: Hole blocking layer
305: Electron transport layer
306: Electron injection layer
400: Negative electrode

BEST MODE

Hereinafter, the present application will be described in detail.

A hetero-cyclic compound according to an exemplary embodiment of the present application is represented by Chemical Formula 1. More specifically, the hetero-cyclic compound represented by Chemical Formula 1 may be used as a material for an organic material layer of an organic light emitting device by the structural characteristics of the core structure and the substituent as described above.

In Chemical Formulae 3 and 4, * denotes a position to be linked to L2 of Chemical Formula 1.

According to an exemplary embodiment of the present application, Chemical Formula 3 may be represented by any one of the following Chemical Formulae.

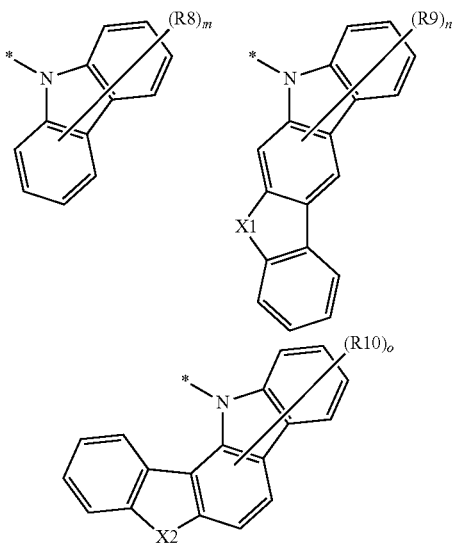

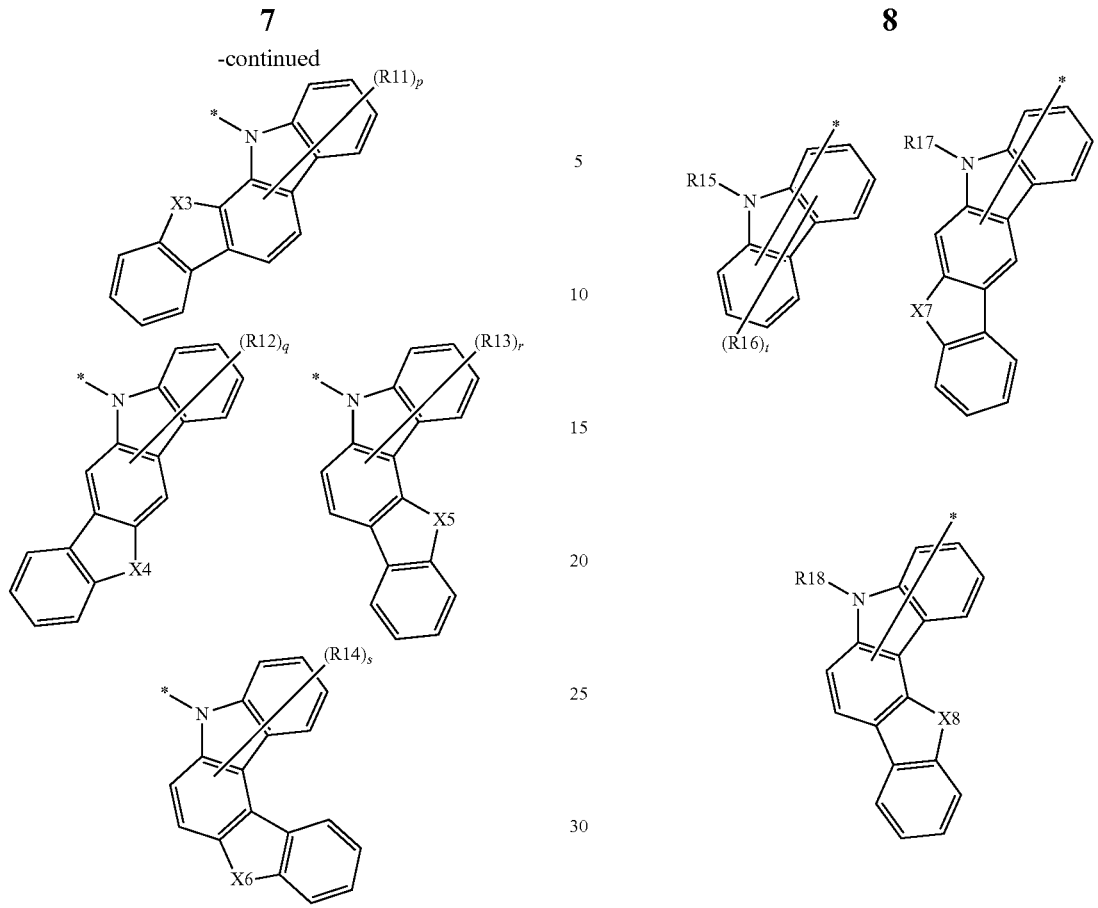

In the structural formulae, X1 to X6 are the same as or different from each other, and each independently NR, S, O, or CR'R", R8 to R14 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups combine with each other to form a substituted or unsubstituted aliphatic or aromatic hydrocarbon ring, R, R', and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, and m is an integer of 0 to 8, and n, o, p, q, r, and s are each independently an integer of 0 to 6.

According to an exemplary embodiment of the present application, Chemical Formula 4 may be represented by any one of the following Chemical Formulae.

In the structural formulae, X7 and X8 are the same as or different from each other, and each independently NR, S, O, or CR'R", R15 to R18 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups combine with each other to form a substituted or unsubstituted aliphatic or aromatic hydrocarbon ring, R, R', and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, and t is an integer of 0 to 7.

According to an exemplary embodiment of the present specification, Chemical Formula 1 may be represented by any one of the following Chemical Formulae 5 to 10.

[Chemical Formula 5]

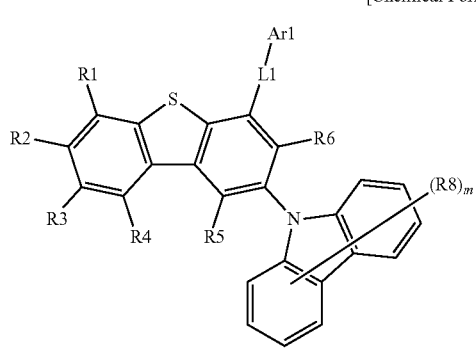

[Chemical Formula 6]

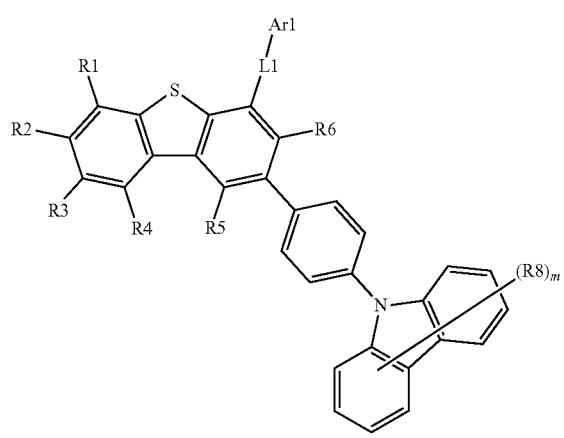

[Chemical Formula 7]

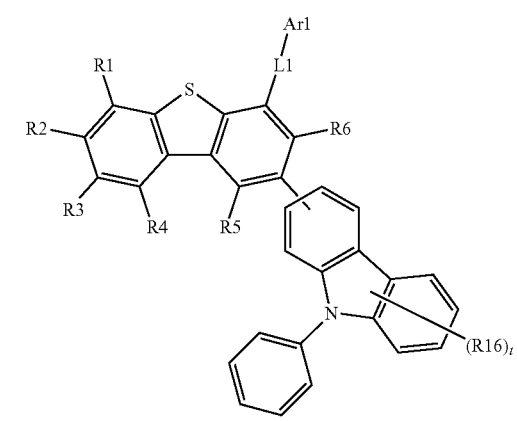

[Chemical Formula 8]

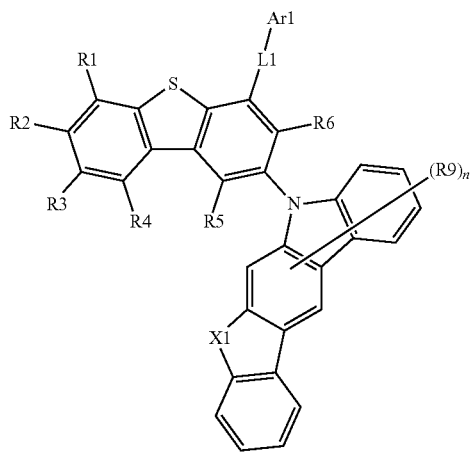

[Chemical Formula 9]

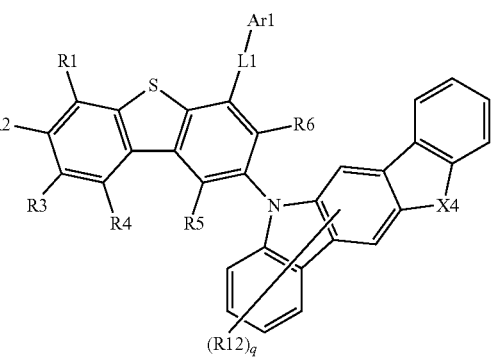

[Chemical Formula 10]

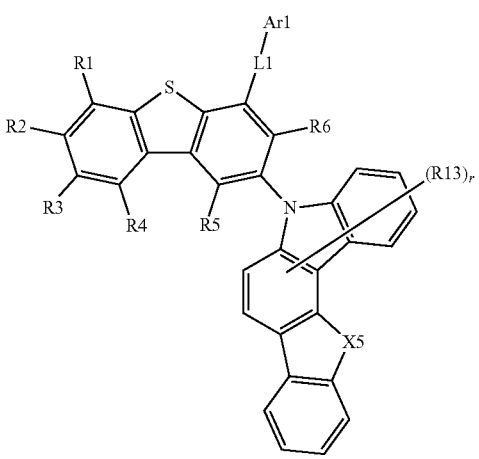

In Chemical Formulae 5 to 10, the definitions of R1 to R6, R8, R9, R12, R13, R16, L1, Ar1, X1, X4, X5, m, n, q, r, and t are the same as those in Chemical Formula 1 and the structural formulae.

In an exemplary embodiment of the present application, R1 to R6 of Chemical Formula 1 may be each independently hydrogen or deuterium.

In an exemplary embodiment of the present application, R8 to R18 may be each independently hydrogen; deuterium; a substituted or unsubstituted $C_6$ to $C_{60}$ aryl group; or a substituted or unsubstituted $C_2$ to $C_{60}$ heteroaryl group.

In an exemplary embodiment of the present application, R, R', and R" of Chemical Formula 1 are the same as or different from each other, and each independently hydrogen; a substituted or unsubstituted $C_1$ to $C_{60}$ alkyl group; or a substituted or unsubstituted $C_6$ to $C_{60}$ aryl group.

Further, the composition for an organic material layer of an organic light emitting device according to an exemplary embodiment of the present application may include both the hetero-cyclic compound represented by Chemical Formula 1 and the compound represented by Chemical Formula 2.

According to an exemplary embodiment of the present application, Chemical Formula 2 may be represented by any one of the following Chemical Formulae 11 to 22.

[Chemical Formula 11]

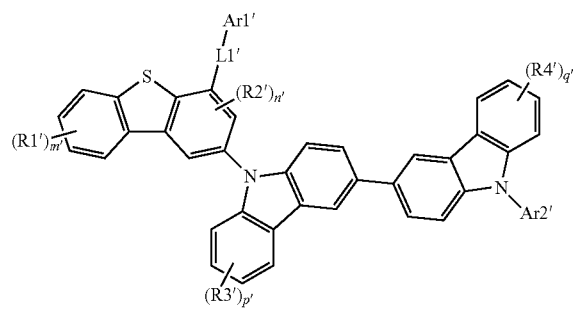

[Chemical Formula 12]

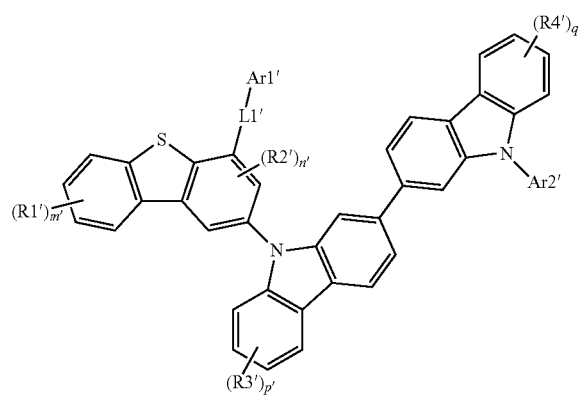

[Chemical Formula 13]

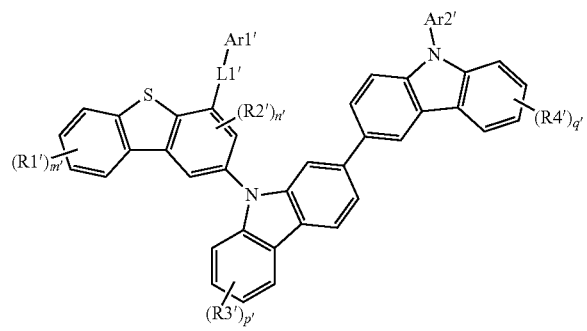

[Chemical Formula 14]

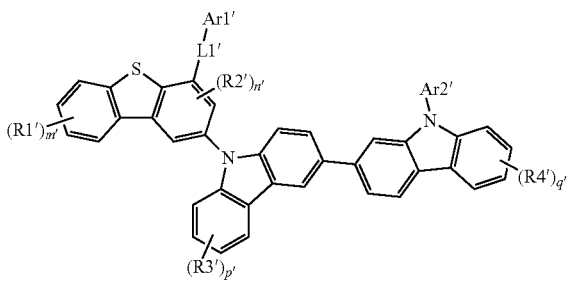

[Chemical Formula 15]

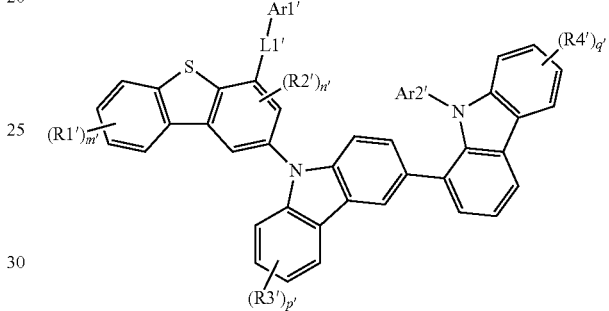

[Chemical Formula 16]

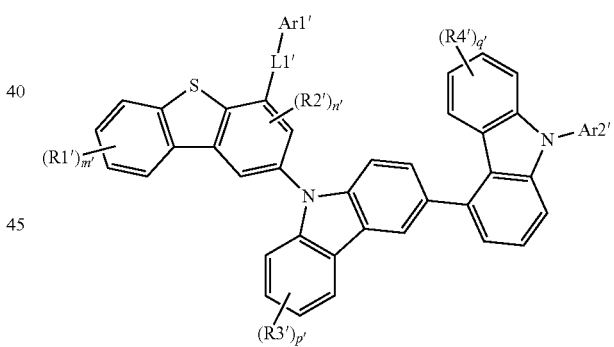

[Chemical Formula 17]

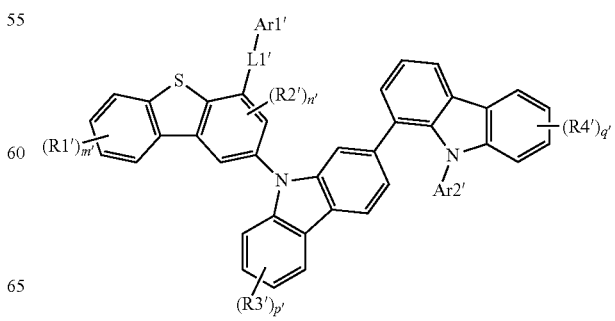

[Chemical Formula 18]

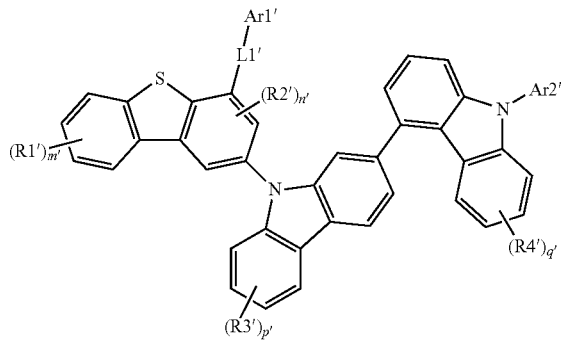

[Chemical Formula 19]

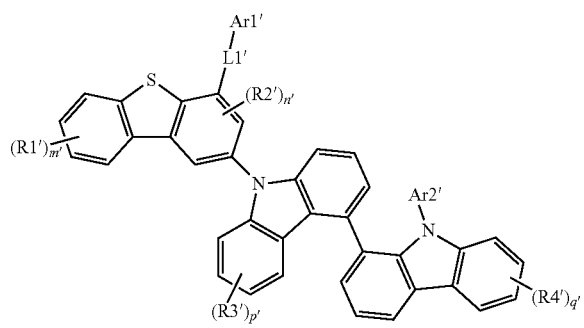

[Chemical Formula 20]

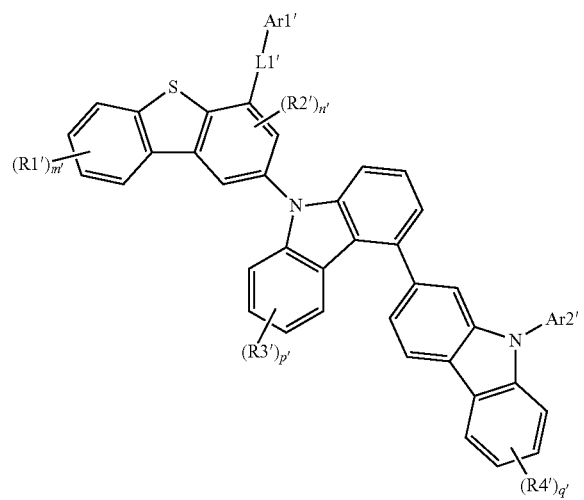

[Chemical Formula 21]

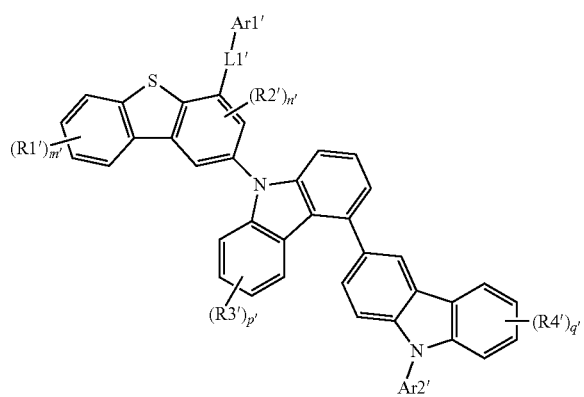

[Chemical Formula 22]

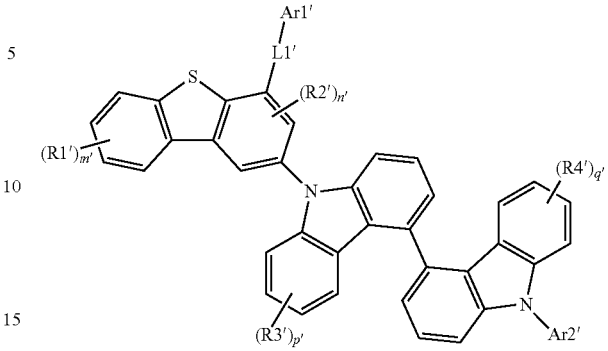

In Chemical Formulae 11 to 22, the definitions of L1, Ar1, Ar2, R1 to R4, m, n, p, and q are the same as those in Chemical Formula 2.

In an exemplary embodiment of the present application, when m', n', p', and q' of Chemical Formula 2 are each independently 2 or more, two or more R1' to R4' may be each the same as or different from each other.

In an exemplary embodiment of the present application, R1' to R4' of Chemical Formula 2 may be each independently hydrogen or deuterium.

In an exemplary embodiment of the present application, Ar1' of Chemical Formula 2 may be a substituted or unsubstituted $C_6$ to $C_{60}$ aryl group; a substituted or unsubstituted $C_2$ to $C_{60}$ heteroaryl group including S; or a substituted or unsubstituted $C_2$ to $C_{60}$ heteroaryl group including O.

In an exemplary embodiment of the present application, Ar1' of Chemical Formula 2 may be a phenyl group, a biphenyl group, a naphthyl group, a fluorene group in which an alkyl group is substituted, a dibenzothiophene group, or a dibenzofuran group.

In an exemplary embodiment of the present application, Ar2' of Chemical Formula 2 may be a substituted or unsubstituted $C_6$ to $C_{60}$ aryl group.

In an exemplary embodiment of the present application, Ar2' of Chemical Formula 2 may be a phenyl group.

In the present application, the substituents of Chemical Formulae 1 and 2 will be more specifically described as follows.

In the present specification, "substituted or unsubstituted" means being unsubstituted or substituted with one or more substituents selected from the group consisting of deuterium; a halogen group; —CN; a $C_1$ to $C_{60}$ alkyl group; a $C_2$ to $C_{60}$ alkenyl group; a $C_2$ to $C_{60}$ alkynyl group; a $C_3$ to $C_{60}$ cycloalkyl group; a $C_2$ to $C_{60}$ heterocycloalkyl group; a $C_6$ to $C_{60}$ aryl group; a $C_2$ to $C_{60}$ heteroaryl group; —SiRR'R"; —P(=O)RR'; a $C_1$ to $C_{20}$ alkylamine group; a $C_6$ to $C_{60}$ arylamine group; and a $C_2$ to $C_{60}$ heteroarylamine group, being unsubstituted or substituted with a substituent to which two or more substituents among the substituents are linked, or being unsubstituted or substituted with a substituent to which two or more substituents selected among the substituents are linked. For example, "the substituent to which two or more substituents are linked" may be a biphenyl group. That is, the biphenyl group may also be an aryl group, and may be interpreted as a substituent to which two phenyl groups are linked. The additional substituents may also be additionally substituted. R, R', and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

According to an exemplary embodiment of the present specification, the "substituted or unsubstituted" is unsubstituted or substituted with one or more substituents selected from the group consisting of deuterium, a halogen group, —CN, SiRR'R", P(=O)RR', a $C_1$ to $C_{20}$ straight-chained or branch-chained alkyl group, a $C_6$ to $C_{60}$ aryl group, and a $C_2$ to $C_{60}$ heteroaryl group, and R, R', and R" are the same as or different from each other, and each independently hydrogen; deuterium; —CN; a $C_1$ to $C_{60}$ alkyl group which is unsubstituted or substituted with deuterium, a halogen group, —CN, a $C_1$ to $C_{20}$ alkyl group, a $C_6$ to $C_{60}$ aryl group, and a $C_2$ to $C_{60}$ heteroaryl group; a $C_3$ to $C_{60}$ cycloalkyl group which is unsubstituted or substituted with deuterium, halogen, —CN, a $C_1$ to $C_{20}$ alkyl group, a $C_6$ to $C_{60}$ aryl group, and a $C_2$ to $C_{60}$ heteroaryl group; a $C_6$ to $C_{60}$ aryl group which is unsubstituted or substituted with deuterium, halogen, —CN, a $C_1$ to $C_{20}$ alkyl group, a $C_6$ to $C_{60}$ aryl group, and a $C_2$ to $C_{60}$ heteroaryl group; or a $C_2$ to $C_{60}$ heteroaryl group which is unsubstituted or substituted with deuterium, halogen, —CN, a $C_1$ to $C_{20}$ alkyl group, a $C_6$ to $C_{60}$ aryl group, and a $C_2$ to $C_{60}$ heteroaryl group.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the halogen may be fluorine, chlorine, bromine or iodine.

In the present specification, the alkyl group includes a straight-chain or branched-chain having 1 to 60 carbon atoms, and may be additionally substituted with another substituent. The number of carbon atoms of the alkyl group may be 1 to 60, specifically 1 to 40, and more specifically 1 to 20. Specific examples thereof include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group, and the like, but are not limited thereto.

In the present specification, the alkenyl group includes a straight-chain or branched-chain having 2 to 60 carbon atoms, and may be additionally substituted with another substituent. The number of carbon atoms of the alkenyl group may be 2 to 60, specifically 2 to 40, and more specifically 2 to 20. Specific examples thereof include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group, and the like, but are not limited thereto.

In the present specification, the alkynyl group includes a straight-chain or branched-chain having 2 to 60 carbon atoms, and may be additionally substituted with another substituent. The number of carbon atoms of the alkynyl group may be 2 to 60, specifically 2 to 40, and more specifically 2 to 20.

In the present specification, the cycloalkyl group includes a monocycle or polycycle having 3 to 60 carbon atoms, and may be additionally substituted with another substituent. Here, the polycycle means a group in which a cycloalkyl group is directly linked to or fused with another cyclic group. Here, another cyclic group may also be a cycloalkyl group, but may also be another kind of cyclic group, for example, a heterocycloalkyl group, an aryl group, a heteroaryl group, and the like. The number of carbon atoms of the cycloalkyl group may be 3 to 60, specifically 3 to 40, and more specifically 5 to 20. Specific examples thereof include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group, and the like, but are not limited thereto.

In the present specification, the heterocycloalkyl group includes O, S, Se, N, or Si as a heteroatom, includes a monocycle or polycycle having 2 to 60 carbon atoms, and may be additionally substituted with another substituent. Here, the polycycle means a group in which a heterocycloalkyl group is directly linked to or fused with another cyclic group. Here, another cyclic group may also be a heterocycloalkyl group, but may also be another kind of cyclic group, for example, a cycloalkyl group, an aryl group, a heteroaryl group, and the like. The number of carbon atoms of the heterocycloalkyl group may be 2 to 60, specifically 2 to 40, and more specifically 3 to 20.

In the present specification, the aryl group includes a monocycle or polycycle having 6 to 60 carbon atoms, and may be additionally substituted with another substituent. Here, the polycycle means a group in which an aryl group is directly linked to or fused with another cyclic group. Here, another cyclic group may also be an aryl group, but may also be another kind of cyclic group, for example, a cycloalkyl group, a heterocycloalkyl group, a heteroaryl group, and the like. The aryl group includes a spiro group. The number of carbon atoms of the aryl group may be 6 to 60, specifically 6 to 40, and more specifically 6 to 25. Specific examples of the aryl group include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused cyclic group thereof, and the like, but are not limited thereto.

In the present specification, the spiro group is a group including a spiro structure, and may have 15 to 60 carbon atoms. For example, the spiro group may include a structure in which a 2,3-dihydro-1H-indene group or a cyclohexane group is spiro-bonded to a fluorenyl group. Specifically, the following spiro group may include any one of the groups of the following structural formulae.

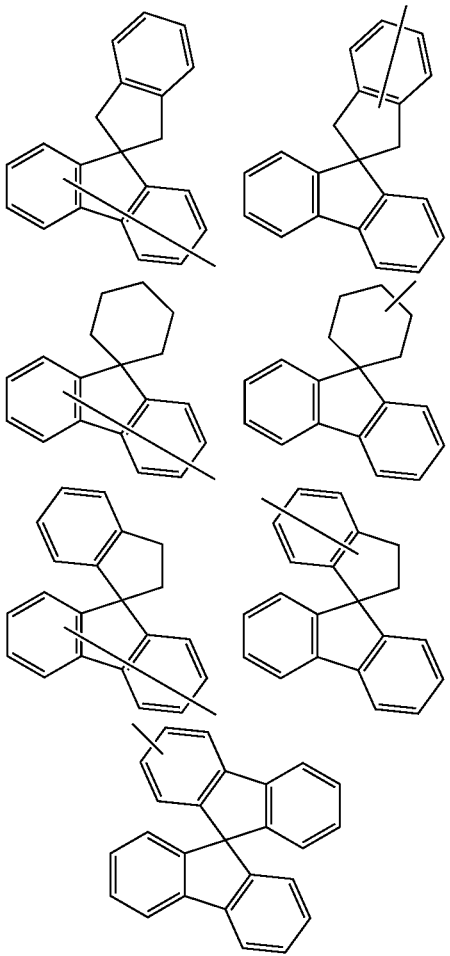

In the present specification, the heteroaryl group includes S, O, Se, N, or Si as a heteroatom, includes a monocycle or polycycle having 2 to 60 carbon atoms, and may be additionally substituted with another substituent. Here, the polycycle means a group in which a heteroaryl group is directly linked to or fused with another cyclic group. Here, another cyclic group may also be a heteroaryl group, but may also be another kind of cyclic group, for example, a cycloalkyl group, a heterocycloalkyl group, an aryl group, and the like. The number of carbon atoms of the heteroaryl group may be 2 to 60, specifically 2 to 40, and more specifically 3 to 25. Specific examples of the heteroaryl group include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxinyl group, a triazinyl group, a tetrazinyl group, a quinolyl group, an isoquinolyl group, a quinazolinyl group, an isoquinazolinyl group, a quinozolilyl group, a naphthyridyl group, an acridinyl group, a phenanthridinyl group, an imidazopyridinyl group, a diaza naphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi (dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepin group, a 9,10-dihydroacridinyl group, a phenanthrazinyl group, a phenothiazinyl group, a phthalazinyl group, a naphthylidinyl group, a phenanthrolinyl group, a benzo[c][1,2,]thiadiazolyl group, a 5,10-dihydrodibenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group, and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group, and the like, but are not limited thereto.

In the present specification, the arylene group means that there are two bonding positions in an aryl group, that is, a divalent group. The above-described description on the aryl group may be applied, except that the arylene groups are each a divalent group. Further, the heteroarylene group means that there are two bonding positions in a heteroaryl group, that is, a divalent group. The above-described description on the heteroaryl group may be applied, except that these are each a divalent group.

According to an exemplary embodiment of the present application, Chemical Formula 1 may be represented by any one of the following compounds, but is not limited thereto.

1-1

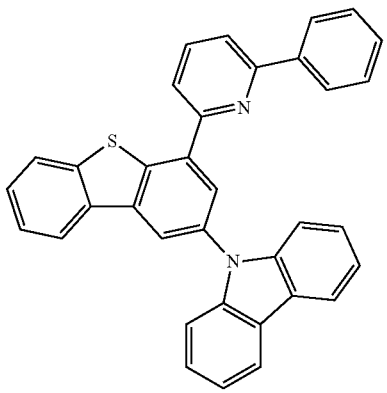

1-2
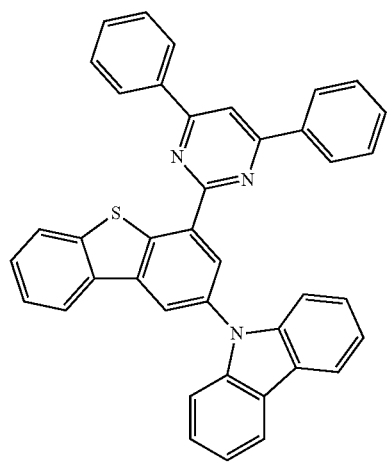
1-3
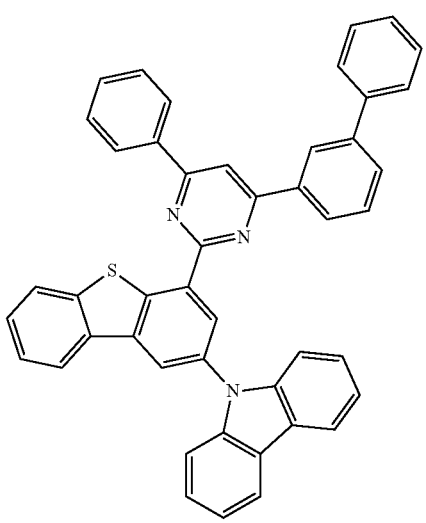
1-4
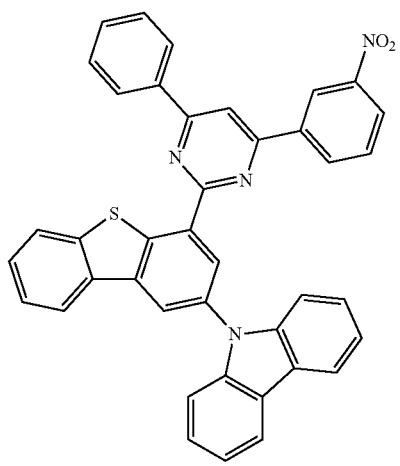
1-5
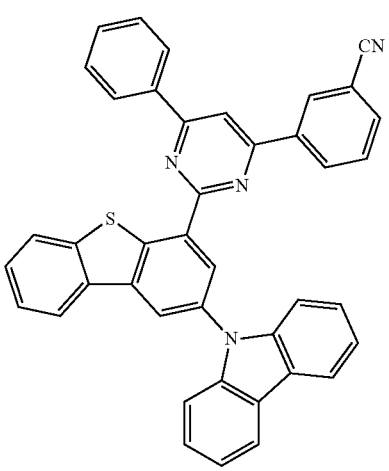
1-6
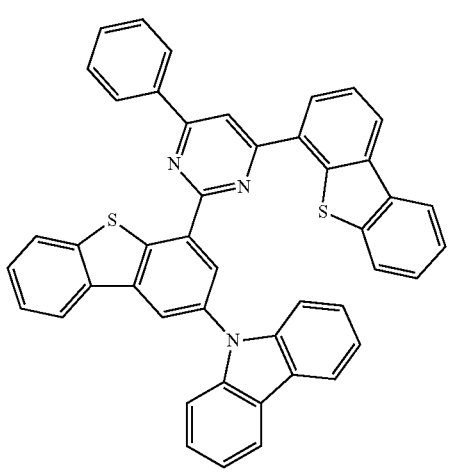
1-7
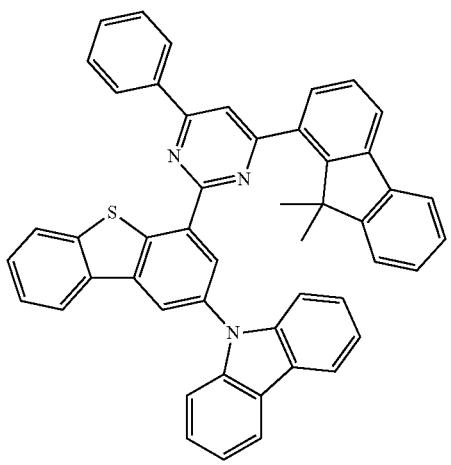

-continued
1-8
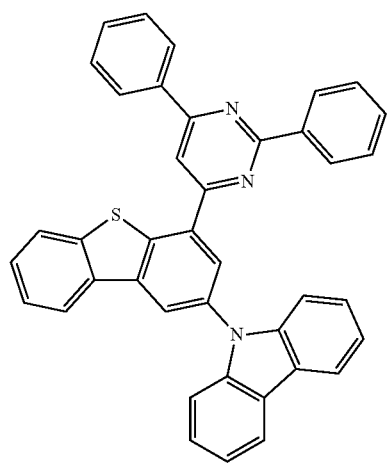
1-9
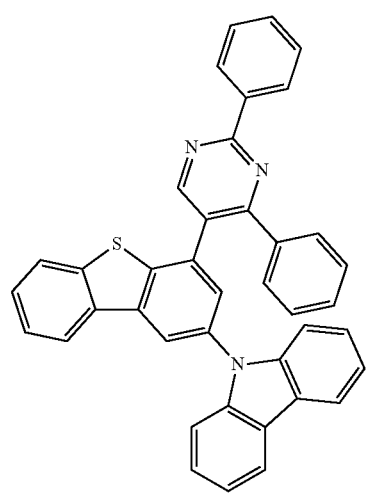
1-10
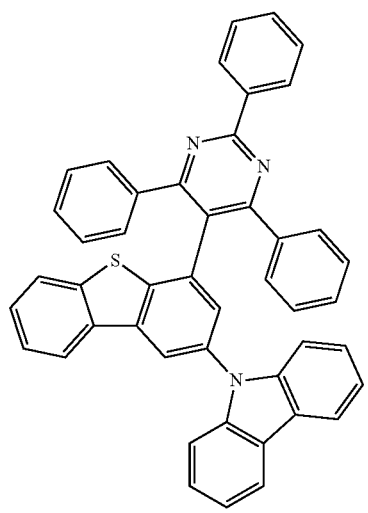
-continued
1-11
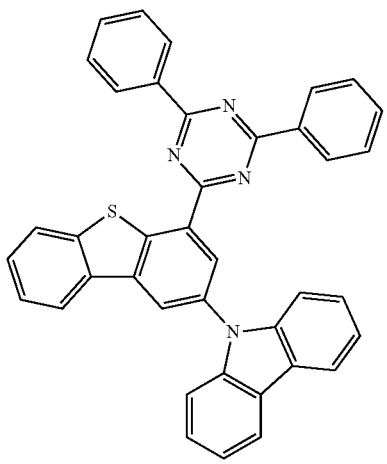
1-12
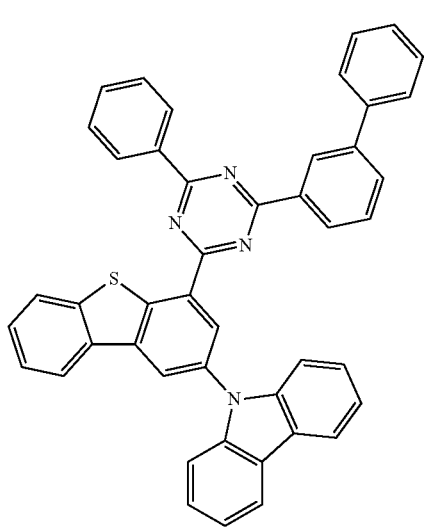
1-13
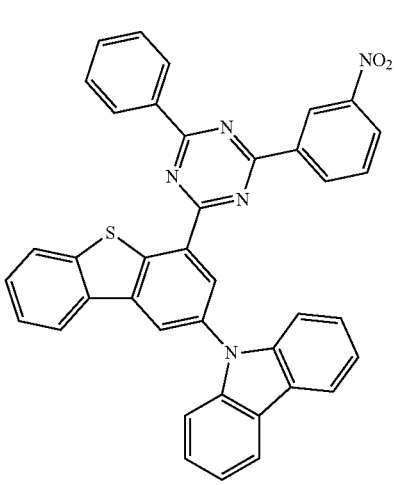

-continued
1-14
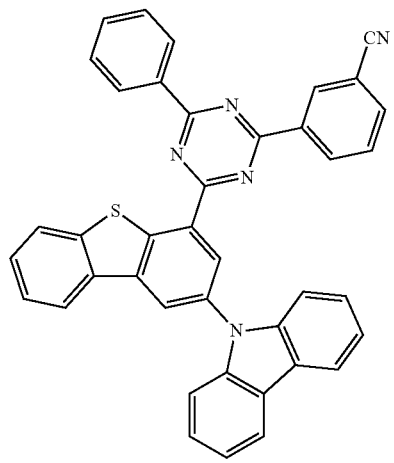
1-15
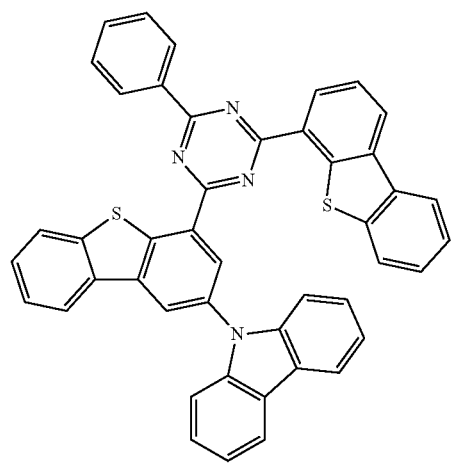
1-16
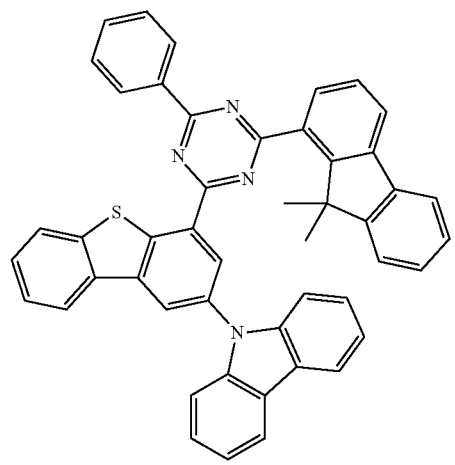
-continued
1-17
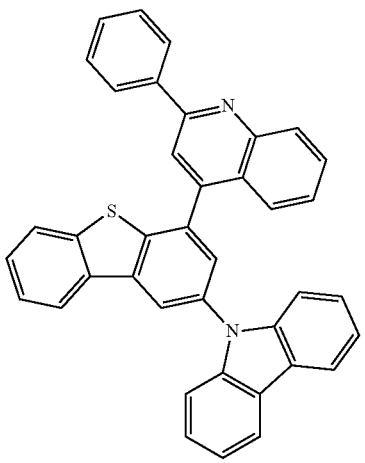
1-18
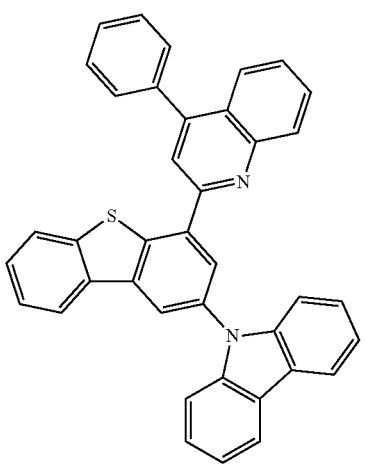
1-19
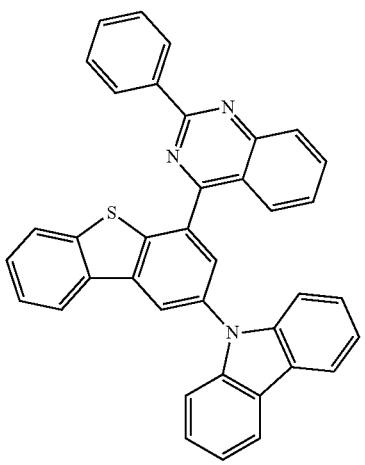

1-20
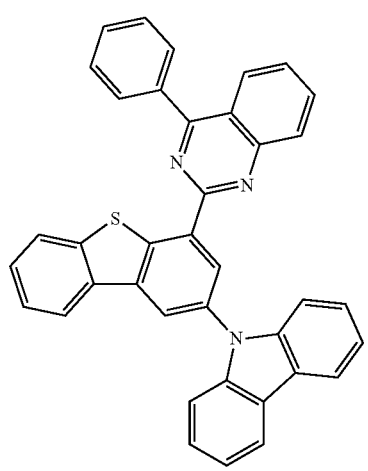
1-21
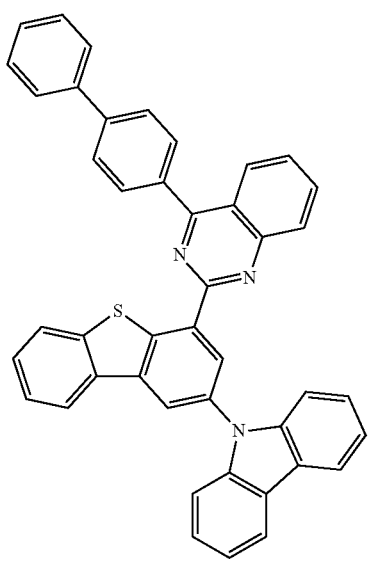
1-22
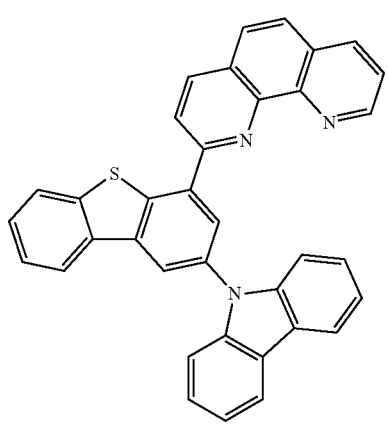
1-23
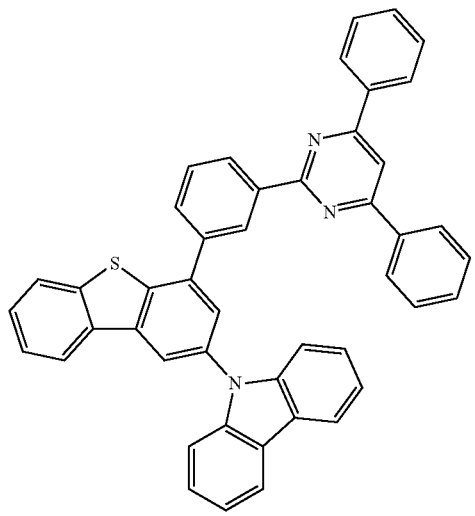
1-24
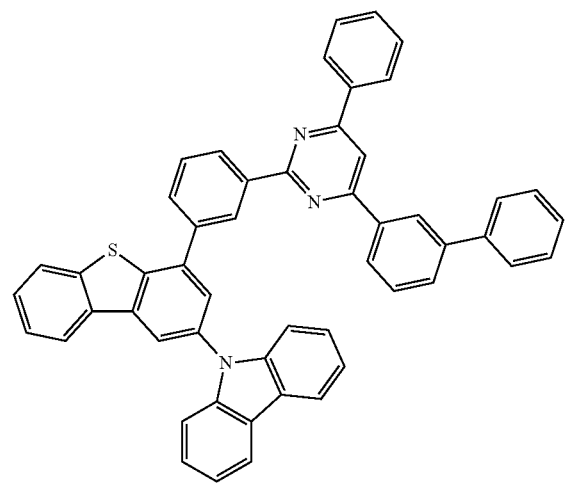
1-25
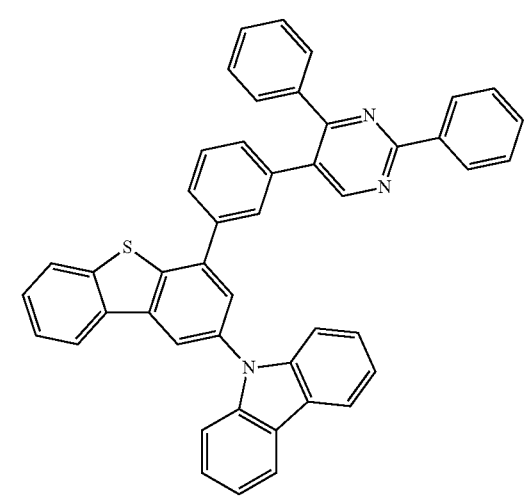

-continued
1-26
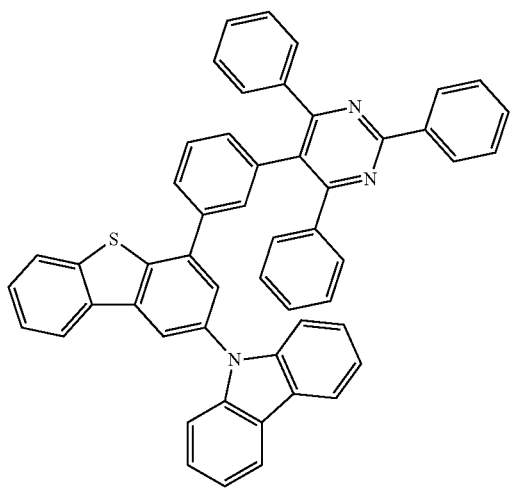
1-27
1-28
1-29
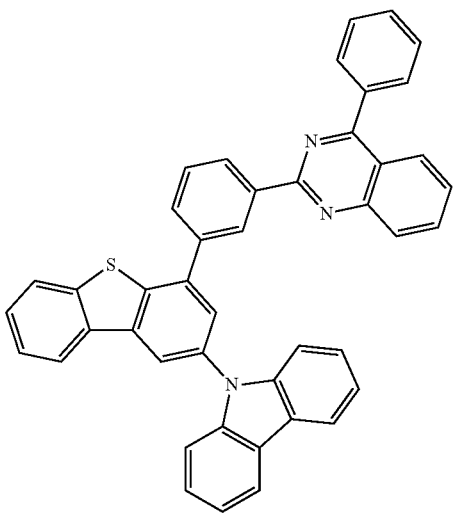
1-30
1-31
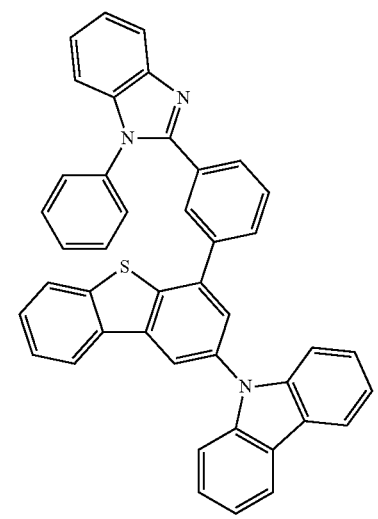

1-32
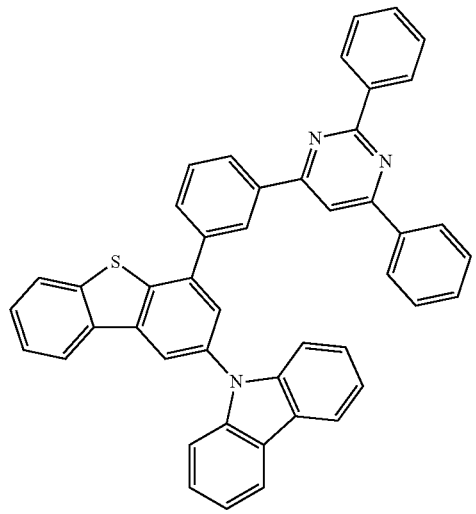
1-33
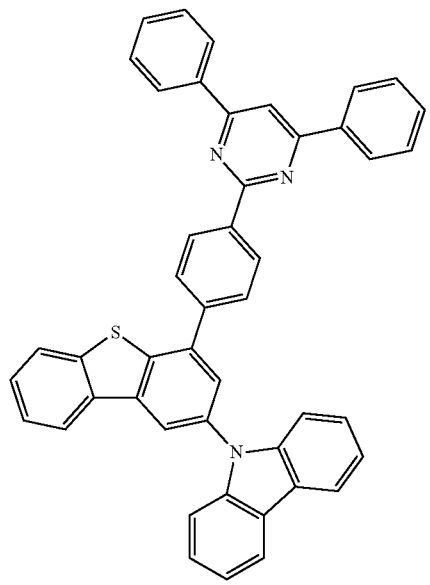
1-34
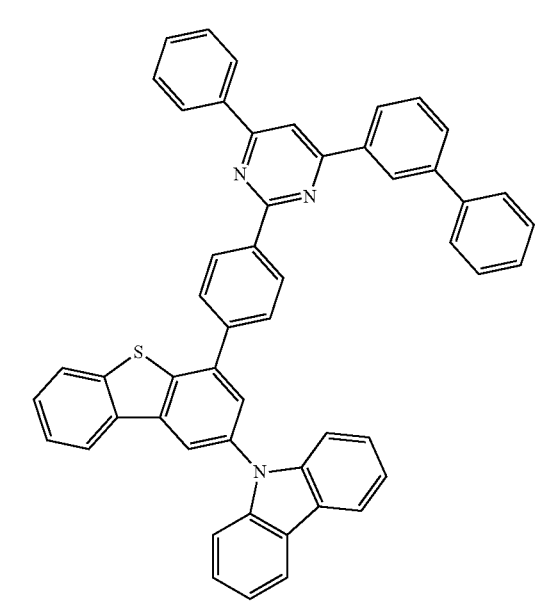
1-35
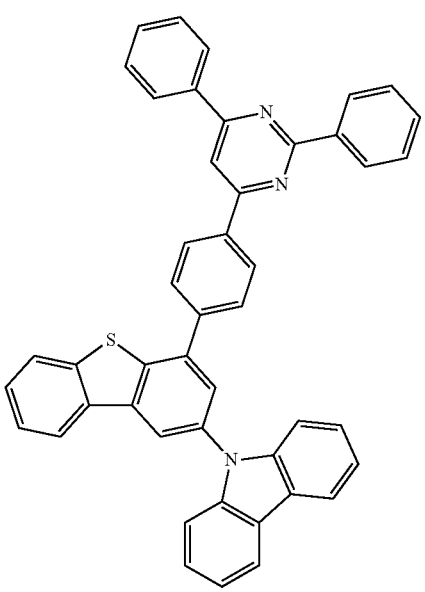

1-36
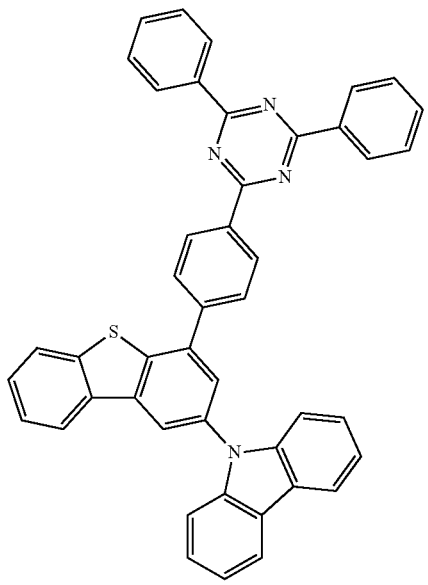
1-37
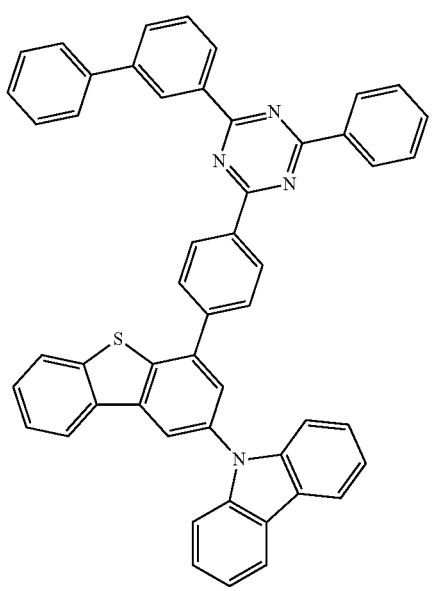
1-38
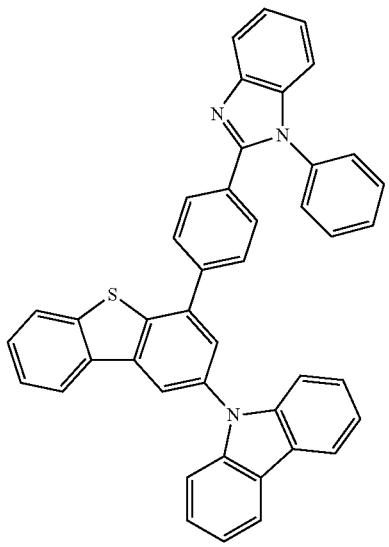
1-39
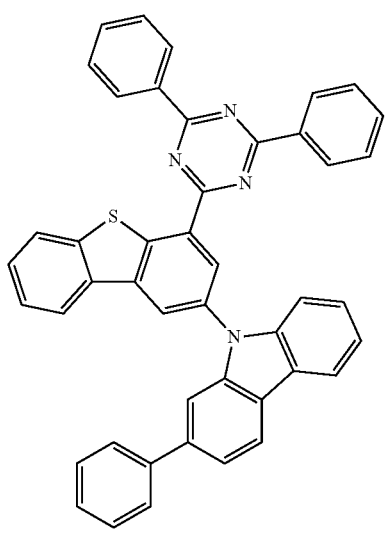
1-40
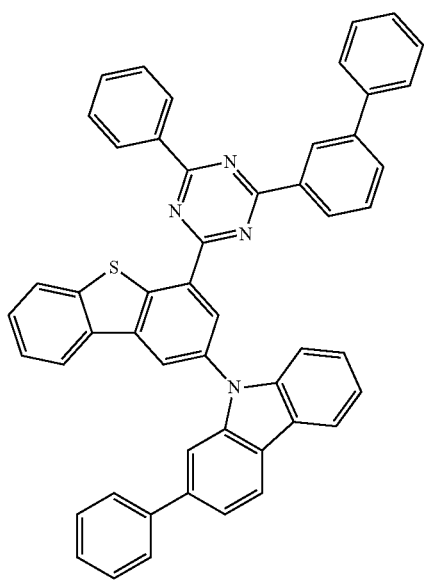

-continued
1-41
1-42
1-43
1-44
1-45
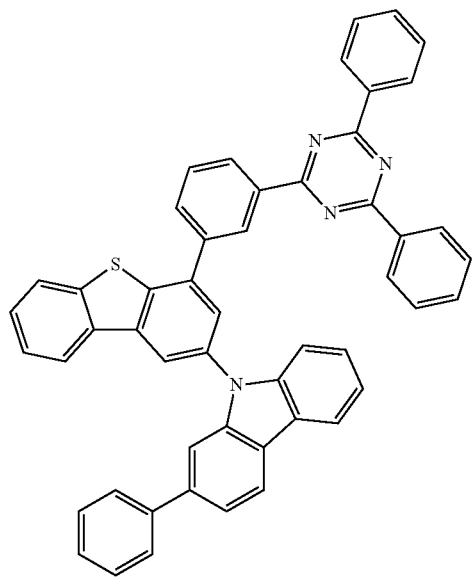
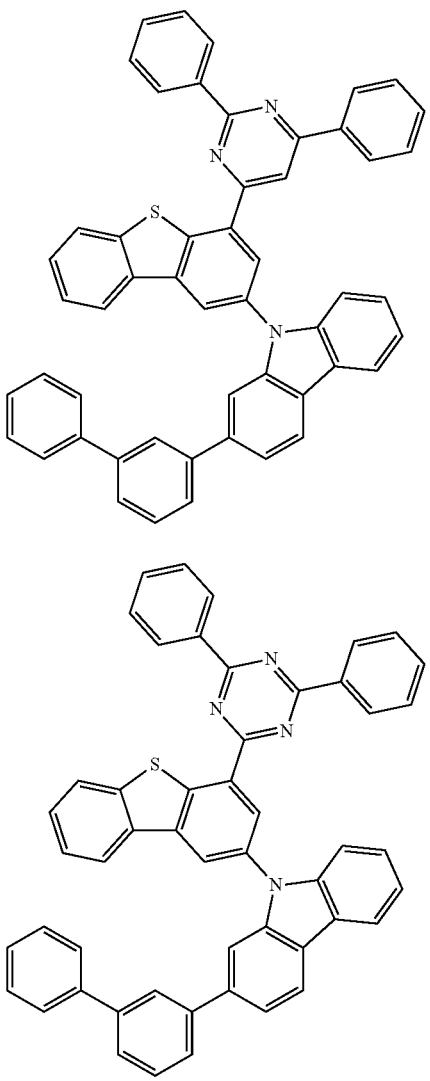
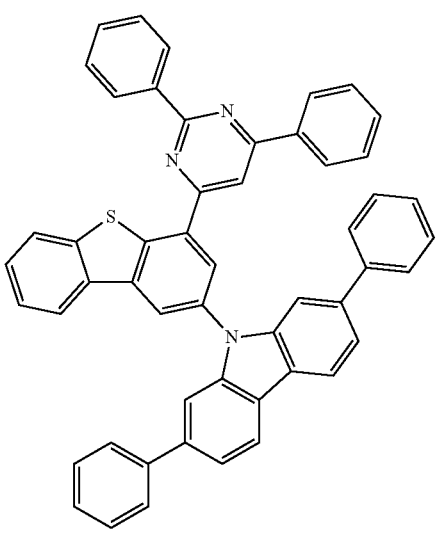

1-46
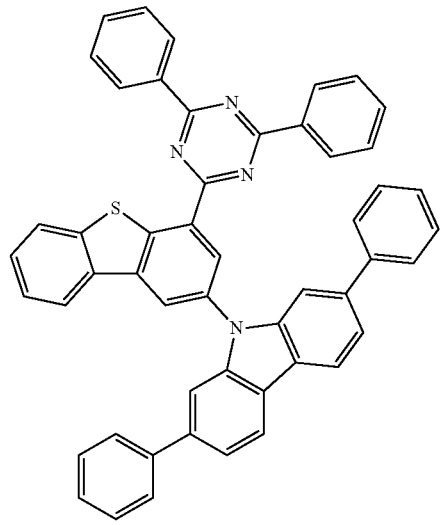
1-47
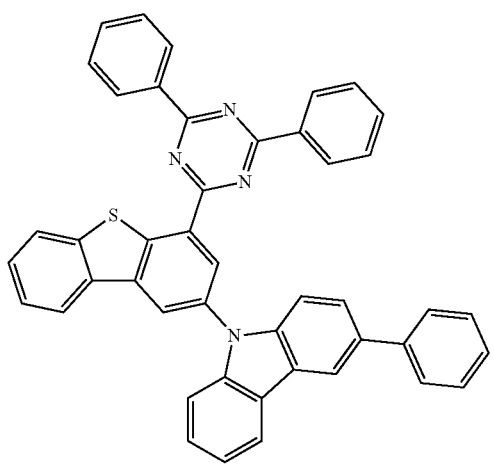
1-48
1-49
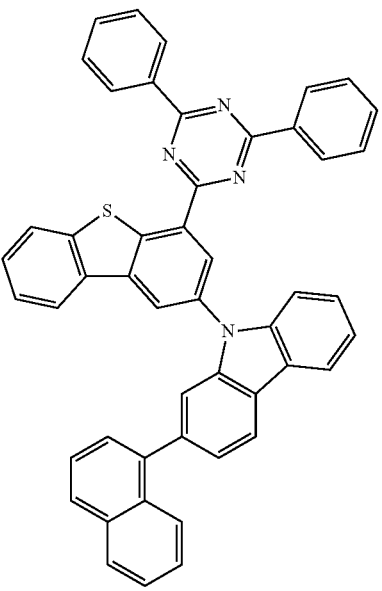
1-50
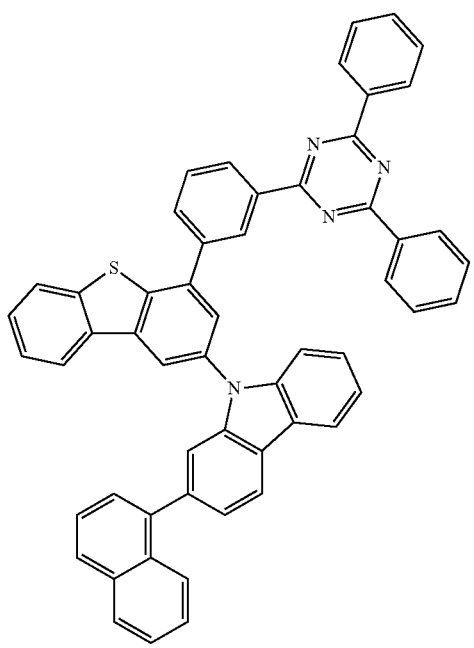

1-51
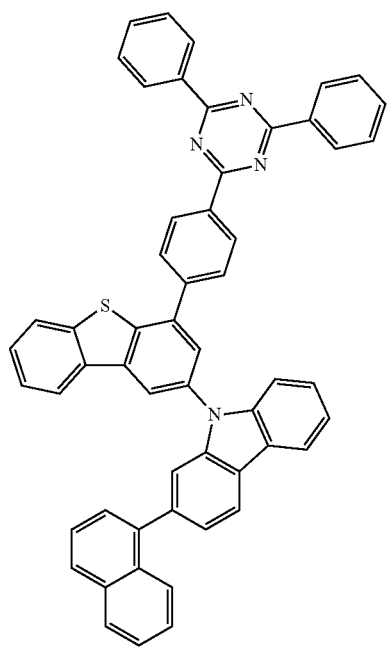
1-52
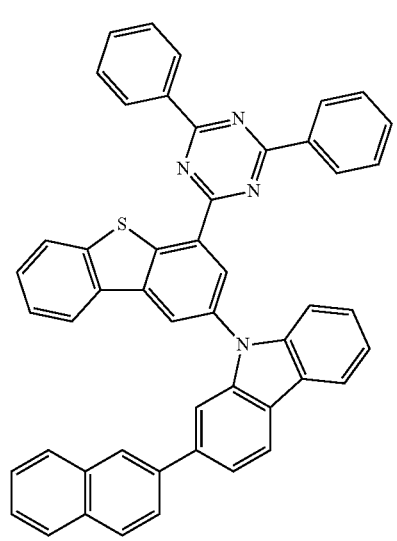
1-53
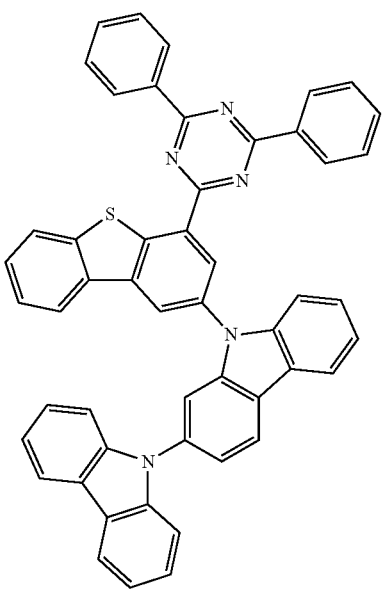
1-54
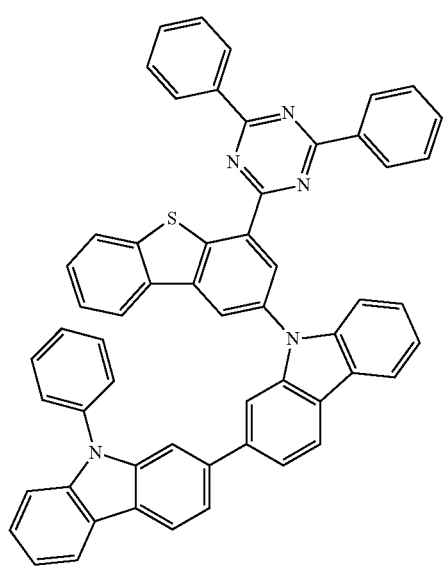

1-55
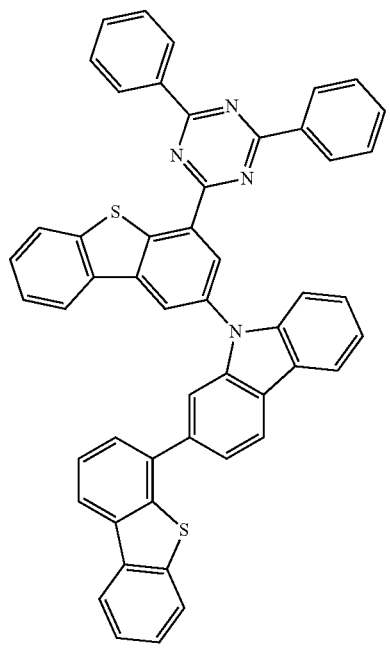
1-56
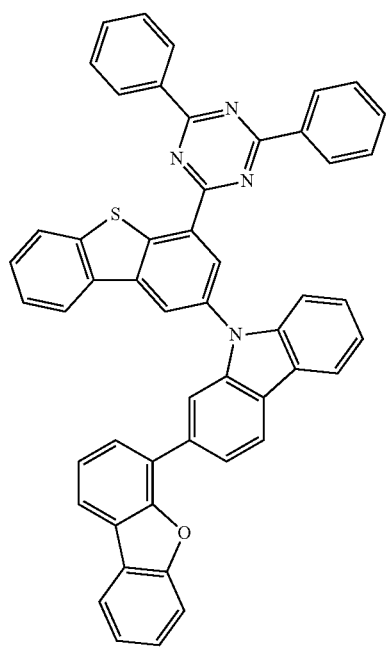
1-57
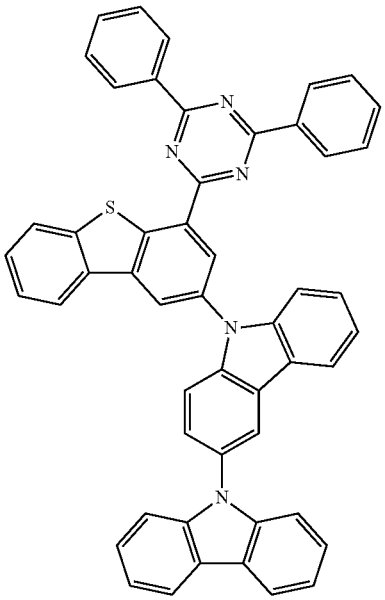
1-58
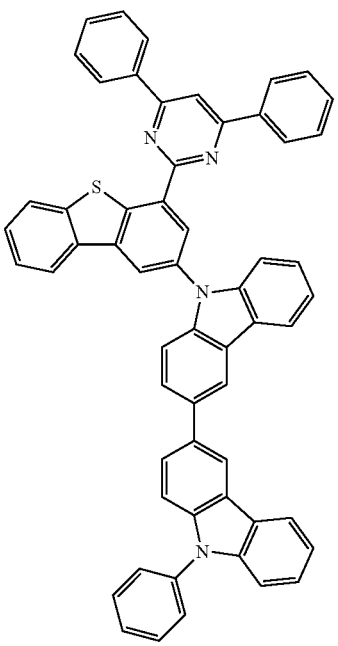

1-59
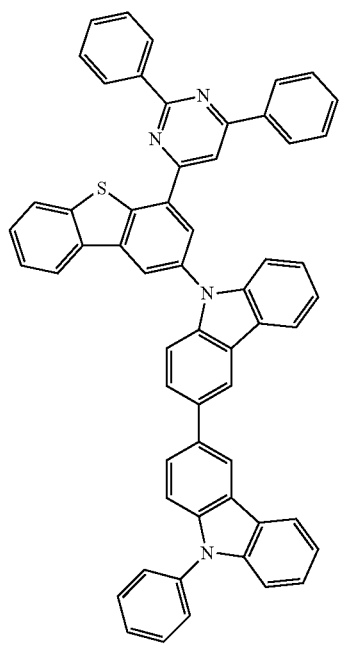
1-61
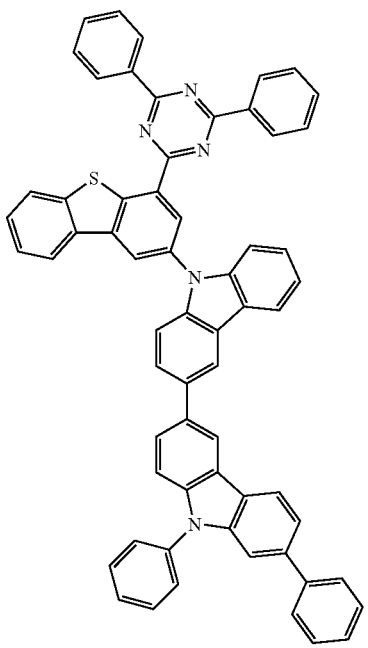
1-60
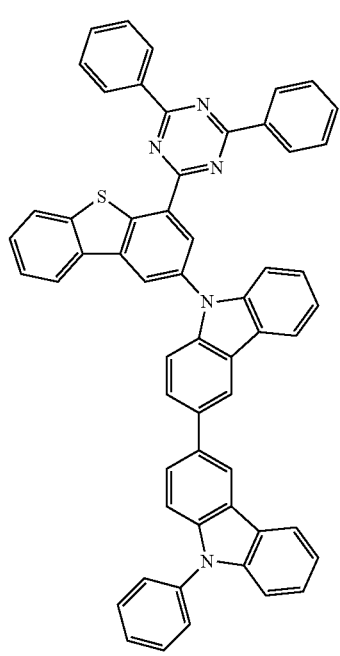
1-62
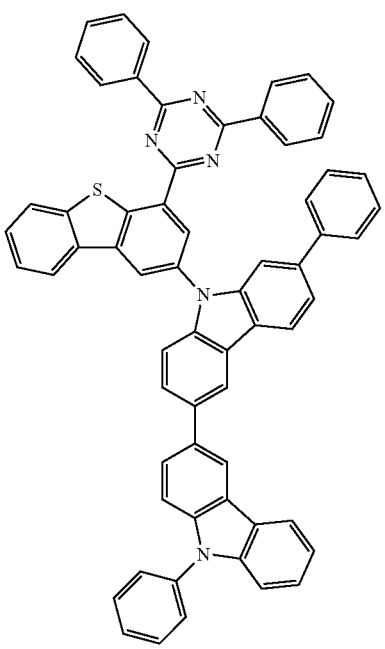

-continued
1-63
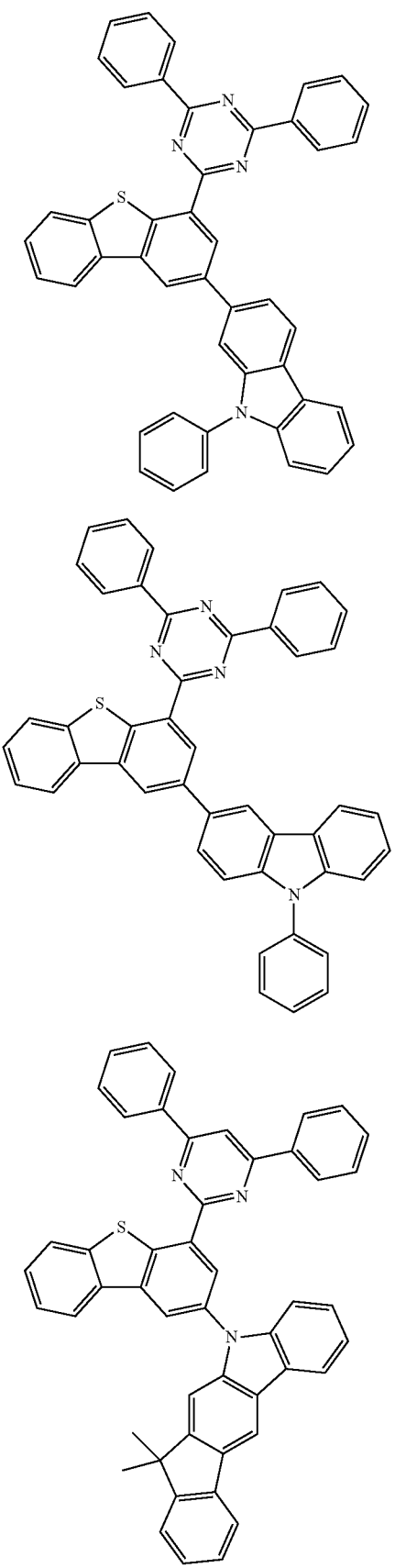
1-64
1-65
1-66
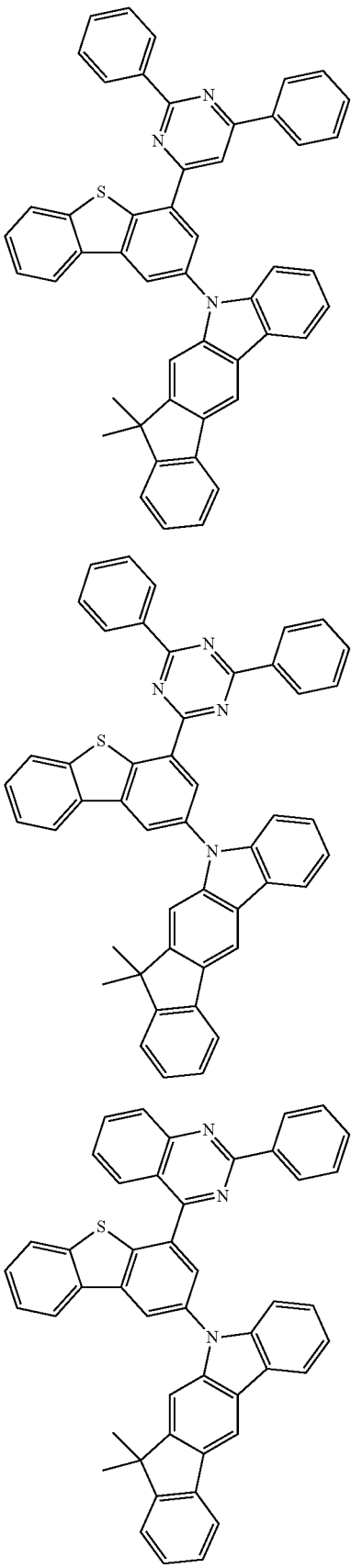
1-67
1-68

1-69
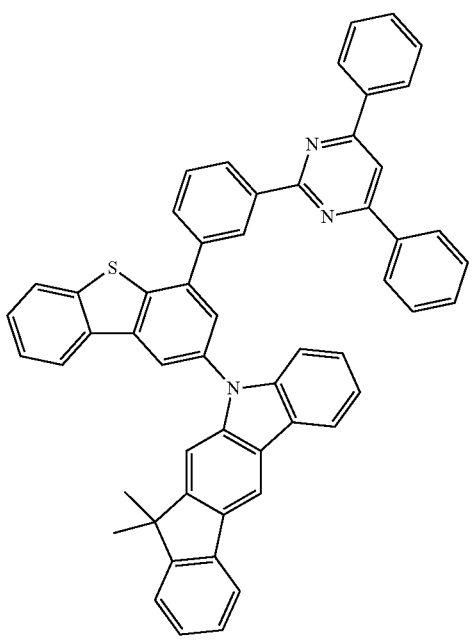
1-71
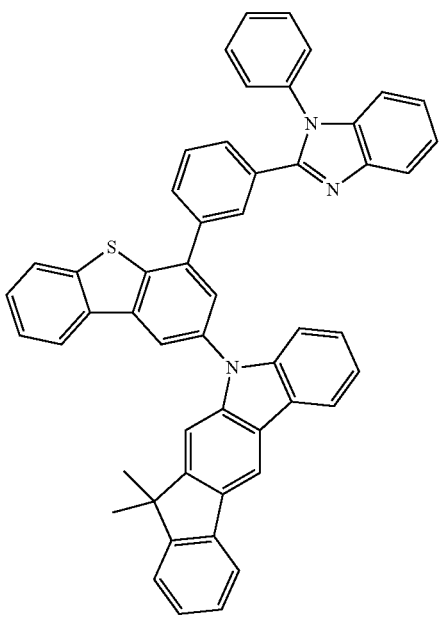
1-70
1-72
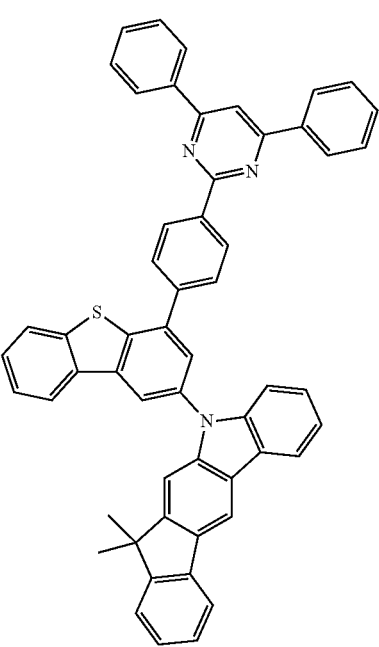

1-73
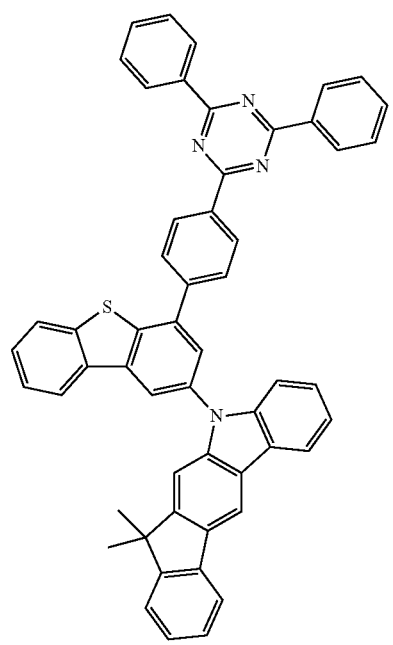
1-74
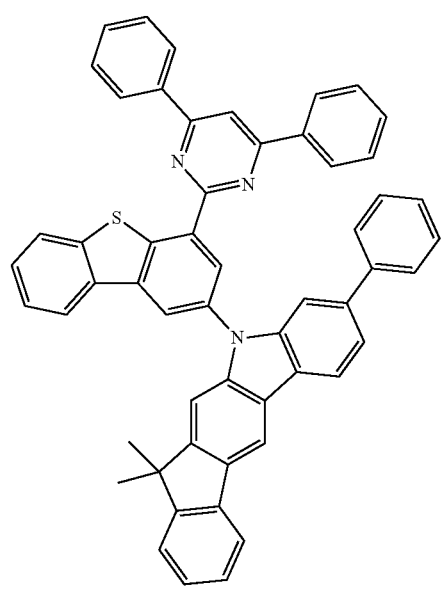
1-75
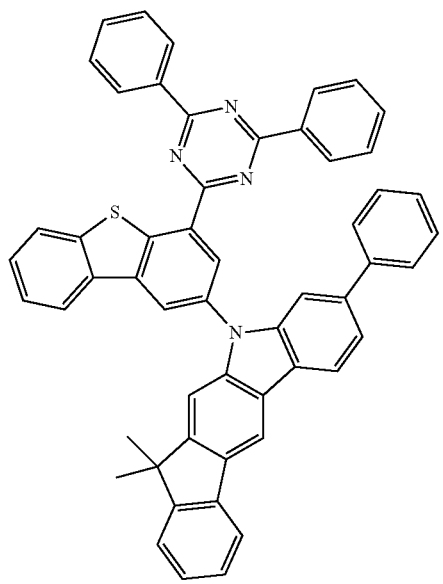
1-76
1-77
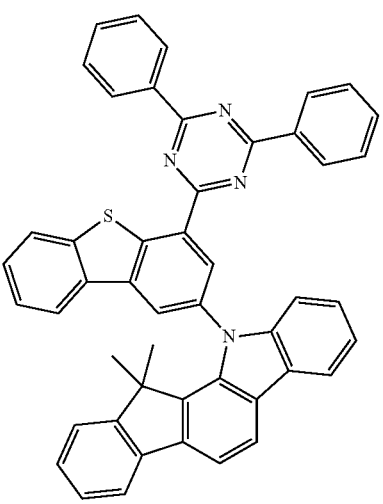

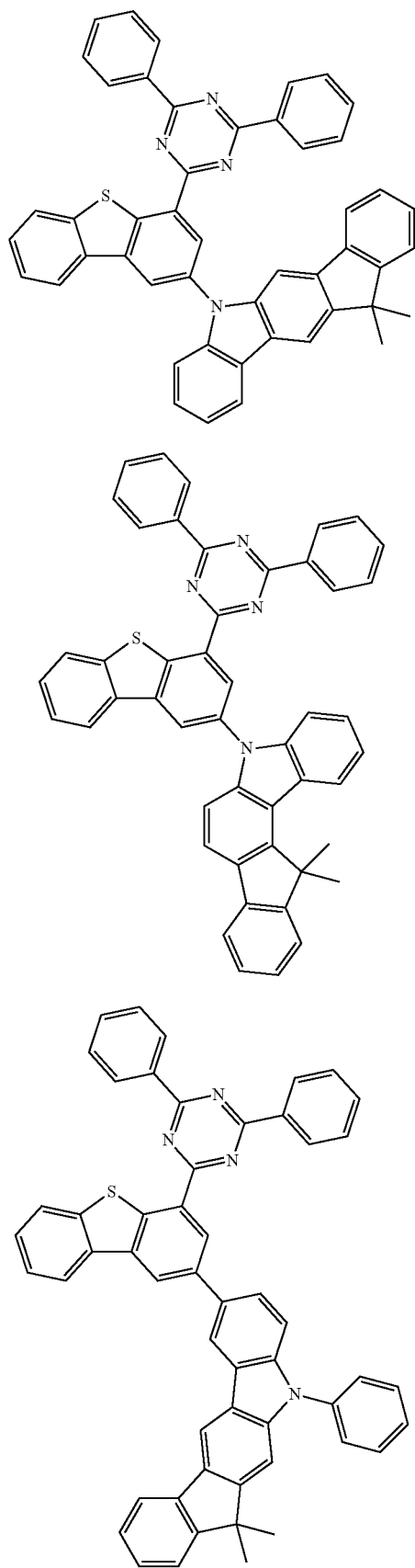
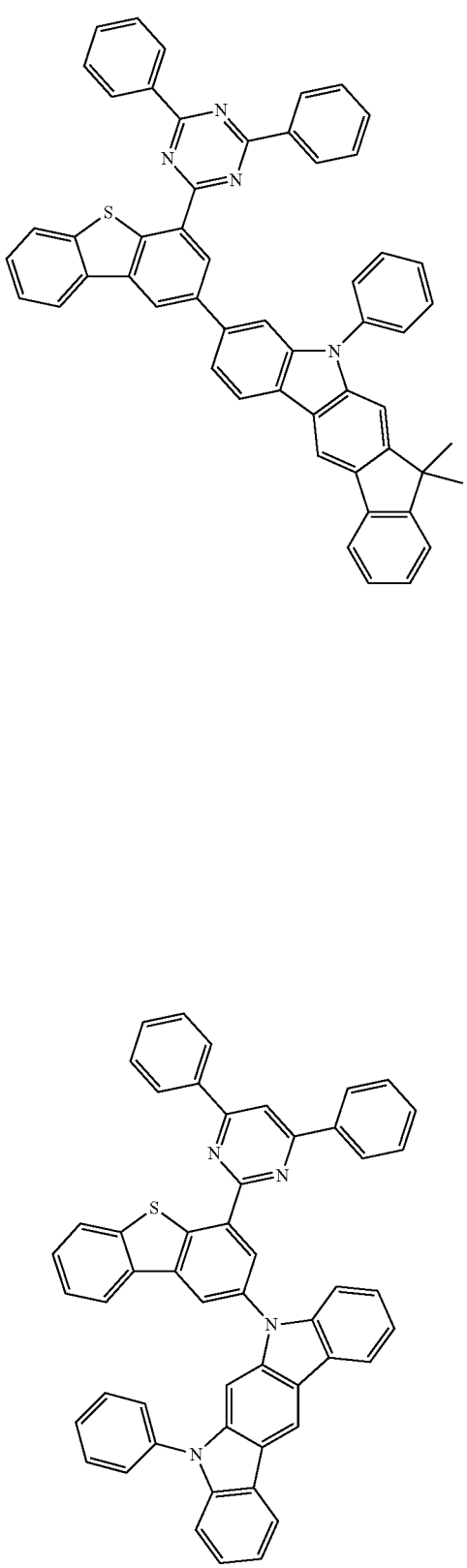

1-83
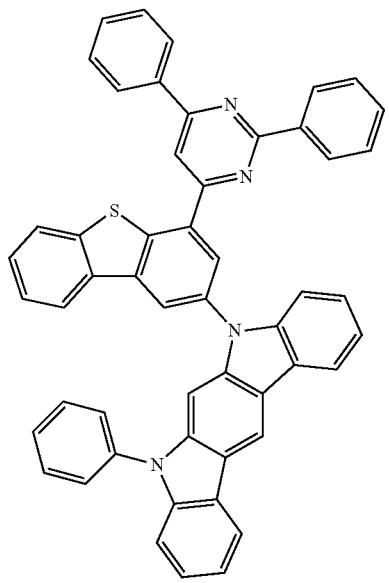
1-85
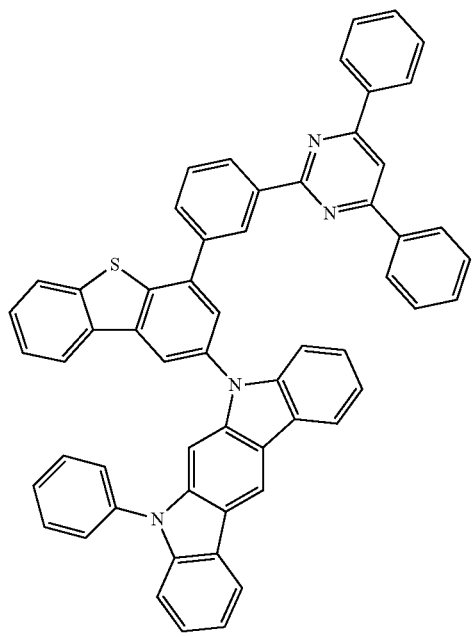
1-84
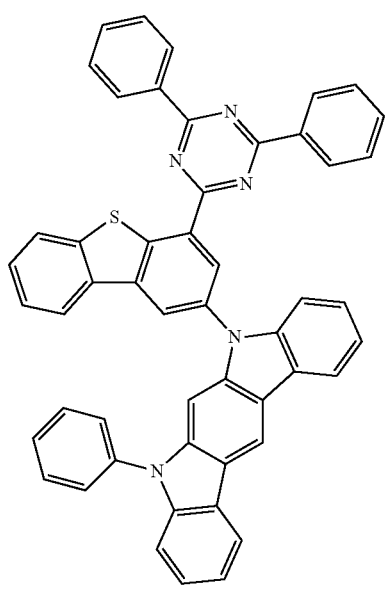
1-86
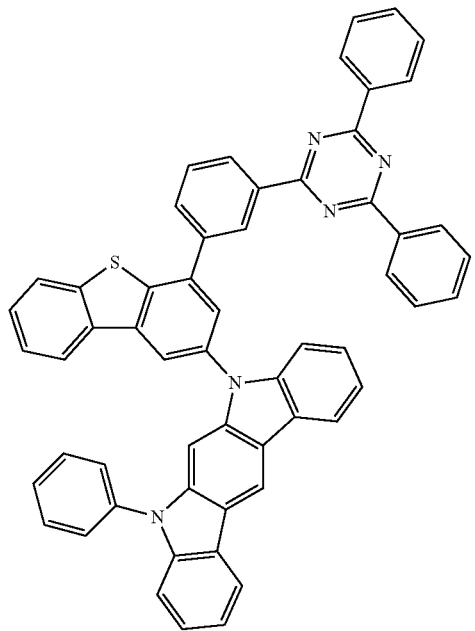

1-87
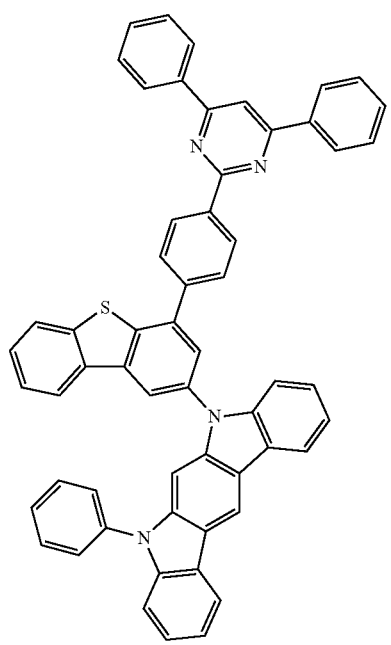
1-89
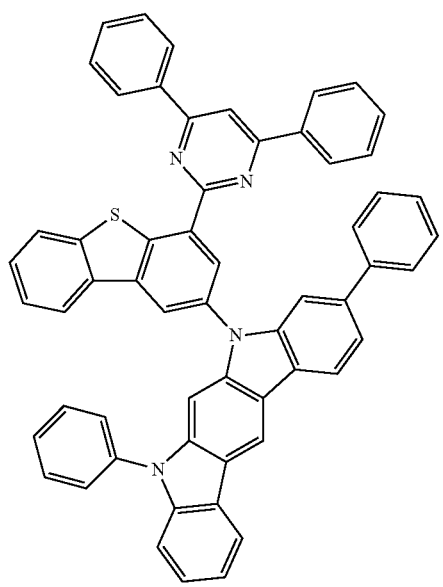
1-88
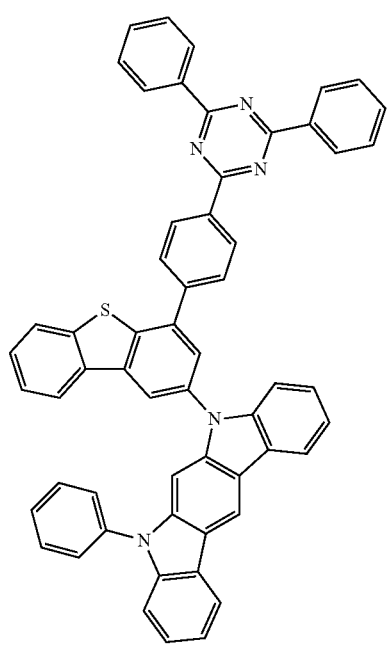
1-90
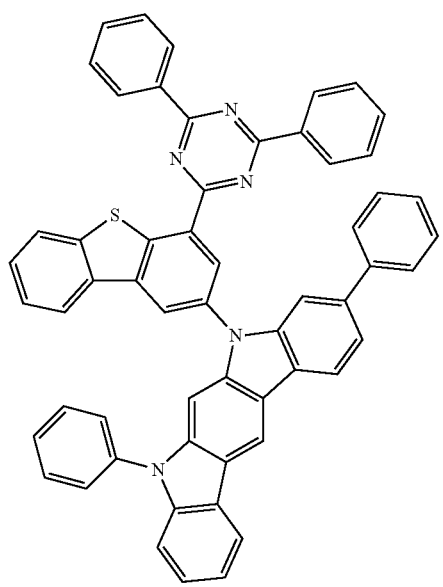

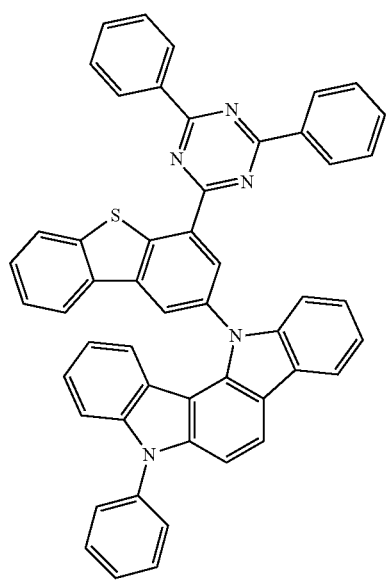
1-91
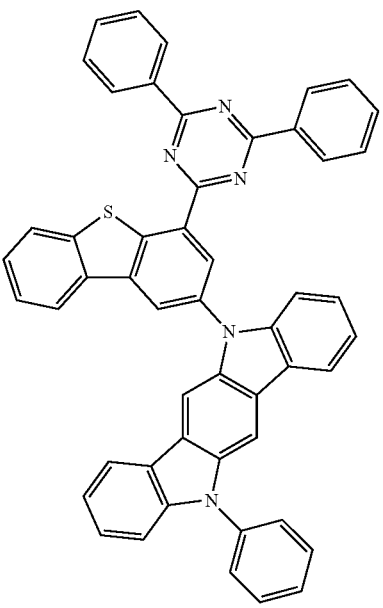
1-93
1-92
1-94
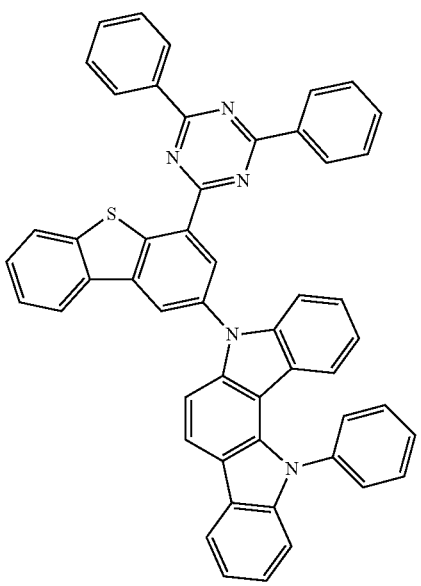

-continued
1-95
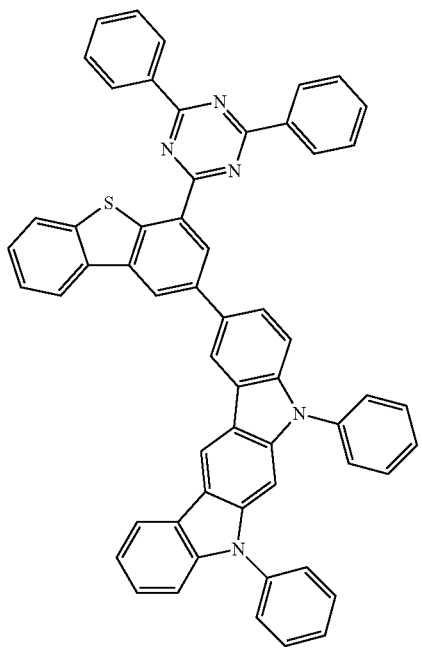
1-97
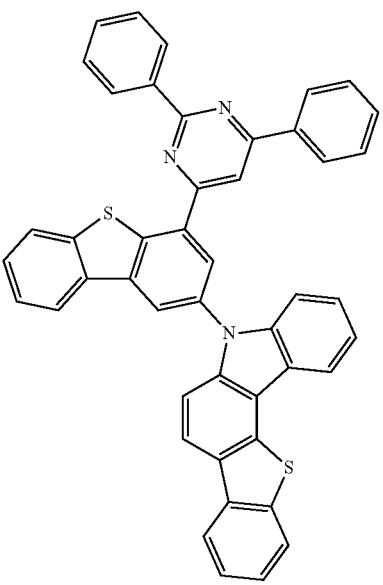
1-96
1-98
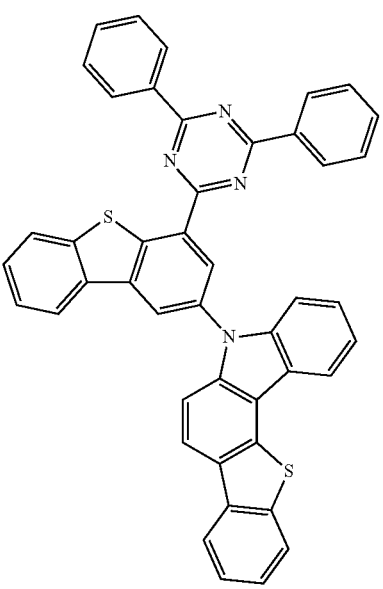

1-99
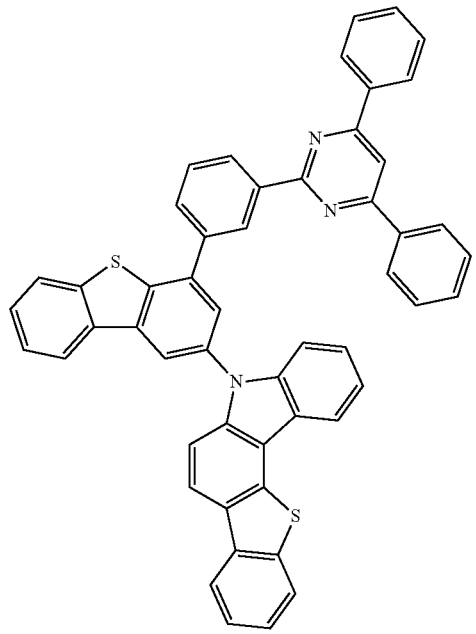
1-101
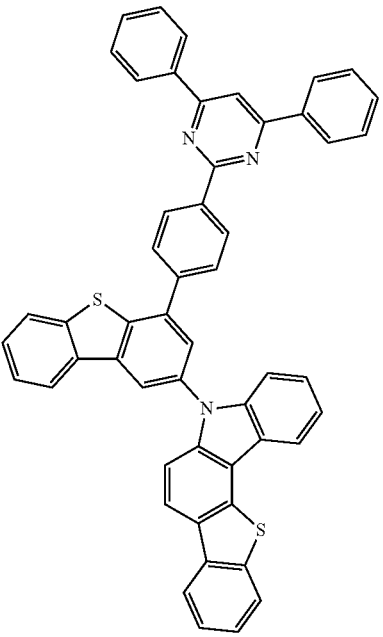
1-100
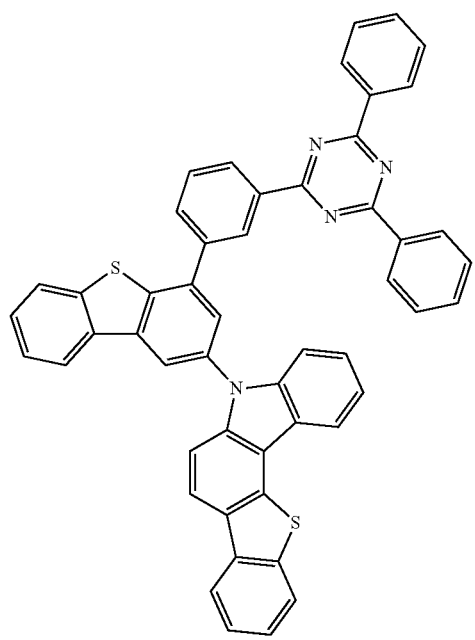
1-102
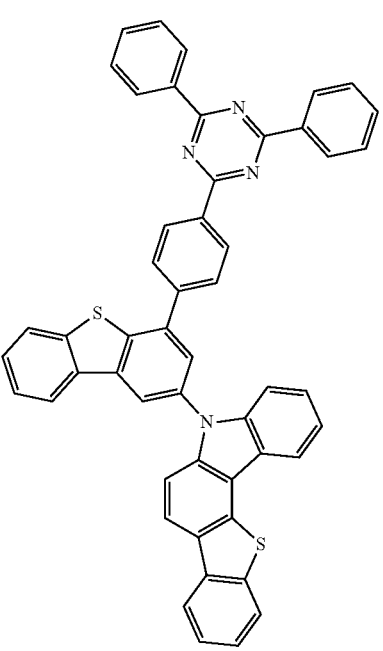

1-103
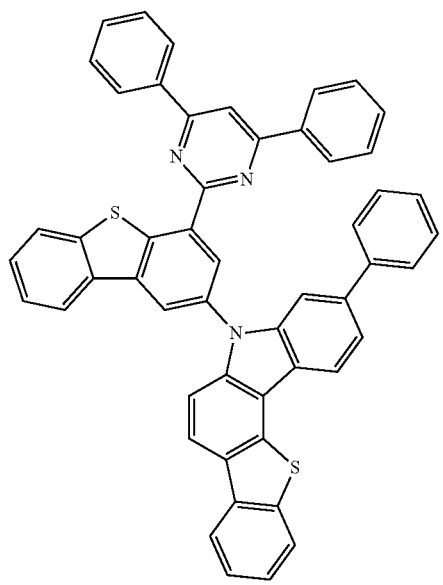
1-104
1-105
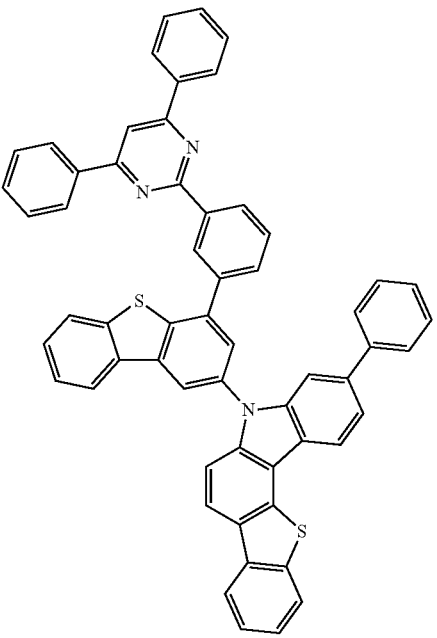
1-106
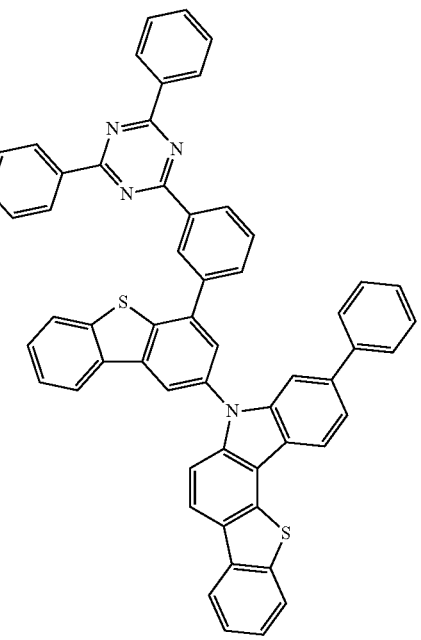

1-107
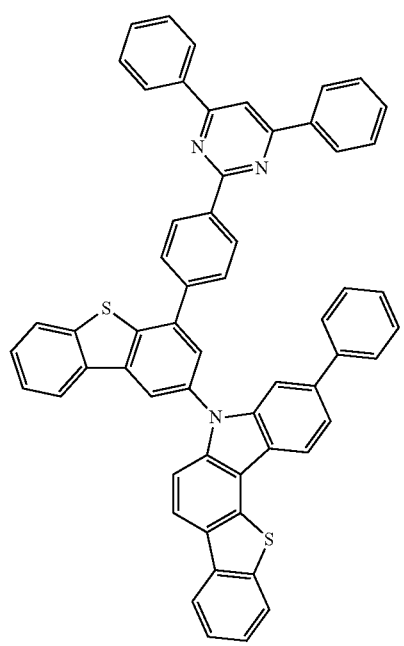
1-108
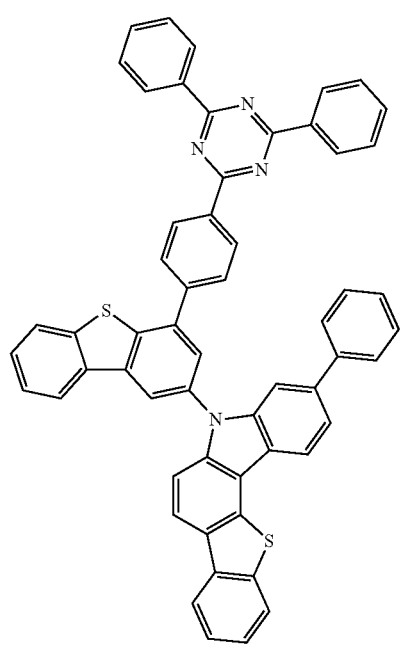
1-109
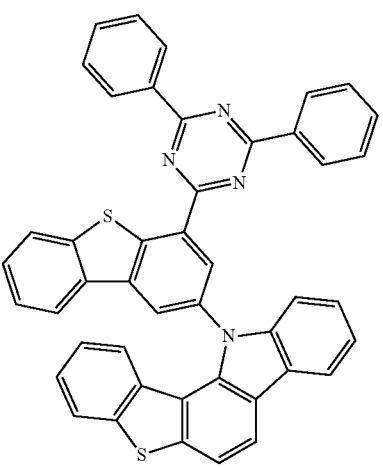
1-110
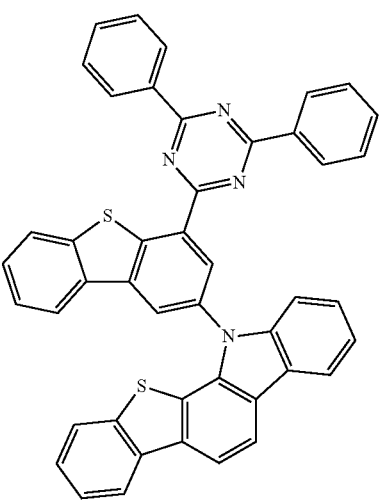
1-111
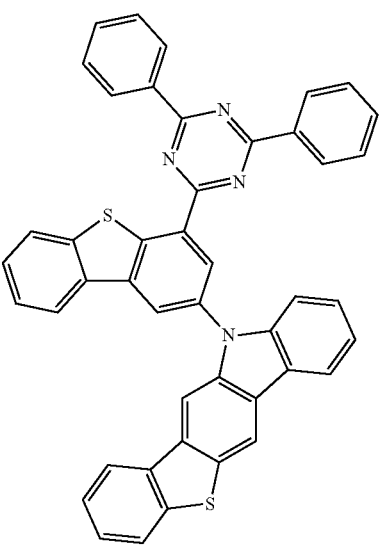

1-112
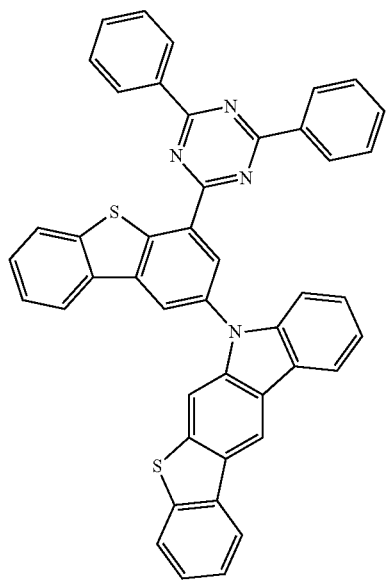
1-113
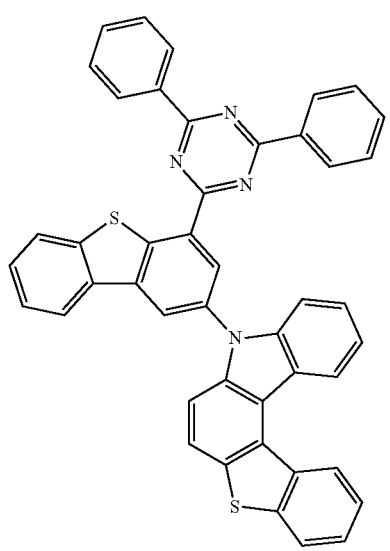
1-114
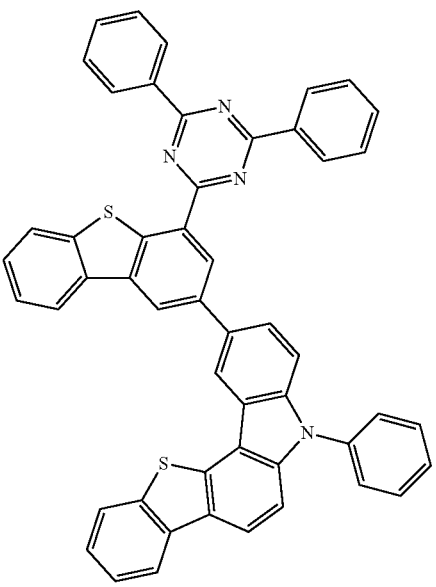
1-115
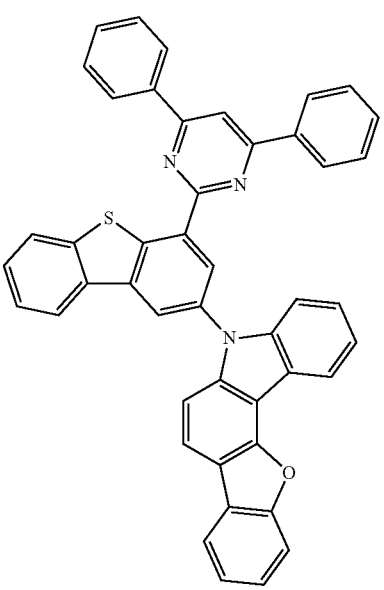

1-116
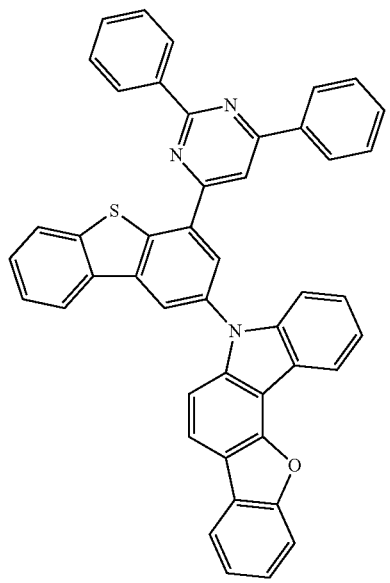
1-118
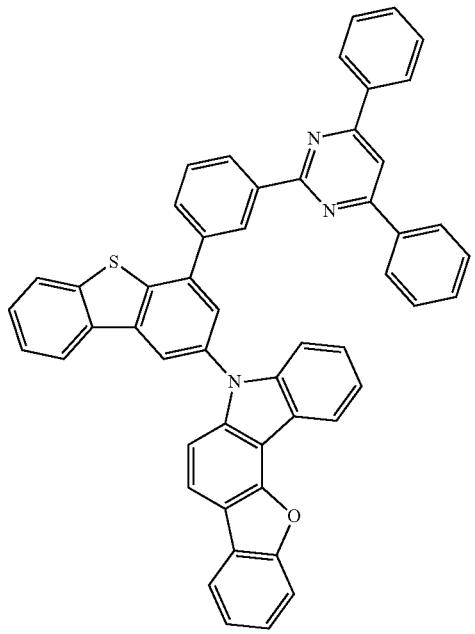
1-117
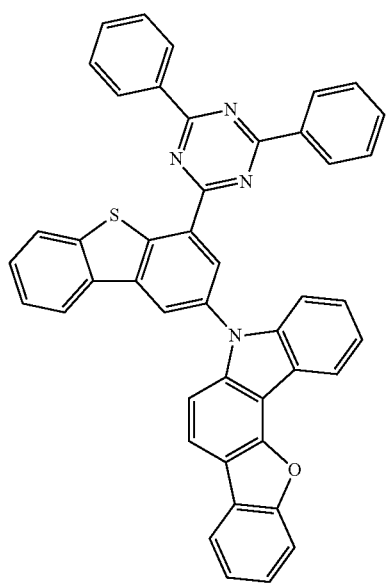
1-119
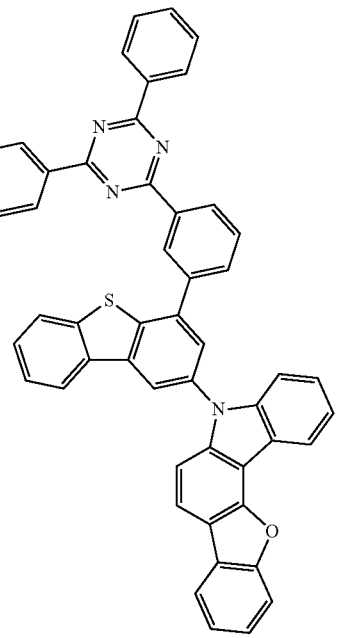

1-120
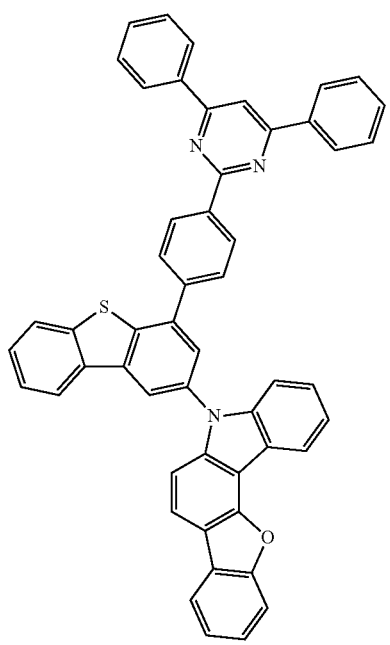
1-122
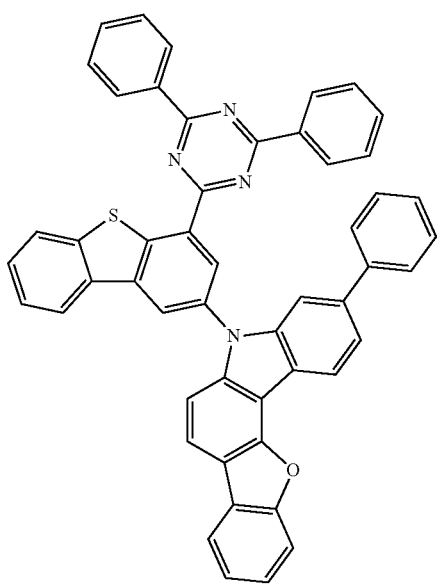
1-121
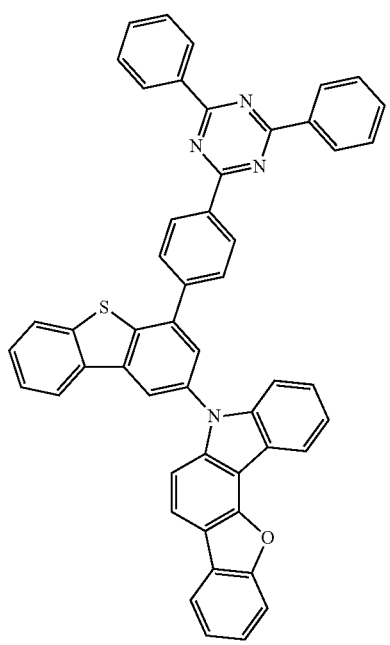
1-123
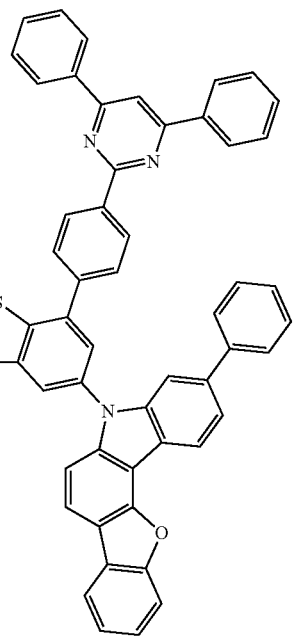

1-124
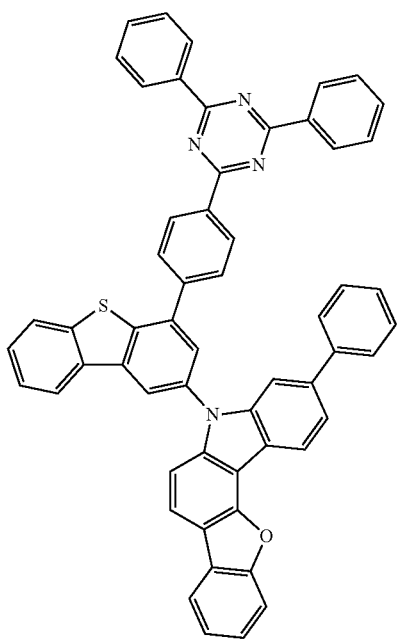
1-125
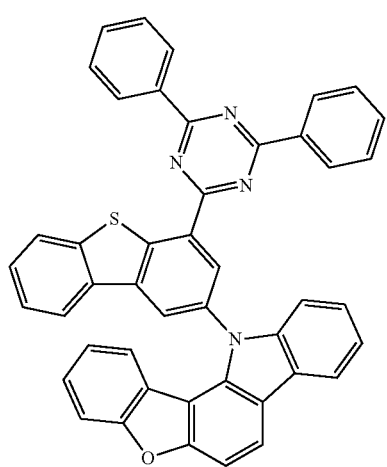
1-126
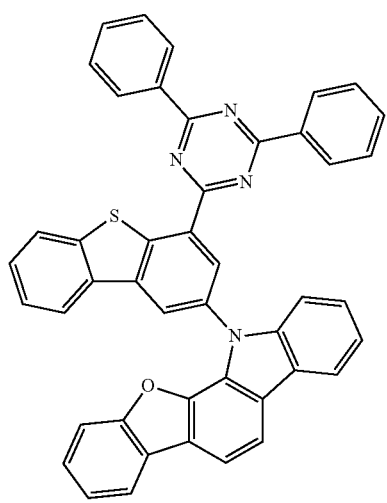
1-127
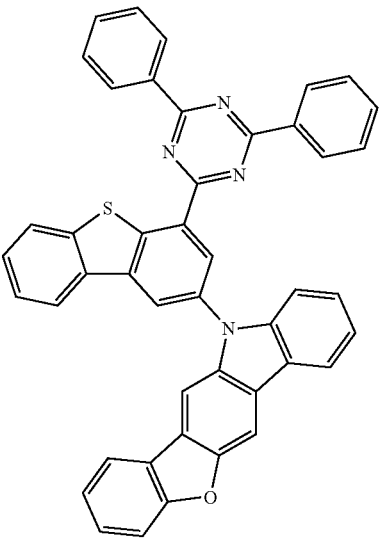
1-128
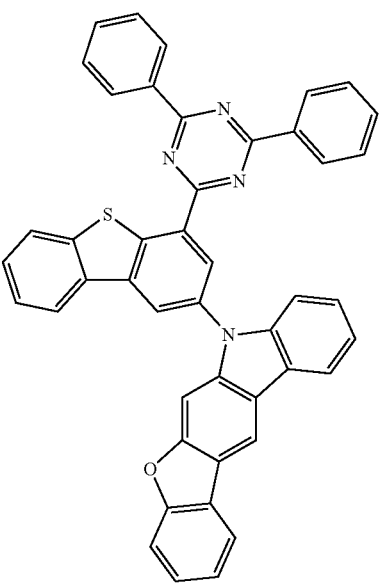
1-129
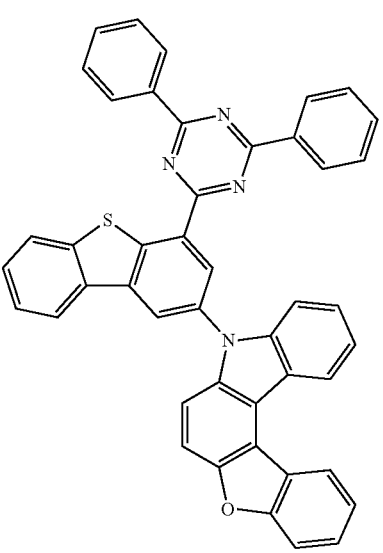

1-130
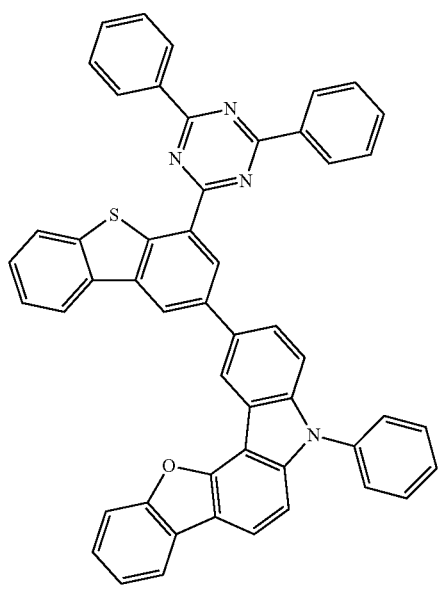
1-131
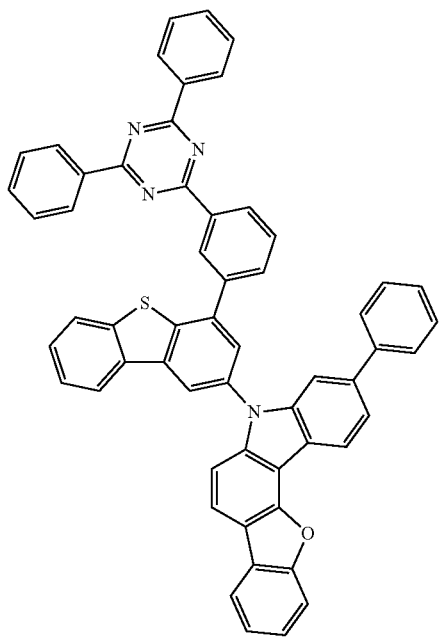
1-132
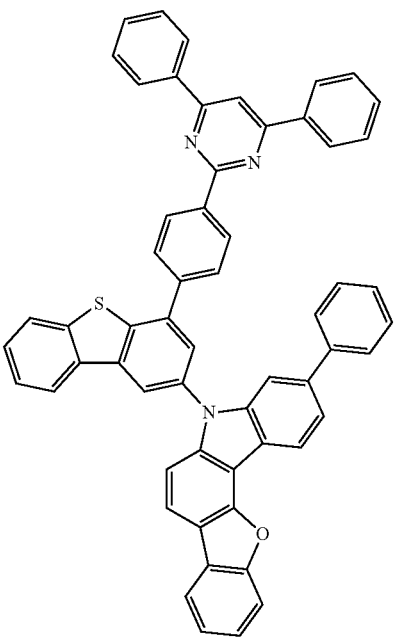
1-133
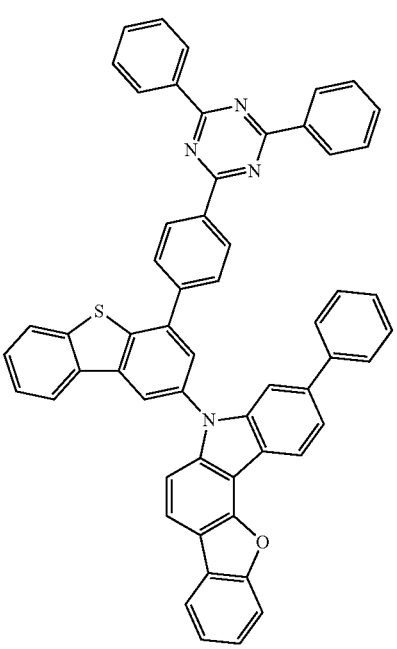

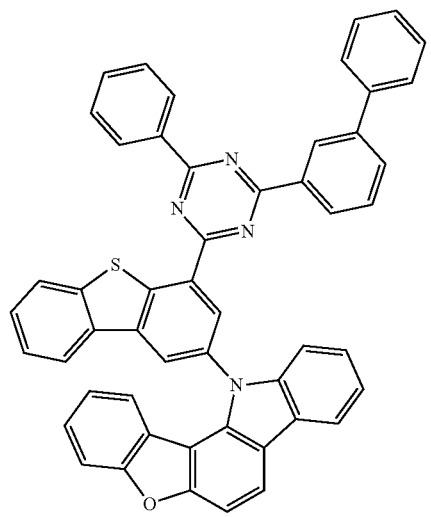
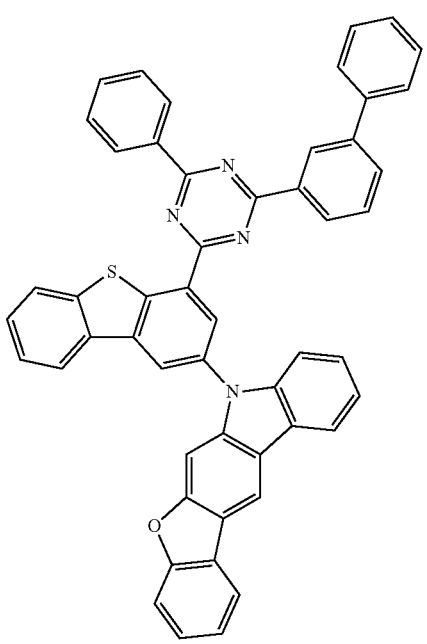

1-139
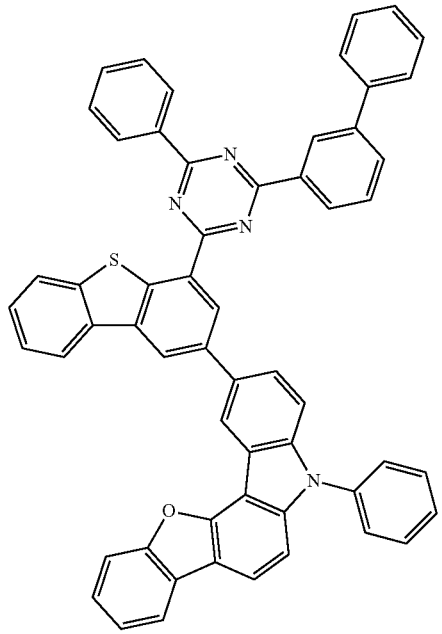
1-140
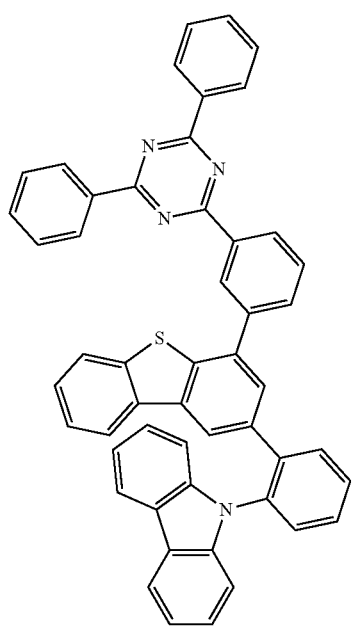
1-141
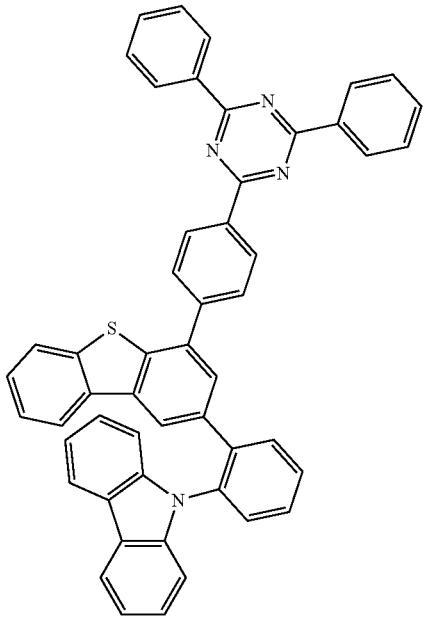
1-142
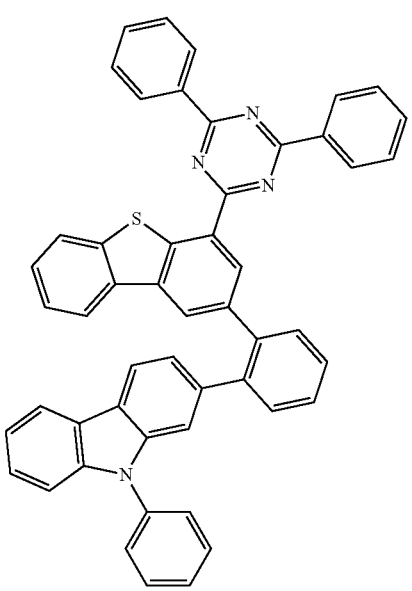

1-143
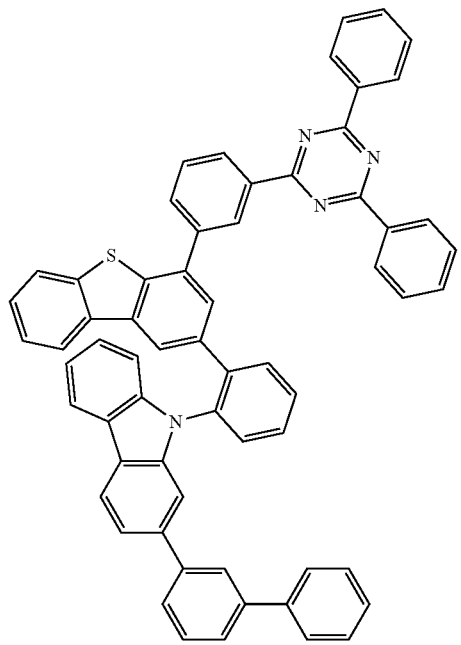
1-145
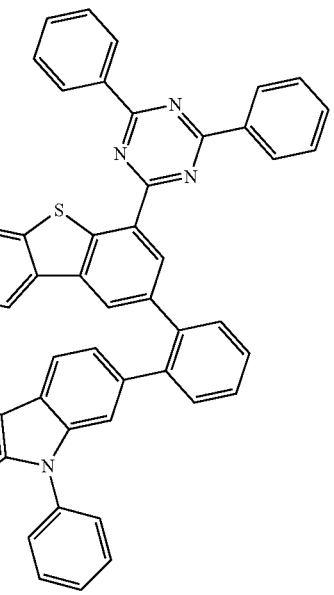
1-144
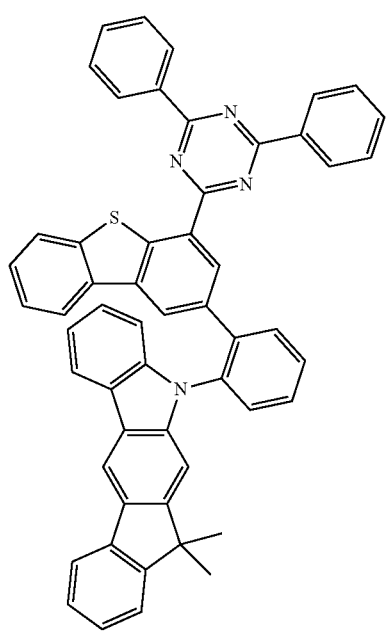
1-146
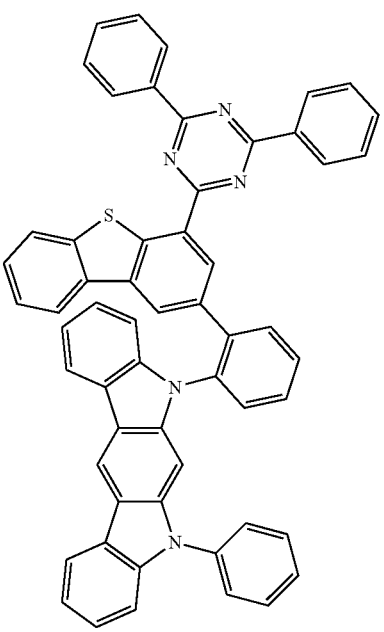

1-147
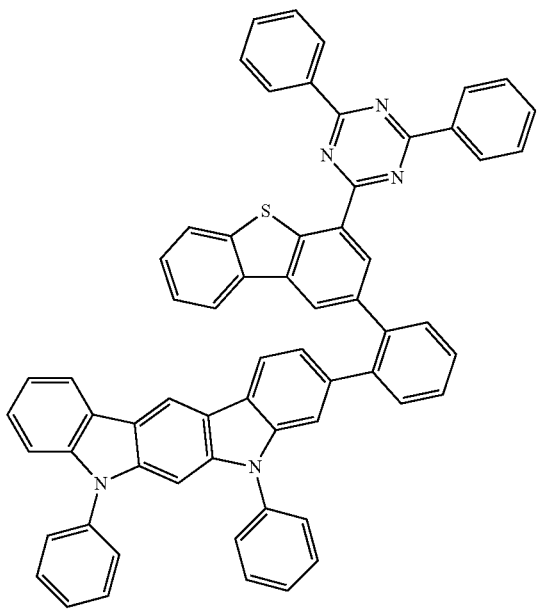
1-148
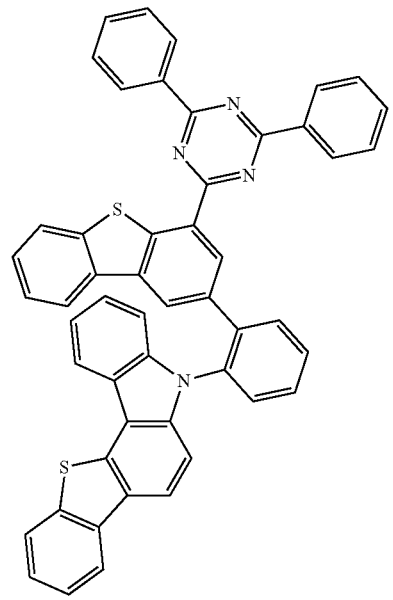
1-149
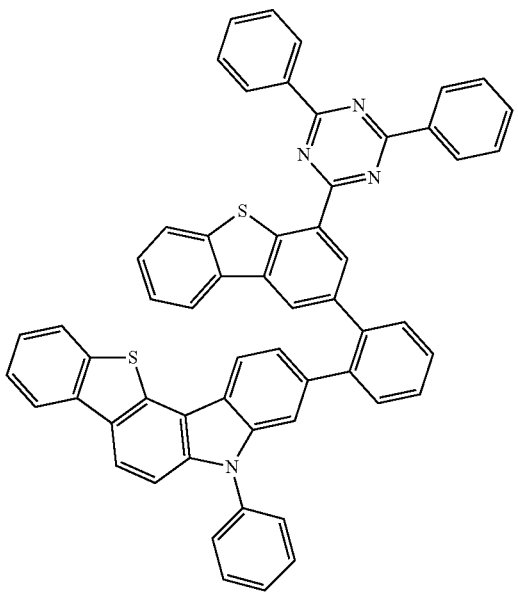
1-150
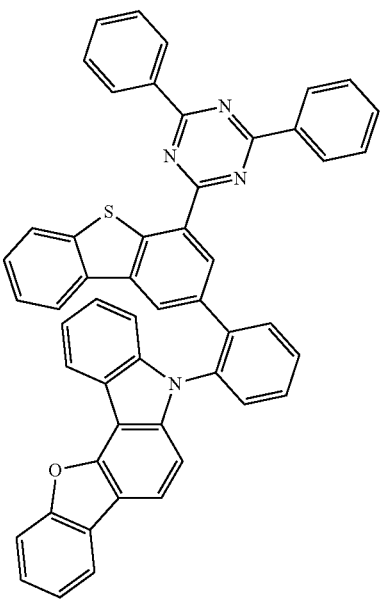

1-151
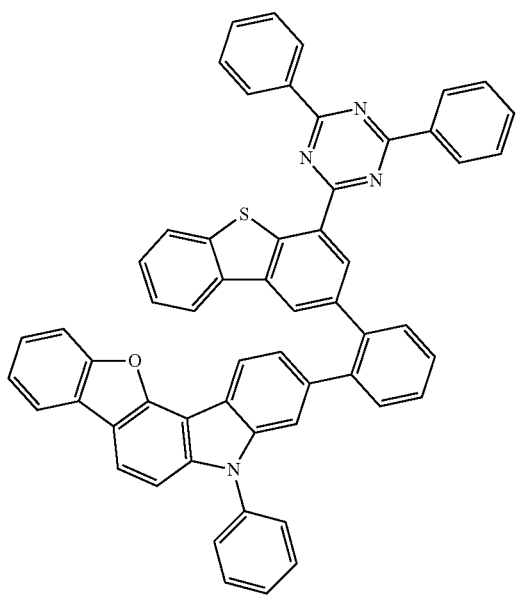
1-153
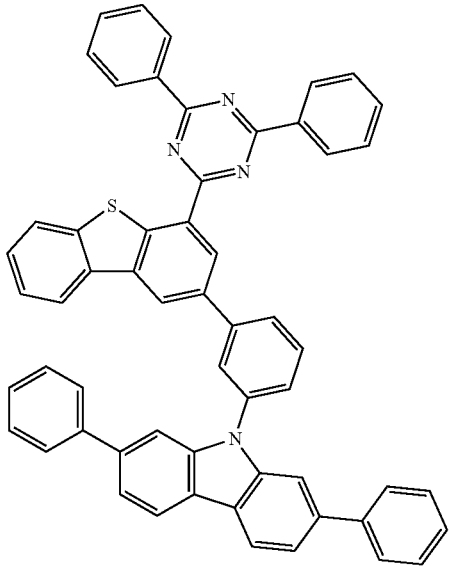
1-152
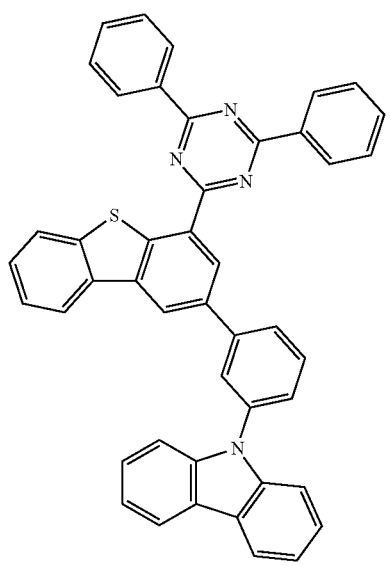
1-154
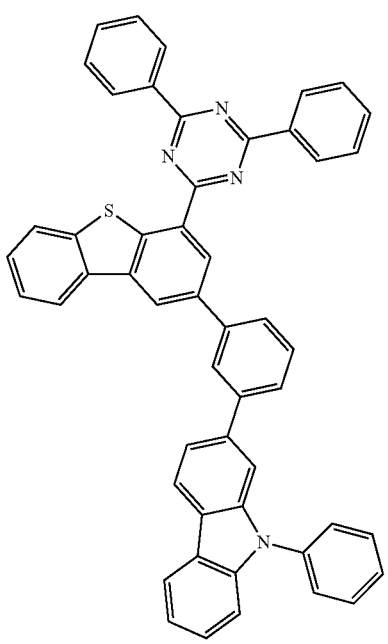

1-155
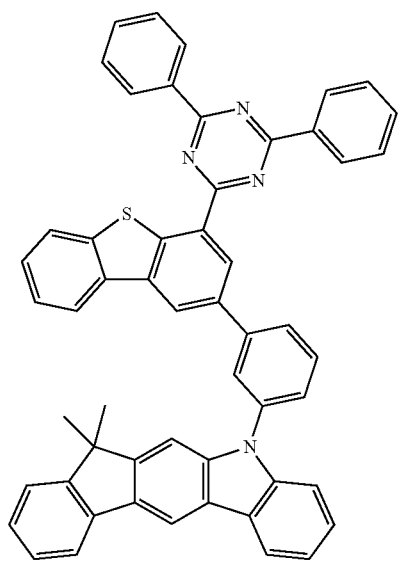
1-157
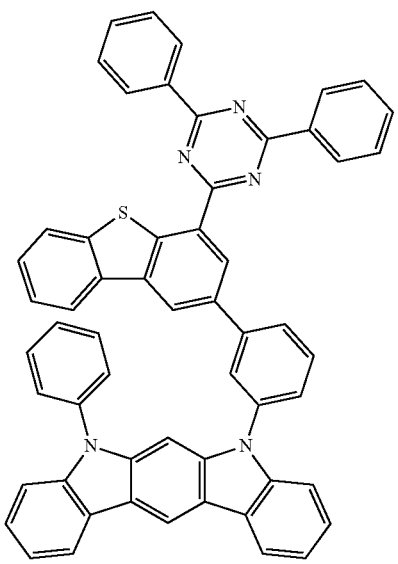
1-156
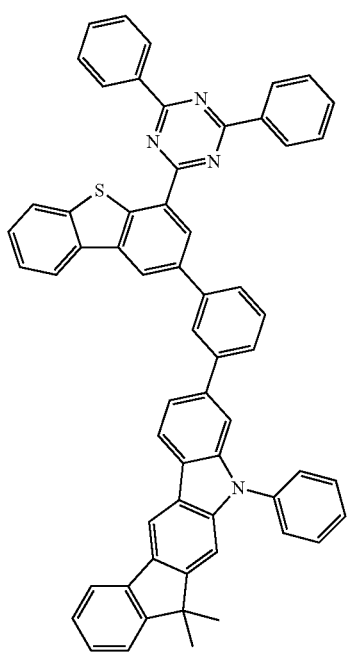
1-158
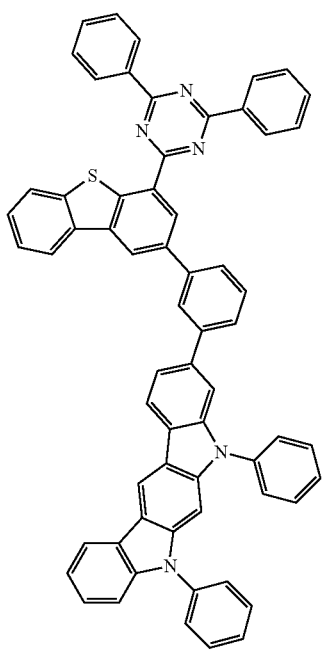

1-159
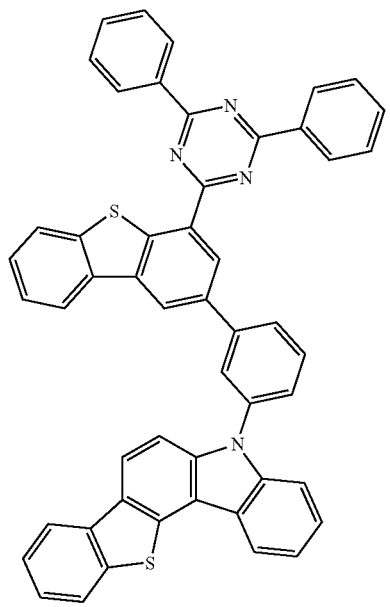
1-161
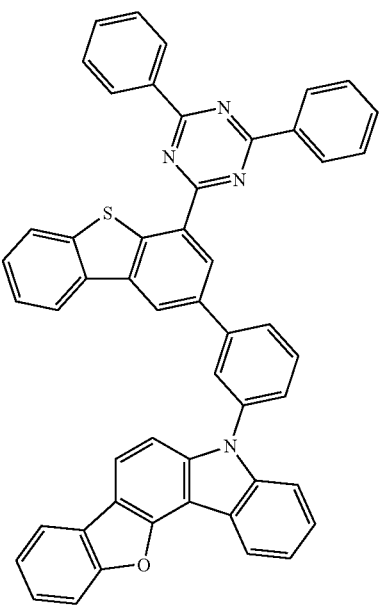
1-160
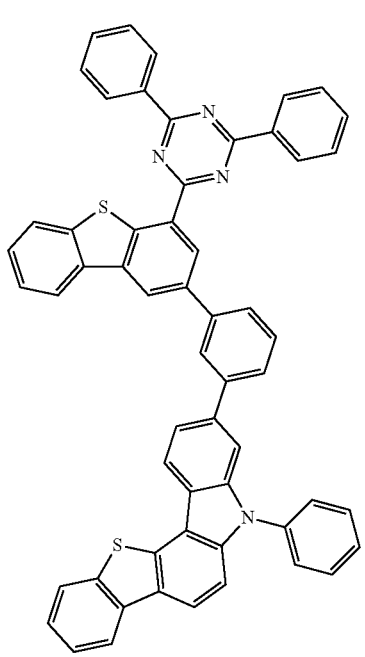
1-162
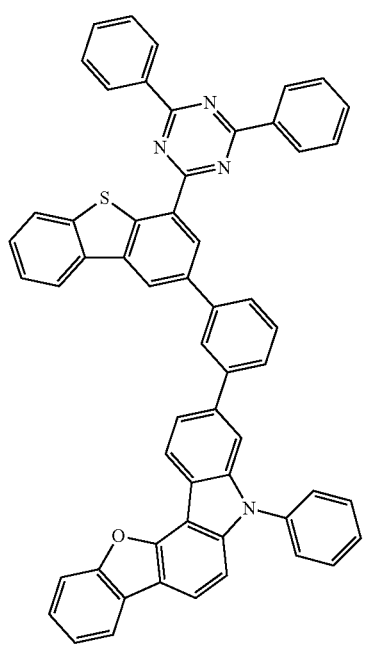

1-163
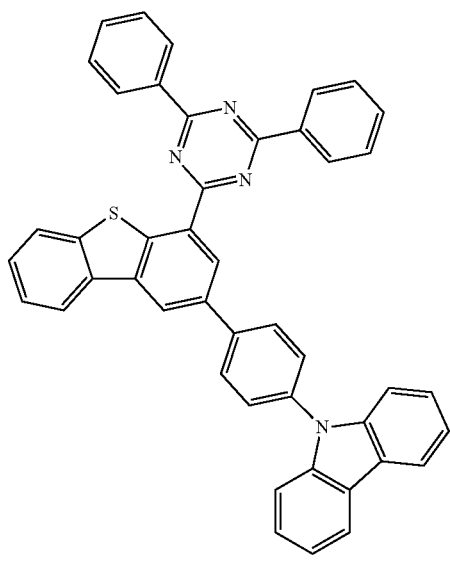
1-165
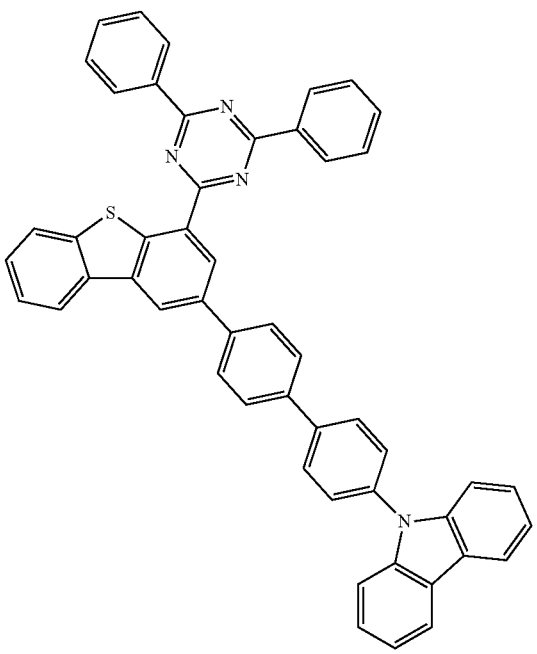
1-164
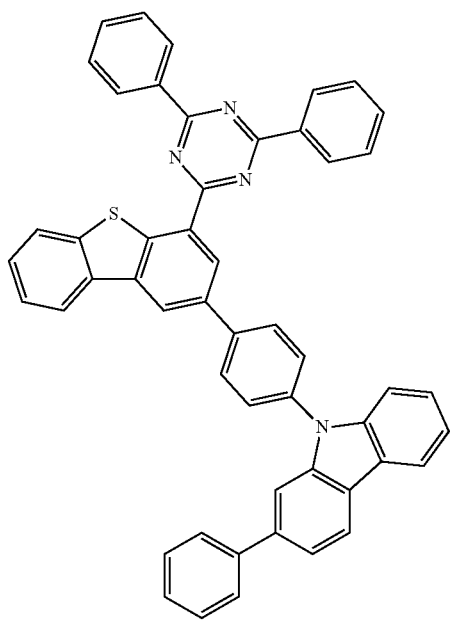
1-166
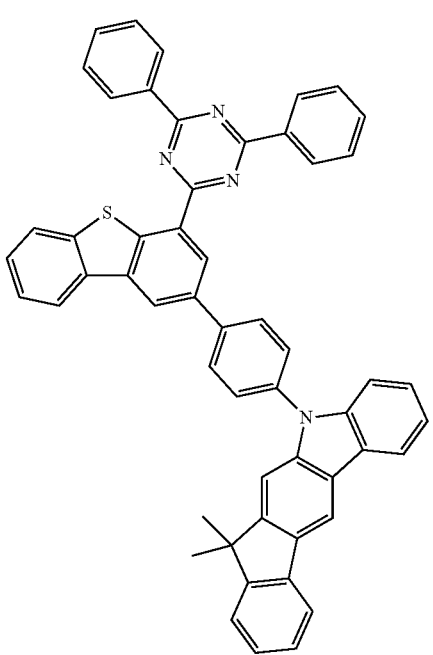

1-167
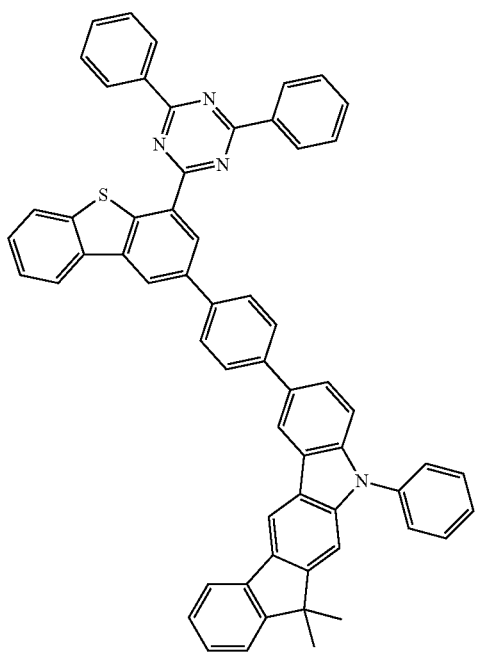
1-169
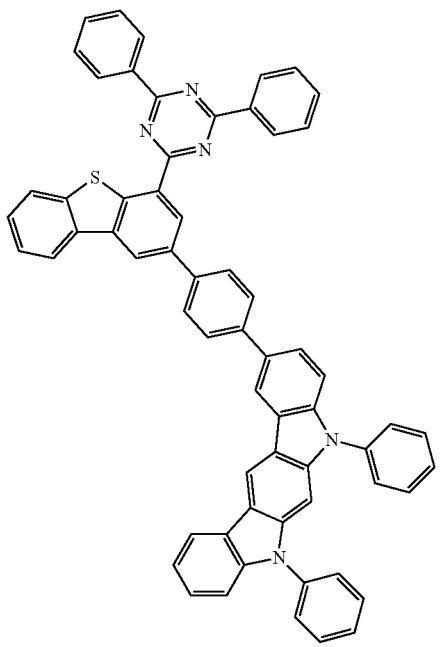
1-168
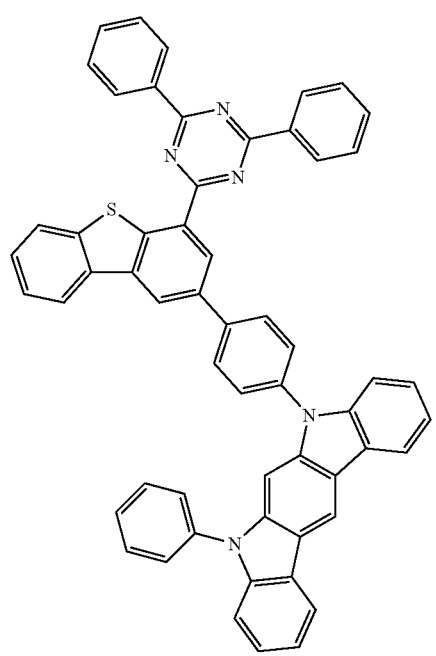
1-170

1-171
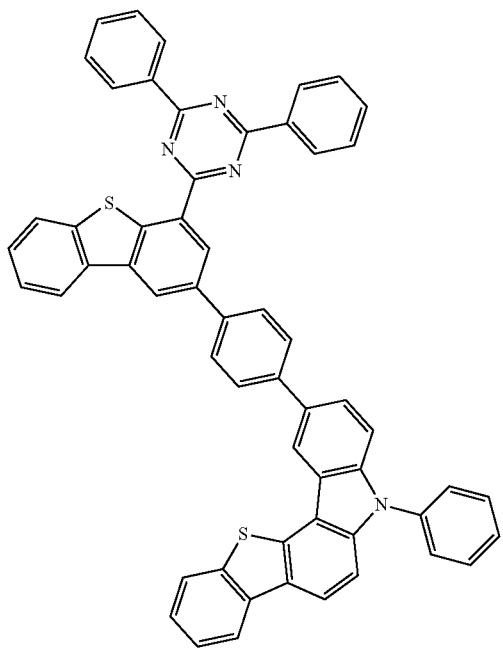
1-173
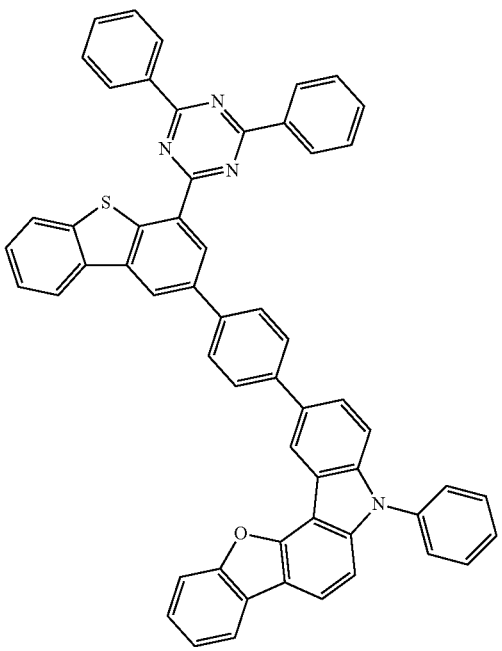
1-172
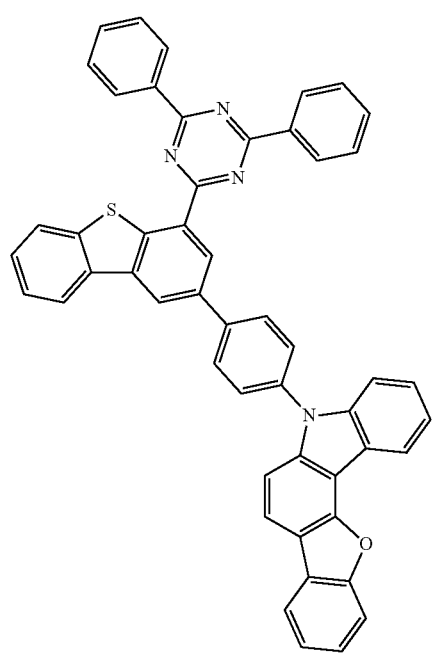
1-174
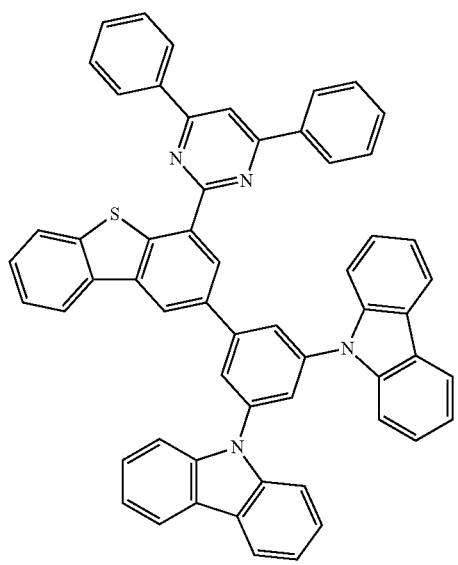

1-175
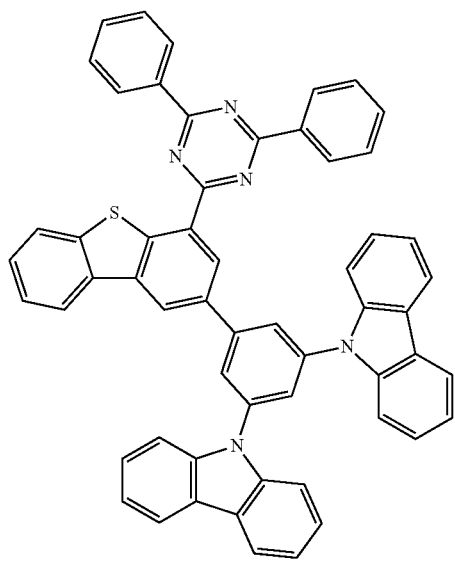
1-177
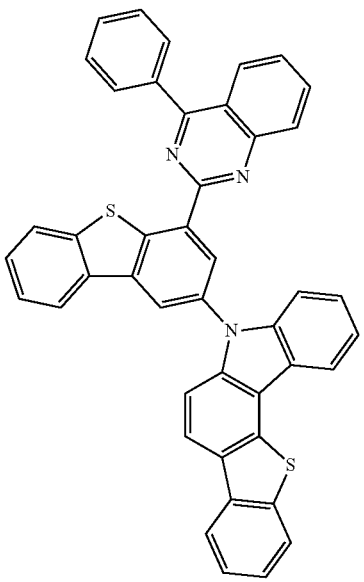
1-176
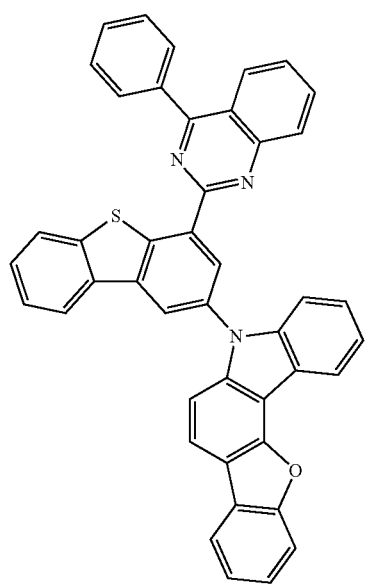
1-178
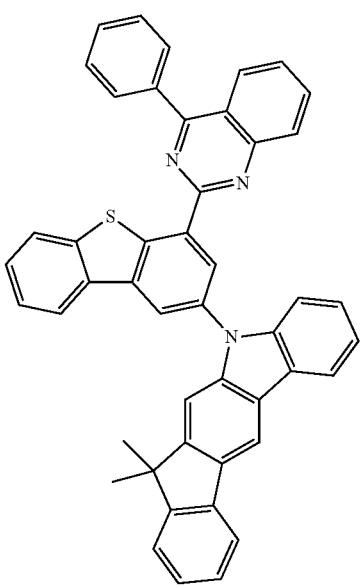

1-179
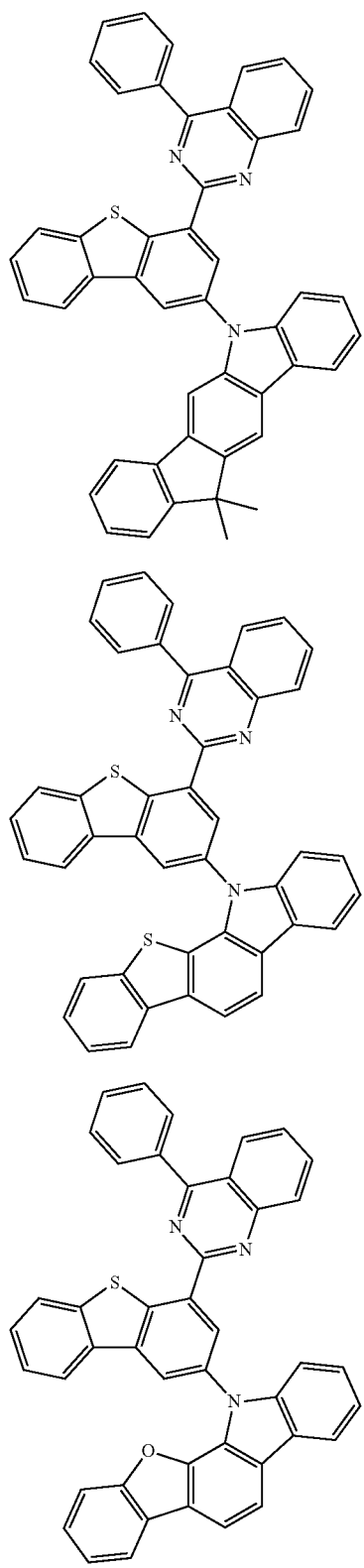
1-180
1-181
2-1
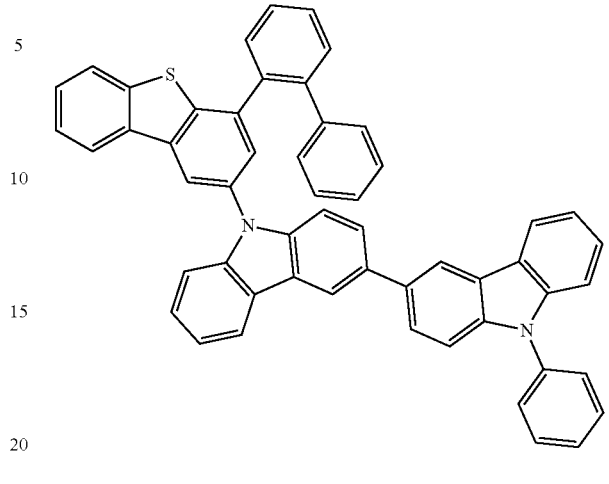
2-2
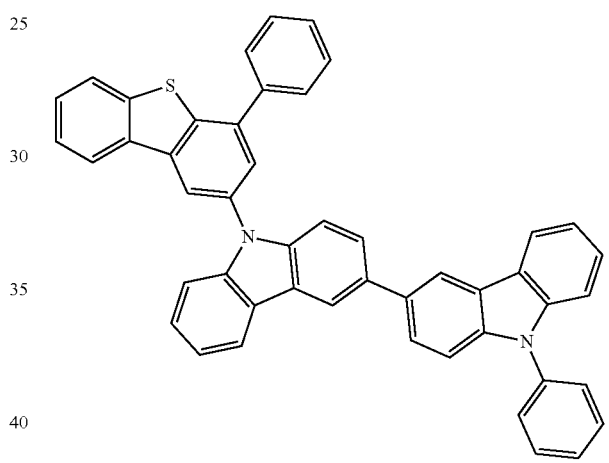
2-3
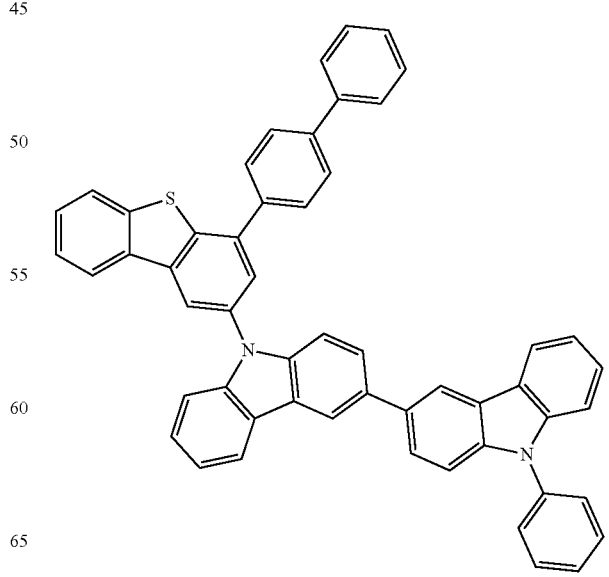
According to an exemplary embodiment of the present application, Chemical Formula 2 may be represented by any one of the following compounds, but is not limited thereto.

2-4
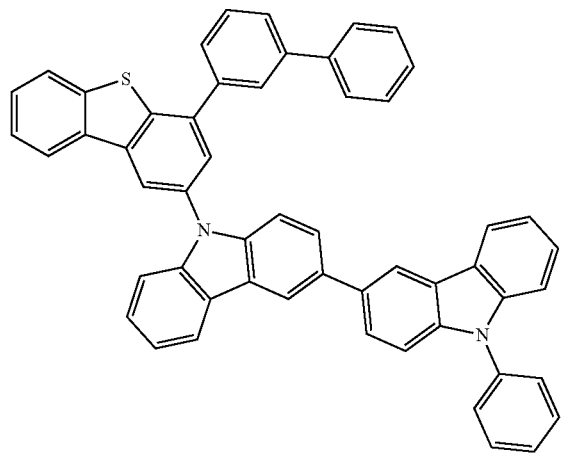
2-5
2-6
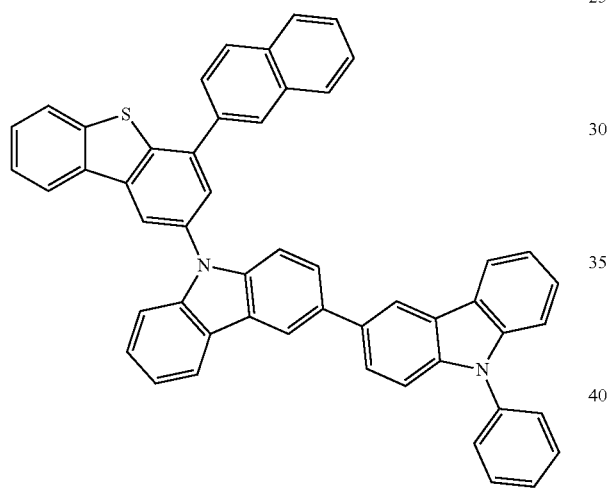
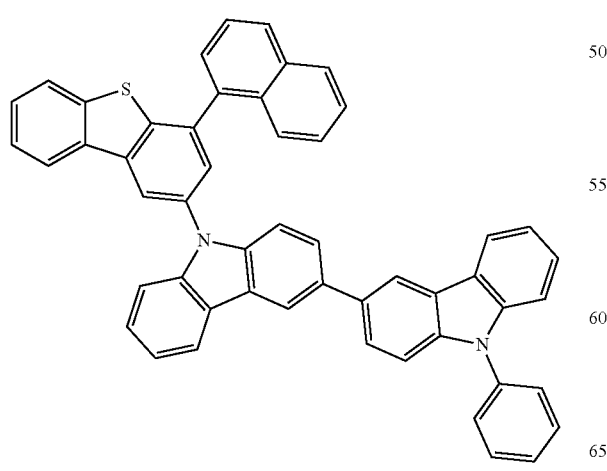
2-7
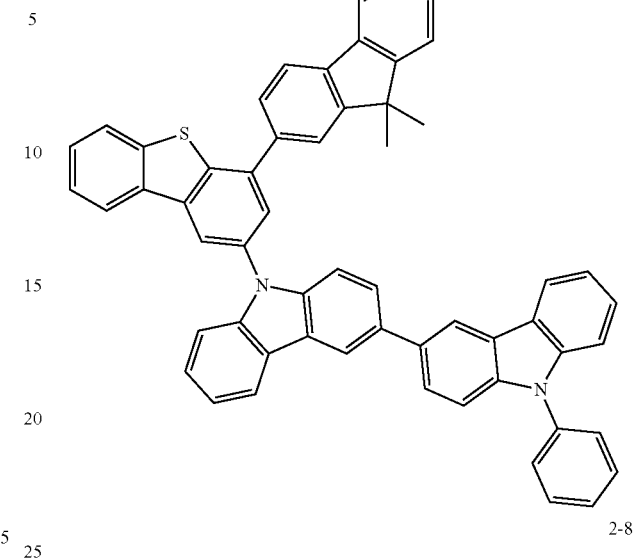
2-8
2-9

-continued
2-10
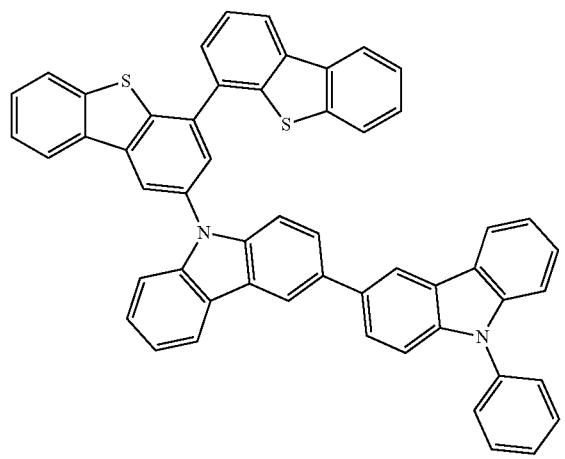
2-11
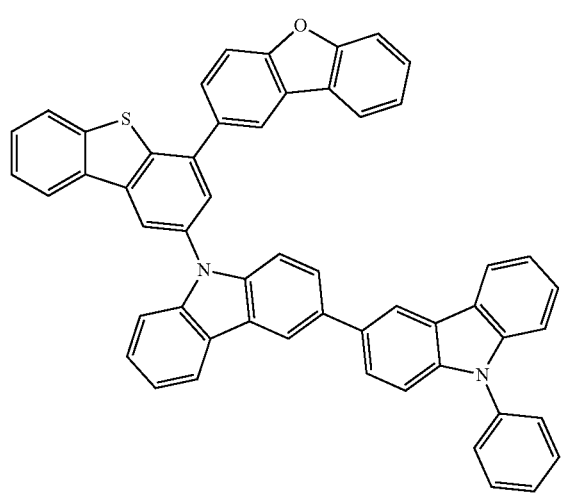
2-12
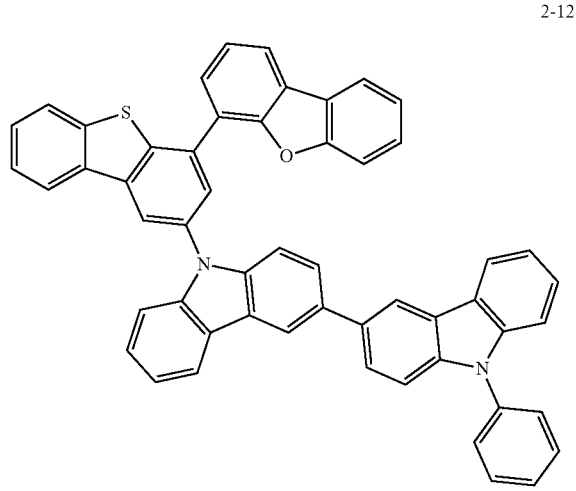
-continued
2-13
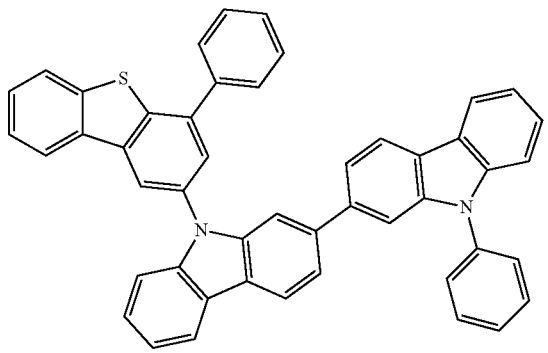
2-14
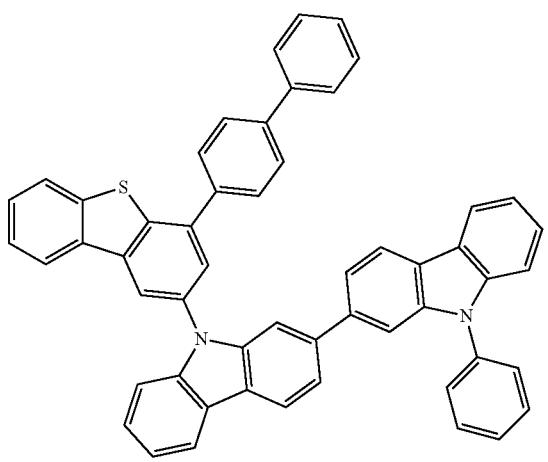
2-15
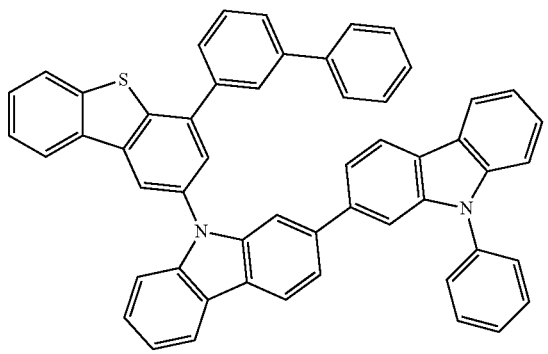
2-16
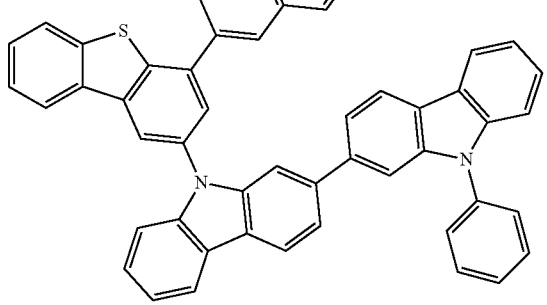

2-17
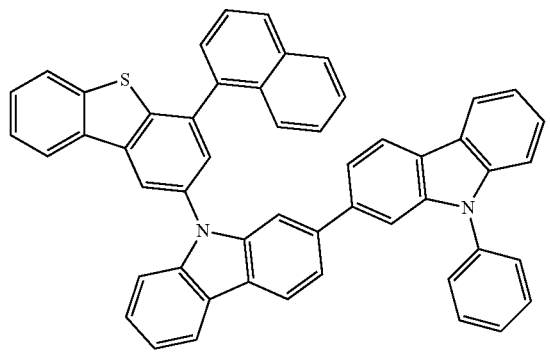
2-18
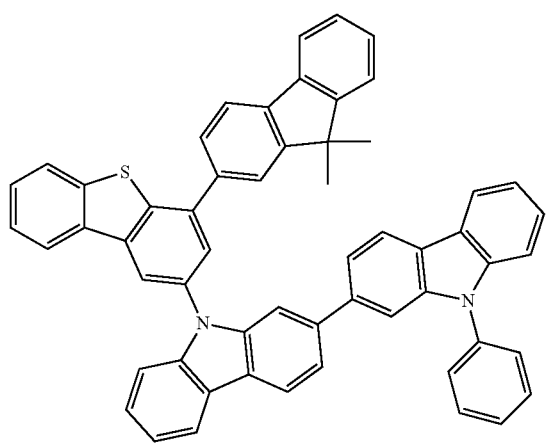
2-19
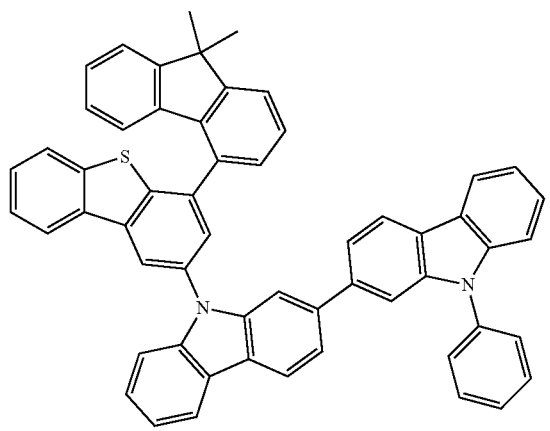
2-20
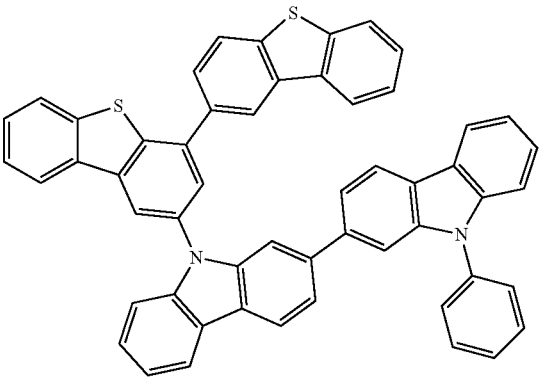
2-21
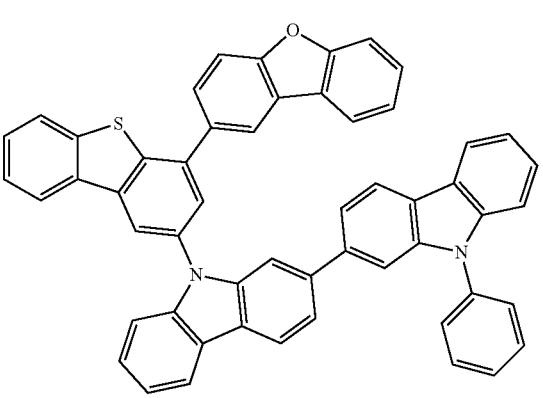
2-22
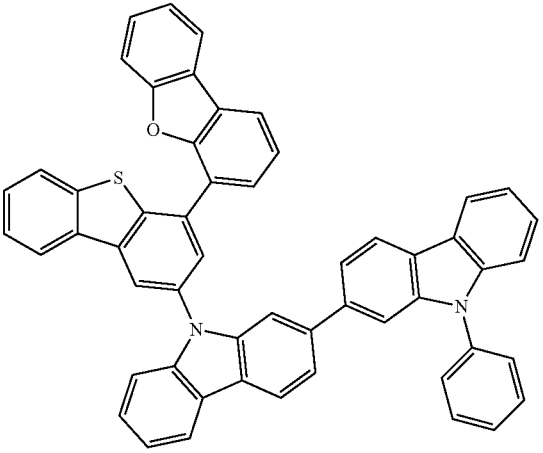

2-23
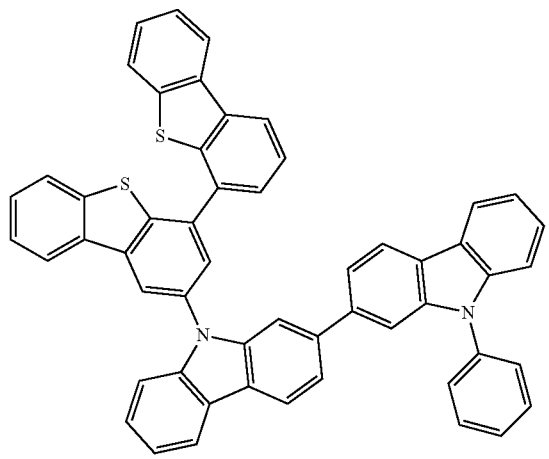
2-24
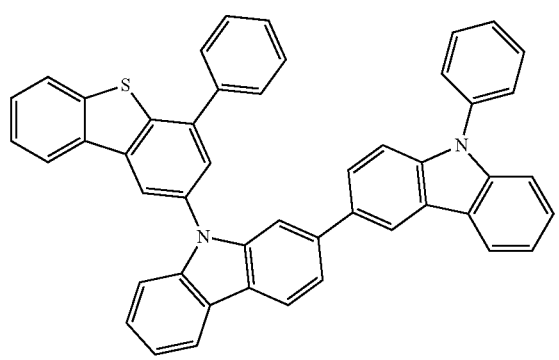
2-25
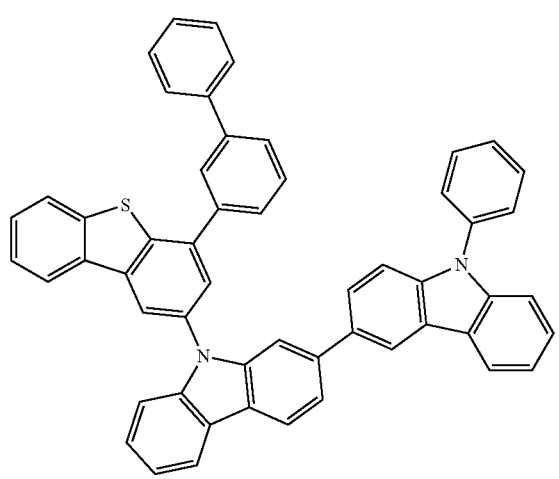
2-26
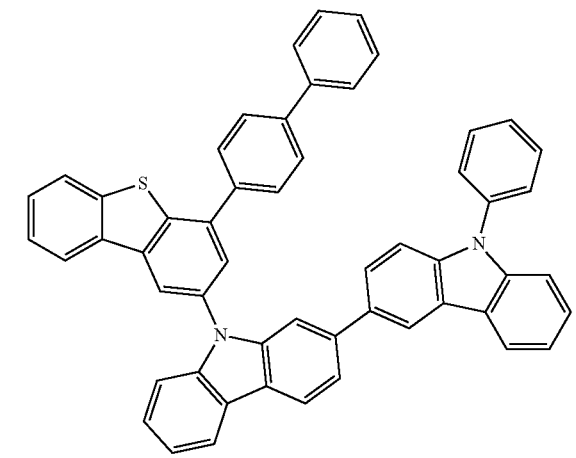
2-27
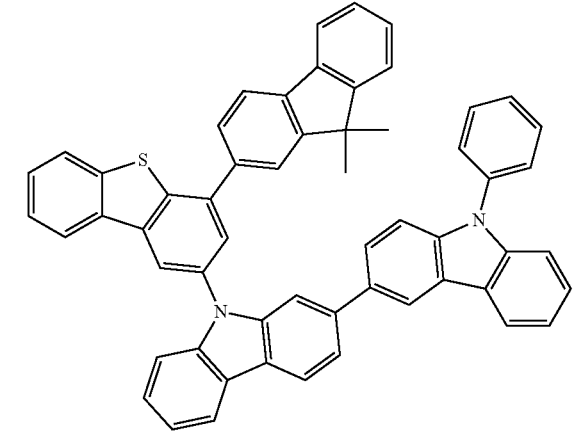
2-28
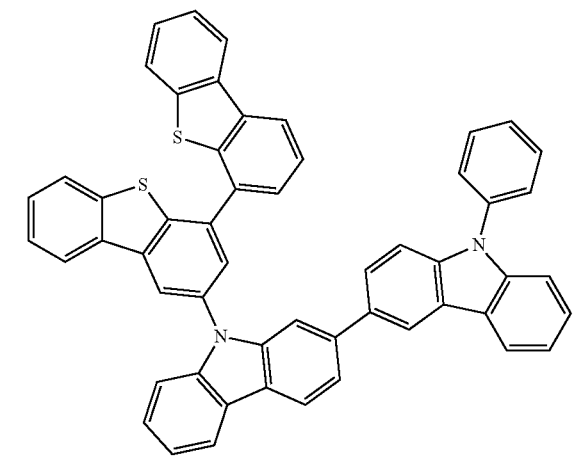

2-29
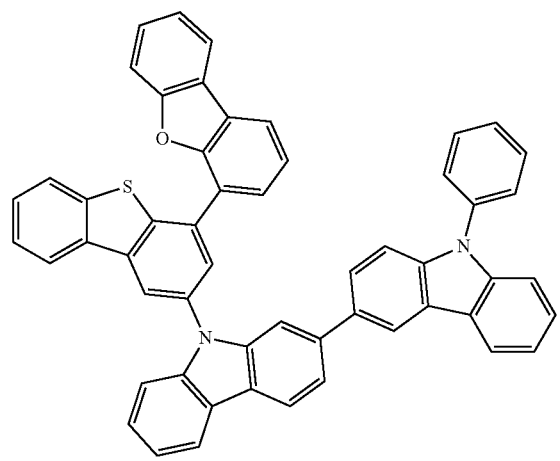
2-32
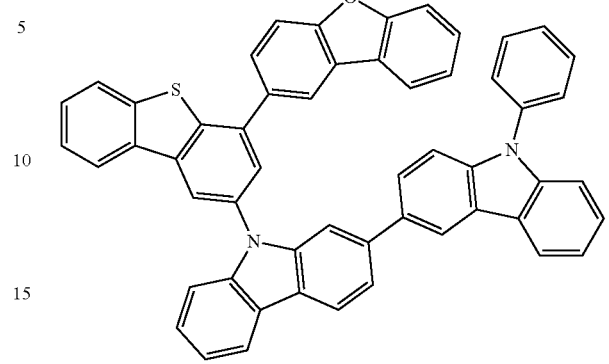
2-30
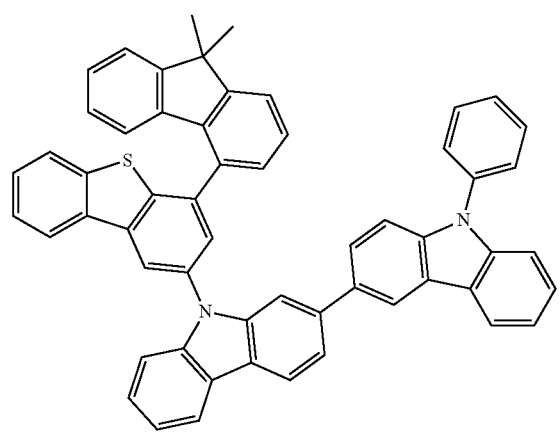
2-33
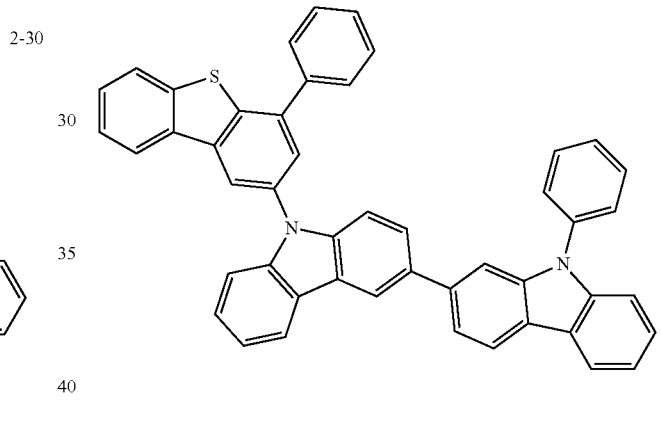
2-31
2-34
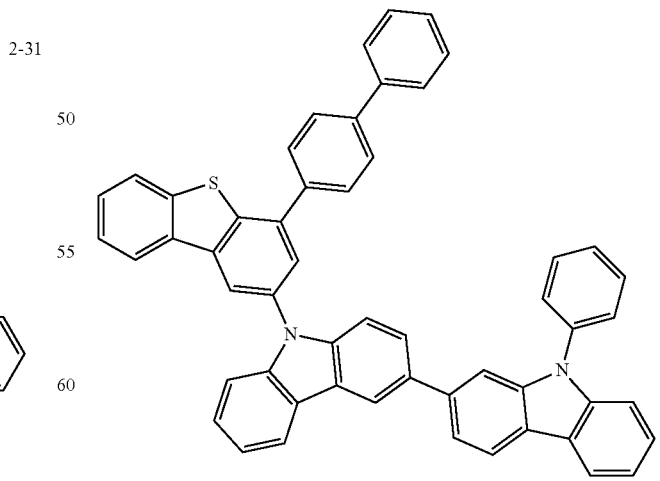

2-35
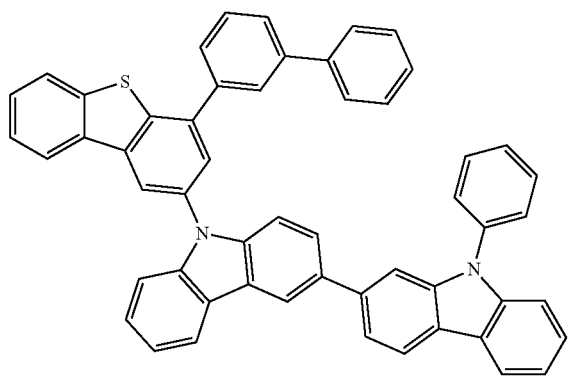
2-36
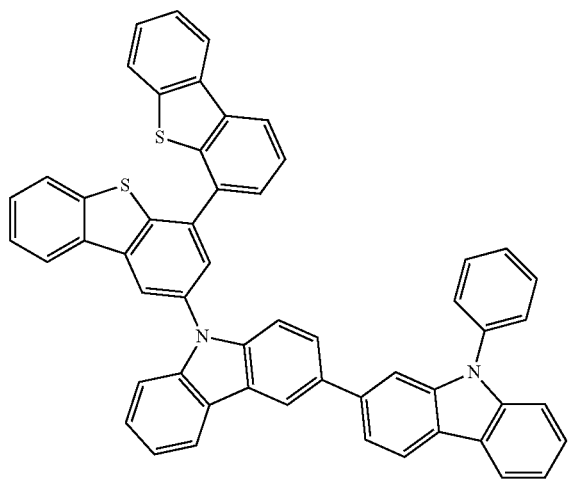
2-37
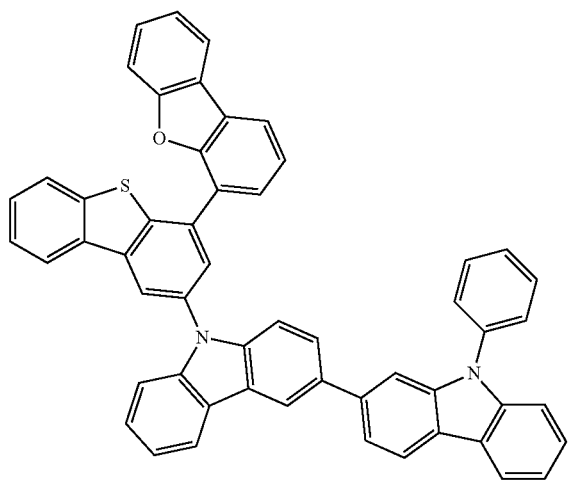
2-38
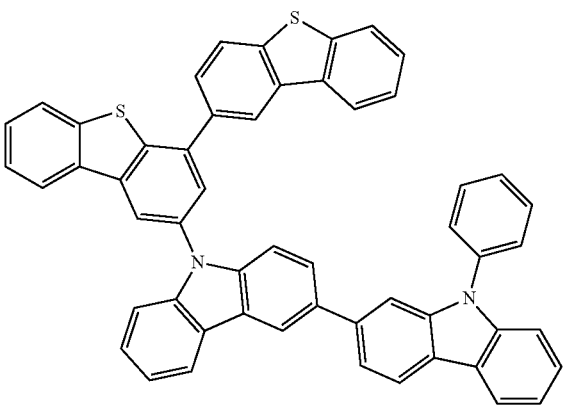
2-39
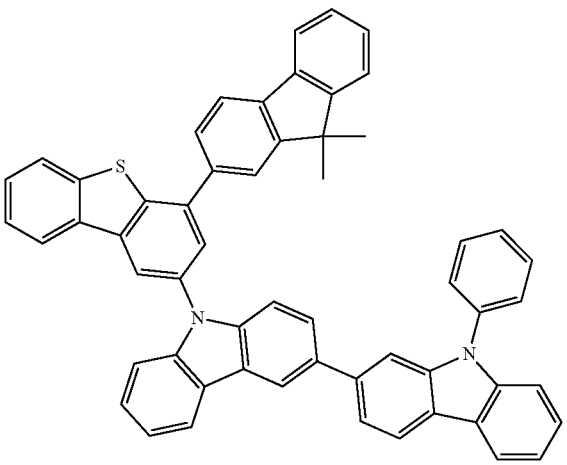
2-40
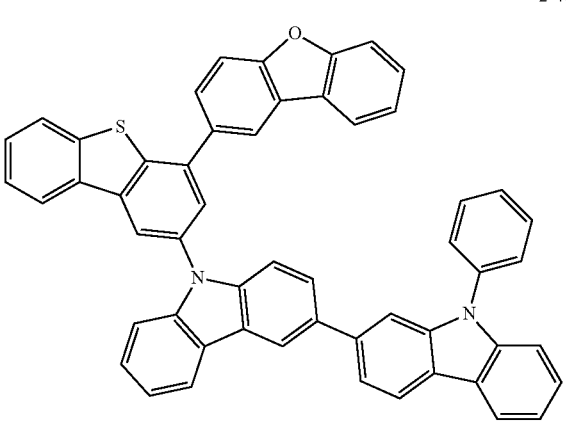

2-41
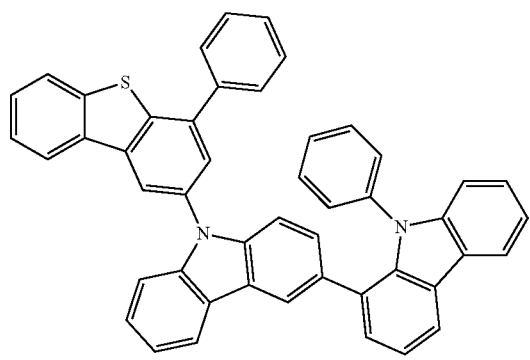
2-42
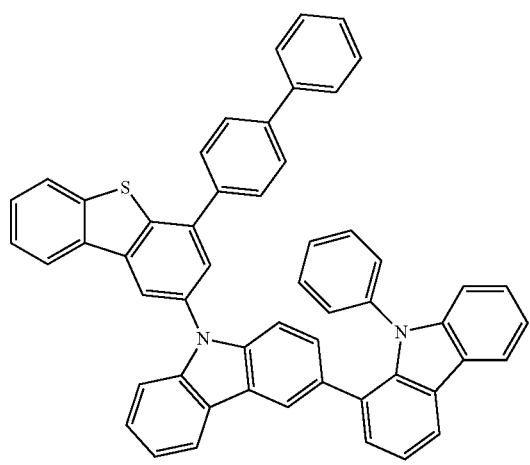
2-43
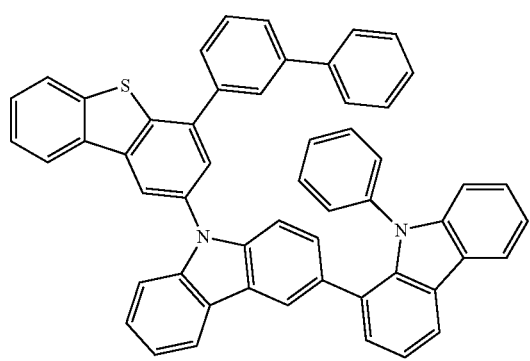
2-44
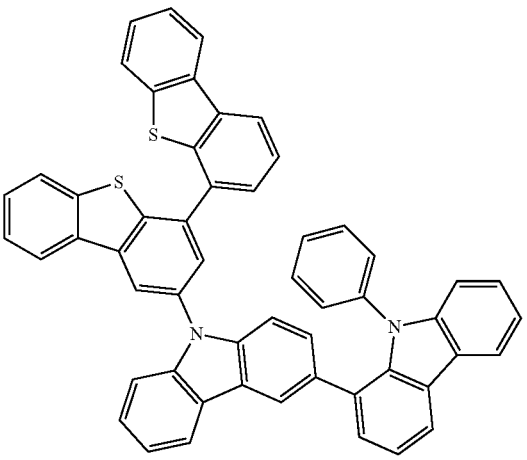
2-45
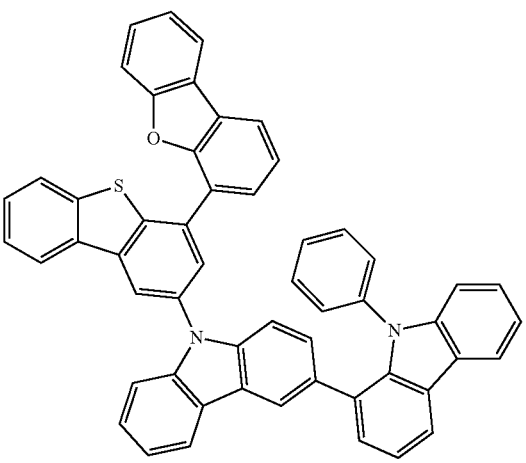
2-46
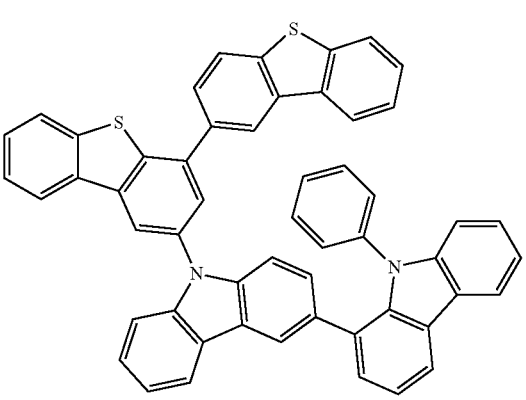

2-47
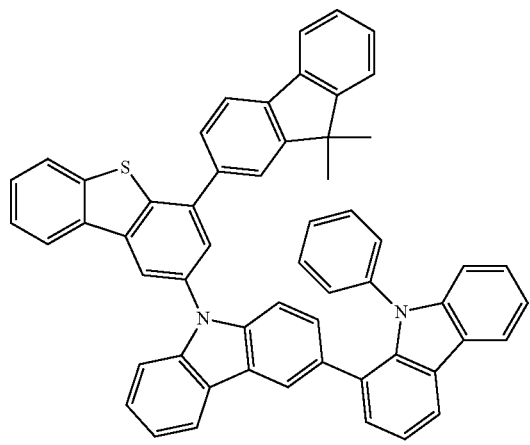
2-50
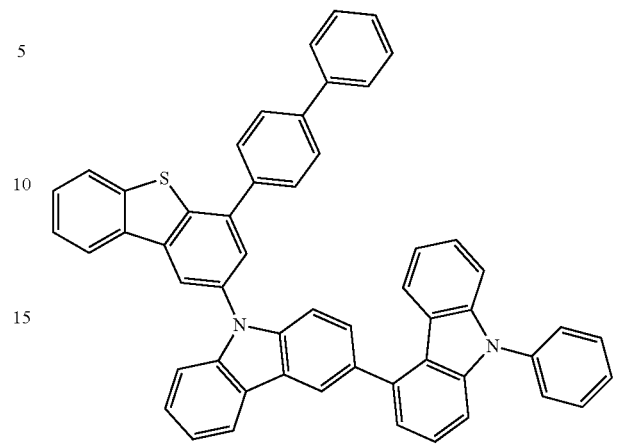
2-48
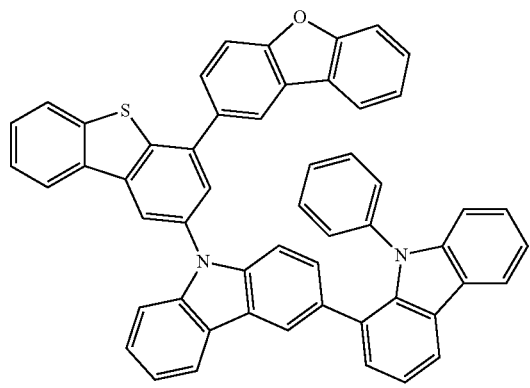
2-51
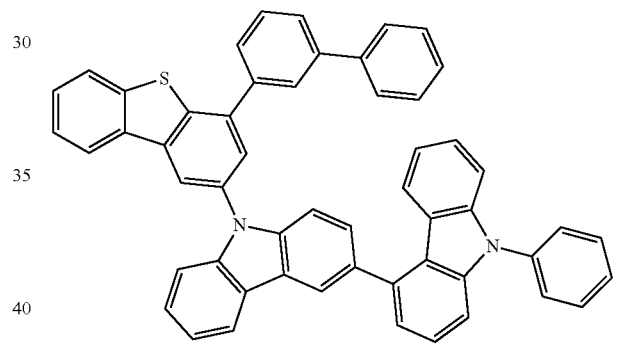
2-49
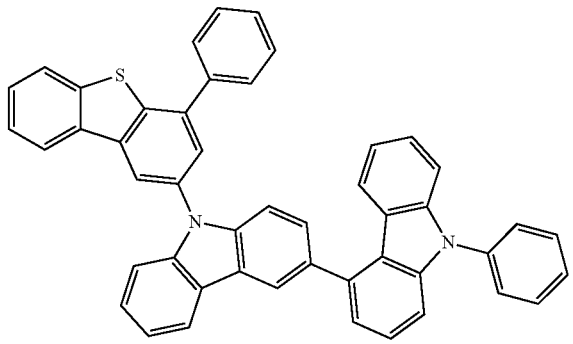
2-52
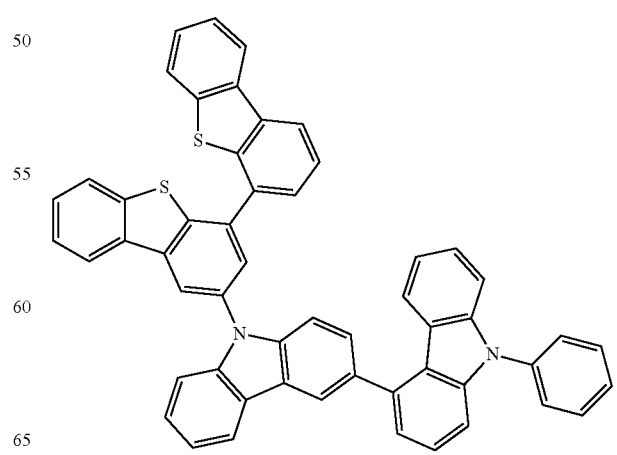

2-53
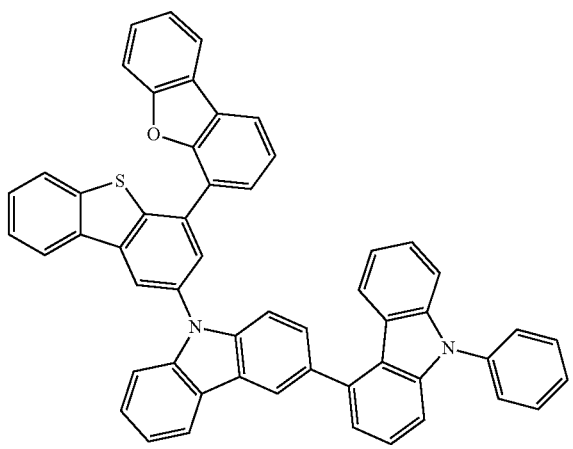
2-56
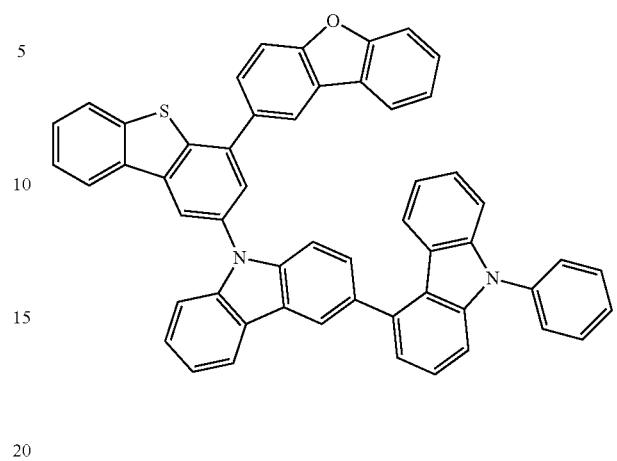
2-54
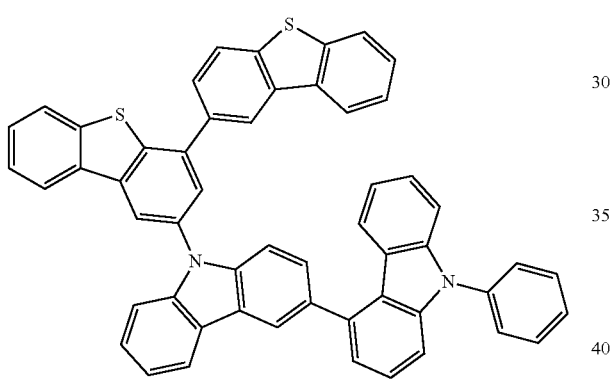
2-57
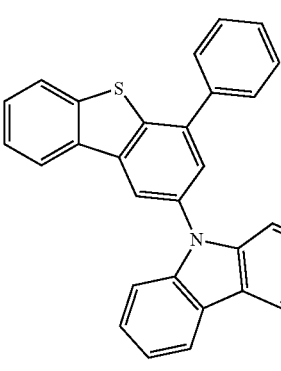
2-55
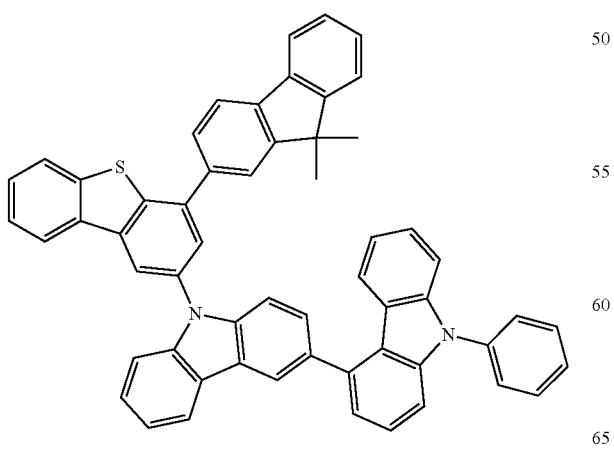
2-58
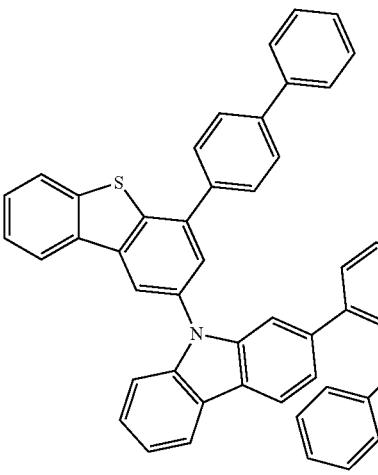

2-59
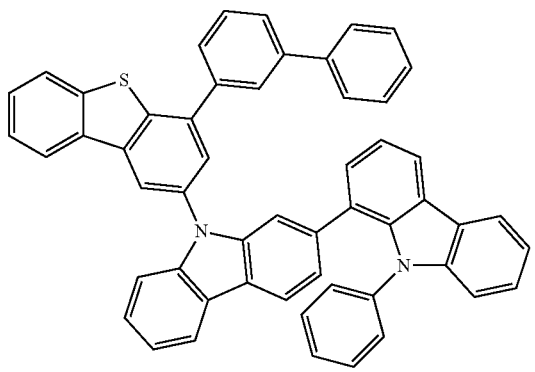
2-60
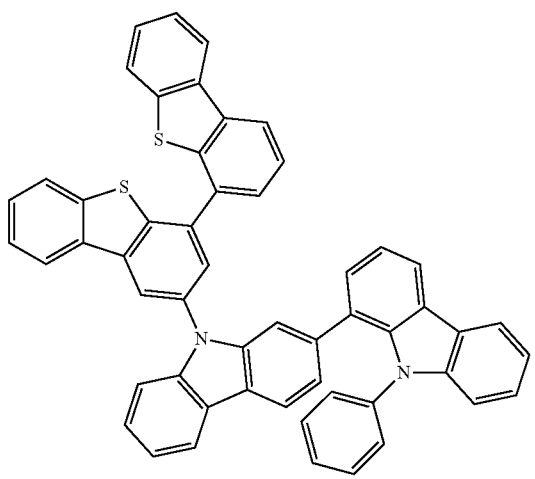
2-61
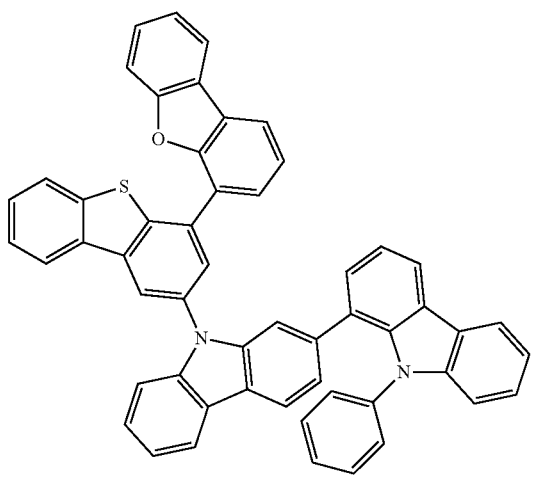
2-62
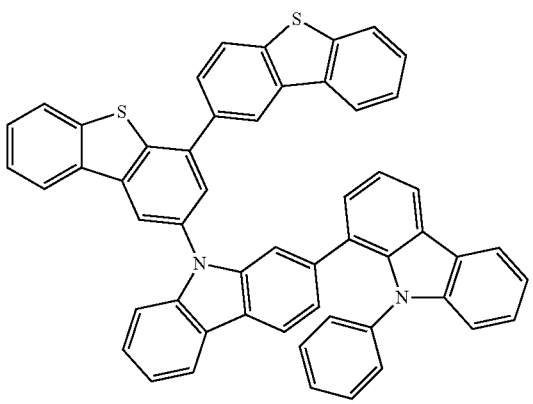
2-63
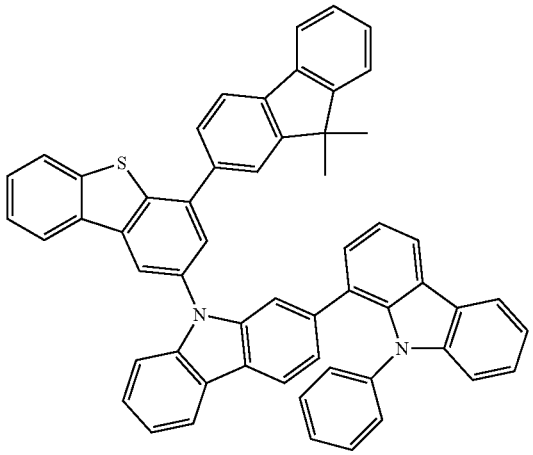
2-64
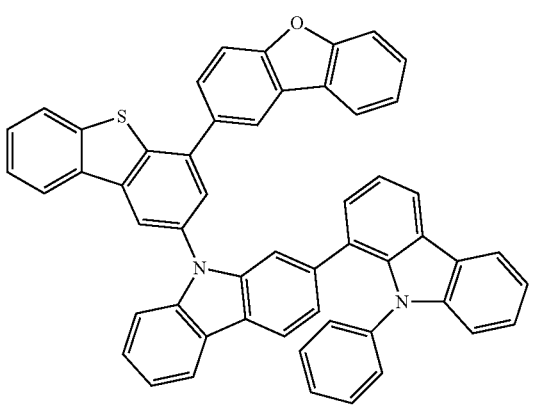

2-65
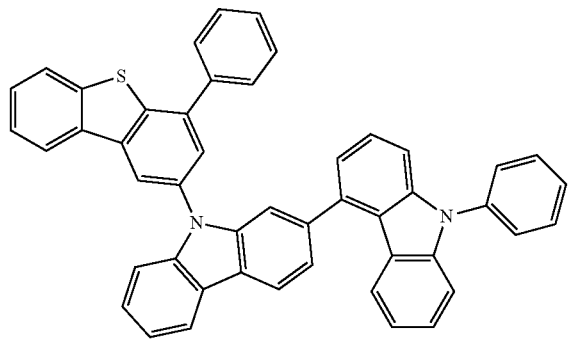
2-66
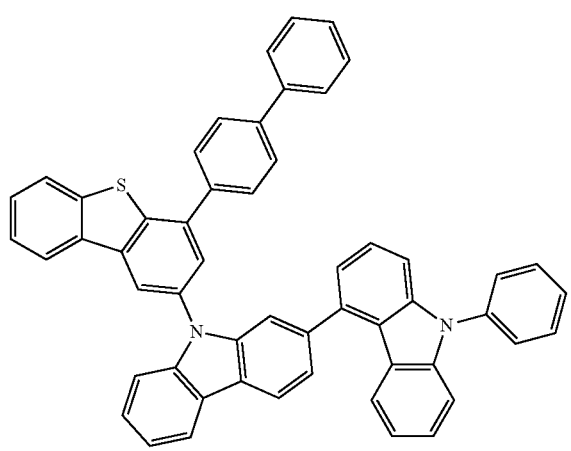
2-67
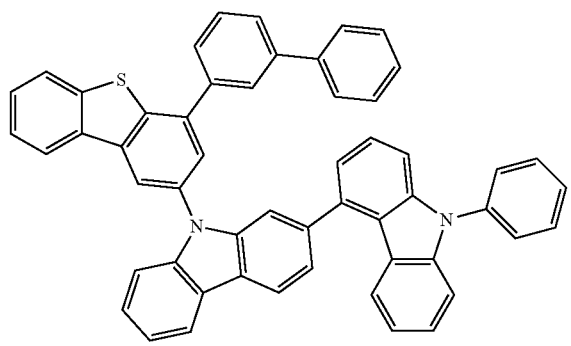
2-68
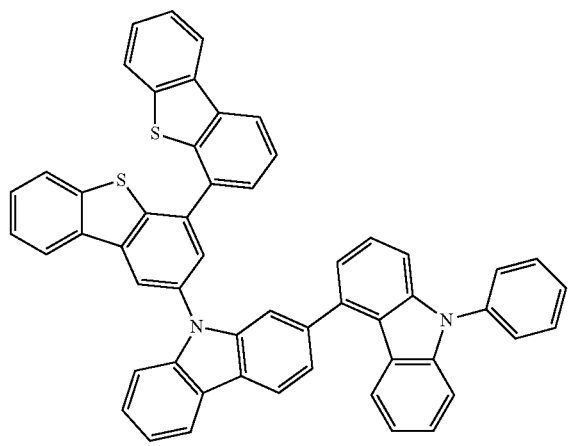
2-69
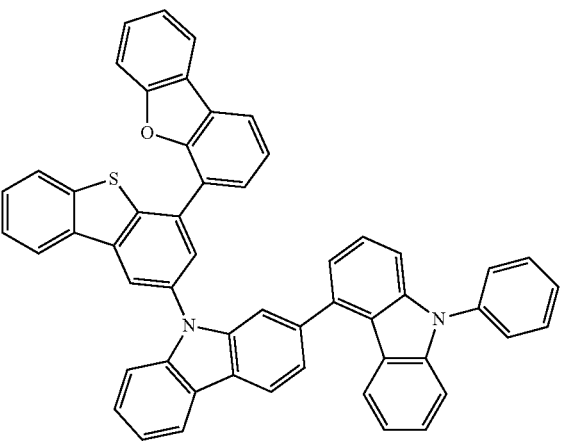
2-70
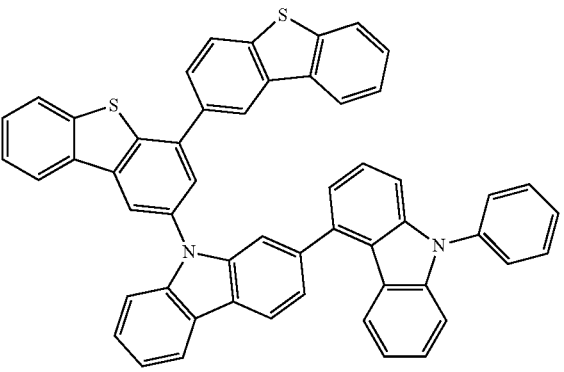
2-71
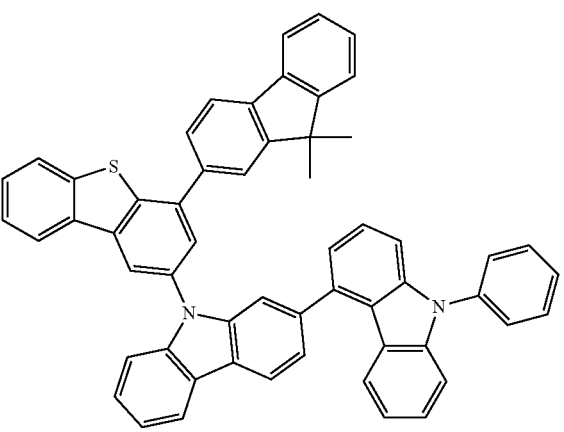

-continued
2-72
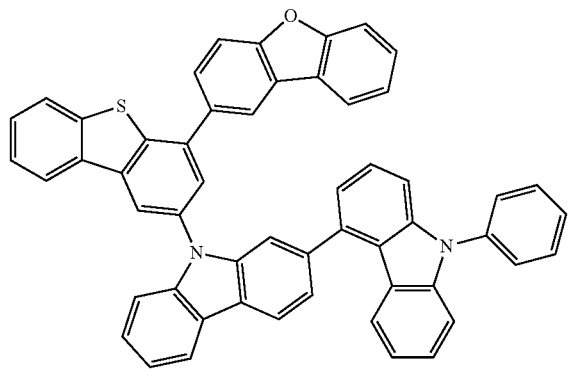
2-73
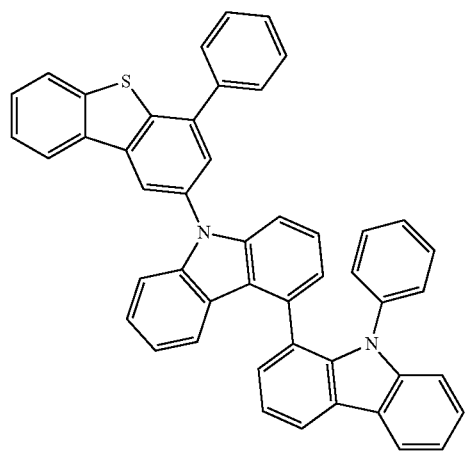
2-74
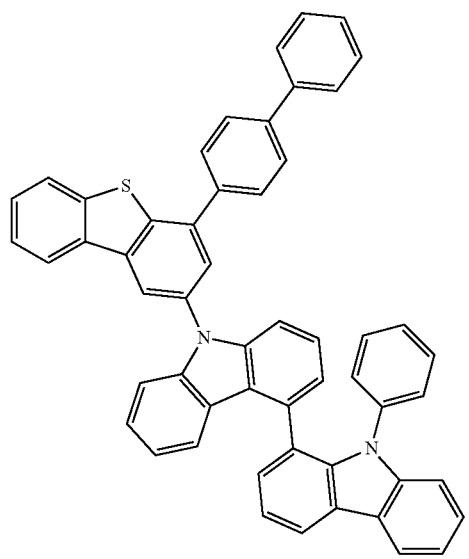
-continued
2-75
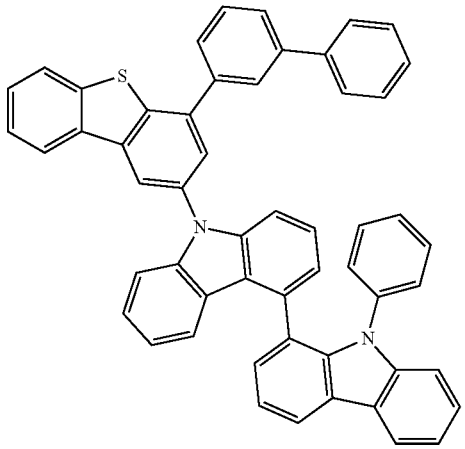
2-76
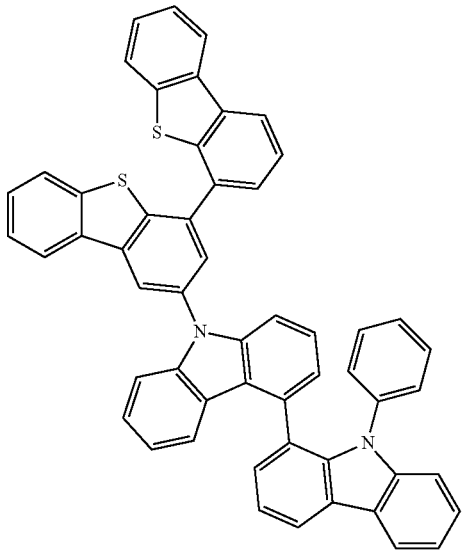
2-77
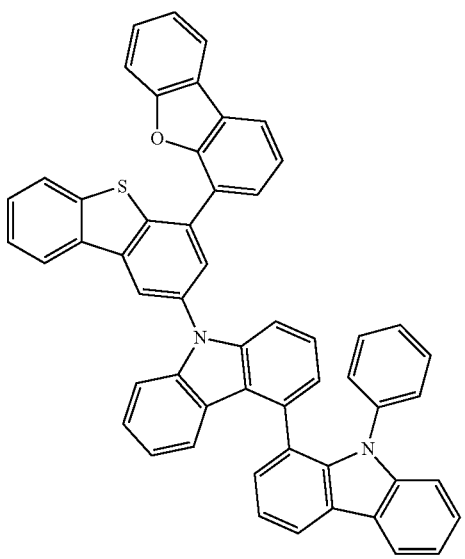

2-78
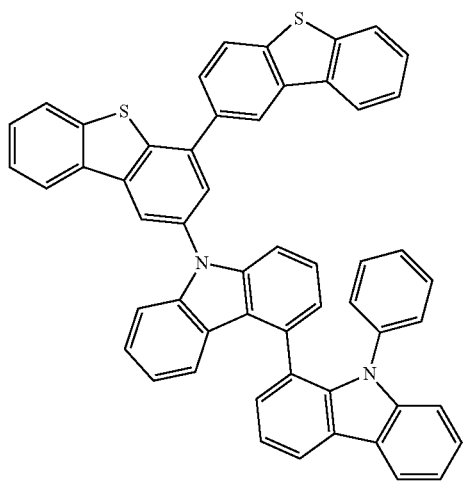
2-79
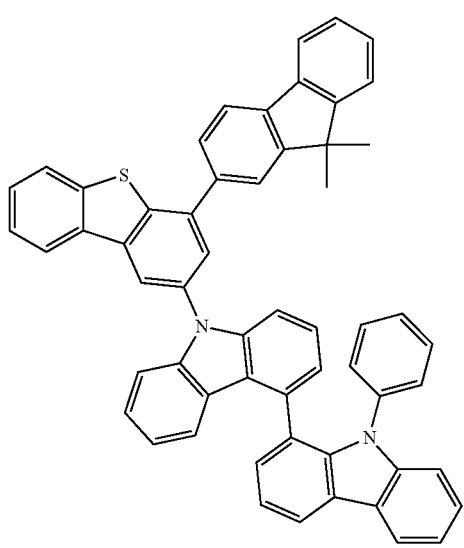
2-80
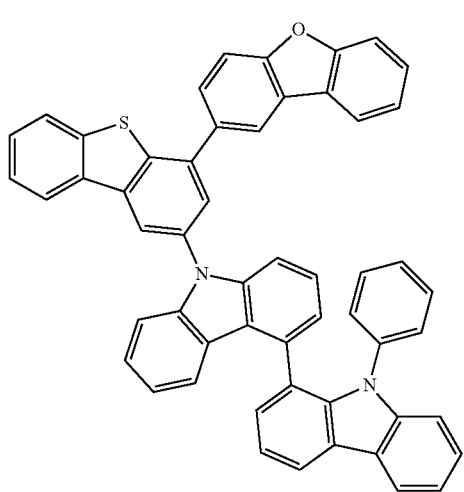
2-81
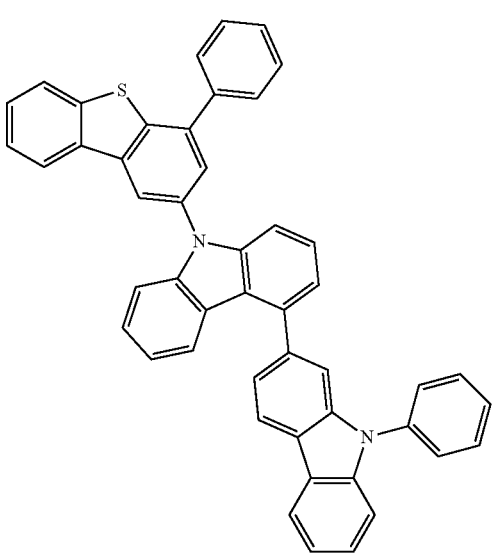
2-82
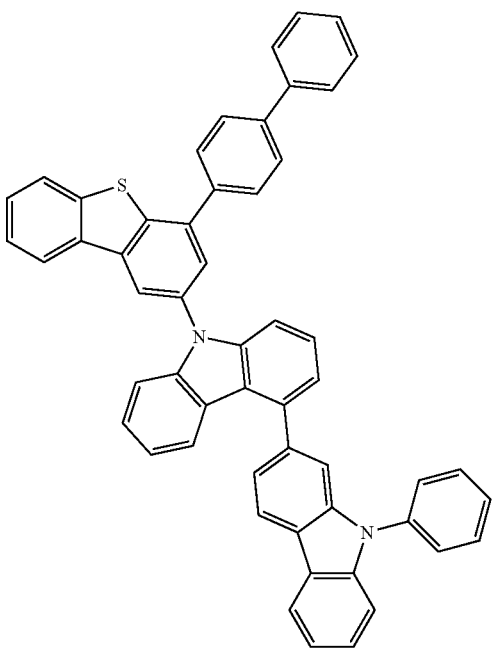

2-83
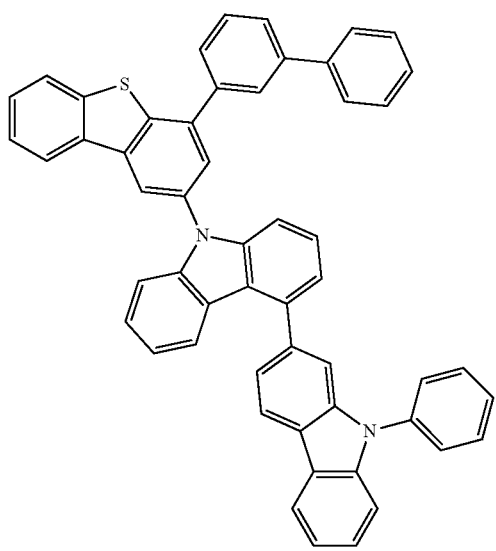
2-85
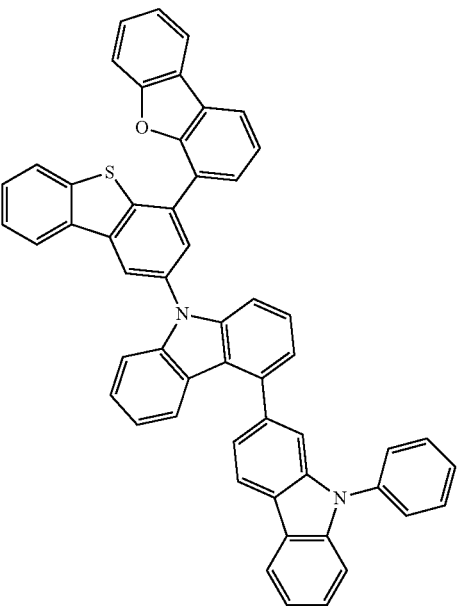
2-84
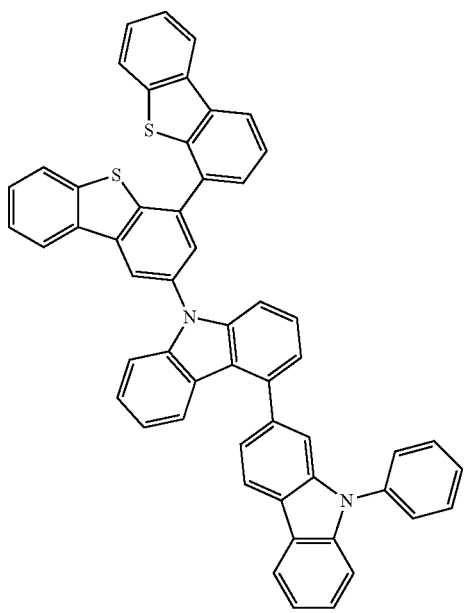
2-86
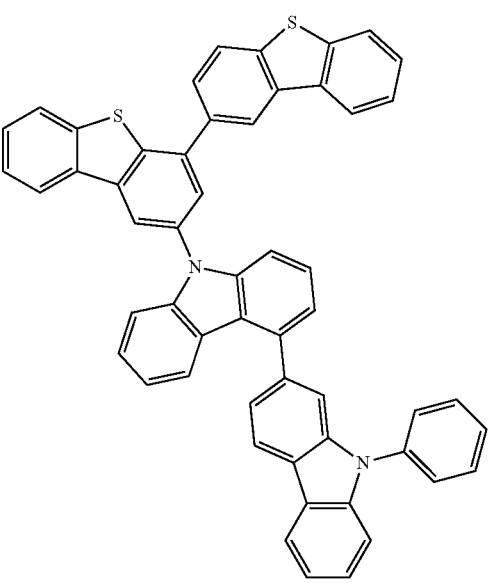

2-87

2-89

2-88

2-90

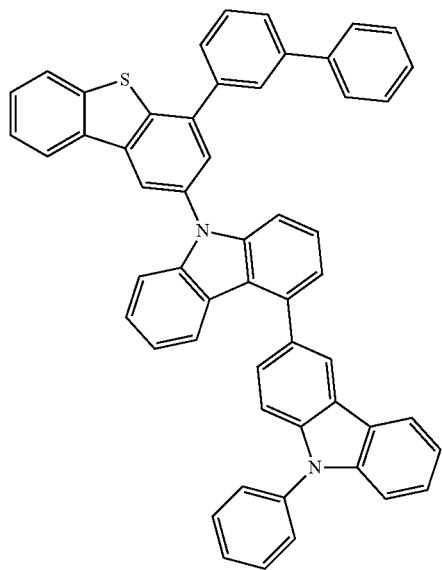
2-91
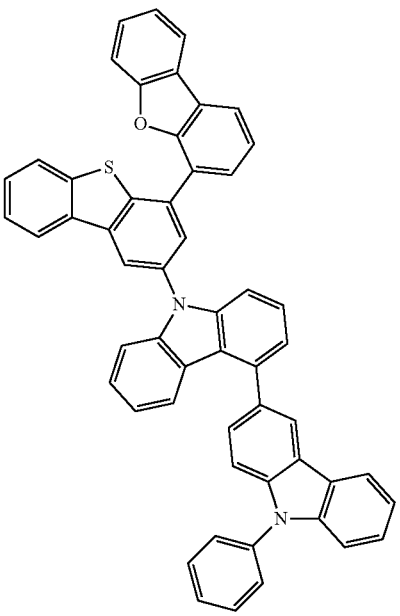
2-93
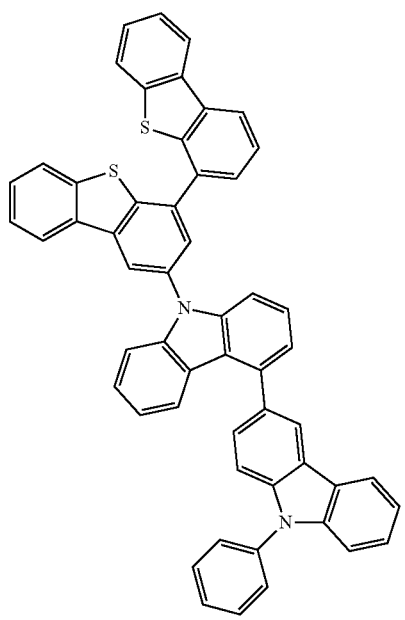
2-92
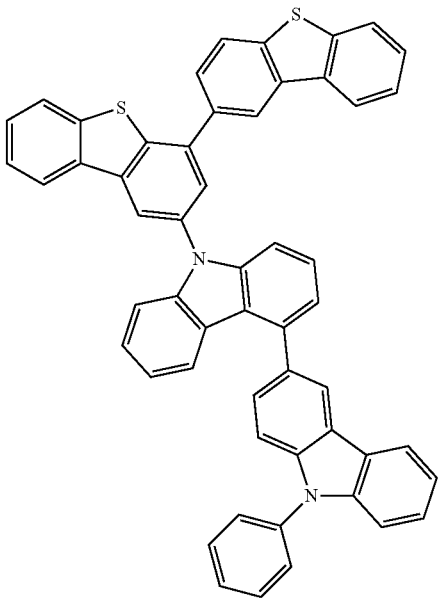
2-94

2-95
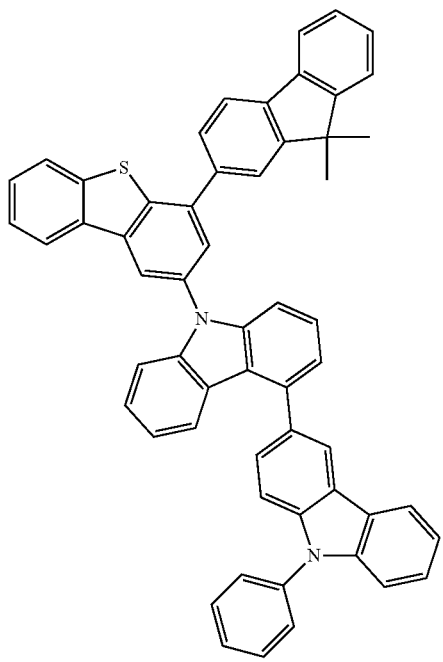
2-97
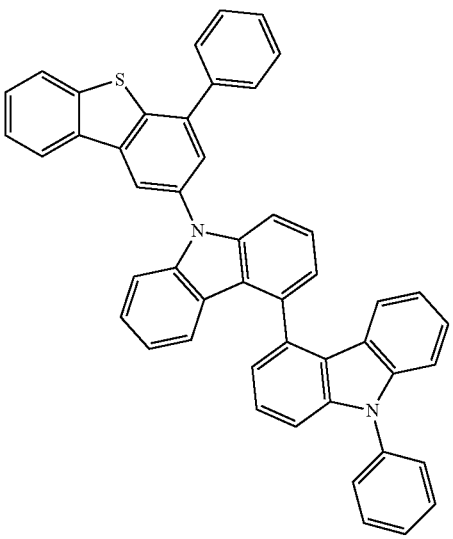
2-96
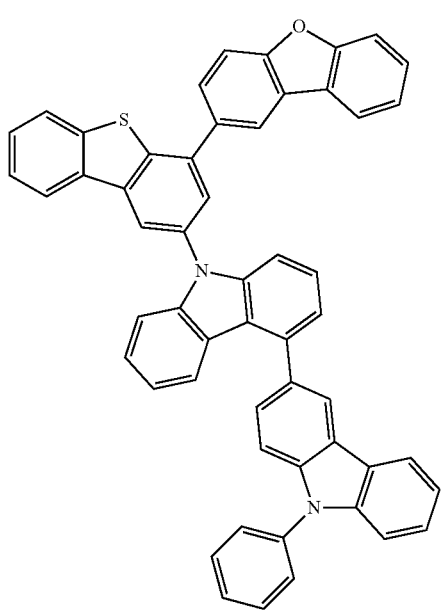
2-98
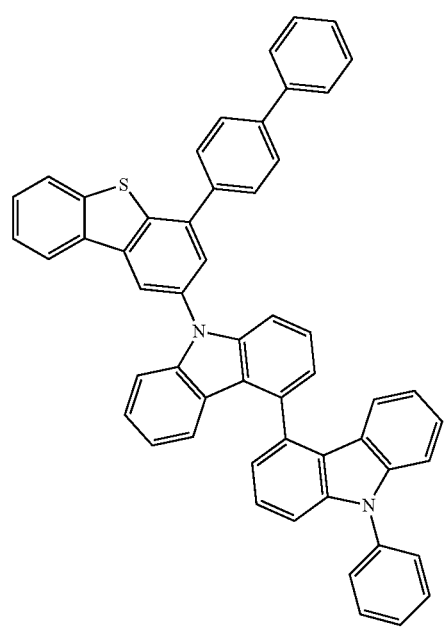

2-99
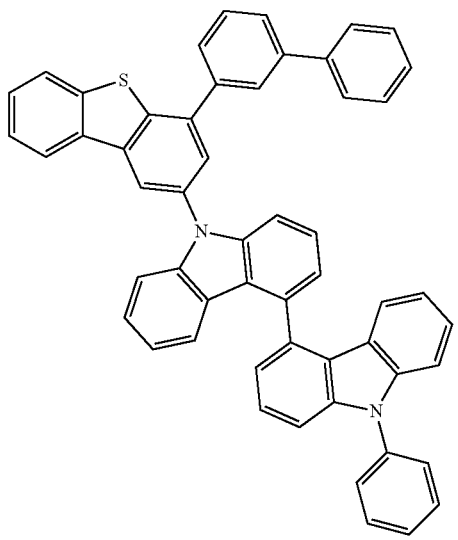
2-101
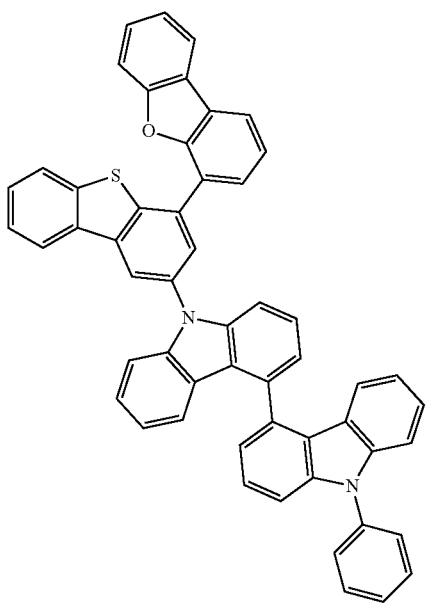
2-100
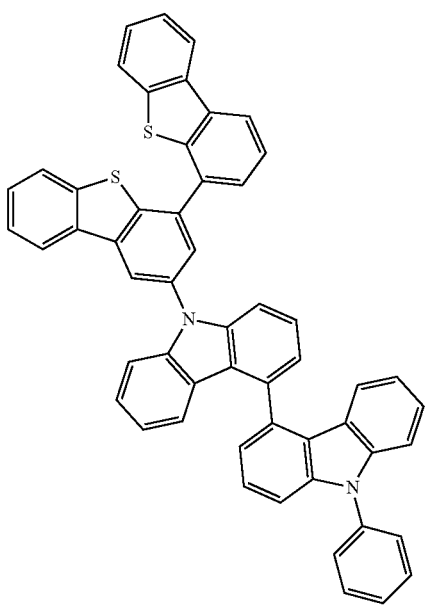
2-102
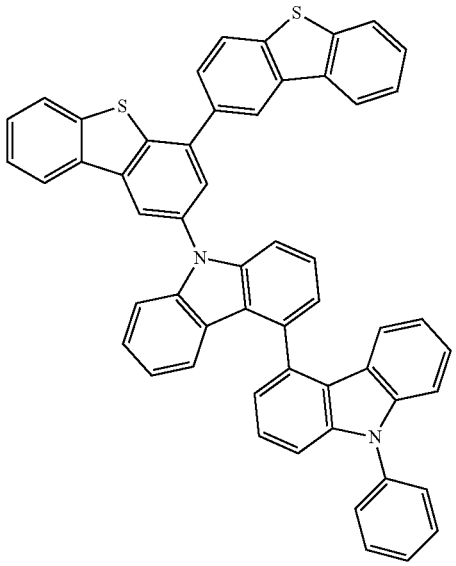

-continued

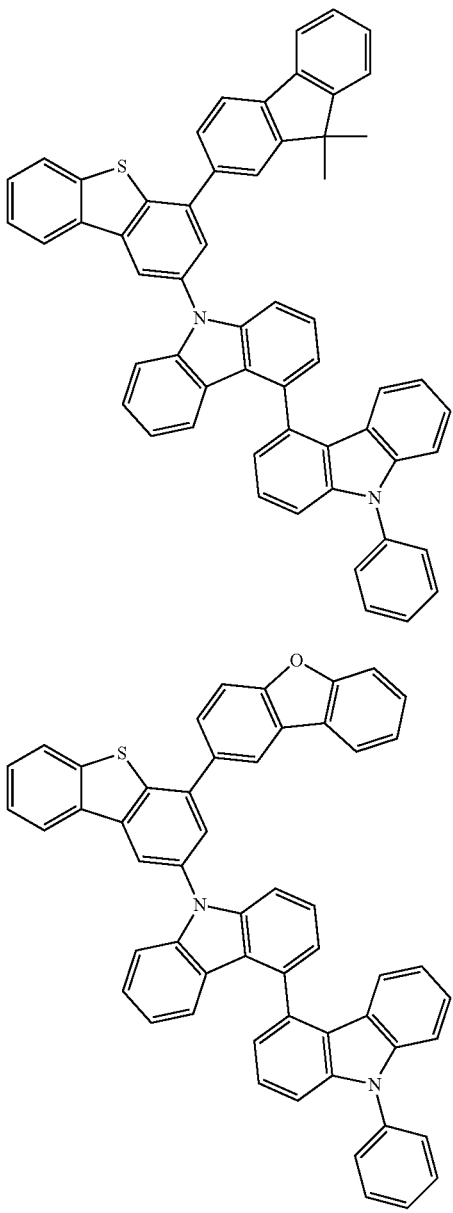

2-103

2-104

Further, it is possible to synthesize a compound having inherent characteristics of a substituent introduced by introducing various substituents into the structures of Chemical Formulae 1 and 2. For example, it is possible to synthesize a material which satisfies conditions required for each organic material layer by introducing a substituent usually used for a hole injection layer material, a material for transporting holes, a light emitting layer material, an electron transport layer material, and a charge generation layer material, which are used for preparing an organic light emitting device, into the core structure.

In addition, it is possible to finely adjust an energy band gap by introducing various substituents into the structures of Chemical Formulae 1 and 2, and meanwhile, it is possible to improve characteristics at the interface between organic materials and diversify the use of material.

Meanwhile, the hetero-cyclic compound has a high glass transition temperature (Tg) and thus has excellent thermal stability. The increase in thermal stability becomes an important factor which provides driving stability to a device.

The hetero-cyclic compound according to an exemplary embodiment of the present application may be prepared by a multi-step chemical reaction. Some intermediate compounds are first prepared, and a compound of Chemical Formula 1 or 2 may be prepared from the intermediate compounds. More specifically, the hetero-cyclic compound according to an exemplary embodiment of the present application may be prepared based on the Preparation Examples to be described below.

Furthermore, another exemplary embodiment of the present application provides a composition for an organic material layer of an organic light emitting device, which includes both the hetero-cyclic compound represented by Chemical Formula 1 and the compound represented by Chemical Formula 2.

The specific contents on the hetero-cyclic compound represented by Chemical Formula 1 and the compound represented by Chemical Formula 2 are the same as those described above.

The weight ratio of the hetero-cyclic compound represented by Chemical Formula 1:the compound represented by Chemical Formula 2 in the composition may be 1:10 to 10:1, 1:8 to 8:1, 1:5 to 5:1, and 1:2 to 2:1, but is not limited thereto.

The composition may be used when an organic material for an organic light emitting device is formed, and particularly, may be more preferably used when a host of a light emitting layer is formed.

The composition is in a form in which two or more compounds are simply mixed, materials in a powder state may also be mixed before an organic material layer of an organic light emitting device is formed, and it is possible to mix compounds in a liquid state at a temperature which is equal to or more than a suitable temperature. The composition is in a solid state at a temperature which is equal to or less than the melting point of each material, and may be maintained as a liquid if the temperature is adjusted.

Another exemplary embodiment of the present application provides an organic light emitting device including the hetero-cyclic compound represented by Chemical Formula 1.

Further, the organic light emitting device according to an exemplary embodiment of the present application includes a positive electrode, a negative electrode, and one or more organic material layers provided between the positive electrode and the negative electrode, in which one or more layers of the organic material layers include the hetero-cyclic compound represented by Chemical Formula 1 and the compound represented by Chemical Formula 2.

The organic light emitting device according to an exemplary embodiment of the present application may be manufactured by typical methods and materials for manufacturing an organic light emitting device, except that the one or more organic material layers are formed by using the hetero-cyclic compound represented by Chemical Formula 1 and the hetero-cyclic compound represented by Chemical Formula 2, which are described above.

The compound represented by Chemical Formula 1 and the hetero-cyclic compound represented by Chemical Formula 2 may be formed as an organic material layer by not only a vacuum deposition method, but also a solution application method when an organic light emitting device is manufactured. Here, the solution application method means spin coating, dip coating, inkjet printing, screen printing, a spray method, roll coating, and the like, but is not limited thereto.

Specifically, the organic light emitting device according to an exemplary embodiment of the present application includes a positive electrode, a negative electrode, and one or more organic material layers provided between the positive electrode and the negative electrode, in which one or more of the organic material layers include the hetero-cyclic compound represented by Chemical Formula 1.

Further, the organic light emitting device according to an exemplary embodiment of the present application includes a positive electrode, a negative electrode, and an one or more organic material layers provided between the positive electrode and the negative electrode, in which one or more layers of the organic material layers include the hetero-cyclic compound represented by Chemical Formula 1 and the hetero-cyclic compound represented by Chemical Formula 2.

FIGS. 1 to 3 exemplify the stacking sequence of the electrodes and the organic material layers of the organic light emitting device according to an exemplary embodiment of the present application. However, the scope of the present application is not intended to be limited by these drawings, and the structure of the organic light emitting device known in the art may also be applied to the present application.

According to FIG. 1, an organic light emitting device in which a positive electrode 200, an organic material layer 300, and a negative electrode 400 are sequentially stacked on a substrate 100 is illustrated. However, the organic light emitting device is not limited only to such a structure, and as in FIG. 2, an organic light emitting device in which a negative electrode, an organic material layer, and a positive electrode are sequentially stacked on a substrate may also be implemented.

FIG. 3 exemplifies a case where an organic material layer is a multilayer. An organic light emitting device according to FIG. 3 includes a hole injection layer 301, a hole transport layer 302, a light emitting layer 303, a hole blocking layer 304, an electron transport layer 305, and an electron injection layer 306. However, the scope of the present application is not limited by the stacking structure as described above, and if necessary, the other layers except for the light emitting layer may be omitted, and another necessary functional layer may be further added.

The organic light emitting device according to the present specification may be manufactured by materials and methods known in the art, except that one or more layers in the organic material layers include the hetero-cyclic compound represented by Chemical Formula 1, or include both the hetero-cyclic compound represented by Chemical Formula 1 and the hetero-cyclic compound represented by Chemical Formula 2.

The hetero-cyclic compound represented by Chemical Formula 1 may alone constitute one or more layers of the organic material layers of the organic light emitting device. However, the hetero-cyclic compound represented by Chemical Formula 1 may be mixed with another material, if necessary, to constitute an organic material layer.

The hetero-cyclic compound represented by Chemical Formula 1 may be used as a material for an electron transport layer, a hole blocking layer, or a light emitting layer, and the like in the organic light emitting device. As an example, the hetero-cyclic compound represented by Chemical Formula 1 may be used as a material for an electron transport layer, a hole transport layer, or a light emitting layer of the organic light emitting device.

Furthermore, the hetero-cyclic compound represented by Chemical Formula 1 may be used as a material for a light emitting layer in the organic light emitting device. As an example, the hetero-cyclic compound represented by Chemical Formula 1 may be used as a material for a phosphorescent host of a light emitting layer in the organic light emitting device.

Further, the organic material layer including the hetero-cyclic compound represented by Chemical Formula 1 and the hetero-cyclic compound represented by Chemical Formula 2 may additionally include another material, if necessary.

The hetero-cyclic compound represented by Chemical Formula 1 and the hetero-cyclic compound represented by chemical Formula 2 may be used as a material for a charge generation layer in the organic light emitting device.

The hetero-cyclic compound represented by Chemical Formula 1 and the hetero-cyclic compound represented by chemical Formula 2 may be used as a material for an electron transport layer, a hole blocking layer, and a light emitting layer, and the like in the organic light emitting device. As an example, the hetero-cyclic compound represented by Chemical Formula 1 and the hetero-cyclic compound represented by Chemical Formula 2 may be used as a material for an electron transport layer, a hole transport layer, or a light emitting layer of the organic light emitting device.

Furthermore, the hetero-cyclic compound represented by Chemical Formula 1 and the compound represented by chemical Formula 2 may be used as a material for a light emitting layer in the organic light emitting device. As an example, the hetero-cyclic compound represented by Chemical Formula 1 and the compound represented by chemical Formula 2 may be used as a material for a phosphorescent host of a light emitting layer in the organic light emitting device.

In the organic light emitting device according to an exemplary embodiment of the present application, materials other than the hetero-cyclic compound of Chemical Formula 1 and the hetero-cyclic compound of Chemical Formula 2 will be exemplified below, but these materials are provided only for exemplification and are not for limiting the scope of the present application, and may be replaced with materials publicly known in the art.

As a material for the positive electrode, materials having a relatively high work function may be used, and a transparent conductive oxide, a metal or a conductive polymer, and the like may be used. Specific examples of the positive electrode material include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as $ZnO:Al$ or $SnO_2:Sb$; a polymer, such as poly(3-methyl compound), poly[3,4-(ethylene-1,2-dioxy) compound] (PEDT), polypyrrole, and polyaniline, and the like, but are not limited thereto.

As a material for the negative electrode, materials having a relatively low work function may be used, and a metal, a metal oxide, or a conductive polymer, and the like may be used. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as $LiF/Al$ or $LiO_2/Al$, and the like, but are not limited thereto.

As a hole injection material, a publicly-known hole injection material may also be used, and it is possible to use, for example, a phthalocyanine compound such as copper phthalocyanine disclosed in U.S. Pat. No. 4,356,429 or starburst-type amine derivatives described in the document [Advanced Material, 6, p. 677 (1994)], for example, tris(4-carbazoyl-9-ylphenyl)amine (TCTA), 4,4',4"-tris[phenyl(m-tolyl)amino]triphenylamine (m-MTDATA), 1,3,5-tris[4-(3-methylphenylphenylamino)phenyl]benzene (m-MTDAPB), polyaniline/dodecylbenzenesulfonic acid or poly(3,4-ethylenedioxythiophene)/poly(4-styrenesulfonate), which is a soluble conductive polymer, polyaniline/camphor sulfonic acid or polyaniline/poly(4-styrene-sulfonate), and the like.

As the hole transport material, a pyrazoline derivative, an arylamine-based derivative, a stilbene derivative, a triphenyldiamine derivative, and the like may be used, and a low-molecular weight or polymer material may also be used.

As the electron transport material, it is possible to use an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, a metal complex of 8-hydroxyquinoline and a derivative thereof, and the like, and a low-molecular weight material and a polymer material may also be used.

As the electron injection material, for example, LiF is representatively used in the art, but the present application is not limited thereto.

As the light emitting material, a red, green, or blue light emitting material may be used, and if necessary, two or more light emitting materials may be mixed and used. In this case, two or more light emitting materials are deposited or used as an individual supply source, or pre-mixed to be deposited and used as one supply source. Further, as the light emitting material, a fluorescent material may also be used, but a phosphorescent material may also be used. As the light emitting material, it is also possible to use alone a material which emits light by combining holes and electrons each injected from the positive electrode and the negative electrode, but materials in which a host material and a dopant material work together to emit light may also be used.

When hosts of the light emitting material are mixed and used, the same series hosts may also be mixed and used, and different series hosts may also be mixed and used. For example, two or more materials selected from n-type host materials or p-type host materials may be used as a host material for a light emitting layer.

The organic light emitting device according to an exemplary embodiment of the present application may be a top emission type, a bottom emission type, or a dual emission type according to the material to be used.

The hetero-cyclic compound according to an exemplary embodiment of the present application may be operated by a principle which is similar to the principle applied to an organic light emitting device, even in an organic electronic device including an organic solar cell, an organic photoconductor, an organic transistor, and the like.

Mode for Invention

Hereinafter, the present specificastion will be described in more detail through the Examples, but these Examples are provided only for exemplifying the present application, and are not intended to limit the scope of the present application.

EXAMPLES

<Preparation Example 1> Preparation of Compound 1-11-2

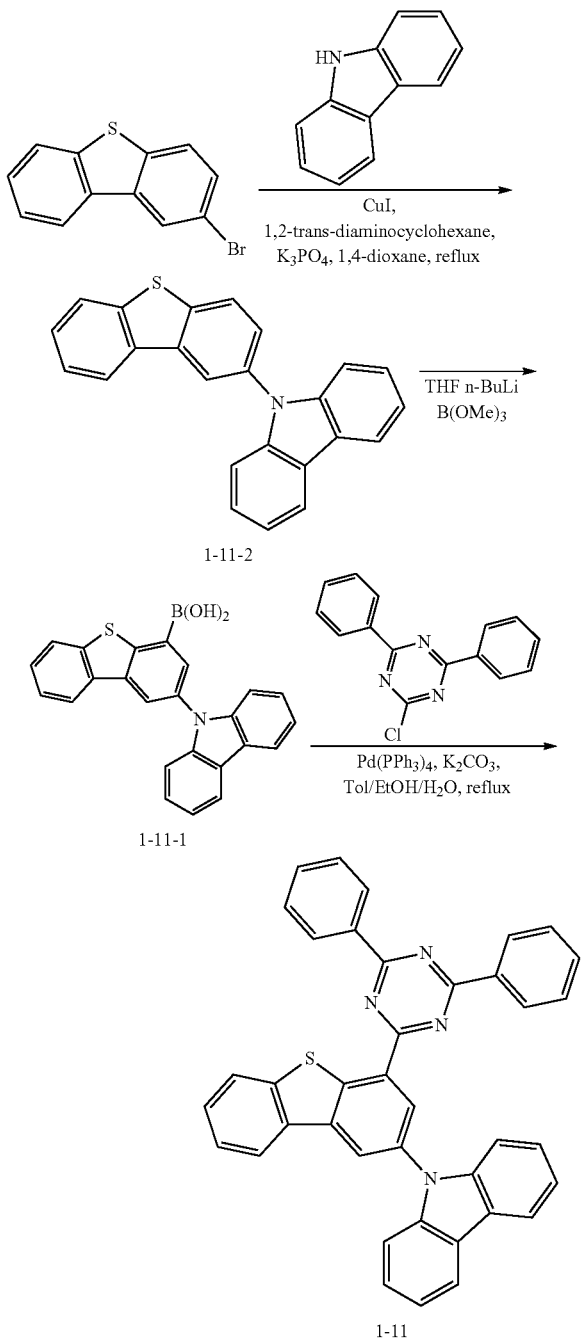

1) Preparation of Compound 1-11-2

5.0 g (19.0 mM) of 2-bromodibenzo[b,d]thiophene, 2.6 g (15.8 mM) of 9H—carbazole, 3.0 g (15.8 mM) of CuI, 1.9 mL (15.8 mM) of trans-1,2-diaminocyclohexane, and 3.3 g (31.6 mM) of $K_3PO_4$ were dissolved in 100 mL of 1,4- oxane, and then the resulting solution was refluxed for 24 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 4.7 g (85%) of Target Compound 1-11-2.

2) Preparation of Compound 1-11-1

7.4 mL (18.6 mM) of 2.5 M n-BuLi was added dropwise to a mixed solution containing 5 g (14.3 mM) of Compound 1-11-2 and 100 mL of THF at −78° C., and the resulting mixture was stirred at room temperature for 1 hour. 4.8 mL (42.9 mM) of trimethyl borate (B(OMe)$_3$) was added dropwise to the reaction mixture, and the resulting mixture was stirred at room temperature for 2 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:MeOH=100:3) and recrystallized with DCM to obtain 3.9 g (70%) of Target Compound 1-11-1.

3) Preparation of Compound 1-11

7.5 g (19.0 mM) of Compound 1-11-1, 5.1 g (19.0 mM) of 2-chloro-4,6-diphenyl-1,3,5-triazine, 1.1 g (0.95 mM) of Pd(PPh$_3$)$_4$, and 5.2 g (38.0 mM) of K$_2$CO$_3$ were dissolved in 100/20/20 mL of toluene/EtOH/H$_2$O, and then the resulting solution was refluxed for 12 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 7.7 g (70%) of Target Compound 1-11.

Target Compound A was prepared and synthesized in the same manner as in the preparation in Preparation Example 1, except that Intermediate A in the following Table 1 was used instead of 9H-carbazole, and Intermediate B in the following Table 1 was used instead of 2-chloro-4,6-diphenyl-1,3,5-triazine in Preparation Example 1.

TABLE 1

| Compound No. | Intermediate A | Intermediate B |
|---|---|---|
| 1-2 | [carbazole structure] | [2-bromo-4,6-diphenylpyrimidine structure] |
| 1-12 | | [2-chloro-4-(biphenyl-3-yl)-6-phenyl-1,3,5-triazine structure] |
| 1-17 | | [4-chloro-2-phenylquinoline structure] |

TABLE 1-continued
1-23 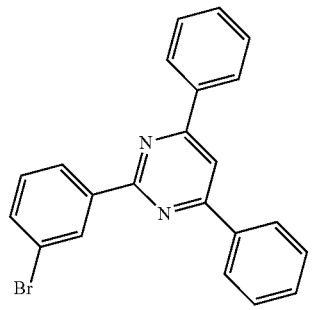 [SMILES: Brc1cccc(-c2nc(-c3ccccc3)cc(-c3ccccc3)n2)c1]
1-27 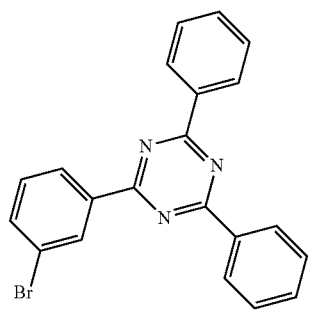 [SMILES: Brc1cccc(-c2nc(-c3ccccc3)nc(-c3ccccc3)n2)c1]
1-33 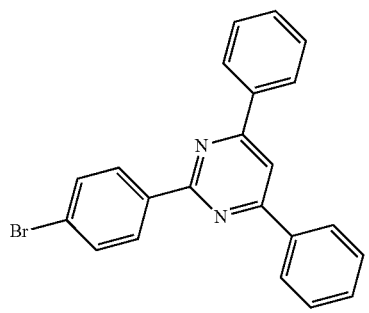 [SMILES: Brc1ccc(-c2nc(-c3ccccc3)cc(-c3ccccc3)n2)cc1]
1-36 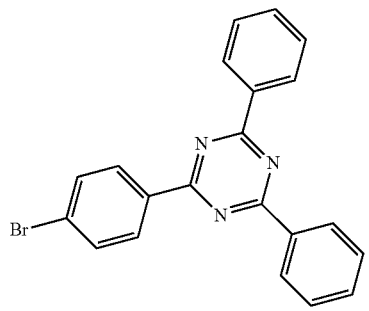 [SMILES: Brc1ccc(-c2nc(-c3ccccc3)nc(-c3ccccc3)n2)cc1]
1-39 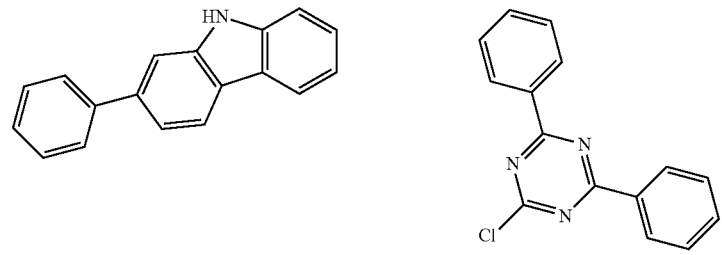

TABLE 1-continued
| 1-40 | 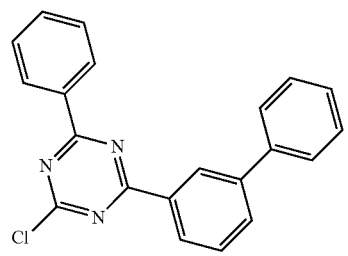 [SMILES: Clc1nc(-c2ccccc2)nc(-c2cccc(-c3ccccc3)c2)n1] |
| 1-41 | 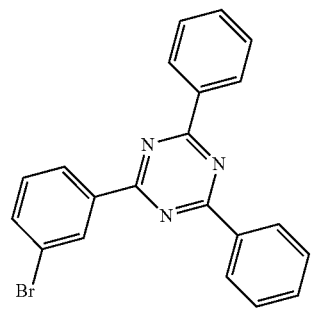 [SMILES: Brc1cccc(-c2nc(-c3ccccc3)nc(-c3ccccc3)n2)c1] |
| 1-42 | 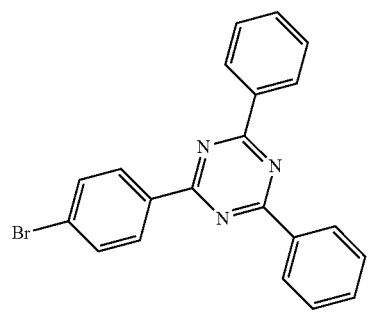 [SMILES: Brc1ccc(-c2nc(-c3ccccc3)nc(-c3ccccc3)n2)cc1] |
| 1-46 | 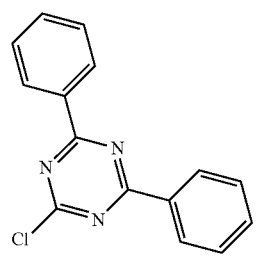 |
| 1-65 | 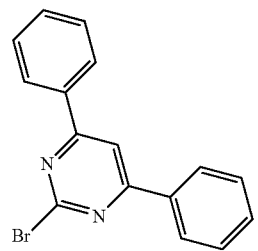 |
| 1-66 | 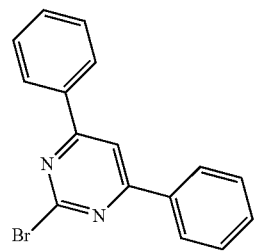 [SMILES: Clc1nc(-c2ccccc2)nc(-c2ccccc2)n1] |

TABLE 1-continued
1-67 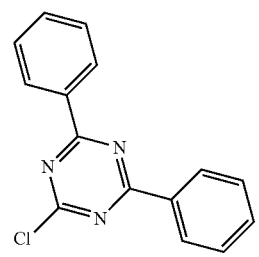 [SMILES: Clc1nc(-c2ccccc2)nc(-c2ccccc2)n1]
1-68 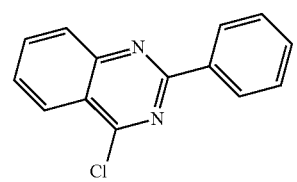 [SMILES: Clc1nc(-c2ccccc2)nc2ccccc12]
1-69 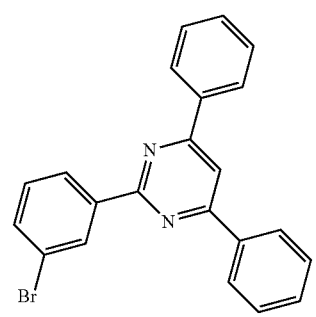 [SMILES: Brc1cccc(-c2nc(-c3ccccc3)cc(-c3ccccc3)n2)c1]
1-70 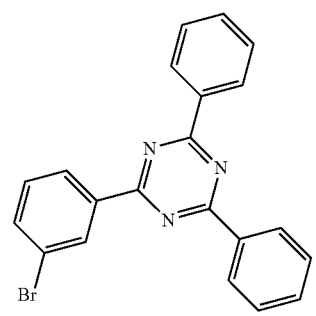
1-71 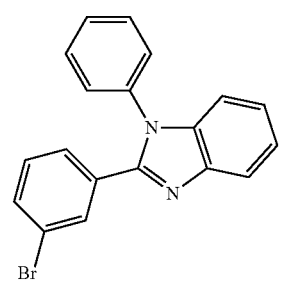 [SMILES: Brc1cccc(-c2nc3ccccc3n2-c2ccccc2)c1]

TABLE 1-continued
1-72 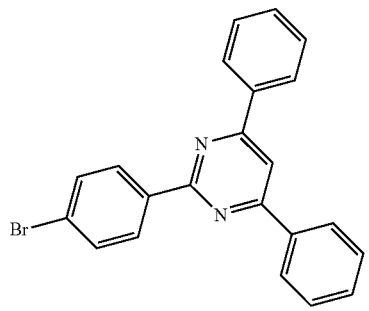 [SMILES: Brc1ccc(-c2nc(-c3ccccc3)cc(-c3ccccc3)n2)cc1]
1-76 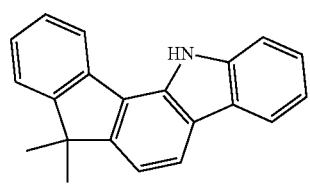 [SMILES: CC1(C)c2ccccc2-c2c1ccc1c2[nH]c2ccccc21] 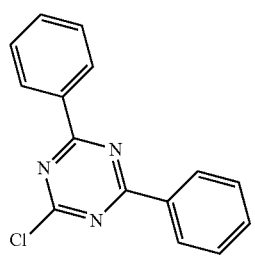 [SMILES: Clc1nc(-c2ccccc2)nc(-c2ccccc2)n1]
1-77 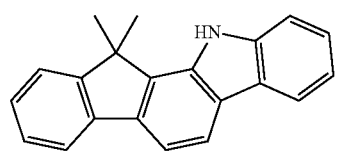 [SMILES: CC1(C)c2ccccc2-c2ccc3c([nH]c4ccccc43)c21]
1-78 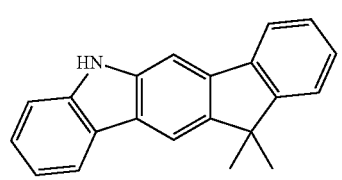 [SMILES: CC1(C)c2ccccc2-c2cc3[nH]c4ccccc4c3cc21]
1-79 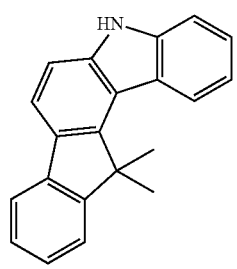 [SMILES: CC1(C)c2ccccc2-c2ccc3[nH]c4ccccc4c3c21]
1-82 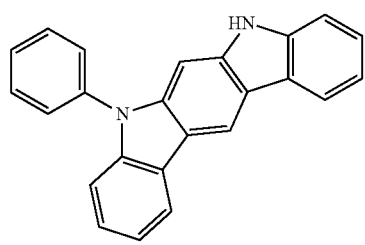 [SMILES: c1ccc(-n2c3ccccc3c3cc4c(cc32)[nH]c2ccccc24)cc1]

TABLE 1-continued
| | | |
|---|---|---|
| 1-83 | | 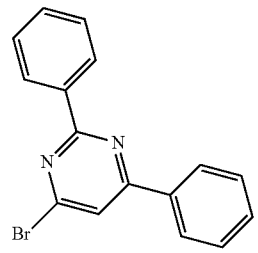 |
| 1-84 | | 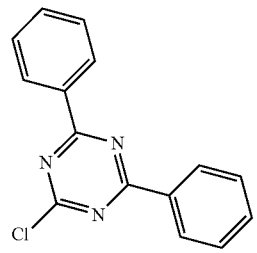 [SMILES: Clc1nc(-c2ccccc2)nc(-c2ccccc2)n1] |
| 1-85 | | 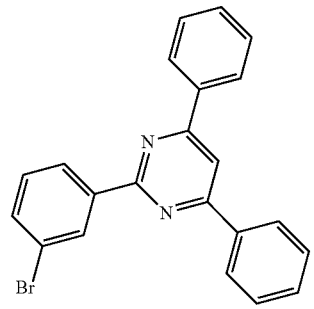 [SMILES: Brc1cccc(-c2nc(-c3ccccc3)cc(-c3ccccc3)n2)c1] |
| 1-86 | | 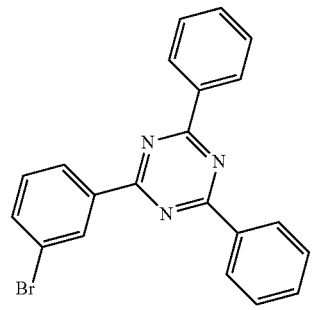 [SMILES: Brc1cccc(-c2nc(-c3ccccc3)nc(-c3ccccc3)n2)c1] |
| 1-91 | 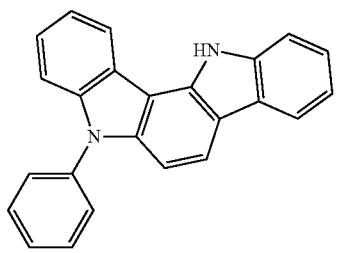 [SMILES: c1ccc(-n2c3ccccc3c3c4[nH]c5ccccc5c4ccc32)cc1] | 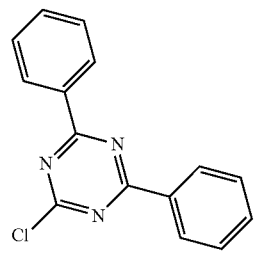 [SMILES: Clc1nc(-c2ccccc2)nc(-c2ccccc2)n1] |
| 1-92 | 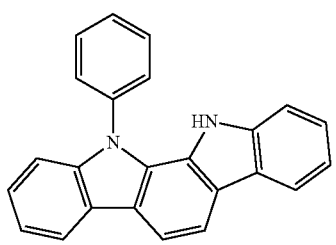 [SMILES: c1ccc(-n2c3ccccc3c3ccc4c5ccccc5[nH]c4c32)cc1] | |

TABLE 1-continued
1-93 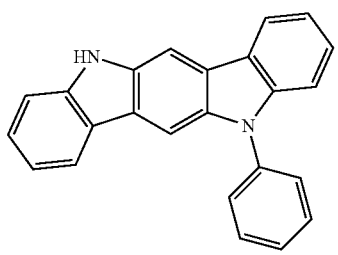 [SMILES: c1ccc(-n2c3ccccc3c3cc4[nH]c5ccccc5c4cc32)cc1]
1-94 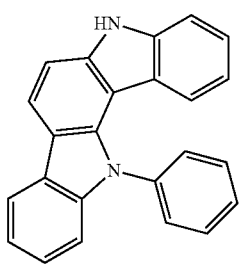 [SMILES: c1ccc(-n2c3ccccc3c3ccc4[nH]c5ccccc5c4c32)cc1]
1-96 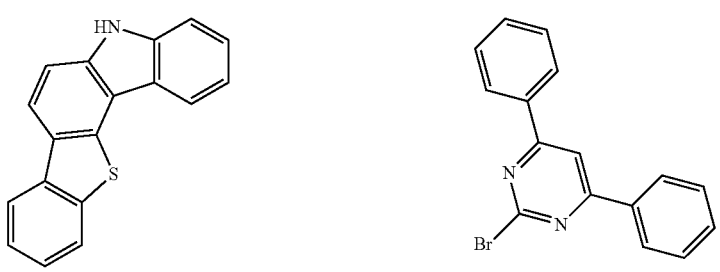
1-98 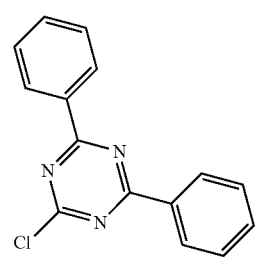 [SMILES: Clc1nc(-c2ccccc2)nc(-c2ccccc2)n1]
1-99 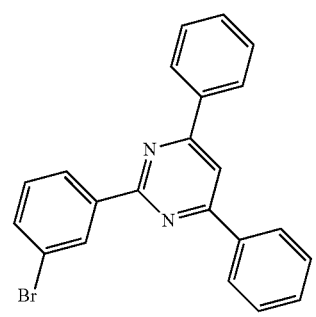 [SMILES: Brc1cccc(-c2nc(-c3ccccc3)cc(-c3ccccc3)n2)c1]

TABLE 1-continued
1-100
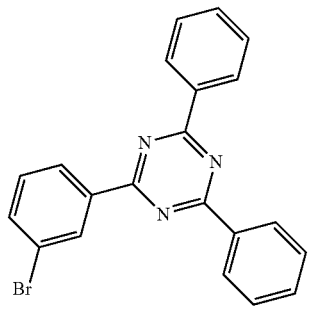 [SMILES: Brc1cccc(-c2nc(-c3ccccc3)nc(-c3ccccc3)n2)c1]
1-109
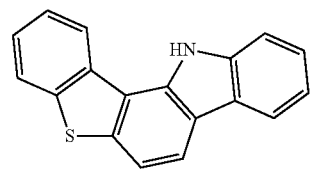 [SMILES: c1ccc2c(c1)[nH]c1c2ccc2sc3ccccc3c21]
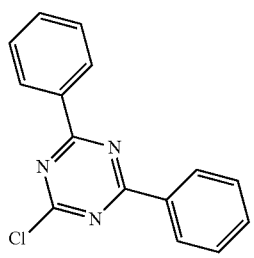 [SMILES: Clc1nc(-c2ccccc2)nc(-c2ccccc2)n1]
1-110
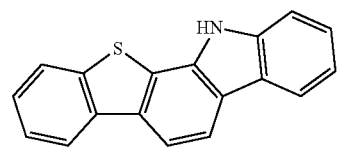
1-111
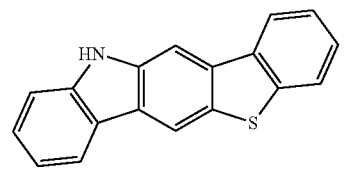 [SMILES: c1ccc2c(c1)[nH]c1cc3c(cc12)sc1ccccc13]
1-112
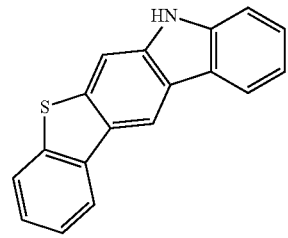
1-113
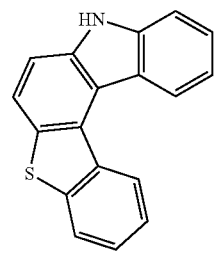 [SMILES: c1ccc2c(c1)[nH]c1ccc3sc4ccccc4c3c12]

TABLE 1-continued
| | | | |
|---|---|---|---|
| 1-117 | 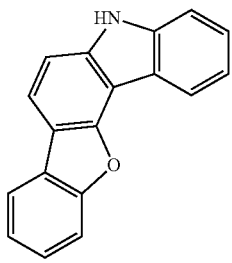 [SMILES: c1ccc2c(c1)[nH]c1ccc3c4ccccc4oc3c12] | | 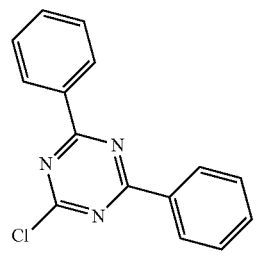 [SMILES: Clc1nc(-c2ccccc2)nc(-c2ccccc2)n1] |
| 1-118 | | | 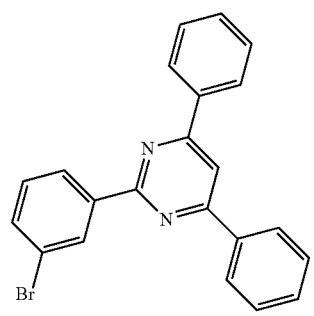 [SMILES: Brc1cccc(-c2nc(-c3ccccc3)cc(-c3ccccc3)n2)c1] |
| 1-119 | | | 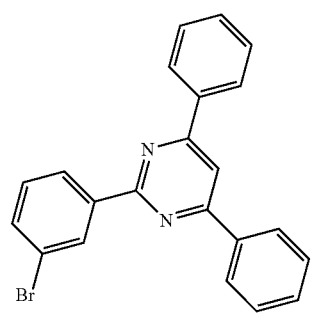 [SMILES: Brc1cccc(-c2nc(-c3ccccc3)cc(-c3ccccc3)n2)c1] |
| 1-125 | 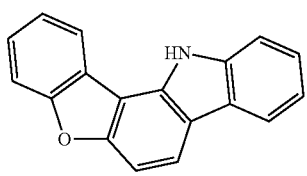 [SMILES: c1ccc2c(c1)[nH]c1c2ccc2oc3ccccc3c21] | | 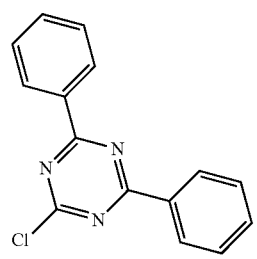 [SMILES: Clc1nc(-c2ccccc2)nc(-c2ccccc2)n1] |
| 1-126 | 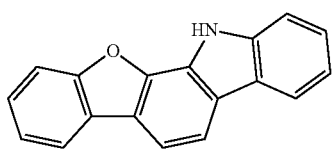 | | |
| 1-127 | 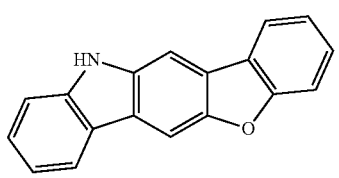 | | |

TABLE 1-continued
1-128 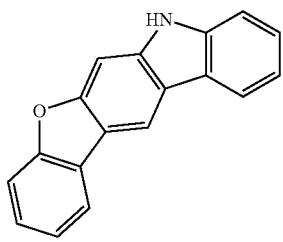 [SMILES: c1ccc2c(c1)[nH]c1cc3oc4ccccc4c3cc12]
1-138 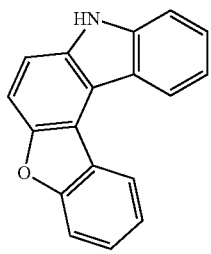 [SMILES: c1ccc2c(c1)[nH]c1ccc3oc4ccccc4c3c12]   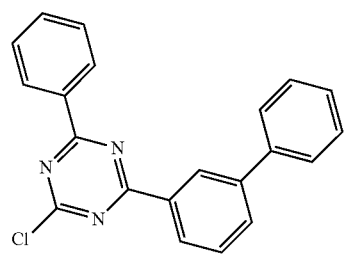 [SMILES: Clc1nc(-c2ccccc2)nc(-c2cccc(-c3ccccc3)c2)n1]
1-176 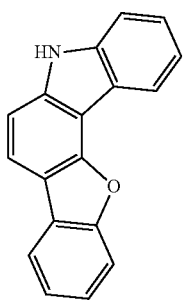 [SMILES: c1ccc2c(c1)[nH]c1ccc3c4ccccc4oc3c12]   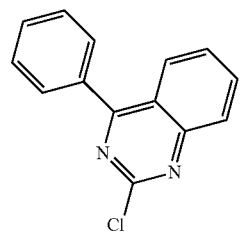 [SMILES: Clc1nc(-c2ccccc2)c2ccccc2n1]
1-177 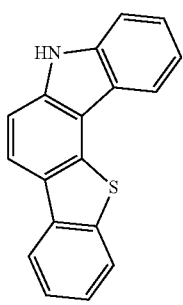 [SMILES: c1ccc2c(c1)[nH]c1ccc3c4ccccc4sc3c12]
1-178 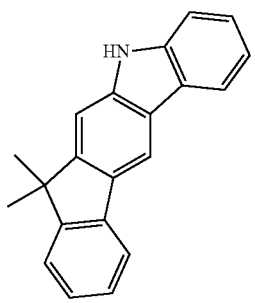 [SMILES: CC1(C)c2ccccc2-c2cc3c(cc21)[nH]c1ccccc13]
1-179 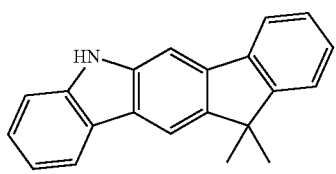 [SMILES: CC1(C)c2ccccc2-c2cc3[nH]c4ccccc4c3cc21]

TABLE 1-continued

| Compound No. | Structure |
|---|---|
| 1-180 | |
| 1-181 | |

| Compound No. | Target Compound A | Total yield |
|---|---|---|
| 1-2 | | 41% |
| 1-12 | | 42% |

TABLE 1-continued
1-17 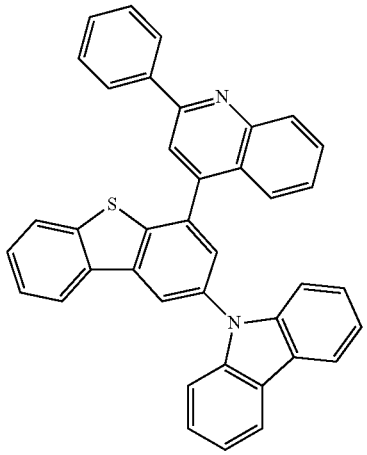 [SMILES: c1ccc(-c2cc(-c3cc(-n4c5ccccc5c5ccccc54)cc4c3sc3ccccc34)c3ccccc3n2)cc1] 43%
1-23 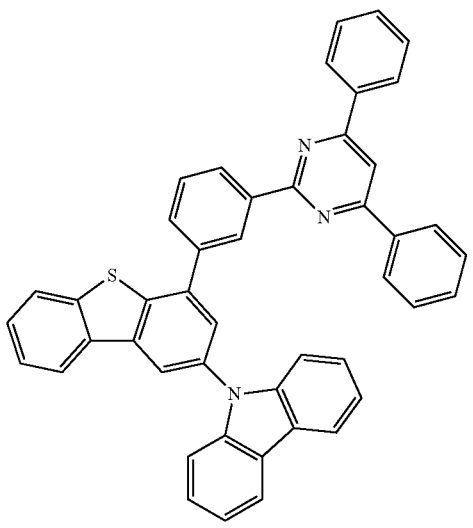 [SMILES: c1ccc(-c2cc(-c3ccccc3)nc(-c3cccc(-c4cc(-n5c6ccccc6c6ccccc65)cc5c4sc4ccccc45)c3)n2)cc1] 46%
1-27 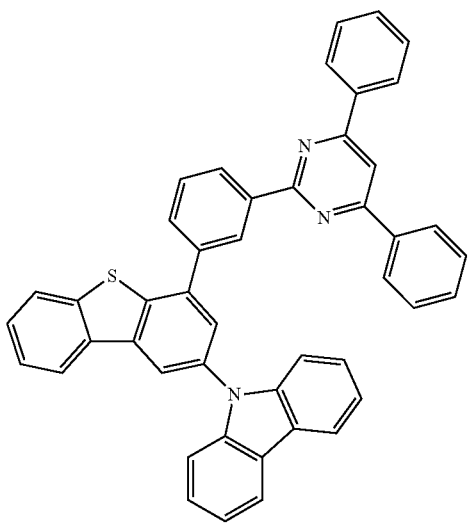 [SMILES: c1ccc(-c2cc(-c3ccccc3)nc(-c3cccc(-c4cc(-n5c6ccccc6c6ccccc65)cc5c4sc4ccccc45)c3)n2)cc1] 45%

TABLE 1-continued
| 1-33 | 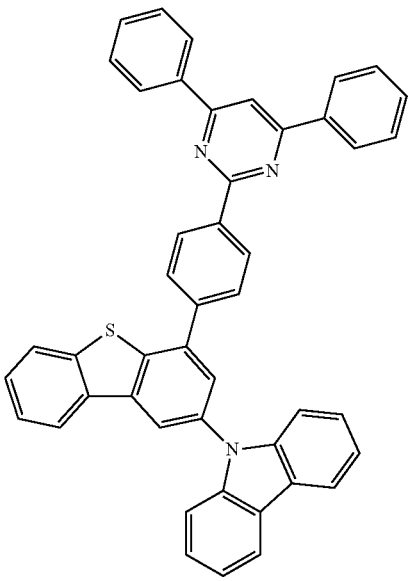 [SMILES: c1ccc(-c2cc(-c3ccccc3)nc(-c3ccc(-c4cc(-n5c6ccccc6c6ccccc65)cc5c4sc4ccccc45)cc3)n2)cc1] | 43% |
| 1-36 | 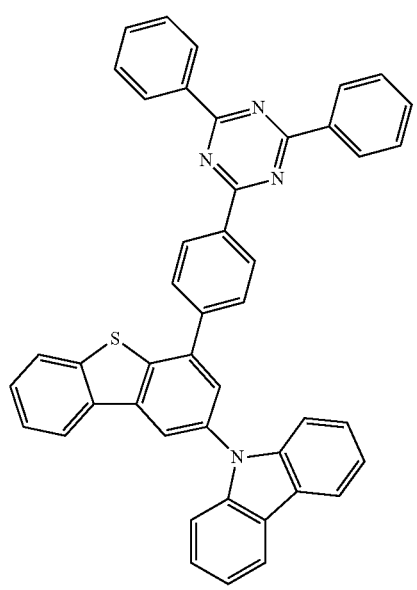 [SMILES: c1ccc(-c2nc(-c3ccccc3)nc(-c3ccc(-c4cc(-n5c6ccccc6c6ccccc65)cc5c4sc4ccccc45)cc3)n2)cc1] | 41% |

TABLE 1-continued
| 1-39 | 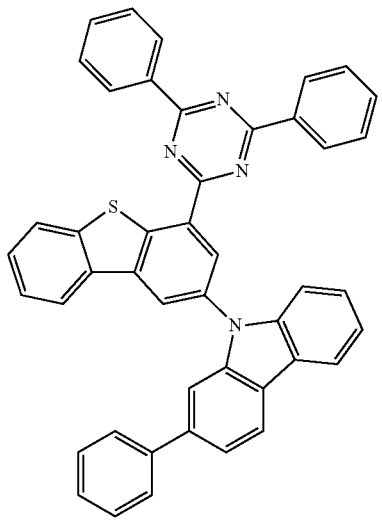 [SMILES: c1ccc(-c2ccc3c4ccccc4n(-c4cc(-c5nc(-c6ccccc6)nc(-c6ccccc6)n5)c5sc6ccccc6c5c4)c3c2)cc1] | 48% |
| 1-40 | 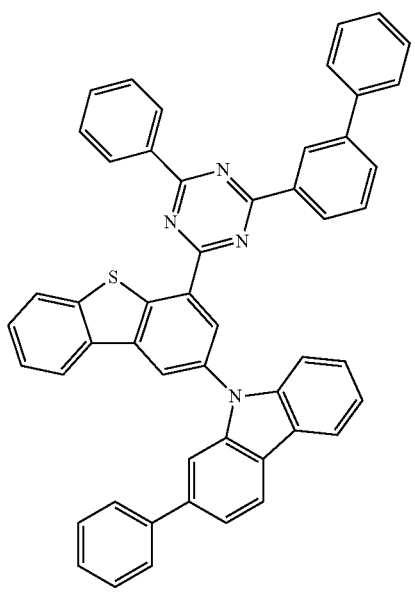 [SMILES: c1ccc(-c2cccc(-c3nc(-c4ccccc4)nc(-c4cc(-n5c6ccccc6c6ccc(-c7ccccc7)cc65)cc5c4sc4ccccc45)n3)c2)cc1] | 49% |

TABLE 1-continued
| 1-41 | 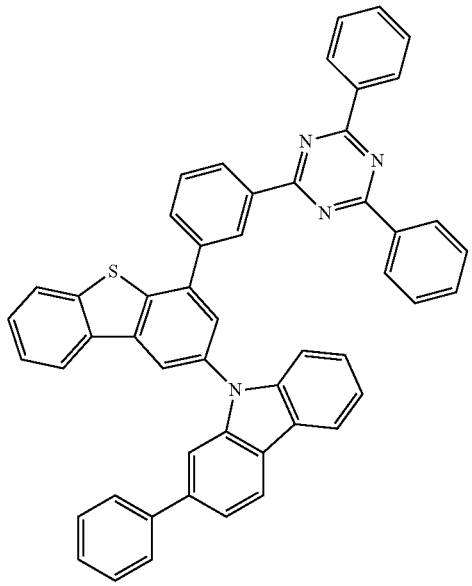 [SMILES: c1ccc(-c2ccc3c4ccccc4n(-c4cc(-c5cccc(-c6nc(-c7ccccc7)nc(-c7ccccc7)n6)c5)c5sc6ccccc6c5c4)c3c2)cc1] | 47% |
|---|---|---|
| 1-42 | 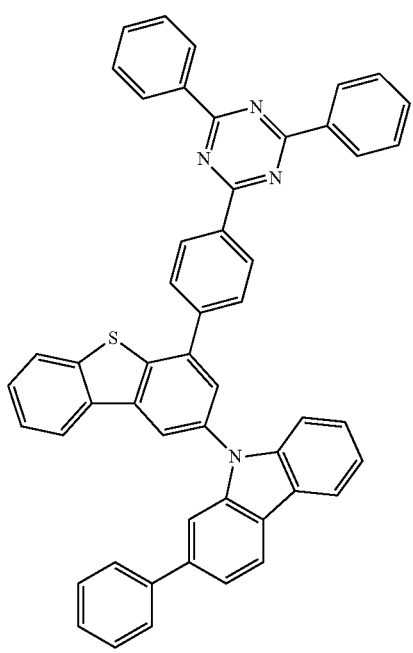 [SMILES: c1ccc(-c2ccc3c4ccccc4n(-c4cc(-c5ccc(-c6nc(-c7ccccc7)nc(-c7ccccc7)n6)cc5)c5sc6ccccc6c5c4)c3c2)cc1] | 45% |

TABLE 1-continued
| 1-46 | 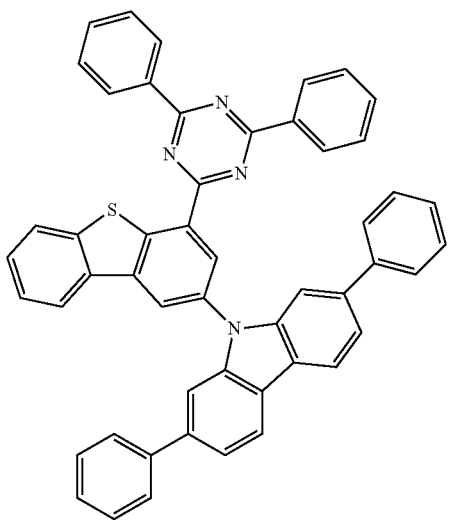 [SMILES: c1ccc(-c2ccc3c4ccc(-c5ccccc5)cc4n(-c4cc(-c5nc(-c6ccccc6)nc(-c6ccccc6)n5)c5sc6ccccc6c5c4)c3c2)cc1] | 48% |
| 1-65 | 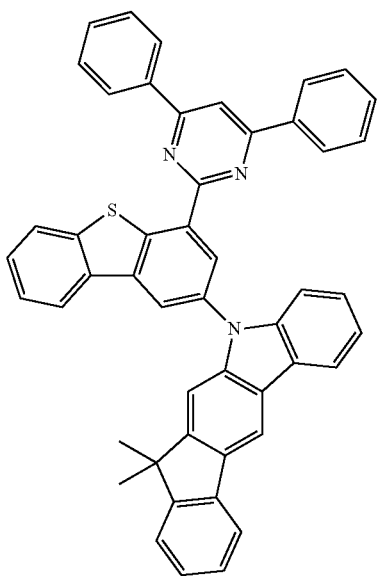 [SMILES: CC1(C)c2ccccc2-c2cc3c4ccccc4n(-c4cc(-c5nc(-c6ccccc6)cc(-c6ccccc6)n5)c5sc6ccccc6c5c4)c3cc21] | 44% |
| 1-66 | 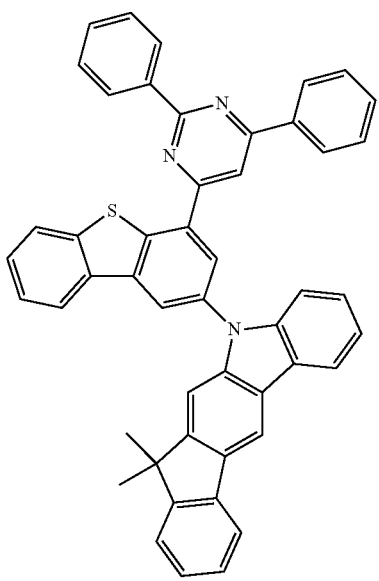 [SMILES: CC1(C)c2ccccc2-c2cc3c4ccccc4n(-c4cc(-c5cc(-c6ccccc6)nc(-c6ccccc6)n5)c5sc6ccccc6c5c4)c3cc21] | 46% |

TABLE 1-continued
| 1-67 | 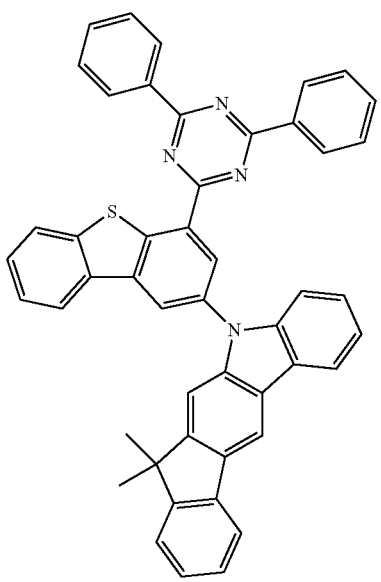 [SMILES: CC1(C)c2ccccc2-c2cc3c4ccccc4n(-c4cc(-c5nc(-c6ccccc6)nc(-c6ccccc6)n5)c5sc6ccccc6c5c4)c3cc21] | 47% |
| 1-68 | 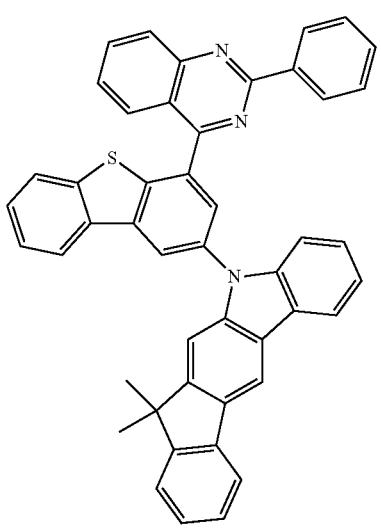 [SMILES: CC1(C)c2ccccc2-c2cc3c4ccccc4n(-c4cc(-c5nc(-c6ccccc6)nc6ccccc56)c5sc6ccccc6c5c4)c3cc21] | 44% |

TABLE 1-continued
| 1-69 | 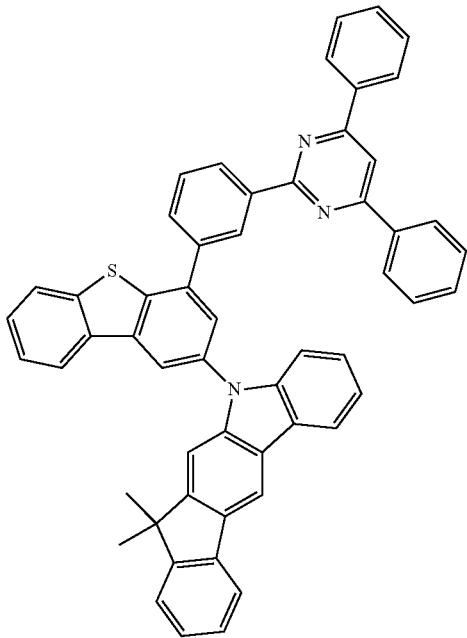 [SMILES: CC1(C)c2ccccc2-c2cc3c4ccccc4n(-c4cc(-c5cccc(-c6nc(-c7ccccc7)cc(-c7ccccc7)n6)c5)c5sc6ccccc6c5c4)c3cc21] | 46% |
| 1-70 | 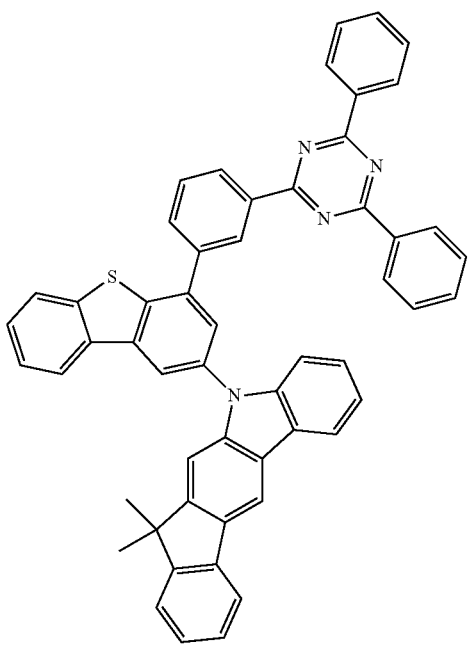 [SMILES: CC1(C)c2ccccc2-c2cc3c4ccccc4n(-c4cc(-c5cccc(-c6nc(-c7ccccc7)nc(-c7ccccc7)n6)c5)c5sc6ccccc6c5c4)c3cc21] | 44% |

TABLE 1-continued
| 1-71 | 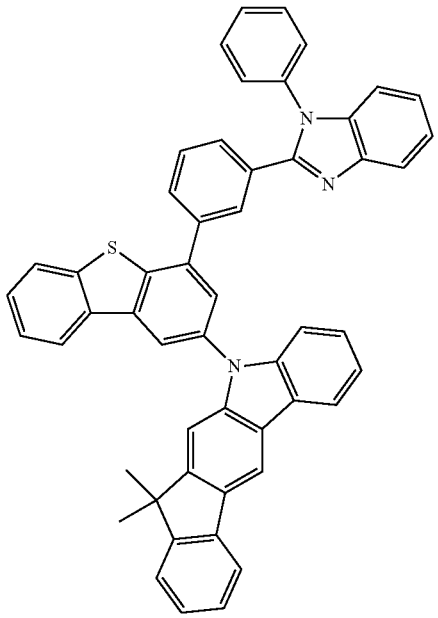 [SMILES: CC1(C)c2ccccc2-c2cc3c4ccccc4n(-c4cc(-c5cccc(-c6nc7ccccc7n6-c6ccccc6)c5)c5sc6ccccc6c5c4)c3cc21] | 43% |
| 1-72 | 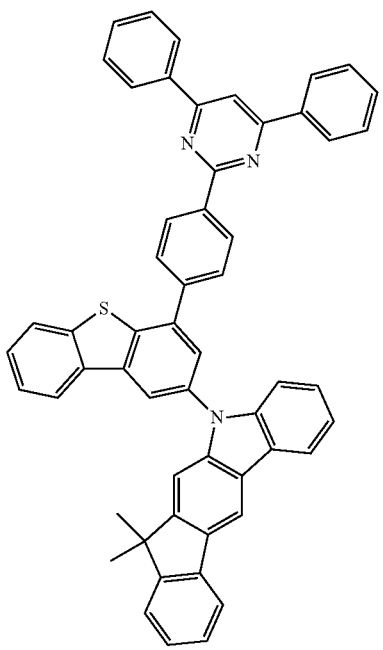 [SMILES: CC1(C)c2ccccc2-c2cc3c4ccccc4n(-c4cc(-c5ccc(-c6nc(-c7ccccc7)cc(-c7ccccc7)n6)cc5)c5sc6ccccc6c5c4)c3cc21] | 42% |

TABLE 1-continued
1-76 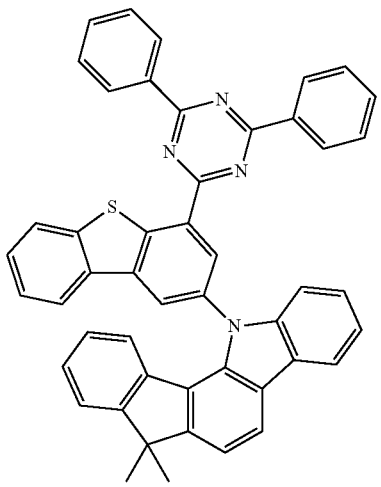 [SMILES: CC1(C)c2ccccc2-c2c1ccc1c3ccccc3n(-c3cc(-c4nc(-c5ccccc5)nc(-c5ccccc5)n4)c4sc5ccccc5c4c3)c21] 45%
1-77 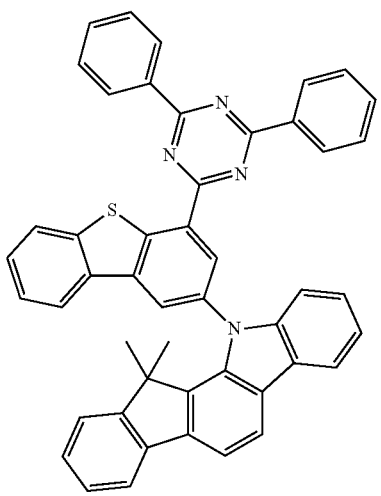 [SMILES: CC1(C)c2ccccc2-c2ccc3c4ccccc4n(-c4cc(-c5nc(-c6ccccc6)nc(-c6ccccc6)n5)c5sc6ccccc6c5c4)c3c21] 46%
1-78 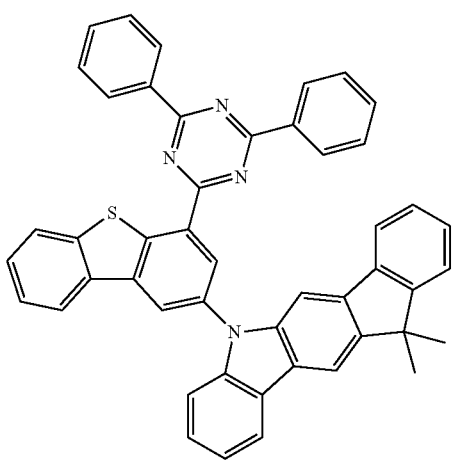 [SMILES: CC1(C)c2ccccc2-c2cc3c(cc21)c1ccccc1n3-c1cc(-c2nc(-c3ccccc3)nc(-c3ccccc3)n2)c2sc3ccccc3c2c1] 47%

TABLE 1-continued
| 1-79 | 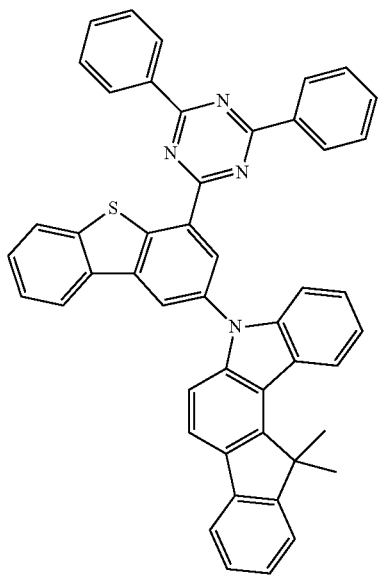 [SMILES: CC1(C)c2ccccc2-c2ccc3c(c21)c1ccccc1n3-c1cc(-c2nc(-c3ccccc3)nc(-c3ccccc3)n2)c2sc3ccccc3c2c1] | 48% |
| 1-82 | 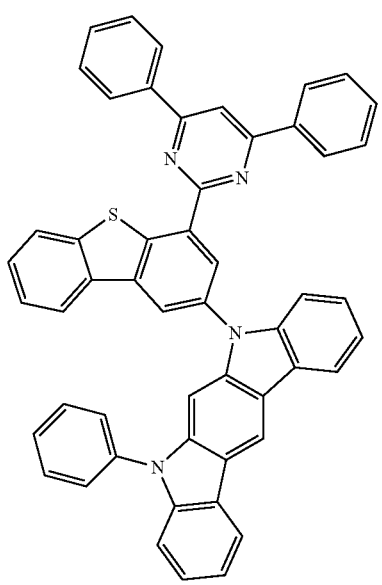 [SMILES: c1ccc(-c2cc(-c3ccccc3)nc(-c3cc(-n4c5ccccc5c5cc6c7ccccc7n(-c7ccccc7)c6cc54)cc4c3sc3ccccc34)n2)cc1] | 49% |

TABLE 1-continued
| 1-83 | 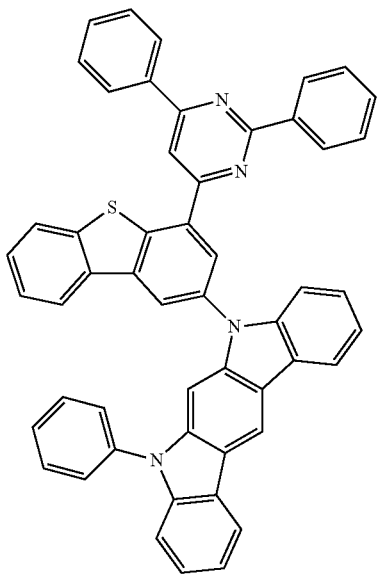 [SMILES: c1ccc(-c2cc(-c3cc(-n4c5ccccc5c5cc6c7ccccc7n(-c7ccccc7)c6cc54)cc4c3sc3ccccc34)nc(-c3ccccc3)n2)cc1] | 43% |
|---|---|---|
| 1-84 | 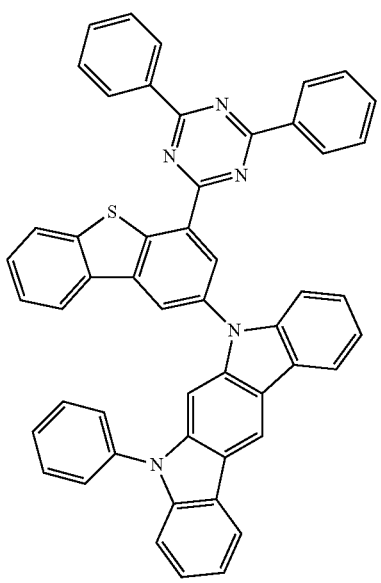 | 44% |

TABLE 1-continued
| 1-85 | 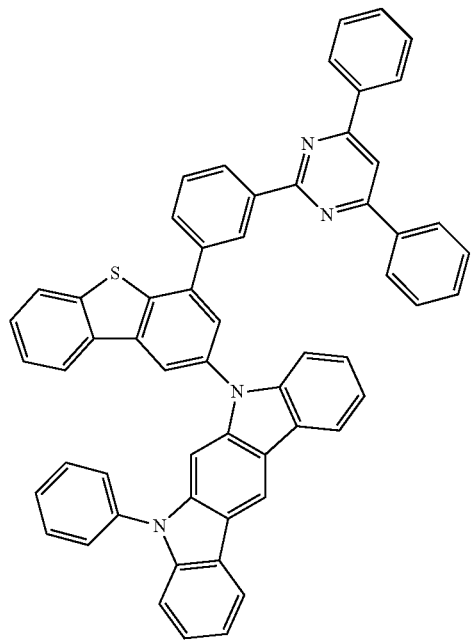 [SMILES: c1ccc(-c2cc(-c3ccccc3)nc(-c3cccc(-c4cc(-n5c6ccccc6c6cc7c8ccccc8n(-c8ccccc8)c7cc65)cc5c4sc4ccccc45)c3)n2)cc1] | 45% |
| 1-86 | 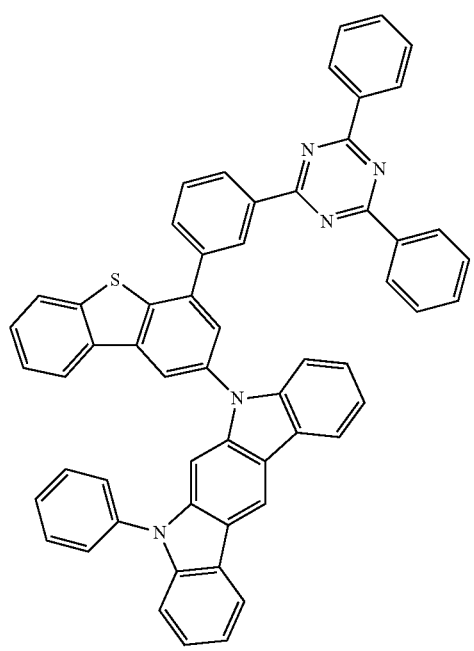 [SMILES: c1ccc(-c2nc(-c3ccccc3)nc(-c3cccc(-c4cc(-n5c6ccccc6c6cc7c8ccccc8n(-c8ccccc8)c7cc65)cc5c4sc4ccccc45)c3)n2)cc1] | 43% |

TABLE 1-continued
| | | |
|---|---|---|
| 1-91 | 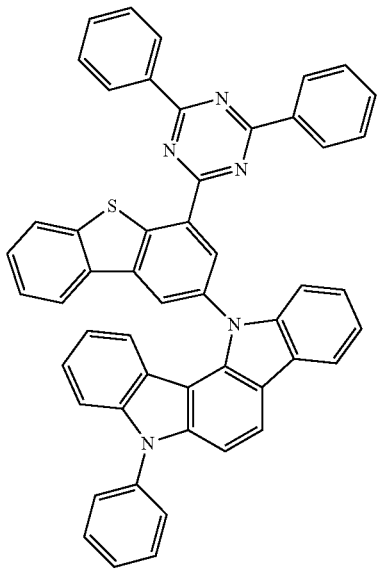 [SMILES: c1ccc(-c2nc(-c3ccccc3)nc(-c3cc(-n4c5ccccc5c5ccc6c(c7ccccc7n6-c6ccccc6)c54)cc4c3sc3ccccc34)n2)cc1] | 46% |
| 1-92 | 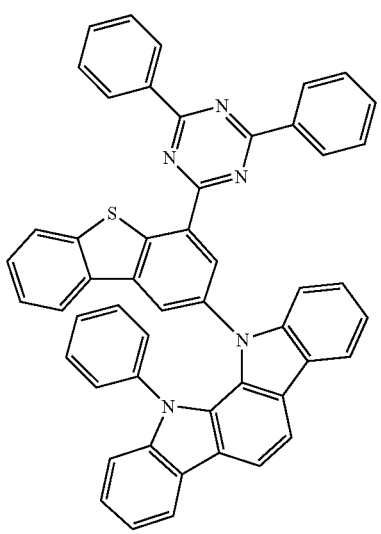 [SMILES: c1ccc(-c2nc(-c3ccccc3)nc(-c3cc(-n4c5ccccc5c5ccc6c7ccccc7n(-c7ccccc7)c6c54)cc4c3sc3ccccc34)n2)cc1] | 47% |

TABLE 1-continued
1-93 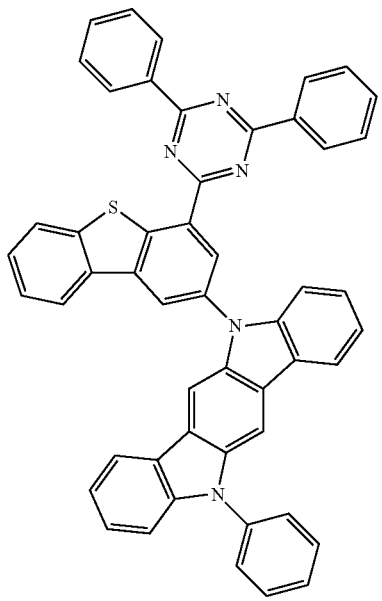 [SMILES: c1ccc(-c2nc(-c3ccccc3)nc(-c3cc(-n4c5ccccc5c5cc6c(cc54)c4ccccc4n6-c4ccccc4)cc4c3sc3ccccc34)n2)cc1] 47%
1-94 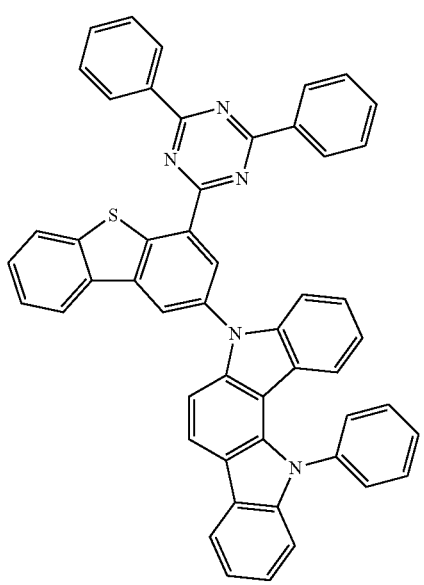 [SMILES: c1ccc(-c2nc(-c3ccccc3)nc(-c3cc(-n4c5ccccc5c5c4ccc4c6ccccc6n(-c6ccccc6)c45)cc4c3sc3ccccc34)n2)cc1] 44%

TABLE 1-continued
| | | |
|---|---|---|
| 1-96 | 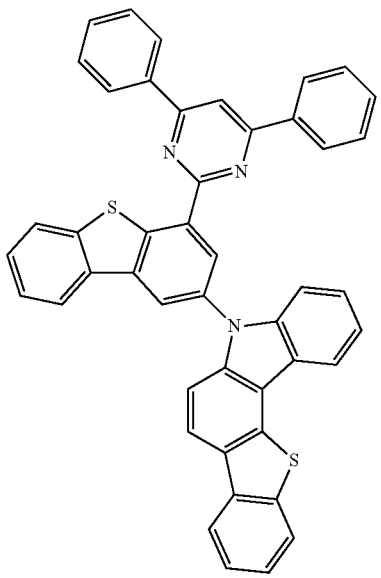 [SMILES: c1ccc(-c2cc(-c3ccccc3)nc(-c3cc(-n4c5ccccc5c5c6sc7ccccc7c6ccc54)cc4c3sc3ccccc34)n2)cc1] | 46% |
| 1-98 | 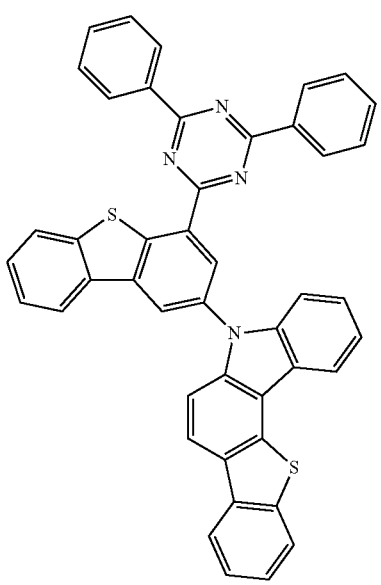 | 43% |

TABLE 1-continued
| 1-99 | 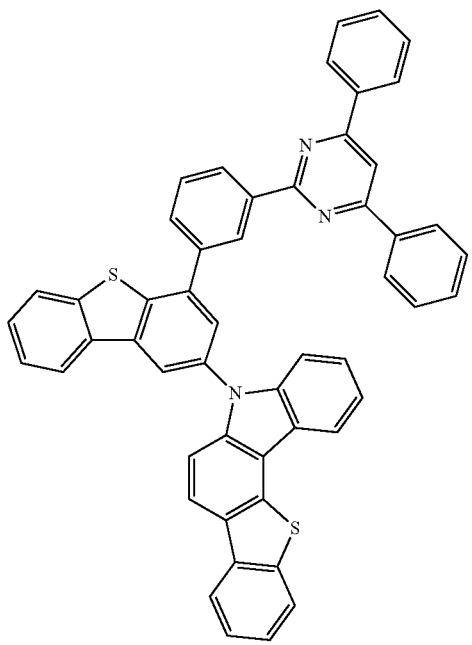 | 43% |
| 1-100 | 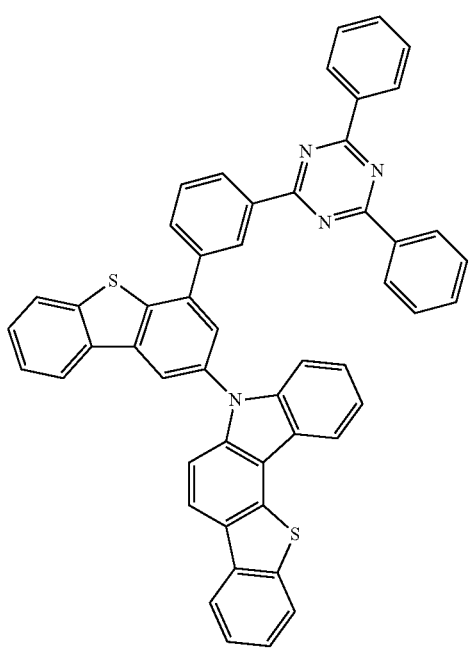 | 42% |

TABLE 1-continued
1-109 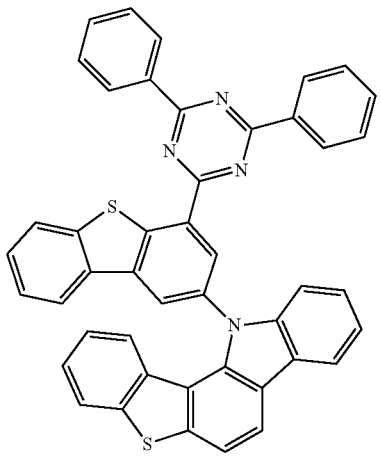 41%
1-110 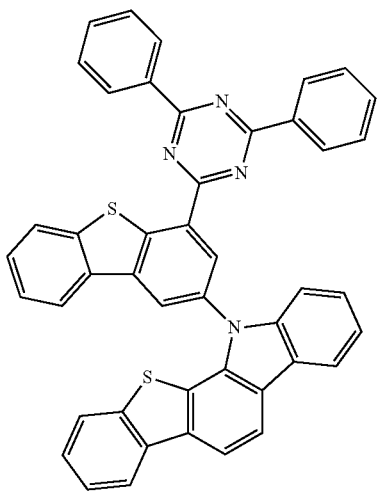 42%
1-111 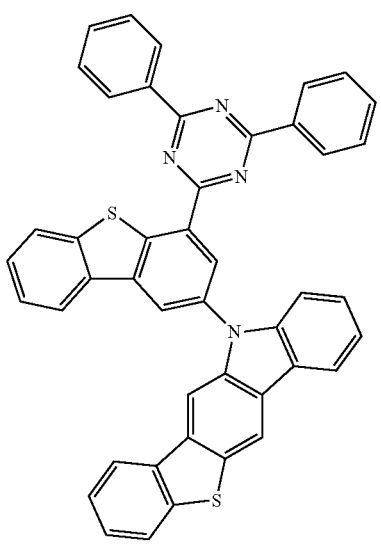 42%

TABLE 1-continued
1-112 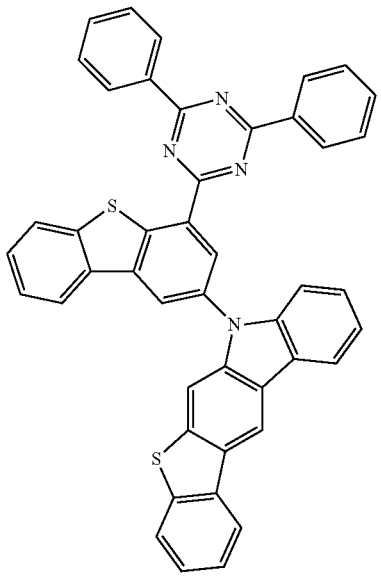 45%
1-113 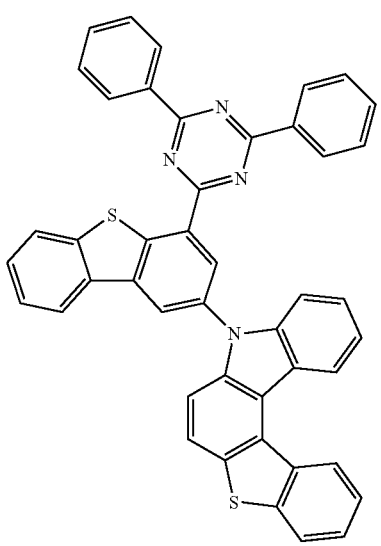 [SMILES: c1ccc(-c2nc(-c3ccccc3)nc(-c3cc(-n4c5ccccc5c5c6c(ccc54)sc4ccccc46)cc4c3sc3ccccc34)n2)cc1] 45%

TABLE 1-continued
| 1-117 | 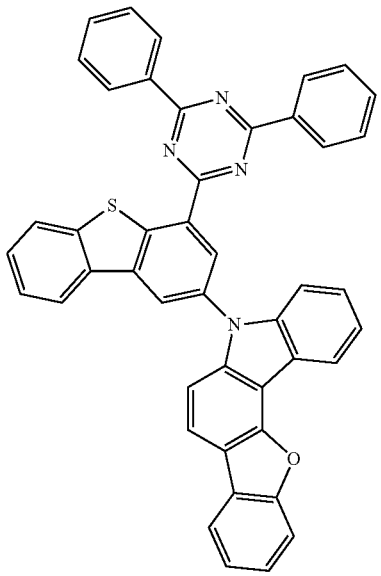 [SMILES: c1ccc(-c2nc(-c3ccccc3)nc(-c3cc(-n4c5ccccc5c5c6oc7ccccc7c6ccc54)cc4c3sc3ccccc34)n2)cc1] | 46% |
| 1-118 | 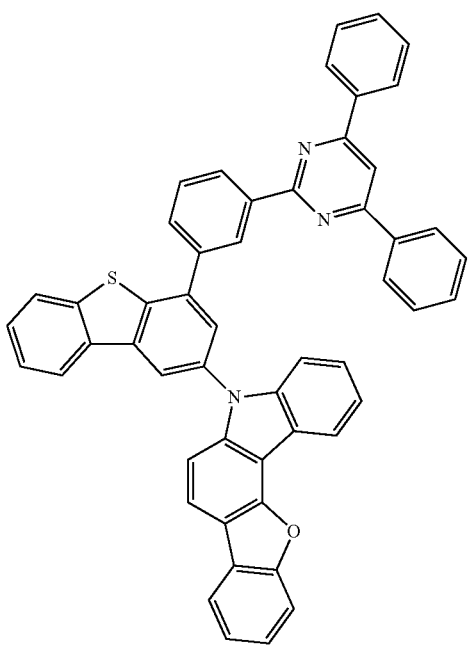 | 49% |

TABLE 1-continued
| 1-119 | 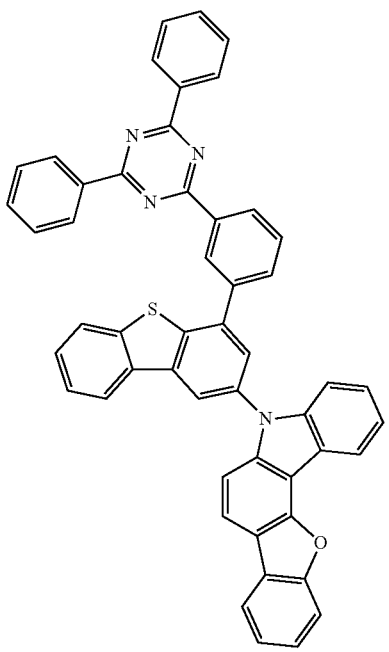 [SMILES: c1ccc(-c2nc(-c3ccccc3)nc(-c3cccc(-c4cc(-n5c6ccccc6c6c7oc8ccccc8c7ccc65)cc5c4sc4ccccc45)c3)n2)cc1] | 46% |
| 1-125 | 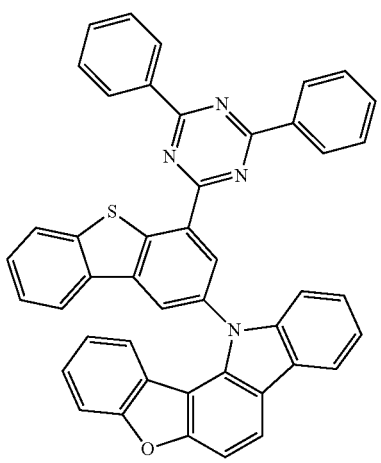 [SMILES: c1ccc(-c2nc(-c3ccccc3)nc(-c3cc(-n4c5ccccc5c5ccc6oc7ccccc7c6c54)cc4c3sc3ccccc34)n2)cc1] | 43% |
| 1-126 | 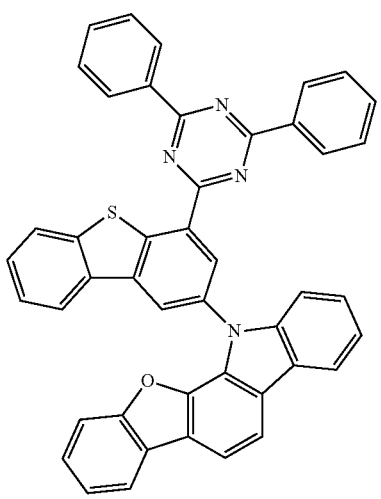 [SMILES: c1ccc(-c2nc(-c3ccccc3)nc(-c3cc(-n4c5ccccc5c5ccc6c7ccccc7oc6c54)cc4c3sc3ccccc34)n2)cc1] | 44% |

TABLE 1-continued
1-127 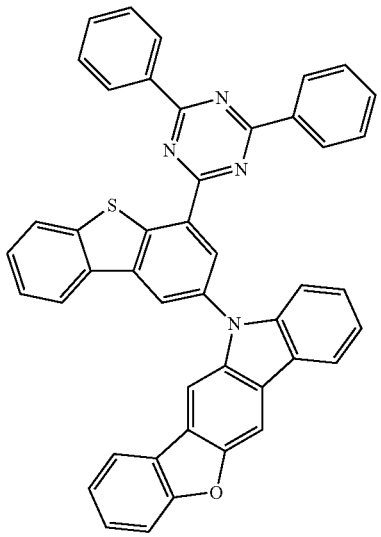 [SMILES: c1ccc(-c2nc(-c3ccccc3)nc(-c3cc(-n4c5ccccc5c5cc6oc7ccccc7c6cc54)cc4c3sc3ccccc34)n2)cc1] 45%
1-128 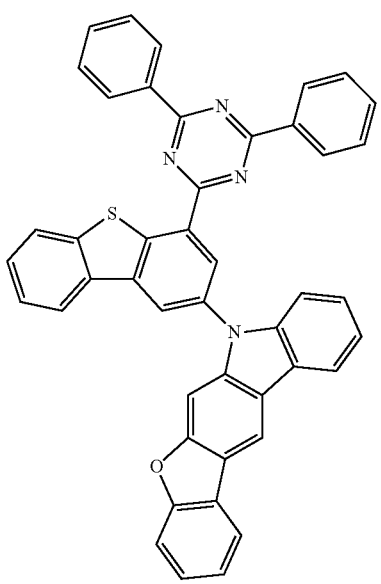 [SMILES: c1ccc(-c2nc(-c3ccccc3)nc(-c3cc(-n4c5ccccc5c5cc6c(cc54)oc4ccccc46)cc4c3sc3ccccc34)n2)cc1] 42%

TABLE 1-continued
| | | |
|---|---|---|
| 1-138 | 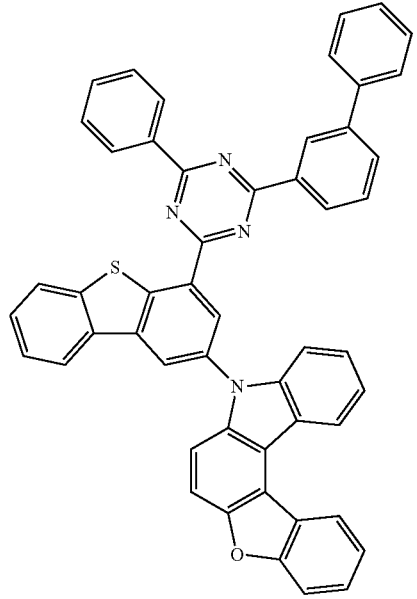 [SMILES: c1ccc(-c2cccc(-c3nc(-c4ccccc4)nc(-c4cc(-n5c6ccccc6c6c7c(ccc65)oc5ccccc57)cc5c4sc4ccccc45)n3)c2)cc1] | 47% |
| 1-176 | 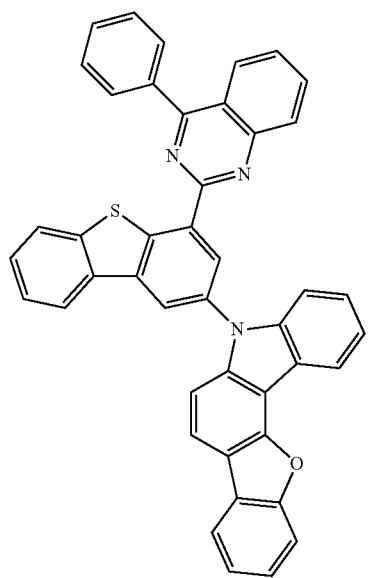 | 48% |

TABLE 1-continued
| 1-177 | 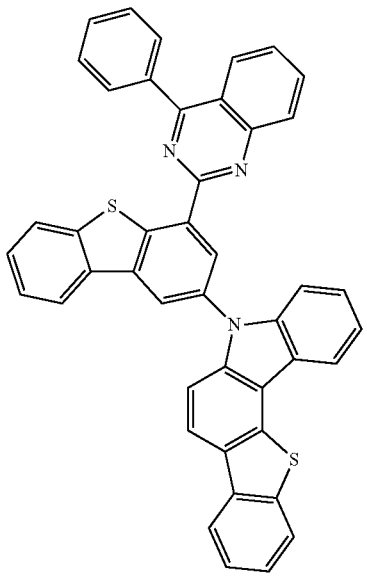 [SMILES: c1ccc(-c2nc(-c3cc(-n4c5ccccc5c5c6sc7ccccc7c6ccc54)cc4c3sc3ccccc34)nc3ccccc23)cc1] | 49% |
| 1-178 | 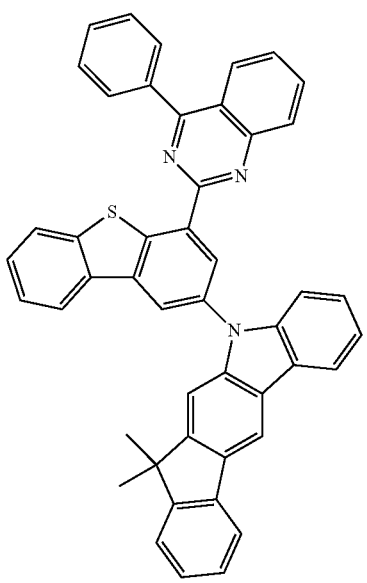 [SMILES: CC1(C)c2ccccc2-c2cc3c4ccccc4n(-c4cc(-c5nc(-c6ccccc6)c6ccccc6n5)c5sc6ccccc6c5c4)c3cc21] | 44% |

TABLE 1-continued
1-179 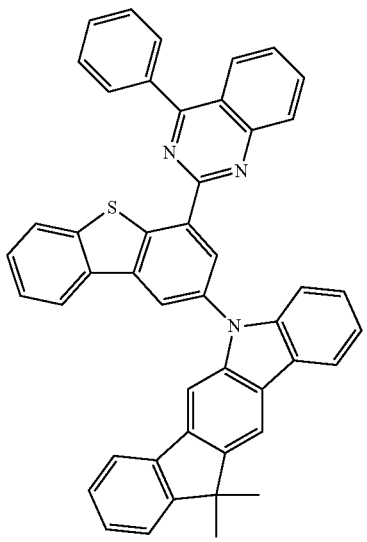 [SMILES: CC1(C)c2ccccc2-c2cc3c(cc21)c1ccccc1n3-c1cc(-c2nc(-c3ccccc3)c3ccccc3n2)c2sc3ccccc3c2c1] 44%
1-180 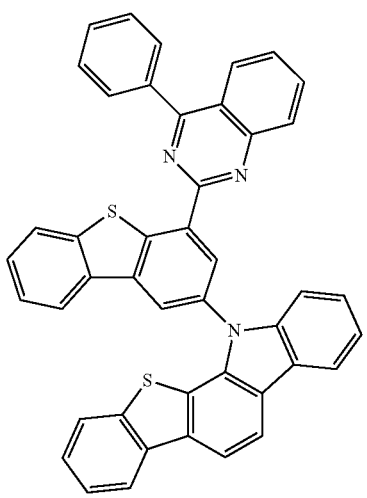 [SMILES: c1ccc(-c2nc(-c3cc(-n4c5ccccc5c5ccc6c7ccccc7oc6c54)cc4c3sc3ccccc34)nc3ccccc23)cc1] 43%
1-181 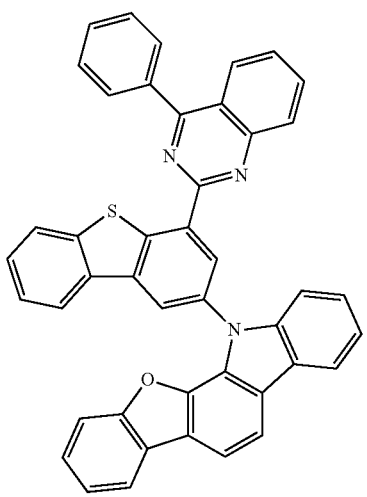 46%

<Preparation Example 2> Preparation of Compound 1-64

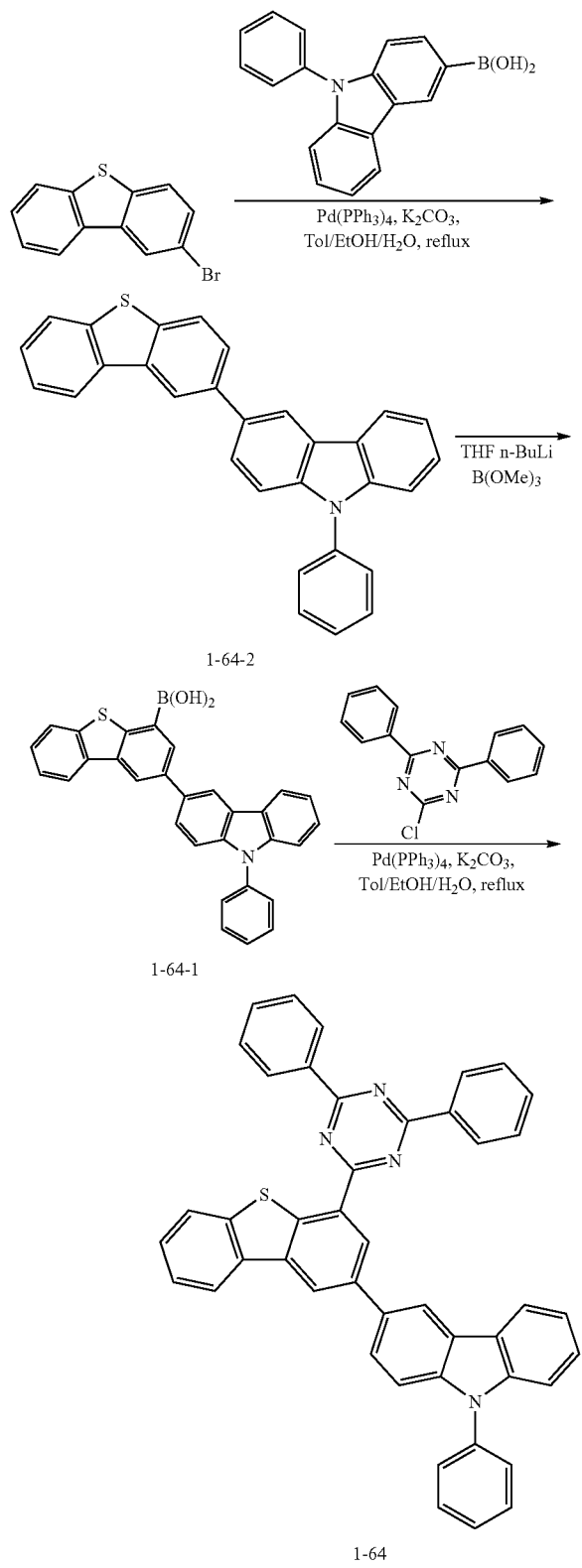

1) Preparation of Compound 1-64-2

5.0 g (19.0 mM) of 2-bromodibenzo[b,d]thiophene, 5.5 g (19.0 mM) of (9-phenyl-9H-carbazol-3-yl)boronic acid, 1.1 g (0.95 mM) of Pd(PPh$_3$)$_4$, and 5.2 g (38.0 mM) of K$_2$CO$_3$ were dissolved in 100/20/20 mL of toluene/EtOH/H$_2$O, and then the resulting solution was refluxed for 12 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with hexane to obtain 5.7 g (70%) of Target Compound 1-64-2.

2) Preparation of Compound 1-64-1

7.4 mL (18.6 mM) of 2.5 M n-BuLi was added dropwise to a mixed solution containing 6.1 g (14.3 mM) of Compound 1-64-2 and 100 mL of THF at −78° C., and the resulting mixture was stirred at room temperature for 1 hour. 4.8 mL (42.9 mM) of trimethyl borate (B(OMe)$_3$) was added dropwise to the reaction mixture, and the resulting mixture was stirred at room temperature for 2 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:MeOH=100:3) and recrystallized with DCM to obtain 4.7 g (70%) of Target Compound 1-64-1.

3) Preparation of Compound 1-64

8.9 g (19.0 mM) of Compound 1-64-1, 5.1 g (19.0 mM) of 2-chloro-4,6-diphenyl-1,3,5-triazine, 1.1 g (0.95 mM) of Pd(PPh$_3$)$_4$, and 5.2 g (38.0 mM) of K$_2$CO$_3$ were dissolved in 100/20/20 mL of toluene/EtOH/H$_2$O, and then the resulting solution was refluxed for 12 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 8.7 g (70%) of Target Compound 1-64.

Target Compound B was prepared and synthesized in the same manner as in the preparation in Preparation Example 2, except that Intermediate C in the following Table 2 was used instead of (9-phenyl-9H-carbazol-3-yl)boronic acid, and Intermediate D in the following Table 2 was used instead of 2-chloro-4,6-diphenyl-1,3,5-triazine in Preparation Example 2.

TABLE 2

| Compound No. | Intermediate C | Intermediate D |
|---|---|---|
| 1-80 | | |
| 1-95 | | |
| 1-114 | | |
| 1-139 | | |
| 1-140 | | |

TABLE 2-continued
1-155 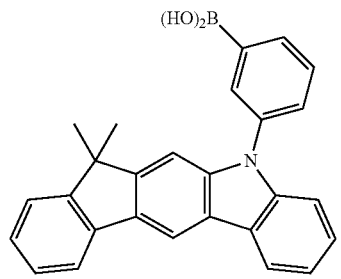 [SMILES: CC1(C)c2ccccc2-c2cc3c4ccccc4n(-c4cccc(B(O)O)c4)c3cc21] 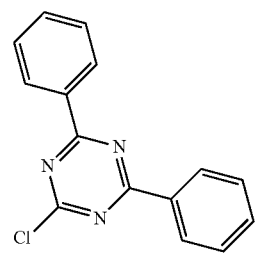 [SMILES: Clc1nc(-c2ccccc2)nc(-c2ccccc2)n1]
1-156 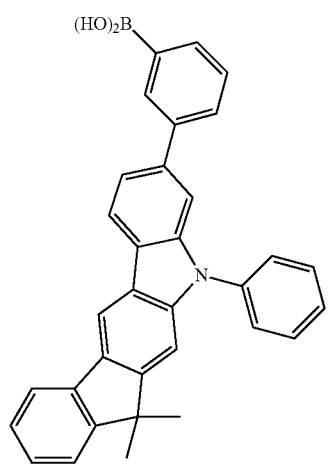 [SMILES: CC1(C)c2ccccc2-c2cc3c4ccc(-c5cccc(B(O)O)c5)cc4n(-c4ccccc4)c3cc21]
1-157 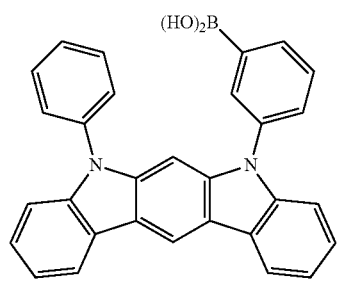 [SMILES: OB(O)c1cccc(-n2c3ccccc3c3cc4c5ccccc5n(-c5ccccc5)c4cc32)c1]
1-158 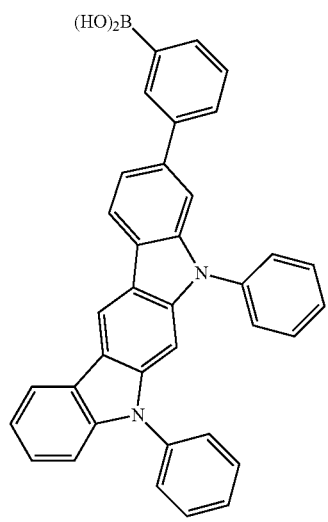 [SMILES: OB(O)c1cccc(-c2ccc3c4cc5c6ccccc6n(-c6ccccc6)c5cc4n(-c4ccccc4)c3c2)c1]

TABLE 2-continued
1-160 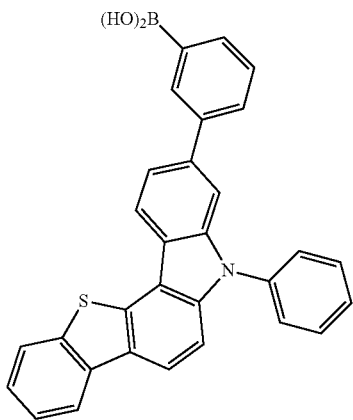 [SMILES: OB(O)c1cccc(-c2ccc3c4c5sc6ccccc6c5ccc4n(-c4ccccc4)c3c2)c1]
1-162 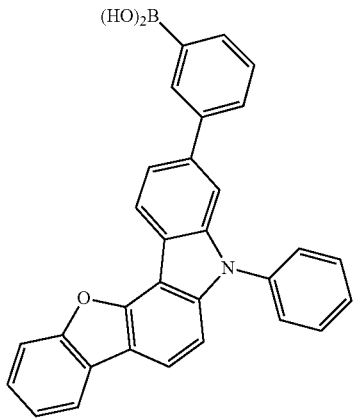 [SMILES: OB(O)c1cccc(-c2ccc3c4c5oc6ccccc6c5ccc4n(-c4ccccc4)c3c2)c1]
1-163 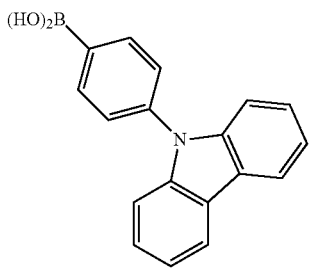 [SMILES: OB(O)c1ccc(-n2c3ccccc3c3ccccc32)cc1]
1-164 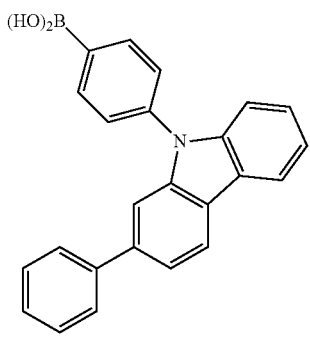 [SMILES: OB(O)c1ccc(-n2c3ccccc3c3ccc(-c4ccccc4)cc32)cc1]

TABLE 2-continued
1-165 (HO)₂B 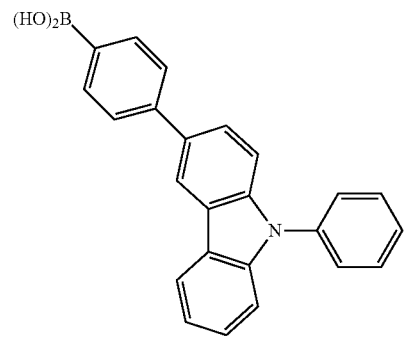 [SMILES: OB(O)c1ccc(-c2ccc3c(c2)c2ccccc2n3-c2ccccc2)cc1]
1-170 (HO)₂B 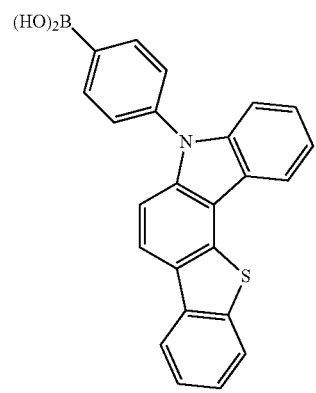
1-172 (HO)₂B 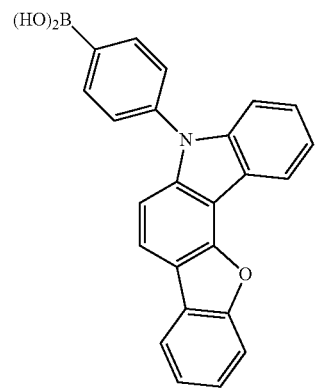 [SMILES: OB(O)c1ccc(-n2c3ccccc3c3c4oc5ccccc5c4ccc32)cc1]
1-174 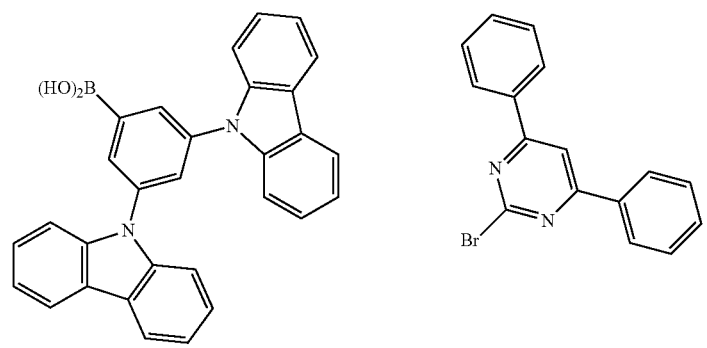

TABLE 2-continued

| Compound No. | Target Compound B | Total yield |
|---|---|---|
| 1-80 | | 34% |
| 1-95 | | 35% |

TABLE 2-continued
| 1-114 | 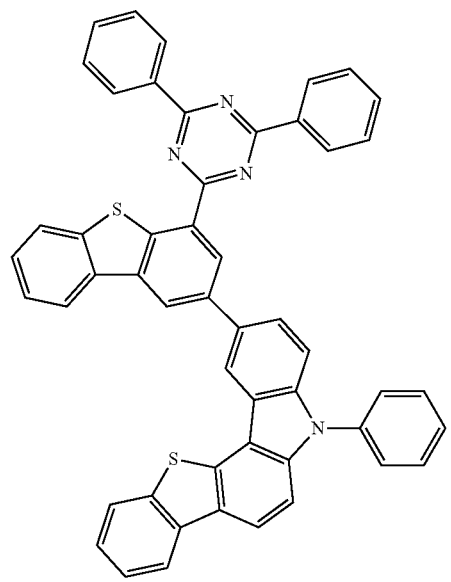 [SMILES: c1ccc(-c2nc(-c3ccccc3)nc(-c3cc(-c4ccc5c(c4)c4c6sc7ccccc7c6ccc4n5-c4ccccc4)cc4c3sc3ccccc34)n2)cc1] | 37% |
| 1-139 | 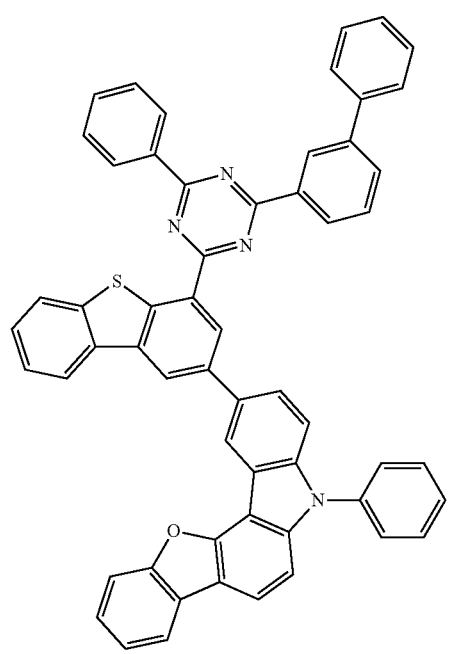 [SMILES: c1ccc(-c2cccc(-c3nc(-c4ccccc4)nc(-c4cc(-c5ccc6c(c5)c5c7oc8ccccc8c7ccc5n6-c5ccccc5)cc5c4sc4ccccc45)n3)c2)cc1] | 36% |

TABLE 2-continued
1-140 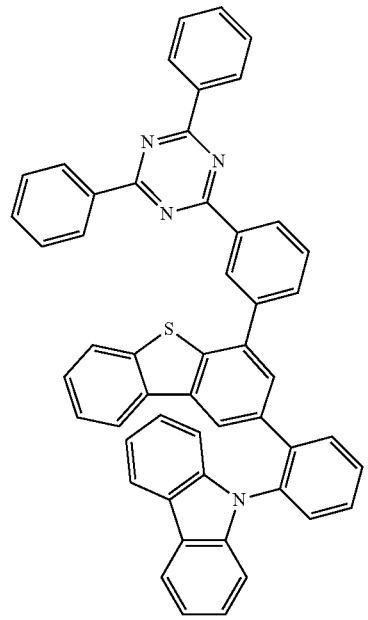 [SMILES: c1ccc(-c2nc(-c3ccccc3)nc(-c3cccc(-c4cc(-c5ccccc5-n5c6ccccc6c6ccccc65)cc5c4sc4ccccc45)c3)n2)cc1] 38%
1-155 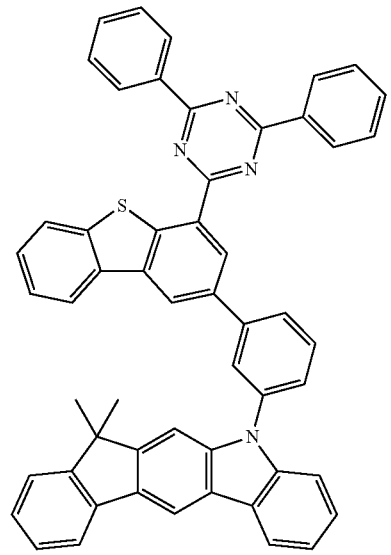 [SMILES: CC1(C)c2ccccc2-c2cc3c4ccccc4n(-c4cccc(-c5cc(-c6nc(-c7ccccc7)nc(-c7ccccc7)n6)c6sc7ccccc7c6c5)c4)c3cc21] 40%

TABLE 2-continued
1-156
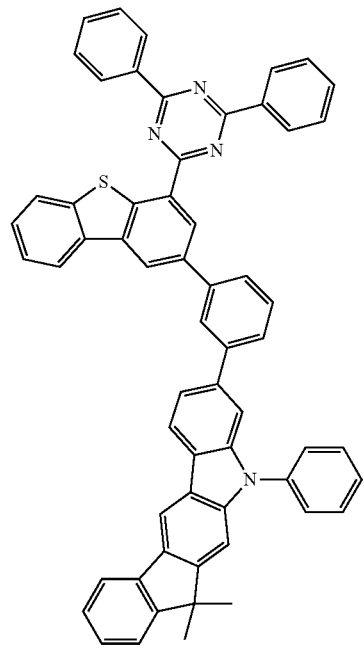 [SMILES: CC1(C)c2ccccc2-c2cc3c4ccc(-c5cccc(-c6cc(-c7nc(-c8ccccc8)nc(-c8ccccc8)n7)c7sc8ccccc8c7c6)c5)cc4n(-c4ccccc4)c3cc21]
39%
1-157
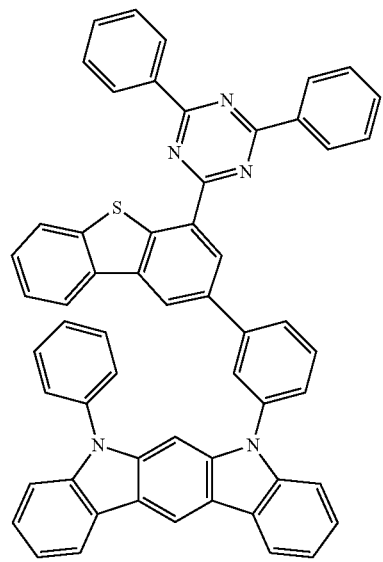 [SMILES: c1ccc(-c2nc(-c3ccccc3)nc(-c3cc(-c4cccc(-n5c6ccccc6c6cc7c8ccccc8n(-c8ccccc8)c7cc65)c4)cc4c3sc3ccccc34)n2)cc1]
39%

TABLE 2-continued
1-158 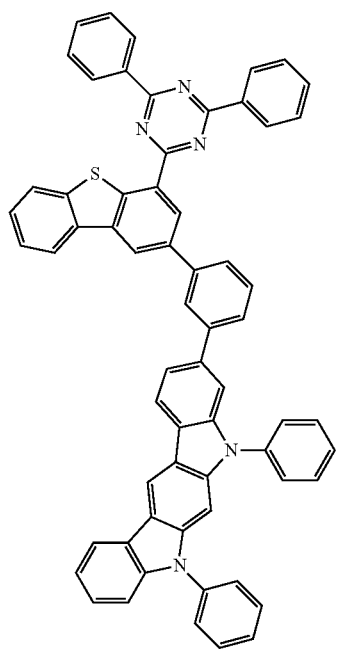 [SMILES: c1ccc(-c2nc(-c3ccccc3)nc(-c3cc(-c4cccc(-c5ccc6c7cc8c9ccccc9n(-c9ccccc9)c8cc7n(-c7ccccc7)c6c5)c4)cc4c3sc3ccccc34)n2)cc1] 37%
1-160 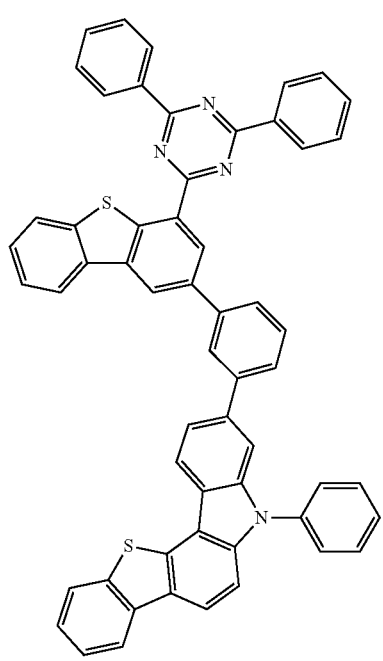 36%

TABLE 2-continued
| 1-162 | 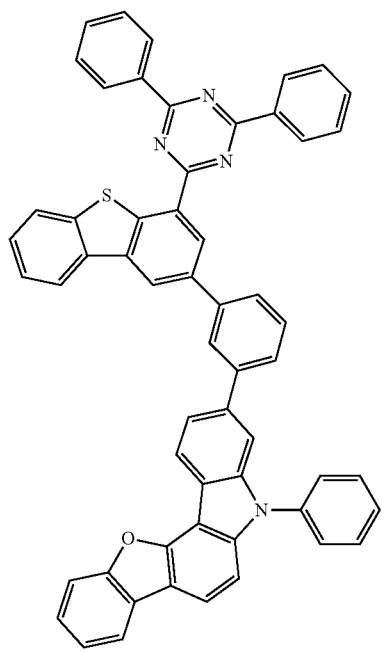 [SMILES: c1ccc(-c2nc(-c3ccccc3)nc(-c3cc(-c4cccc(-c5ccc6c7c8sc9ccccc9c8ccc7n(-c7ccccc7)c6c5)c4)cc4c3sc3ccccc34)n2)cc1] | 37% |
| 1-163 | 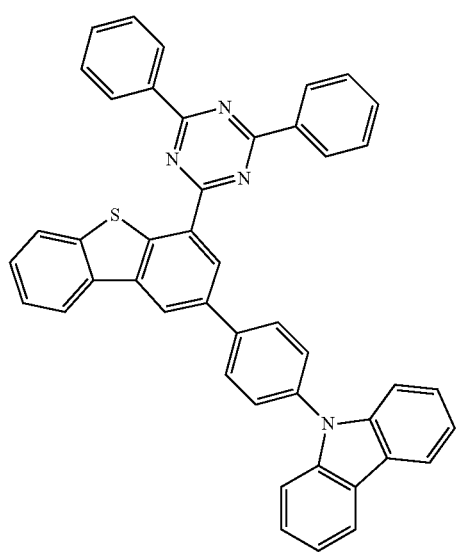 [SMILES: c1ccc(-c2nc(-c3ccccc3)nc(-c3cc(-c4ccc(-n5c6ccccc6c6ccccc65)cc4)cc4c3sc3ccccc34)n2)cc1] | 33% |

TABLE 2-continued
| 1-164 | 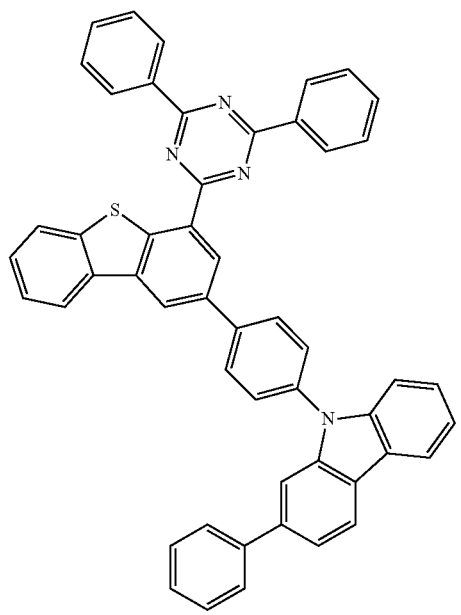 [SMILES: c1ccc(-c2ccc3c4ccccc4n(-c4ccc(-c5cc(-c6nc(-c7ccccc7)nc(-c7ccccc7)n6)c6sc7ccccc7c6c5)cc4)c3c2)cc1] | 34% |
| 1-165 | 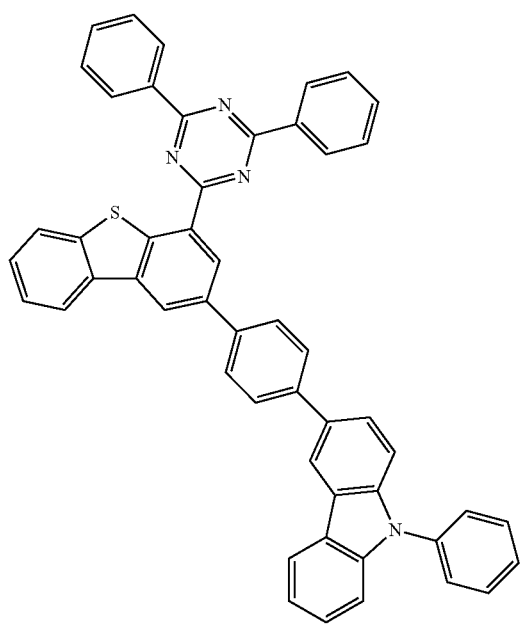 [SMILES: c1ccc(-c2nc(-c3ccccc3)nc(-c3cc(-c4ccc(-c5ccc6c(c5)c5ccccc5n6-c5ccccc5)cc4)cc4c3sc3ccccc34)n2)cc1] | 36% |

TABLE 2-continued
1-170 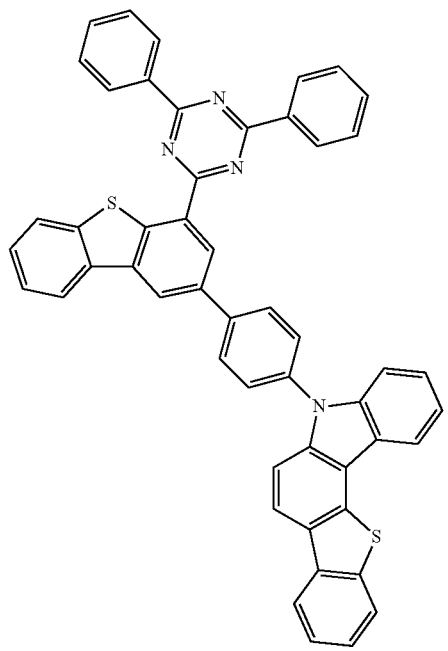 37%
1-172 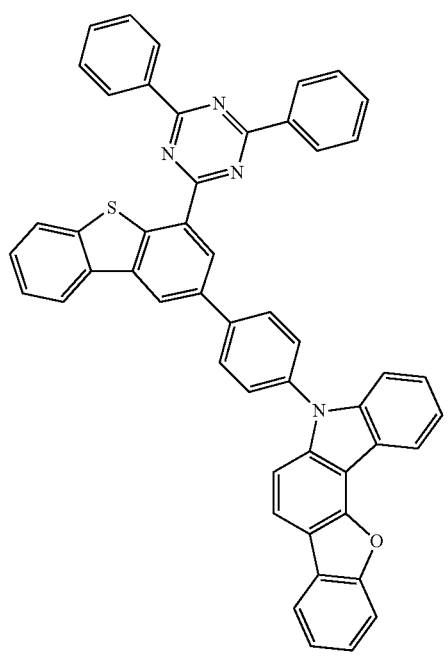 [SMILES: c1ccc(-c2nc(-c3ccccc3)nc(-c3cc(-c4ccc(-n5c6ccccc6c6c7sc8ccccc8c7ccc65)cc4)cc4c3sc3ccccc34)n2)cc1] 33%

TABLE 2-continued
1-174
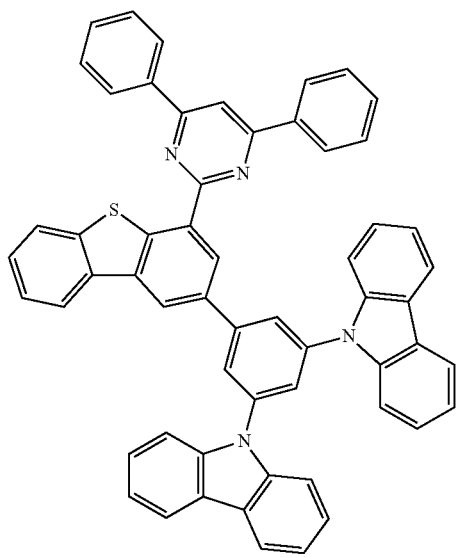 [SMILES: c1ccc(-c2cc(-c3ccccc3)nc(-c3cc(-c4cc(-n5c6ccccc6c6ccccc65)cc(-n5c6ccccc6c6ccccc65)c4)cc4c3sc3ccccc34)n2)cc1]
38%
<Preparation Example 3> Synthesis of Compound 2-2
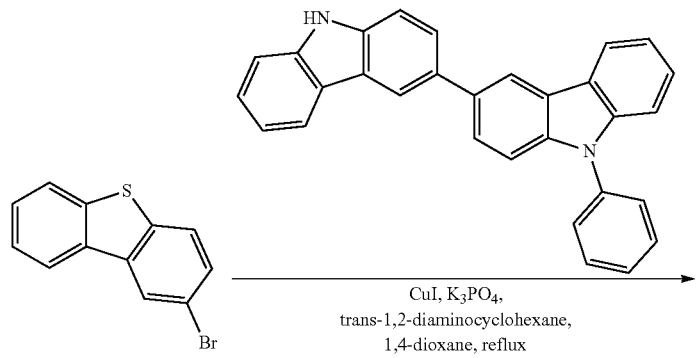
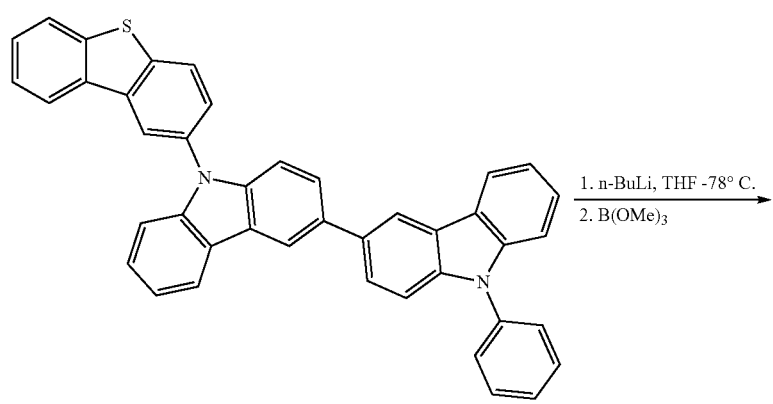
2-2-2

-continued

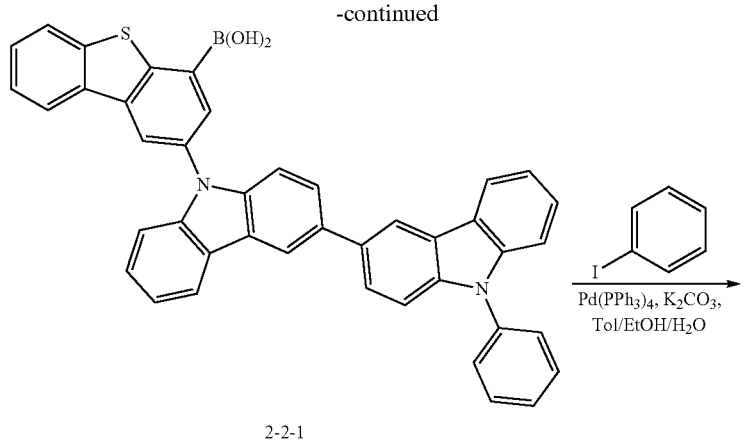

2-2-1

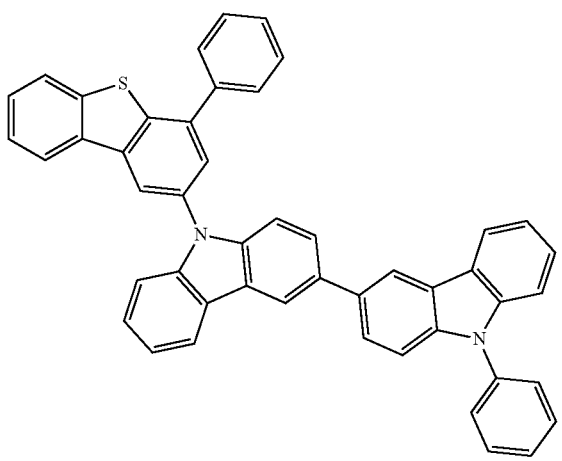

2-2

1) Preparation of Compound 2-2-2 (Ref 1)

4.2 g (15.8 mM) of 2-bromodibenzo[b,d]thiophene, 6.5 g (15.8 mM) of 9-phenyl-9H,9'H-3,3'-bicarbazole, 3.0 g (15.8 mM) of CuI, 1.9 mL (15.8 mM) of trans-1,2-diaminocyclohexane, and 3.3 g (31.6 mM) of $K_3PO_4$ were dissolved in 100 mL of 1,4-oxane, and then the resulting solution was refluxed for 24 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:Hex=1:3) and recrystallized with methanol to obtain 7.9 g (85%) of Target Compound 2-2-2.

2) Preparation of Compound 2-2-1

7.4 mL (18.6 mmol) of 2.5 M n-BuLi was added dropwise to a mixed solution containing 8.4 g (14.3 mmol) of Compound 2-2-1 and 100 mL of THF at −78° C., and the resulting mixture was stirred at room temperature for 1 hour. 4.8 mL (42.9 mmol) of trimethyl borate was added dropwise to the reaction mixture, and the resulting mixture was stirred at room temperature for 2 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:MeOH=100:3) and recrystallized with DCM to obtain 3.9 g (70%) of Target Compound 2-2-1.

3) Preparation of Compound 2-2

6.7 g (10.5 mM) of Compound 2-2-1, 2.1 g (10.5 mM) of iodobenzene, 606 mg (0.52 mM) of $Pd(PPh_3)_4$, and 2.9 g (21.0 mM) of $K_2CO_3$ were dissolved in 100/20/20 mL of toluene/EtOH/$H_2O$, and then the resulting solution was refluxed for 12 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:Hex=1:3) and recrystallized with methanol to obtain 4.9 g (70%) of Target Compound 2-2.

<Preparation Example 4> Synthesis of Compound 2-3

Target Compound 2-3 (83%) was obtained by performing the preparation in the same manner as in the preparation of Compound 2-2, except that 4-iodo-1,1'-biphenyl was used instead of iodobenzene in the preparation of Compound 2-2.

<Preparation Example 5> Synthesis of Compound Ref 2

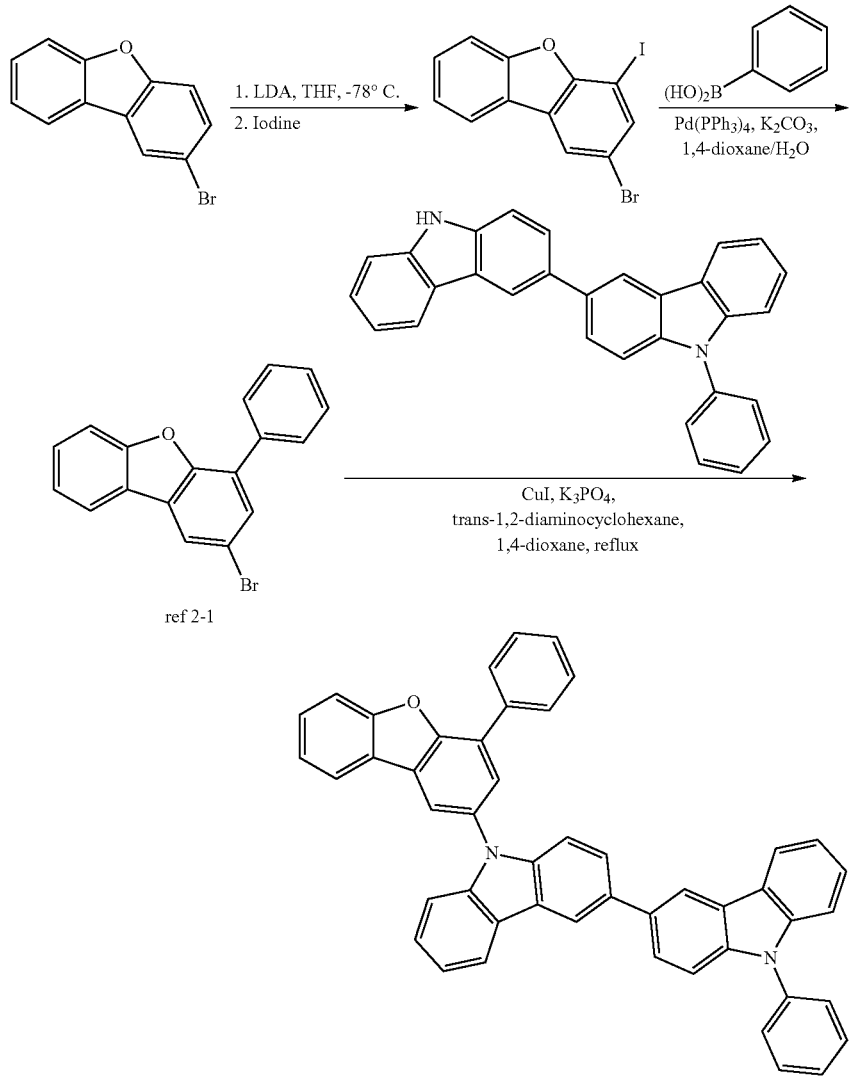

1) Preparation of Compound ref 2-2

88.0 mL (157.8 mM) of 1.8 M LDA was added dropwise to a mixed solution containing 30.0 g (121.4 mM) of 2-bromodibenzofuran and 300 mL of THF at −78° C., and the resulting mixture was stirred at room temperature for 1 hour. 11.0 g (42.9 mmol) of iodine was put into the reaction mixture, and the resulting mixture was stirred at room temperature for 2 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM) and recrystallized with MeOH to obtain 23.1 g (51%) of Target Compound ref 2-2.

2) Preparation of Compound Ref 2-1

3.9 g (10.5 mM) of Compound ref 2-2, 1.3 g (10.5 mM) of phenylboronic acid, 606 mg (0.52 mM) of Pd(PPh$_3$)$_4$, and 2.9 g (21.0 mM) of K$_2$CO$_3$ were dissolved in 100/20/20 mL of toluene/EtOH/H$_2$O, and then the resulting solution was refluxed for 12 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 2.4 g (70%) of Target Compound ref 2-1.

3) Preparation of Compound ref 2

5.1 g (15.8 mM) of Compound ref 2-1, 6.5 g (15.8 mM) of 9-phenyl-9H,9'H-3,3'-bicarbazole, 3.0 g (15.8 mM) of CuI, 1.9 mL (15.8 mM) of trans-1,2-diaminocyclohexane, and 3.3 g (31.6 mM) of K$_3$PO$_4$ were dissolved in 100 mL of 1,4-oxane, and then the resulting solution was refluxed for 24 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 8.7 g (85%) of Target Compound ref 2.

<Preparation Example 6> Preparation of Compound Ref 3

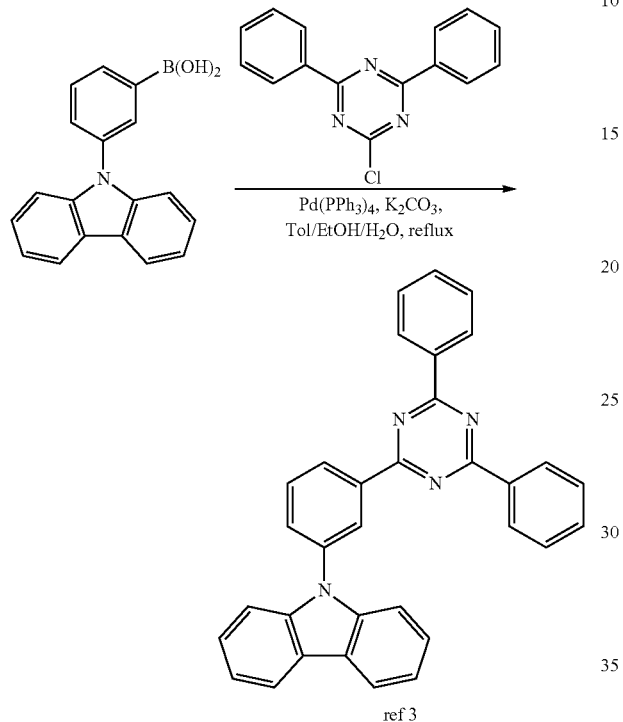

ref 3

5.5 g (19.0 mmol) of (3-(9H-carbazol-9-yl)phenyl)boronic acid, 5.1 g (19.0 mM) of 2-chloro-4,6-diphenyl-1,3,5-triazine, 1.1 g (0.95 mM) of Pd(PPh$_3$)$_4$, and 5.2 g (38.0 mM) of K$_2$CO$_3$ were dissolved in 100/20/20 mL of toluene/ethanol/H$_2$O, and then the resulting solution was refluxed for 12 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 6.3 g (70%) of Target Compound ref 3.

<Preparation Example 7> Synthesis of Compound 2-7

Compound 2-7 was obtained by using 2-bromo-9,9-dimethyl-9H-fluorene instead of iodobenzene in the preparation of Compound 2-2 (yield 69%).

<Preparation Example 8> Synthesis of Compound 2-9

Compound 2-9 was obtained by using 2-bromodibenzo[b,d]thiophene instead of iodobenzene in the preparation of Compound 2-2 (yield 72%).

<Preparation Example 9> Synthesis of Compound 2-11

Compound 2-11 was obtained by using 2-bromodibenzo[b,d]furan instead of iodobenzene in the preparation of Compound 2-2 (yield 68%).

<Preparation Example 10> Preparation of Compound Ref 4

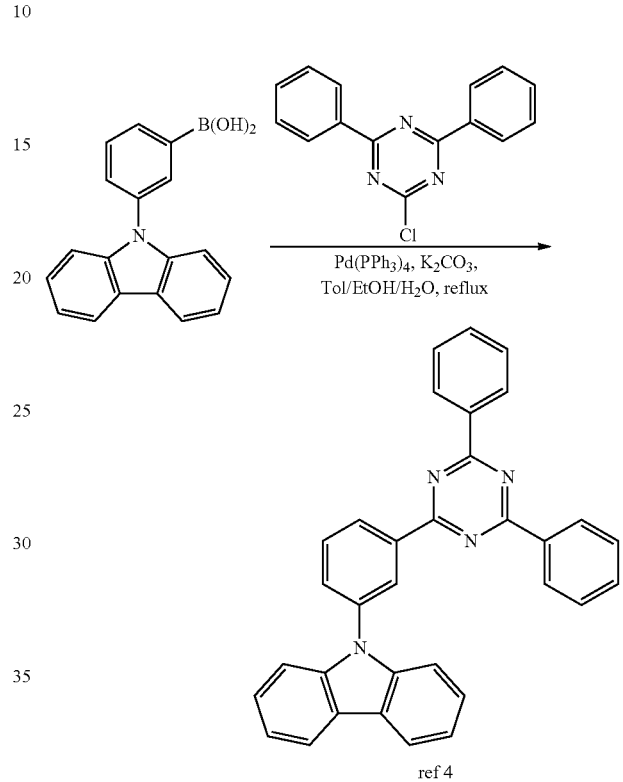

ref 4

5.5 g (19.0 mmol) of (3-(9H-carbazol-9-yl)phenyl)boronic acid, 5.1 g (19.0 mM) of 2-chloro-4,6-diphenyl-1,3,5-triazine, 1.1 g (0.95 mM) of Pd(PPh$_3$)$_4$, and 5.2 g (38.0 mM) of K$_2$CO$_3$ were dissolved in 100/20/20 mL of toluene/ethanol/H$_2$O, and then the resulting solution was refluxed for 12 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 6.3 g (70%) of Compound ref 4.

<Preparation Example 11> Preparation of Compound Ref 5

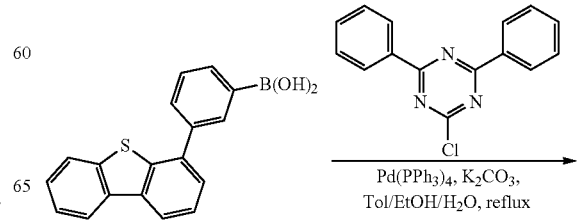

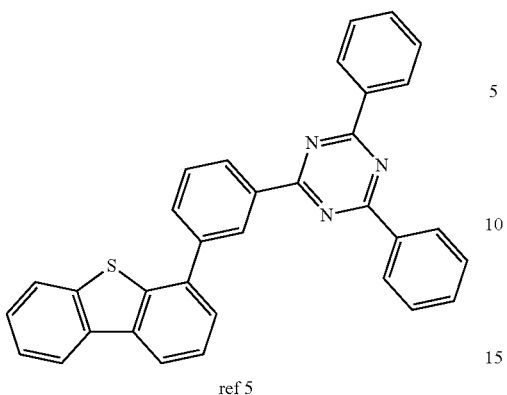

ref 5

5.8 g (19.0 mM) of (3-(dibenzo[b,d]thiophene-4-yl)phenyl)boronic acid, 5.1 g (19.0 mM) of 2-chloro-4,6-diphenyl-1,3,5-triazine, 1.1 g (0.95 mM) of Pd(PPh$_3$)$_4$, and 5.2 g (38.0 mM) of K$_2$CO$_3$ were dissolved in 100/20/20 mL of toluene/ethanol/H$_2$O, and then the resulting solution was refluxed for 12 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 6.5 g (70%) of Compound ref 5.

<Preparation Example 12> Synthesis of Compound Ref 6

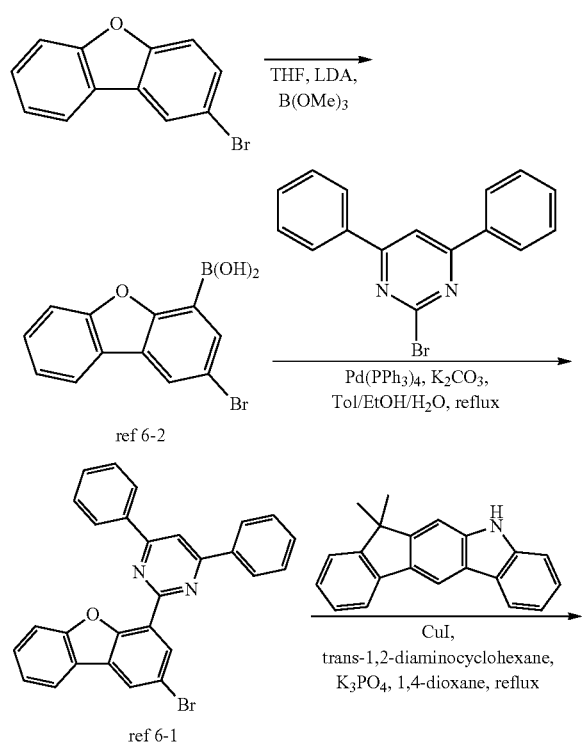

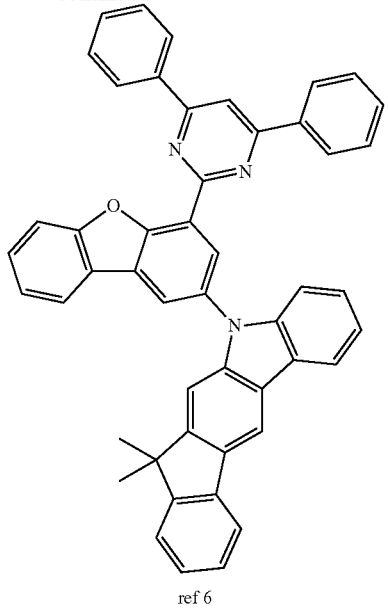

ref 6

1) Preparation of Compound ref 6-2

11.4 mL (22.8 mM) of 2.0 M lithium diisopropylamine was added dropwise to a mixed solution containing 4.7 g (19.0 mM) of 2-bromodibenzo[b,d]furan and 100 mL of THF at −78° C., and the resulting mixture was stirred at −78° C. for 1 hour. 4.8 mL (42.9 mM) of trimethyl borate was added dropwise to the reaction mixture, and the resulting mixture was stirred at room temperature for 2 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:MeOH=100:3) and recrystallized with DCM to obtain 3.9 g (70%) of Compound ref 6-2.

2) Preparation of Compound Ref 6-1

5.5 g (19.0 mM) of Compound ref 6-2, 5.9 g (19.0 mM) of 2-bromo-4,6-diphenylpyrimidine, 1.1 g (0.95 mM) of Pd(PPh$_3$)$_4$, and 5.2 g (38.0 mM) of K$_2$CO$_3$ were dissolved in 100/20/20 mL of toluene/ethanol/H$_2$O, and then the resulting solution was refluxed for 12 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with hexane to obtain 6.3 g (70%) of Compound ref 6-1.

3) Preparation of Compound Ref 6

9.1 g (19.0 mM) of Compound ref 6-1, 4.5 g (15.8 mM) of 7,7-dimethyl-5,7-dihydroindeno[2,1-b]carbazole, 3.0 g (15.8 mM) of CuI, 1.9 mL (15.8 mM) of trans-1,2-diaminocyclohexane, and 3.3 g (31.6 mM) of K$_3$PO$_4$ were dissolved in 100 mL of 1,4-oxane, and then the resulting solution was refluxed for 24 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 9.1 g (85%) of Compound ref 6.

<Preparation Example 13> Synthesis of Compound Ref 7

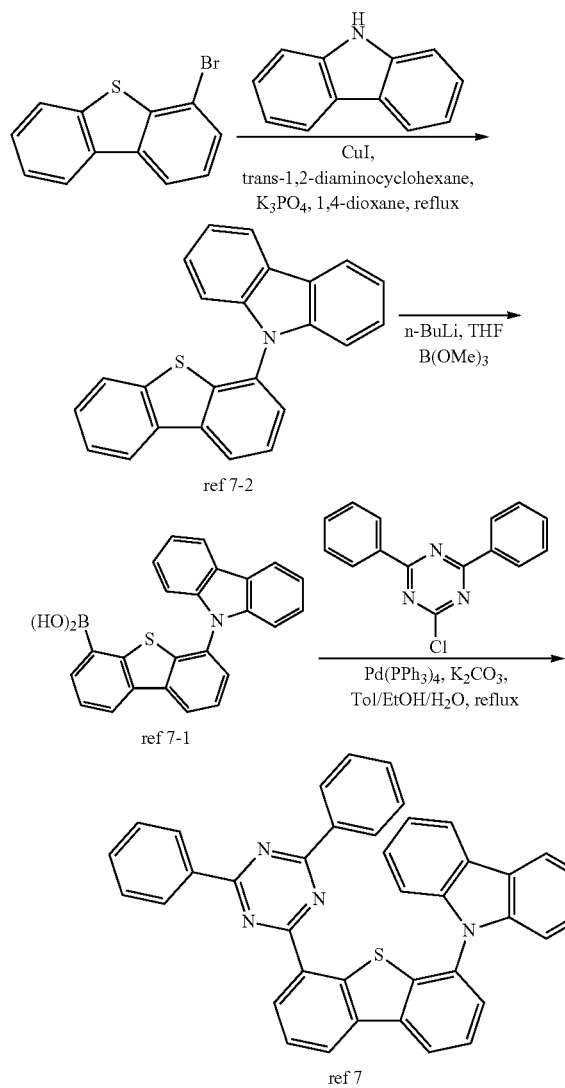

1) Preparation of Compound Ref 7-2

5.0 g (19.0 mM) of 4-bromodibenzo[b,d]thiophene, 2.6 g (15.8 mM) of 9H-carbazole, 3.0 g (15.8 mM) of CuI, 1.9 mL (15.8 mM) of trans-1,2-diaminocyclohexane, and 3.3 g (31.6 mM) of $K_3PO_4$ were dissolved in 100 mL of 1,4-oxane, and then the resulting solution was refluxed for 24 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:Hex=1:3) and recrystallized with methanol to obtain 4.7 g (85%) of Compound ref 7-2.

2) Preparation of Compound Ref 7-1

7.4 mL (18.6 mM) of 2.5 M n-BuLi was added dropwise to a mixed solution containing 5.0 g (14.3 mM) of Compound ref 7-2 and 100 mL of THF at −78° C., and the resulting mixture was stirred at room temperature for 1 hour. 4.8 mL (42.9 mM) of trimethyl borate was added dropwise to the reaction mixture, and the resulting mixture was stirred at room temperature for 2 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:MeOH=100:3) and recrystallized with DCM to obtain 3.9 g (70%) of Target Compound ref 7-1.

3) Preparation of Compound Ref 7

7.5 g (19.0 mM) of Compound ref 7-1, 5.1 g (19.0 mM) of 2-chloro-4,6-diphenyl-1,3,5-triazine, 1.1 g (0.95 mM) of $Pd(PPh_3)_4$, and 5.2 g (38.0 mM) of $K_2CO_3$ were dissolved in 100/20/20 mL of toluene/ethanol/$H_2O$, and then the resulting solution was refluxed for 12 hours. After the reaction was completed, distilled water and DCM were added thereto at room temperature, extraction was performed, the organic layer was dried over $MgSO_4$, and then the solvent was removed by a rotary evaporator. The reactant was purified by column chromatography (DCM:Hex=1:3) and recrystallized with methanol to obtain 7.7 g (70%) of Compound ref 7.

<Preparation Example 14> Synthesis of Compound Ref 8

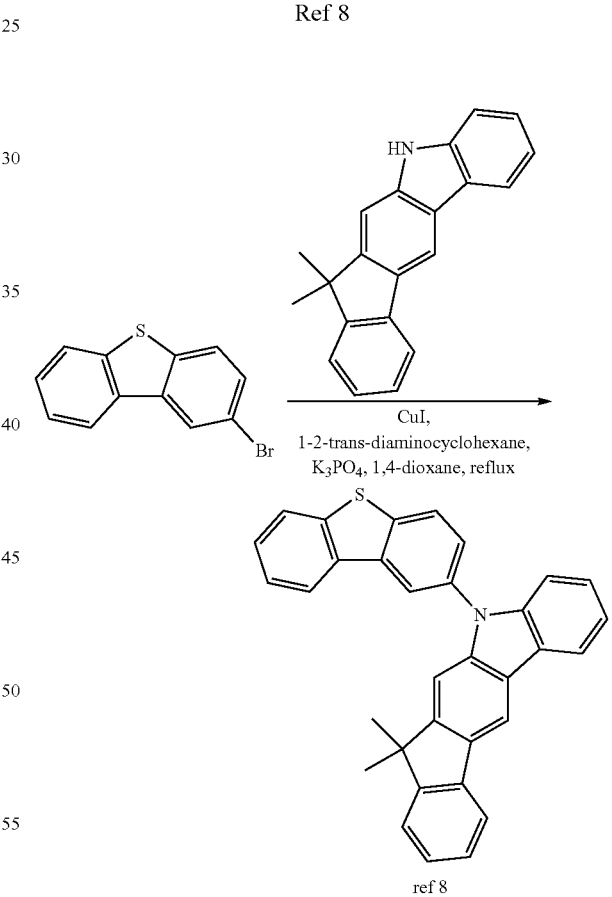

5.0 g (19.0 mM) of 2-bromodibenzo[b,d]thiophene, 4.5 g (15.8 mM) of 7,7-dimethyl-5,7-dihydroindeno[2,1-b]carbazole, 3.0 g (15.8 mM) of CuI, 1.9 mL (15.8 mM) of trans-1,2-diaminocyclohexane, and 3.3 g (31.6 mM) of $K_3PO_4$ were dissolved in 100 mL of 1,4-oxane, and then the resulting solution was refluxed for 24 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 7.3 g (85%) of Compound ref 8.

<Preparation Example 15> Synthesis of Compound Ref 9

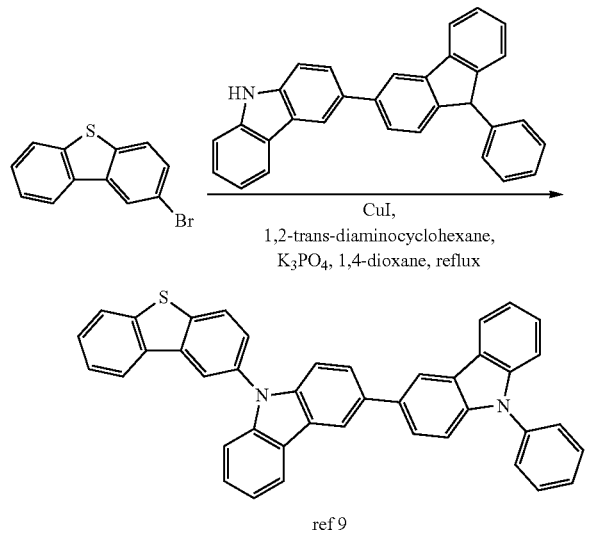

ref 9

4.2 g (15.8 mM) of 2-bromodibenzo[b,d]thiophene, 6.5 g (15.8 mM) of 9-phenyl-9H,9'H-3,3'-bicarbazole, 3.0 g (15.8 mM) of CuI, 1.9 mL (15.8 mM) of trans-1,2-diaminocyclohexane, and 3.3 g (31.6 mM) of K$_3$PO$_4$ were dissolved in 100 mL of 1,4-oxane, and then the resulting solution was refluxed for 24 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with methanol to obtain 7.9 g (85%) of Compound ref 9.

Compounds were prepared in the same manner as in the Preparation Examples, and the synthesis confirmation results thereof are shown in Tables 3 to 23.

TABLE 3

HOMO = −5.5 − ($E_{ox}$(Compound 1-2) − $E_{ox}$(NPB)) (eV)
Band gap = 1240/UV absorption edge(404 nm) (eV)

| | $E_{ox}$ | HOMO | Band gap | LUMO |
|---|---|---|---|---|
| NPB | 0.81 | | | |
| Compound 1-2 | 1.45 | −6.14 | 3.07 | −3.07 |

TABLE 4

HOMO = −5.5 − ($E_{ox}$(Compound 1-11) − $E_{ox}$(NPB)) (eV)
Band gap = 1240/UV absorption edge(432 nm) (eV)

| | $E_{ox}$ | HOMO | Band gap | LUMO |
|---|---|---|---|---|
| NPB | 0.80 | | | |
| Compound 1-11 | 1.48 | −6.18 | 2.87 | −3.31 |

TABLE 5

HOMO = −5.5 − ($E_{ox}$(Compound 1-23) − $E_{ox}$(NPB)) (eV)
Band gap = 1240/UV absorption edge(367 nm) (eV)

| | $E_{ox}$ | HOMO | Band gap | LUMO |
|---|---|---|---|---|
| NPB | 0.82 | | | |
| Compound 1-23 | 1.38 | −6.06 | 3.38 | −2.68 |

TABLE 6

HOMO = −5.5 − ($E_{ox}$(Compound 1-27) − $E_{ox}$(NPB)) (eV)
Band gap = 1240/UV absorption edge(369 nm) (eV)

| | $E_{ox}$ | HOMO | Band gap | LUMO |
|---|---|---|---|---|
| NPB | 0.80 | | | |
| Compound 1-27 | 1.37 | −6.07 | 3.36 | −2.71 |

TABLE 7

HOMO = −5.5 − ($E_{ox}$(Compound 1-33) − $E_{ox}$(NPB)) (eV)
Band gap = 1240/UV absorption edge(378 nm) (eV)

| | $E_{ox}$ | HOMO | Band gap | LUMO |
|---|---|---|---|---|
| NPB | 0.83 | | | |
| Compound 1-33 | 1.45 | −6.11 | 3.28 | −3.82 |

TABLE 8

HOMO = −5.5 − ($E_{ox}$(Compound 1-39) − $E_{ox}$(NPB)) (eV)
Band gap = 1240/UV absorption edge(433 nm) (eV)

| | $E_{ox}$ | HOMO | Band gap | LUMO |
|---|---|---|---|---|
| NPB | 0.76 | | | |
| Compound 1-39 | 1.41 | −6.15 | 2.86 | −3.29 |

TABLE 9

HOMO = −5.5 − (E$_{ox}$(Compound 1-41) − E$_{ox}$(NPB)) (eV)
Band gap = 1240/UV absorption edge(366 nm) (eV)

| | E$_{ox}$ | HOMO | Band gap | LUMO |
|---|---|---|---|---|
| NPB | 0.78 | | | |
| Compound 1-41 | 1.40 | −6.12 | 3.39 | −2.73 |

TABLE 10

HOMO = −5.5 − (E$_{ox}$(Compound 1-65) − E$_{ox}$(NPB)) (eV)
Band gap = 1240/UV absorption edge(416 nm) (eV)

| | E$_{ox}$ | HOMO | Band gap | LUMO |
|---|---|---|---|---|
| NPB | 0.79 | | | |
| Compound 1-65 | 1.22 | −5.93 | 2.98 | −2.95 |

TABLE 11

HOMO = −5.5 − (E$_{ox}$ (Compound 1-66) − E$_{ox}$ (NPB)) (eV)
Band gap = 1240/UV absorption edge (425 nm) (eV)

| | E$_{ox}$ | HOMO | Band gap | LUMO |
|---|---|---|---|---|
| NPB | 0.77 | | | |
| Compound 1-66 | 1.19 | −5.93 | 2.92 | −3.01 |

TABLE 12

HOMO = −5.5 − (E$_{ox}$ (Compound 1-67) − E$_{ox}$ (NPB)) (eV)
Band gap = 1240/UV absorption edge (452 nm) (eV)

| | E$_{ox}$ | HOMO | Band gap | LUMO |
|---|---|---|---|---|
| NPB | 0.76 | | | |
| Compound 1-67 | 1.16 | −5.89 | 2.74 | −3.15 |

TABLE 13

HOMO = −5.5 − (E$_{ox}$ (Compound 1-69) − E$_{ox}$ (NPB)) (eV)
Band gap = 1240/UV absorption edge (371 nm) (eV)

| | E$_{ox}$ | HOMO | Band gap | LUMO |
|---|---|---|---|---|
| NPB | 0.78 | | | |
| Compound 1-69 | 1.13 | −5.86 | 3.34 | −2.52 |

TABLE 14

HOMO = −5.5 − (E$_{ox}$ (Compound 1-70) − E$_{ox}$ (NPB)) (eV)
Band gap = 1240/UV absorption edge (371 nm) (eV)

| | E$_{ox}$ | HOMO | Band gap | LUMO |
|---|---|---|---|---|
| NPB | 0.76 | | | |
| Compound 1-70 | 1.14 | −5.88 | 3.34 | −2.54 |

TABLE 15

HOMO = −5.5 − (E$_{ox}$ (Compound 1-71) − E$_{ox}$ (NPB)) (eV)
Band gap = 1240/UV absorption edge (371 nm) (eV)

| | E$_{ox}$ | HOMO | Band gap | LUMO |
|---|---|---|---|---|
| NPB | 0.77 | | | |
| Compound 1-71 | 1.15 | −5.88 | 3.34 | −2.54 |

TABLE 16

HOMO = −5.5 − (E$_{ox}$ (Compound 1-78) − E$_{ox}$ (NPB)) (eV)
Band gap = 1240/UV absorption edge (438 nm) (eV)

| | E$_{ox}$ | HOMO | Band gap | LUMO |
|---|---|---|---|---|
| NPB | 0.78 | | | |
| Compound 1-78 | 1.30 | −6.02 | 2.83 | −3.19 |

TABLE 17

HOMO = −5.5 − (E$_{ox}$ (Compound 1-82) − E$_{ox}$ (NPB)) (eV)
Band gap = 1240/UV absorption edge (426 nm) (eV)

| | E$_{ox}$ | HOMO | Band gap | LUMO |
|---|---|---|---|---|
| NPB | 0.78 | | | |
| Compound 1-82 | 1.09 | −5.81 | 2.91 | −2.90 |

TABLE 18

HOMO = −5.5 − (E$_{ox}$ (Compound 1-84) − E$_{ox}$ (NPB)) (eV)
Band gap = 1240/UV absorption edge (463 nm) (eV)

| | E$_{ox}$ | HOMO | Band gap | LUMO |
|---|---|---|---|---|
| NPB | 0.77 | | | |
| Compound 1-84 | 1.08 | −5.80 | 2.68 | −3.12 |

TABLE 19

| | $E_{ox}$ | HOMO | Band gap | LUMO |
|---|---|---|---|---|
| \multicolumn{5}{c}{HOMO = −5.5 − ($E_{ox}$ (Compound 1-99) − $E_{ox}$ (NPB)) (eV)} |
| \multicolumn{5}{c}{Band gap = 1240/UV absorption edge (364 nm) (eV)} |
| NPB | 0.83 | | | |
| Compound 1-99 | 1.36 | −6.03 | 3.41 | −2.62 |

TABLE 20

| Compound | Td (signal value: 95%) | Tg |
|---|---|---|
| Compound 1-2 | 442.04° C. | — |
| Compound 1-11 | 426.38° C. | — |
| Compound 1-23 | 473.62° C. | 141.91° C. |
| Compound 1-27 | 464.07° C. | — |
| Compound 1-33 | 478.83° C. | 153.06° C. |
| Compound 1-39 | 460.32° C. | 151.88° C. |
| Compound 1-41 | 484.24° C. | 157.88° C. |
| Compound 1-65 | 467.84° C. | 179.13° C. |
| Compound 1-66 | 463.00° C. | 179.38° C. |
| Compound 1-67 | 461.79° C. | 185.05° C. |
| Compound 1-69 | 492.45° C. | 179.99° C. |
| Compound 1-70 | 482.96° C. | 185.05° C. |
| Compound 1-71 | 461.10° C. | 169.72° C. |
| Compound 1-78 | 462.82° C. | 180.63° C. |
| Compound 1-82 | 495.17° C. | — |
| Compound 1-84 | 492.52° C. | 188.83° C. |
| Compound 1-99 | 523.67° C. | 176.50° C. |

TABLE 21

| Compound | $^1$H NMR (CDCl$_3$, 200 Mz) |
|---|---|
| 1-2 | δ = 9.26 (1H, d), 8.51 (1H, d), 8.41~8.39 (4H, m), 8.23 (2H, d), 8.18 (1H, d), 8.13 (1H, s), 8.06 (1H, d), 7.62~7.43 (12H, m), 7.34 (2H, t) |
| 1-11 | δ = 9.32 (1H, d), 8.90~8.88 (4H, m), 8.61 (1H, d), 8.25 (2H, d), 8.21 (1H, d), 8.12 (1H, d), 7.65~7.45 (12H, m), 7.37 (2H, t) |
| 1-12 | δ = 8.55 (1H, d), 8.45~8.36 (4H, m), 8.19 (1H, d), 7.93~8.00 (4H, m), 7.73~7.77 (4H, m), 7.35~7.61 (12H, m), 7.20~7.20 (2H, m) |
| 1-17 | δ = 8.55 (1H, d), 8.45 (1H, d), 8.30 (2H, d), 7.90~8.12 (6H, m), 7.78 (1H, t), 7.47~7.69 (10H, m), 7.25~7.33 (3H, m) |
| 1-23 | δ = 8.55 (1H, d), 8.45~8.38 (2H, m), 8.23~8.19 (2H, m), 8.00~7.93 (8H, m), 7.77~7.73 (2H, m), 7.58~7.49 (11H, m), 7.35 (1H, t), 7.20~7.16 (2H, m) |
| 1-27 | δ = 9.27 (1H, d), 8.89 (1H, d), 8.79 (4H, m), 8.41 (1H, d), 8.21 (3H, m), 8.05 (1H, d), 7.93 (1H, d), 7.87 (1H, d), 7.77 (1H, t), 7.64~7.46 (12H, m), 7.32 (2H, t) |
| 1-33 | δ = 8.92 (2H, d), 8.36 (1H, d), 8.32 (4H, m), 8.21~8.16 (3H, m), 8.07 (1H, s), 8.01 (2H, d), 7.94 (1H, d), 7.61~7.44 (12H, m), 7.32 (2H, t) |
| 1-36 | δ = 8.55 (1H, d), 8.45 (1H, d), 8.36 (4H, d), 8.19 (1H, d), 8.00~7.93 (5H, m), 7.77 (1H, s), 7.58~7.49 (10H, m), 7.35 (1H, t), 7.25~7.16 (4H, m) |
| 1-39 | δ = 9.35 (1H, s), 8.90 (4H, d), 8.64 (1H, s), 8.30~8.20 (3H, m), 8.13 (1H, d), 7.71 (1H, s), 7.66~7.45 (14H, m), 7.38~7.33 (3H, m) |
| 1-40 | δ = 9.38 (1H, s), 9.24 (1H, s), 8.87 (3H, d), 8.64 (1H, s), 8.30~8.21 (3H, m), 8.08 (1H, d), 7.90 (1H, d), 7.80 (2H, d), 7.72~7.32 (19H, d) |
| 1-41 | δ = 9.30 (1H, s), 8.90 (1H, d), 8.80 (4H, d), 8.43 (1H, s), 8.26~8.20 (3H, m), 8.03 (1H, d), 7.93 (1H, d), 7.87 (1H, s), 7.77 (1H, t), 7.72 (1H, s), 7.67 (1H, d), 7.60~7.47 (11H, m), 7.41~7.29 (4H, m) |
| 1-42 | δ = 8.55 (1H, d), 8.45 (1H, d), 8.36~8.31 (5H, m), 8.00~7.91 (6H, m), 7.77~7.74 (4H, m), 7.56~7.35 (12H, m), 7.25 (2H, d), 7.16 (1H, t) |
| 1-46 | δ = 8.62 (1H, d), 8.45 (1H, d), 8.36~8.31 (5H, m), 8.22 (1H, m), 8.00 (1H, s), 7.93~7.91 (2H, m), 7.77~7.74 (7H, m), 7.50~7.41 (14H, m) |
| 1-64 | δ = 8.55 (1H, d), 8.45 (1H, d), 8.36 (4H, d), 8.22 (1H, s), 7.99~7.89 (5H, m), 7.77 (1H, d), 7.62~7.49 (13H, m), 7.35 (1H, t), 7.16 (1H, t) |
| 1-65 | δ = 9.33 (1H, d), 8.59 (1H, d), 8.53 (1H, s), 8.42 (4H, m), 8.28 (1H, d), 8.22 (1H, d), 8.15 (1H, s), 8.09 (1H, d), 7.90 (1H, d), 7.59~7.51 (10H, m), 7.50~7.34 (4H, m), 7.17 (1H, m), 1.53~1.50 (6H, d) |
| 1-66 | δ = 8.96 (2H, d), 8.60 (1H, s), 8.53 (1H, s), 8.46 (1H, s), 8.29~8.23 (4H, m), 8.19 (1H, s), 8.10 (1H, d), 7.90 (1H, d), 7.66~7.59 (4H, m), 7.56~7.51 (4H, m), 7.47~7.38 (6H, m), 7.31 (1H, m), 1.53~1.50 (6H, d) |
| 1-67 | δ = 9.39 (1H, s), 8.90 (4H, d), 8.68 (1H, s), 8.54 (1H, s), 8.30 (1H, d), 8.25 (1H, d), 8.15 (1H, d), 7.91 (1H, d), 7.64~7.52 (10H, m), 7.47~7.35 (4H, m), 7.29 (1H, t), 1.53~1.50 (6H, d) |
| 1-68 | δ = 8.55 (1H, d), 8.45 (1H, d), 8.24 (1H, d), 7.94~7.88 (3H, m), 7.80~7.74 (4H, m), 7.57~7.49 (7H, m), 7.38~7.33 (3H, m), 7.24~7.16 (4H, m), 7.05 (1H, m), 1.69 (6H, s) |
| 1-69 | δ = 9.26 (1H, s), 8.84 (1H, d), 8.49 (1H, s), 8.43 (1H, s), 8.31 (4H, m), 8.25~8.20 (2H, m), 8.07 (1H, s), 7.95 (2H, t), 7.88 (2H, s), 7.73 (1H, t), 7.55 (10H, m), 7.45~7.28 (5H, m), 1.53~1.50 (6H, d) |
| 1-70 | δ = 9.26 (1H, s), 8.84 (1H, d), 8.49 (1H, s), 8.43 (1H, s), 8.31 (4H, m), 8.25~8.20 (2H, m), 8.07 (1H, s), 7.71 (1H, t), 7.55 (10H, m), 7.45~7.28 (5H, m), 1.53~1.50 (6H, d) |
| 1-71 | δ = 8.54 (1H, s), 8.33 (1H, s), 8.30 (1H, d), 8.15 (1H, d), 7.96 (1H, d), 7.89 (4H, t), 7.78 (1H, s), 7.59~7.50 (3H, m), 7.44~7.25 (11H, m), 7.23~7.14 (4H, m), 6.85 (1H, t), 1.53~1.50 (6H, d) |
| 1-72 | δ = 8.55 (1H, d), 8.45 (1H, d), 8.24~8.23 (2H, m), 8.00~7.88 (10H, m), 7.77~7.74 (2H, m), 7.56~7.49 (10H, m), 7.38~7.35 (2H, m), 7.25 (2H, d), 7.16 (1H, t), 1.69 (6H, s) |
| 1-78 | δ = 9.36 (1H, s), 8.89 (2H, d), 8.64 (1H, s), 8.27~8.21 (3H, m), 8.13 (1H, d), 7.79 (1H, s), 7.67~7.50 (9H, m), 7.47~7.35 (4H, m), 7.30~7.17 (2H, m), 1.69 (6H, s) |
| 1-82 | δ = 9.31 (1H, s), 8.92 (1H, s), 8.57 (1H, s), 8.43 (4H, m), 8.35 (1H, d), 8.31 (1H, d), 8.18 (2H, m), 8.05 (1H, d), 7.63~7.47 (11H, m), 7.45~7.28 (7H, m), 7.20 (1H, m) |

TABLE 21-continued

| Compound | $^1$H NMR (CDCl$_3$, 200 Mz) |
|---|---|
| 1-83 | δ = 8.55 (1H, d), 8.45 (1H, d), 8.35 (2H, d), 8.23~8.19 (2H, m), 8.00~7.93 (5H, m), 7.77 (1H, s), 7.62~7.49 (16H, m), 7.40~7.35 (2H, m), 7.20~7.16 (2H, m) |
| 1-84 | δ = 9.39 (1H, s), 8.92 (1H, s), 8.90 (4H, m), 8.62 (1H, s), 8.37~8.33 (2H, m), 8.19 (1H, d), 8.11 (1H, d), 7.67~7.47 (11H, m), 7.45~7.28 (7H, m), 7.30 (2H, m), 7.20 (1H, m) |
| 1-93 | δ = 8.55 (1H, d), 8.45 (1H, d), 8.28 (4H, d), 8.12 (1H, d), 7.90~7.98 (3H, m), 7.29~7.69 (21H, m) |
| 1-96 | δ = 8.55 (1H, d), 8.45 (2H, m), 8.23 (1H, s), 7.90~8.08 (5H, m), 7.79 (4H, d), 7.69 (1H, s), 7.25~7.52 (13H, m) |
| 1-98 | δ = 8.55 (1H, d), 8.45 (1H, d), 8.36 (4H, d), 8.05~7.93 (5H, m), 7.77 (1H, s), 7.56~7.49 (10H, m), 7.35~7.33 (2H, m), 7.16 (1H, t) |
| 1-99 | δ = 9.25 (1H, s), 8.85 (1H, s), 8.45 (1H, s), 8.38 (1H, d), 8.32 (4H, m), 8.22 (3H, m), 8.07 (1H, s), 8.00 (2H, t), 7.94 (2H, m), 7.76~7.66 (3H, m), 7.66~7.47 (12H, m) |
| 1-100 | δ = 8.55 (1H, d), 8.45 (2H, m), 8.28 (4H, d), 8.24 (1H, d), 7.90~8.05 (5H, m), 7.69~7.70 (2H, m), 7.23~7.57 (15H, m) |
| 1-110 | 9.31 (1H, s), 9.29 (1H, s), 8.81 (4H, d), 8.30~8.58 (7H, m), 7.30~7.79 (13H, m) |
| 1-117 | δ = 8.55 (1H, d), 8.45 (1H, d), 8.28 (4H, d), 7.89~7.94 (5H, m), 7.66~7.69 (2H, m), 7.25~7.52 (12H, m), 7.13 (1H, d) |
| 1-119 | δ = 8.57 (1H, d), 8.46 (1H, d), 8.28 (4H, d), 8.24 (1H, d), 7.89~7.98 (5H, m), 7.66~7.70 (3H, m), 7.25~7.57 (14H, m), 7.13 (1H, d) |
| 1-126 | δ = 8.56 (1H, d), 8.45 (1H, d), 8.28 (4H, d), 7.89~7.98 (5H, m), 7.66~7.69 (2H, m), 7.25~7.53 (13H, m) |
| 1-163 | δ = 8.55 (1H, d), 8.45 (1H, d), 8.36 (4H, d), 8.22~8.19 (2H, m), 7.99~7.91 (8H, m), 7.58~7.49 (10H, m), 7.35 (1H, t), 7.20~7.16 (2H, m) |
| 1-170 | δ = 8.55 (1H, d), 8.45 (2H, m), 8.28 (4H, d), 7.94~8.05 (5H, m), 7.75~7.79 (3H, m), 7.68 (2H, d), 7.25~7.53 (13H, m) |
| 1-172 | δ = 8.57 (1H, d), 8.45 (1H, d), 8.28 (4H, d), 7.89~7.98 (5H, m), 7.66~7.79 (6H, m), 7.25~7.52 (12H, m) |
| 1-176 | δ = 8.58 (1H, d), 8.45 (1H, d), 8.16 (1H, d), 7.79~7.94 (9H, m), 7.25~7.69 (12H, m) |
| 1-177 | δ = 8.55 (1H, d), 8.45~8.46 (2H, m), 8.16 (1H, d), 7.83~8.05 (9H, m), 7.69 (1H, s), 7.25~7.58 (11H, m) |
| 1-178 | δ = 8.55 (1H, d), 8.45 (1H, d), 8.09~8.16 (2H, m), 7.79~7.98 (7H, m), 7.24~7.69 (13H, m), 1.72 (6H, s) |
| 1-179 | δ = 8.57 (1H, d), 8.47 (1H, d), 8.09~8.16 (3H, m), 7.79~7.98 (7H, m), 7.69 (1H, s), 7.24~7.61 (12H, m), 1.72 (6H, s) |
| 1-180 | δ = 8.54 (1H, d), 8.44~8.46 (2H, m), 8.16 (1H, d), 7.79~8.05 (9H, m), 7.69 (1H, s), 7.25~7.60 (11H, m) |
| 1-181 | δ = 8.55 (1H, d), 8.45 (1H, d), 8.16 (1H, d), 7.79~7.98 (9H, m), 7.25~7.69 (13H, m) |
| 2-2 | δ = 8.55 (1H, d), 8.45 (1H, d), 8.30 (1H, d), 8.19 (1H, d), 8.13 (1H, d), 8.00~7.89 (6H, m), 7.77 (2H, m), 7.62~7.35 (15H, m), 7.20~7.16 (2H, m) |
| 2-3 | δ = 8.55 (1H, d), 8.45 (1H, d), 8.30 (1H, d), 8.19 (1H, d), 8.13 (1H, d), 8.00~7.89 (6H, m), 7.77 (4H, m), 7.62~7.41 (13H, m), 7.25~7.16 (6H, m) |
| 2-7 | δ = 8.55 (1H, d), 8.45 (1H, d), 8.30 (1H, d), 8.19~8.09 (3H, m), 8.00~7.89 (8H, m), 7.78~7.77 (3H, m), 7.62~7.49 (10H, m), 7.38~7.16 (5H, m), 1.69 (6H, s) |
| 2-9 | δ = 8.55 (1H, d), 8.45 (2H, m), 8.30 (1H, d), 8.19~8.12 (4H, m), 8.00~7.89 (8H, m), 7.77 (2H, m), 7.62~7.49 (11H, m), 7.35 (1H, t), 7.21~7.16 (2H, m) |
| 2-11 | δ = 8.55 (1H, d), 8.45 (1H, d), 8.30 (1H, d), 8.19 (1H, d), 8.13 (1H, d), 8.00~7.77 (12H, m), 7.62~7.31 (13H, m), 7.20~7.16 (2H, m) |

TABLE 22

| Compound | FD-MS | Compound | FD-MS |
|---|---|---|---|
| 1-2 | m/z = 579.18 (C$_{40}$H$_{25}$N$_3$S = 579.72) | 1-11 | m/z = 580.17 (C$_{39}$H$_{24}$N$_4$S = 580.71) |
| 1-12 | m/z = 656.20 (C$_{45}$H$_{28}$N$_4$S = 656.81) | 1-17 | m/z = 552.17 (C$_{39}$H$_{24}$N$_2$S = 552.69) |
| 1-23 | m/z = 655.21 (C$_{46}$H$_{29}$N$_3$S = 655.81) | 1-27 | m/z = 656.20 (C$_{45}$H$_{28}$N$_4$S = 656.80) |
| 1-33 | m/z = 655.21 (C$_{46}$H$_{29}$N$_3$S = 655.81) | 1-36 | m/z = 656.20 (C$_{45}$H$_{28}$N$_4$S = 656.80) |
| 1-39 | m/z = 656.20 (C$_{45}$H$_{28}$N$_4$S = 656.80) | 1-40 | m/z = 732.23 (C$_{51}$H$_{32}$N$_4$S = 732.90) |
| 1-41 | m/z = 732.23 (C$_{51}$H$_{32}$N$_4$S = 732.89) | 1-42 | m/z = 732.23 (C$_{51}$H$_{32}$N$_4$S = 732.89) |
| 1-46 | m/z = 732.23 (C$_{51}$H$_{32}$N$_4$S = 732.89) | 1-64 | m/z = 656.20 (C$_{45}$H$_{28}$N$_4$S = 656.80) |
| 1-65 | m/z = 695.24 (C$_{49}$H$_{33}$N$_3$S = 695.87) | 1-66 | m/z = 695.24 (C$_{49}$H$_{33}$N$_3$S = 695.87) |
| 1-67 | m/z = 696.23 (C$_{48}$H$_{32}$N$_4$S = 696.86) | 1-68 | m/z = 669.22 (C$_{47}$H$_{31}$N$_3$S = 669.83) |
| 1-69 | m/z = 771.27 (C$_{55}$H$_{37}$N$_3$S = 771.97) | 1-70 | m/z = 772.27 (C$_{54}$H$_{36}$N$_4$S = 772.96) |
| 1-71 | m/z = 733.26 (C$_{52}$H$_{35}$N$_3$S = 733.93) | 1-72 | m/z = 772.27 (C$_{54}$H$_{36}$N$_4$S = 772.96) |
| 1-78 | m/z = 696.23 (C$_{48}$H$_{32}$N$_4$S = 696.86) | 1-82 | m/z = 744.23 (C$_{52}$H$_{32}$N$_4$S = 744.90) |
| 1-83 | m/z = 744.23 (C$_{52}$H$_{32}$N$_4$S = 744.90) | 1-84 | m/z = 745.23 (C$_{51}$H$_{31}$N$_5$S = 745.89) |
| 1-93 | m/z = 745.23 (C$_{51}$H$_{31}$N$_5$S = 745.89) | 1-96 | m/z = 685.16 (C$_{46}$H$_{27}$N$_3$S$_2$ = 685.86) |
| 1-98 | m/z = 686.16 (C$_{45}$H$_{26}$N$_4$S$_2$ = 686.84) | 1-99 | m/z = 761.20 (C$_{51}$H$_{31}$N$_3$S$_2$ = 761.95) |
| 1-100 | m/z = 762.19 (C$_{51}$H$_{30}$N$_4$S$_2$ = 762.94) | 1-110 | m/z = 686.16 (C$_{45}$H$_{26}$N$_4$S$_2$ = 686.84) |
| 1-117 | m/z = 670.18 (C$_{45}$H$_{26}$N$_4$OS = 670.78) | 1-119 | m/z = 746.21 (C$_{51}$H$_{30}$N$_4$OS = 746.88) |
| 1-126 | m/z = 670.18 (C$_{45}$H$_{26}$N$_4$OS = 670.78) | 1-163 | m/z = 656.80 (C$_{45}$H$_{28}$N$_4$S = 656.20) |
| 1-170 | m/z = 762.19 (C$_{51}$H$_{30}$N$_4$S$_2$ = 762.94) | 1-172 | m/z = 746.21 (C$_{51}$H$_{30}$N$_4$OS = 746.88) |
| 1-176 | m/z = 643.17 (C$_{44}$H$_{25}$N$_3$OS = 643.75) | 1-177 | m/z = 659.15 (C$_{44}$H$_{25}$N$_3$S$_2$ = 659.82) |

TABLE 22-continued

| Compound | FD-MS | Compound | FD-MS |
| --- | --- | --- | --- |
| 1-178 | m/z = 669.22 ($C_{47}H_{31}N_3S$ = 669.83) | 1-179 | m/z = 669.22 ($C_{47}H_{31}N_3S$ = 669.83) |
| 1-180 | m/z = 659.15 ($C_{44}H_{25}N_3S_2$ = 659.82) | 1-181 | m/z = 643.17 ($C_{44}H_{25}N_3OS$ = 643.75) |

TABLE 23

| Compound | FD-Mass | Compound | FD-Mass |
| --- | --- | --- | --- |
| 2-1 | m/z = 742.94 (C54H34N2S = 742.24) | 2-2 | m/z = 666.84 (C48H30N2S = 666.21) |
| 2-3 | m/z = 742.94 (C54H34N2S = 742.24) | 2-4 | m/z = 742.94 (C54H34N2S = 742.24) |
| 2-5 | m/z = 716.90 (C52H32N2S = 716.23) | 2-6 | m/z = 716.90 (C52H32N2S = 716.23) |
| 2-7 | m/z = 783.00 (C57H38N2S = 782.28) | 2-8 | m/z = 783.00 (C57H38N2S = 782.28) |
| 2-9 | m/z = 772.98 (C54H32N2S2 = 772.20) | 2-10 | m/z = 772.98 (C54H32N2S2 = 772.20) |
| 2-11 | m/z = 756.92 (C54H32N2OS = 756.22) | 2-12 | m/z = 756.92 (C54H32N2OS = 756.22) |
| 2-13 | m/z = 666.84 (C48H30N2S = 666.21) | 2-14 | m/z = 742.94 (C54H34N2S = 742.24) |
| 2-15 | m/z = 742.94 (C54H34N2S = 742.24) | 2-16 | m/z = 716.90 (C52H32N2S = 716.23) |
| 2-17 | m/z = 716.90 (C52H32N2S = 716.23) | 2-18 | m/z = 783.00 (C57H38N2S = 782.28) |
| 2-19 | m/z = 783.00 (C57H38N2S = 782.28) | 2-20 | m/z = 772.98 (C54H32N2S2 = 772.20) |
| 2-21 | m/z = 756.92 (C54H32N2OS = 756.22) | 2-22 | m/z = 756.92 (C54H32N2OS = 756.22) |
| 2-23 | m/z = 772.98 (C54H32N2S2 = 772.20) | 2-24 | m/z = 666.84 (C48H30N2S = 666.21) |
| 2-25 | m/z = 742.94 (C54H34N2S = 742.24) | 2-26 | m/z = 742.94 (C54H34N2S = 742.24) |
| 2-27 | m/z = 783.00 (C57H38N2S = 782.28) | 2-28 | m/z = 772.98 (C54H32N2S2 = 772.20) |
| 2-29 | m/z = 756.92 (C54H32N2OS = 756.22) | 2-30 | m/z = 772.98 (C54H32N2S2 = 772.20) |
| 2-31 | m/z = 783.00 (C57H38N2S = 782.28) | 2-32 | m/z = 756.92 (C54H32N2OS = 756.22) |
| 2-33 | m/z = 666.84 (C48H30N2S = 666.21) | 2-34 | m/z = 742.94 (C54H34N2S = 742.24) |
| 2-35 | m/z = 742.94 (C54H34N2S = 742.24) | 2-36 | m/z = 772.98 (C54H32N2S2 = 772.20) |
| 2-37 | m/z = 756.92 (C54H32N2OS = 756.22) | 2-38 | m/z = 772.98 (C54H32N2S2 = 772.20) |
| 2-39 | m/z = 783.00 (C57H38N2S = 782.28) | 2-40 | m/z = 756.92 (C54H32N2OS = 756.22) |
| 2-41 | m/z = 666.84 (C48H30N2S = 666.21) | 2-42 | m/z = 742.94 (C54H34N2S = 742.24) |
| 2-43 | m/z = 742.94 (C54H34N2S = 742.24) | 2-44 | m/z = 772.98 (C54H32N2S2 = 772.20) |
| 2-45 | m/z = 756.92 (C54H32N2OS = 756.22) | 2-46 | m/z = 772.98 (C54H32N2S2 = 772.20) |
| 2-47 | m/z = 783.00 (C57H38N2S = 782.28) | 2-48 | m/z = 756.92 (C54H32N2OS = 756.22) |
| 2-49 | m/z = 666.84 (C48H30N2S = 666.21) | 2-50 | m/z = 742.94 (C54H34N2S = 742.24) |
| 2-51 | m/z = 742.94 (C54H34N2S = 742.24) | 2-52 | m/z = 772.98 (C54H32N2S2 = 772.20) |
| 2-53 | m/z = 756.92 (C54H32N2OS = 756.22) | 2-54 | m/z = 772.98 (C54H32N2S2 = 772.20) |
| 2-55 | m/z = 783.00 (C57H38N2S = 782.28) | 2-56 | m/z = 756.92 (C54H32N2OS = 756.22) |
| 2-57 | m/z = 666.84 (C48H30N2S = 666.21) | 2-58 | m/z = 742.94 (C54H34N2S = 742.24) |
| 2-59 | m/z = 742.94 (C54H34N2S = 742.24) | 2-60 | m/z = 772.98 (C54H32N2S2 = 772.20) |
| 2-61 | m/z = 756.92 (C54H32N2OS = 756.22) | 2-62 | m/z = 772.98 (C54H32N2S2 = 772.20) |
| 2-63 | m/z = 783.00 (C57H38N2S = 782.28) | 2-64 | m/z = 756.92 (C54H32N2OS = 756.22) |
| 2-65 | m/z = 666.84 (C48H30N2S = 666.21) | 2-66 | m/z = 742.94 (C54H34N2S = 742.24) |
| 2-67 | m/z = 742.94 (C54H34N2S = 742.24) | 2-68 | m/z = 772.98 (C54H32N2S2 = 772.20) |
| 2-69 | m/z = 756.92 (C54H32N2OS = 756.22) | 2-70 | m/z = 772.98 (C54H32N2S2 = 772.20) |
| 2-71 | m/z = 783.00 (C57H38N2S = 782.28) | 2-72 | m/z = 756.92 (C54H32N2OS = 756.22) |
| 2-73 | m/z = 666.84 (C48H30N2S = 666.21) | 2-74 | m/z = 742.94 (C54H34N2S = 742.24) |
| 2-75 | m/z = 742.94 (C54H34N2S = 742.24) | 2-76 | m/z = 772.98 (C54H32N2S2 = 772.20) |
| 2-77 | m/z = 756.92 (C54H32N2OS = 756.22) | 2-78 | m/z = 772.98 (C54H32N2S2 = 772.20) |
| 2-79 | m/z = 783.00 (C57H38N2S = 782.28) | 2-80 | m/z = 756.92 (C54H32N2OS = 756.22) |
| 2-81 | m/z = 666.84 (C48H30N2S = 666.21) | 2-82 | m/z = 742.94 (C54H34N2S = 742.24) |
| 2-83 | m/z = 742.94 (C54H34N2S = 742.24) | 2-84 | m/z = 772.98 (C54H32N2S2 = 772.20) |
| 2-85 | m/z = 756.92 (C54H32N2OS = 756.22) | 2-86 | m/z = 772.98 (C54H32N2S2 = 772.20) |
| 2-87 | m/z = 783.00 (C57H38N2S = 782.28) | 2-88 | m/z = 756.92 (C54H32N2OS = 756.22) |
| 2-89 | m/z = 666.84 (C48H30N2S = 666.21) | 2-90 | m/z = 742.94 (C54H34N2S = 742.24) |
| 2-91 | m/z = 742.94 (C54H34N2S = 742.24) | 2-92 | m/z = 772.98 (C54H32N2S2 = 772.20) |
| 2-93 | m/z = 756.92 (C54H32N2OS = 756.22) | 2-94 | m/z = 772.98 (C54H32N2S2 = 772.20) |
| 2-95 | m/z = 783.00 (C57H38N2S = 782.28) | 2-96 | m/z = 756.92 (C54H32N2OS = 756.22) |
| 2-97 | m/z = 666.84 (C48H30N2S = 666.21) | 2-98 | m/z = 742.94 (C54H34N2S = 742.24) |
| 2-99 | m/z = 742.94 (C54H34N2S = 742.24) | 2-100 | m/z = 772.98 (C54H32N2S2 = 772.20) |
| 2-101 | m/z = 756.92 (C54H32N2OS = 756.22) | 2-102 | m/z = 772.98 (C54H32N2S2 = 772.20) |
| 2-103 | m/z = 783.00 (C57H38N2S = 782.28) | 2-104 | m/z = 756.92 (C54H32N2OS = 756.22) |

Table 21 shows NMR values, and Tables 22 and 23 show measured values by field desorption mass spectrometry (FD-MS).

FIG. 4 illustrates a measurement graph of LTPL of Compound 1-2 at a wavelength of 363 nm.

FIG. 5 illustrates a measurement graph of PL of Compound 1-2 at a wavelength of 238 nm.

FIG. 6 illustrates a UV absorption spectrum of Compound 1-2.

FIG. 7 illustrates a measurement graph of LTPL of Compound 1-11 at a wavelength of 339 nm.

FIG. 8 illustrates a measurement graph of PL of Compound 1-11 at a wavelength of 234 nm.

FIG. 9 illustrates a UV absorption spectrum of Compound 1-11.

FIG. 10 illustrates a measurement graph of LTPL of Compound 1-23 at a wavelength of 241 nm.

FIG. 11 illustrates a measurement graph of PL of Compound 1-23 at a wavelength of 241 nm.

FIG. 12 illustrates a UV absorption spectrum of Compound 1-23.

FIG. 13 illustrates a measurement graph of LTPL of Compound 1-27 at a wavelength of 340 nm.

FIG. 14 illustrates a measurement graph of PL of Compound 1-27 at a wavelength of 241 nm.

FIG. 15 illustrates a UV absorption spectrum of Compound 1-27.

FIG. 16 illustrates a measurement graph of LTPL of Compound 1-33 at a wavelength of 291 nm.

FIG. 17 illustrates a measurement graph of PL of Compound 1-33 at a wavelength of 239 nm.

FIG. 18 illustrates a UV absorption spectrum of Compound 1-33.

FIG. 19 illustrates a measurement graph of LTPL of Compound 1-39 at a wavelength of 259 nm.

FIG. 20 illustrates a measurement graph of PL of Compound 1-39 at a wavelength of 259 nm.

FIG. 21 illustrates a UV absorption spectrum of Compound 1-39.

FIG. 22 illustrates a measurement graph of LTPL of Compound 1-41 at a wavelength of 260 nm.

FIG. 23 illustrates a measurement graph of PL of Compound 1-41 at a wavelength of 260 nm.

FIG. 24 illustrates a UV absorption spectrum of Compound 1-41.

FIG. 25 illustrates a measurement graph of LTPL of Compound 1-65 at a wavelength of 361 nm.

FIG. 26 illustrates a measurement graph of PL of Compound 1-65 at a wavelength of 235 nm.

FIG. 27 illustrates a UV absorption spectrum of Compound 1-65.

FIG. 28 illustrates a measurement graph of LTPL of Compound 1-66 at a wavelength of 360 nm.

FIG. 29 illustrates a measurement graph of PL of Compound 1-66 at a wavelength of 307 nm.

FIG. 30 illustrates a UV absorption spectrum of Compound 1-66.

FIG. 31 illustrates a measurement graph of LTPL of Compound 1-67 at a wavelength of 361 nm.

FIG. 32 illustrates a measurement graph of PL of Compound 1-67 at a wavelength of 266 nm.

FIG. 33 illustrates a UV absorption spectrum of Compound 1-67.

FIG. 34 illustrates a measurement graph of LTPL of Compound 1-69 at a wavelength of 344 nm.

FIG. 35 illustrates a measurement graph of PL of Compound 1-69 at a wavelength of 308 nm.

FIG. 36 illustrates a UV absorption spectrum of Compound 1-69.

FIG. 37 illustrates a measurement graph of LTPL of Compound 1-70 at a wavelength of 344 nm.

FIG. 38 illustrates a measurement graph of PL of Compound 1-70 at a wavelength of 267 nm.

FIG. 39 illustrates a UV absorption spectrum of Compound 1-70.

FIG. 40 illustrates a measurement graph of LTPL of Compound 1-71 at a wavelength of 344 nm.

FIG. 41 illustrates a measurement graph of PL of Compound 1-71 at a wavelength of 241 nm.

FIG. 42 illustrates a UV absorption spectrum of Compound 1-71.

FIG. 43 illustrates a measurement graph of LTPL of Compound 1-78 at a wavelength of 361 nm.

FIG. 44 illustrates a measurement graph of PL of Compound 1-78 at a wavelength of 263 nm.

FIG. 45 illustrates a UV absorption spectrum of Compound 1-78.

FIG. 46 illustrates a measurement graph of LTPL of Compound 1-82 at a wavelength of 344 nm.

FIG. 47 illustrates a measurement graph of PL of Compound 1-82 at a wavelength of 307 nm.

FIG. 48 illustrates a UV absorption spectrum of Compound 1-82.

FIG. 49 illustrates a measurement graph of LTPL of Compound 1-84 at a wavelength of 363 nm.

FIG. 50 illustrates a measurement graph of PL of Compound 1-84 at a wavelength of 298 nm.

FIG. 51 illustrates a UV absorption spectrum of Compound 1-84.

FIG. 52 illustrates a measurement graph of LTPL of Compound 1-99 at a wavelength of 355 nm.

FIG. 53 illustrates a measurement graph of PL of Compound 1-99 at a wavelength of 355 nm.

FIG. 54 illustrates a UV absorption spectrum of Compound 1-99.

Experimental Example

Experimental Example 1

1) Manufacture of Organic Light Emitting Device

A glass substrate, in which ITO was thinly coated to have a thickness of 1,500 Å, was ultrasonically washed with distilled water. When the washing with distilled water is finished, the glass substrate was ultrasonically washed with a solvent such as acetone, methanol, and isopropyl alcohol, dried and then was subjected to UVO treatment for 5 minutes by using UV in a UV washing machine. Thereafter, the substrate was transferred to a plasma washing machine (PT), and then was subjected to plasma treatment in a vacuum state for an ITO work function and in order to remove a residual film, and was transferred to a thermal deposition equipment for organic deposition.

As the common layers, the hole injection layer 4,4',4"-tris[2-naphthyl(phenyl)amino]triphenylamine (2-TNATA) and the hole transport layer N,N'-di(1-naphthyl)-N,N'-diphenyl-(1,1'-biphenyl)-4,4'-diamine (NPB) were formed on the ITO transparent electrode (positive electrode).

A light emitting layer was thermally vacuum deposited thereon as follows. The light emitting layer was deposited to have a thickness of 400 Å by using a compound described in the following Table 24 as a host and tris(2-phenylpyridine)iridium (Ir(ppy)$_3$) as a green phosphorescent dopant to dope the host with Ir(ppy)$_3$ in an amount of 7%. Thereafter, BCP as a hole blocking layer was deposited to have a thickness of 60 Å, and Alq$_3$ as an electron transport layer was deposited to have a thickness of 200 Å thereon. Finally, an organic electroluminescence device was manufactured by depositing lithium fluoride (LiF) to have a thickness of 10 Å on the electron transport layer to form an electron injection layer, and then depositing an aluminum (Al) negative electrode to have a thickness of 1,200 Å on the electron injection layer to form a negative electrode.

Meanwhile, all the organic compounds required for manufacturing an OLED device were subjected to vacuum sublimed purification under $10^{-6}$ to $10^{-8}$ torr for each material, and used for the manufacture of OLED.

2) Driving Voltage and Light Emitting Efficiency of Organic Electroluminescence Device For the organic electroluminescence device manufactured as described above, electroluminescence (EL) characteristics were measured by M7000 manufactured by McScience Inc., and based on the measurement result thereof, $T_{90}$ was measured by a lifetime measurement equipment (M6000) manufactured by McScience Inc. when the reference brightness was 6,000 cd/m². Characteristics of the organic electroluminescence device of the present invention are as shown in the following Table 24.

TABLE 24

|  | Compound | Driving voltage (V) | Efficiency (cd/A) | Color coordinate (x, y) | Lifetime ($T_{90}$) |
|---|---|---|---|---|---|
| Example 1 | 1-2 | 4.05 | 67.2 | (0.294, 0.654) | 142 |
| Example 2 | 1-11 | 3.90 | 68.9 | (0.293, 0.653) | 151 |
| Example 3 | 1-17 | 3.82 | 60.5 | (0.283, 0.643) | 186 |
| Example 4 | 1-23 | 4.39 | 64.1 | (0.296, 0.654) | 123 |
| Example 5 | 1-27 | 4.19 | 66.1 | (0.297, 0.653) | 133 |
| Example 6 | 1-33 | 4.40 | 63.2 | (0.305, 0.654) | 120 |
| Example 7 | 1-39 | 3.88 | 69.9 | (0.296, 0.652) | 154 |
| Example 8 | 1-41 | 4.11 | 76.6 | (0.296, 0.675) | 137 |
| Example 9 | 1-64 | 4.00 | 75.6 | (0.296, 0.674) | 134 |
| Example 10 | 1-65 | 3.83 | 68.3 | (0.272, 0.683) | 149 |
| Example 11 | 1-66 | 4.02 | 67.1 | (0.293, 0.654) | 145 |
| Example 12 | 1-67 | 3.80 | 70.2 | (0.284, 0.682) | 160 |
| Example 13 | 1-69 | 4.26 | 65.4 | (0.295, 0.693) | 127 |
| Example 14 | 1-70 | 4.39 | 67.0 | (0.296, 0.701) | 140 |
| Example 15 | 1-71 | 4.25 | 64.7 | (0.295, 0.675) | 130 |
| Example 16 | 1-76 | 4.22 | 68.7 | (0.294, 0.676) | 133 |
| Example 17 | 1-77 | 3.91 | 75.5 | (0.280, 0.678) | 148 |
| Example 18 | 1-78 | 3.81 | 72.5 | (0.281, 0.679) | 158 |
| Example 19 | 1-79 | 3.96 | 67.2 | (0.273, 0.688) | 137 |
| Example 20 | 1-80 | 3.79 | 73.1 | (0.295, 0.659) | 169 |
| Example 21 | 1-82 | 3.91 | 68.2 | (0.274, 0.684) | 147 |
| Example 22 | 1-84 | 3.70 | 70.1 | (0.293, 0.656) | 156 |
| Example 23 | 1-85 | 3.99 | 69.2 | (0.273, 0.687) | 147 |
| Example 24 | 1-86 | 3.71 | 78.1 | (0.295, 0.658) | 170 |
| Example 25 | 1-91 | 3.98 | 61.2 | (0.274, 0.683) | 158 |
| Example 26 | 1-92 | 3.73 | 76.1 | (0.293, 0.655) | 159 |
| Example 27 | 1-93 | 3.81 | 67.6 | (0.286, 0.650) | 137 |
| Example 28 | 1-94 | 4.20 | 66.7 | (0.293, 0.664) | 152 |
| Example 29 | 1-95 | 3.90 | 79.2 | (0.294, 0.662) | 199 |
| Example 30 | 1-96 | 3.79 | 69.3 | (0.272, 0.683) | 149 |
| Example 31 | 1-98 | 3.71 | 65.3 | (0.271, 0.681) | 179 |
| Example 32 | 1-99 | 4.23 | 62.7 | (0.293, 0.654) | 145 |
| Example 33 | 1-100 | 3.93 | 74.2 | (0.294, 0.652) | 190 |
| Example 34 | 1-109 | 3.82 | 69.4 | (0.301, 0.693) | 187 |
| Example 35 | 1-110 | 4.12 | 64.4 | (0.302, 0.693) | 227 |
| Example 36 | 1-111 | 3.88 | 68.9 | (0.286, 0.685) | 177 |
| Example 37 | 1-112 | 3.93 | 64.9 | (0.272, 0.673) | 169 |
| Example 38 | 1-113 | 4.25 | 67.7 | (0.293, 0.654) | 195 |
| Example 39 | 1-114 | 3.11 | 70.2 | (0.314, 0.692) | 178 |
| Example 40 | 1-117 | 3.80 | 67.5 | (0.276, 0.651) | 190 |
| Example 41 | 1-118 | 3.79 | 69.3 | (0.272, 0.683) | 149 |
| Example 42 | 1-119 | 4.29 | 65.1 | (0.285, 0.695) | 180 |
| Example 43 | 1-125 | 3.73 | 67.0 | (0.276, 0.689) | 190 |
| Example 44 | 1-126 | 4.09 | 72.5 | (0.301, 0.685) | 198 |
| Example 45 | 1-127 | 3.81 | 67.6 | (0.286, 0.650) | 137 |
| Example 46 | 1-128 | 3.91 | 68.2 | (0.274, 0.684) | 147 |
| Example 47 | 1-138 | 3.70 | 70.1 | (0.293, 0.656) | 156 |
| Example 48 | 1-139 | 4.11 | 76.6 | (0.296, 0.675) | 137 |
| Example 49 | 1-140 | 4.00 | 75.6 | (0.296, 0.674) | 134 |
| Example 50 | 1-155 | 3.83 | 68.3 | (0.272, 0.683) | 149 |
| Example 51 | 1-156 | 4.05 | 67.2 | (0.294, 0.654) | 142 |
| Example 52 | 1-157 | 3.90 | 68.9 | (0.293, 0.653) | 151 |
| Example 53 | 1-158 | 3.82 | 60.5 | (0.283, 0.643) | 186 |
| Example 54 | 1-160 | 3.73 | 67.0 | (0.276, 0.689) | 190 |
| Example 55 | 1-162 | 3.71 | 78.1 | (0.295, 0.658) | 170 |
| Example 56 | 1-164 | 3.78 | 68.9 | (0.286, 0.685) | 177 |
| Example 57 | 1-165 | 4.29 | 65.1 | (0.285, 0.695) | 180 |
| Example 58 | 1-170 | 4.21 | 68.2 | (0.294, 0.644) | 217 |
| Example 59 | 1-172 | 3.81 | 70.1 | (0.313, 0.706) | 186 |

TABLE 24-continued

|  | Compound | Driving voltage (V) | Efficiency (cd/A) | Color coordinate (x, y) | Lifetime ($T_{90}$) |
|---|---|---|---|---|---|
| Example 60 | 1-174 | 3.73 | 67.0 | (0.276, 0.689) | 190 |
| Example 61 | 1-176 | 3.78 | 68.9 | (0.286, 0.685) | 177 |
| Example 62 | 1-177 | 3.83 | 64.9 | (0.272, 0.673) | 169 |
| Example 63 | 1-178 | 4.25 | 67.7 | (0.293, 0.654) | 195 |
| Example 64 | 1-179 | 3.81 | 70.2 | (0.314, 0.692) | 178 |
| Example 65 | 1-180 | 3.89 | 65.4 | (0.295, 0.693) | 167 |
| Example 66 | 1-181 | 3.73 | 67.0 | (0.276, 0.689) | 190 |
| Comparative Example 1 | CBP | 5.23 | 41.1 | (0.285, 0.681) | 50 |
| Comparative Example 2 | ref 4 | 4.82 | 58.8 | (0.294, 0.654) | 55 |
| Comparative Example 3 | ref 5 | 4.20 | 62.3 | (0.284, 0.695) | 31 |
| Comparative Example 4 | ref 6 | 4.66 | 61.2 | (0.296, 0.676) | 80 |
| Comparative Example 5 | ref 7 | 4.10 | 59.7 | (0.276, 0.684) | 82 |
| Comparative Example 6 | ref 8 | 4.92 | 52.2 | (0.286, 0.644) | 65 |
| Comparative Example 7 | ref 9 | 4.91 | 56.3 | (0.286, 0.644) | 73 |

As can be seen from the results in Table 24, the organic electroluminescence device using a light emitting layer material of the organic electroluminescence device of the present invention had a low driving voltage, an enhanced light emitting efficiency, and a significantly improved lifetime compared to those in Comparative Examples 1 to 7.

Meanwhile, when phenylene is positioned between carbazole and triazine as in Comparative Example 2, the lifetime is reduced because electrons in the LUMO region fail to be stabilized. Further, when there is no carbazole as in Comparative Example 3, the hole mobility deteriorates, and the equilibrium between holes and electrons in the light emitting layer collapses, thereby leading to a decrease in lifetime. In addition, in the case of a compound including dibenzofuran as in Comparative Example 4, the lifetime is reduced because electrons in the LUMO region fail to be stabilized. Furthermore, when a substituent is bonded to the 2nd and 6th positions of dibenzothiophene as in Comparative Example 5, the equilibrium between holes and electrons in the light emitting layer collapses, thereby leading to a decrease in lifetime. Further, as in Comparative Examples 6 and 7, when a heteroaryl group including at least one N is not bonded to the position of Ar1 of Chemical Formula 1 of the present invention, the equilibrium between holes and electrons collapses because there is no substituent which stabilizes electrons, and as a result, a result of reducing the efficiency or lifetime is obtained.

<Experimental Example 2> Manufacture of Organic Light Emitting Device

A glass substrate, in which ITO was thinly coated to have a thickness of 1,500 Å, was ultrasonically washed with distilled water. When the washing with distilled water is finished, the glass substrate was ultrasonically washed with a solvent such as acetone, methanol, and isopropyl alcohol, dried and then was subjected to UVO treatment for 5 minutes by using UV in a UV washing machine. Thereafter, the substrate was transferred to a plasma washing machine (PT), and then was subjected to plasma treatment in a vacuum state for an ITO work function and in order to remove a residual film, and was transferred to a thermal deposition equipment for organic deposition.

As the common layers, the hole injection layer 4,4',4''-tris[2-naphthyl(phenyl)amino]triphenylamine (2-TNATA) and the hole transport layer N,N'-di(1-naphthyl)-N,N'-diphenyl-(1,1'-biphenyl)-4,4'-diamine (NPB) were formed on the ITO transparent electrode (positive electrode).

A light emitting layer was thermally vacuum deposited thereon as follows. The light emitting layer was deposited to have a thickness of 400 Å by using a compound described in Chemical Formula 1 and a compound described in Chemical Formula 2 as hosts from the individual supply source, and was deposited by doping the host with Ir(ppy)$_3$ as a green phosphorescent dopant in an amount of 7%. Thereafter, BCP as a hole blocking layer was deposited to have a thickness of 60 Å, and Alq$_3$ as an electron transport layer was deposited to have a thickness of 200 Å thereon. Finally, an organic electroluminescence device was manufactured by depositing lithium fluoride (LiF) to have a thickness of 10 Å on the electron transport layer to form an electron injection layer, and then depositing an aluminum (Al) negative electrode to have a thickness of 1,200 Å on the electron injection layer to form a negative electrode.

Meanwhile, all the organic compounds required for manufacturing an OLED device were subjected to vacuum sublimed purification under $10^{-6}$ to $10^{-8}$ torr for each material, and used for the manufacture of OLED.

<Experimental Example 3> Manufacture of Organic Light Emitting Device

A glass substrate, in which ITO was thinly coated to have a thickness of 1,500 Å, was ultrasonically washed with distilled water. When the washing with distilled water is finished, the glass substrate was ultrasonically washed with a solvent such as acetone, methanol, and isopropyl alcohol, dried and then was subjected to UVO treatment for 5 minutes by using UV in a UV washing machine. Thereafter, the substrate was transferred to a plasma washing machine (PT), and then was subjected to plasma treatment in a vacuum state for an ITO work function and in order to remove a residual film, and was transferred to a thermal deposition equipment for organic deposition.

As the common layers, the hole injection layer 4,4',4''-tris[2-naphthyl(phenyl)amino]triphenylamine (2-TNATA) and the hole transport layer N,N'-di(1-naphthyl)-N,N'-diphenyl-(1,1'-biphenyl)-4,4'-diamine (NPB) were formed on the ITO transparent electrode (positive electrode).

A light emitting layer was thermally vacuum deposited thereon as follows. The light emitting layer was deposited to have a thickness of 400 Å by pre-mixing a compound described in Chemical Formula 1 and a compound described in Chemical Formula 2 as hosts, and then was deposited from one supply source by doping the host with Ir(ppy)$_3$ as a green phosphorescent dopant in an amount of 7%. Thereafter, BCP as a hole blocking layer was deposited to have a thickness of 60 Å, and Alq₃ as an electron transport layer was deposited to have a thickness of 200 Å thereon. Finally, an organic electroluminescence device was manufactured by depositing lithium fluoride (LiF) to have a thickness of 10 Å on the electron transport layer to form an electron injection layer, and then depositing an aluminum (Al) negative electrode to have a thickness of 1,200 Å on the electron injection layer to form a negative electrode.

Meanwhile, all the organic compounds required for manufacturing an OLED device were subjected to vacuum sublimed purification under $10^{-6}$ to $10^{-8}$ torr for each material, and used for the manufacture of OLED.

The driving voltages and light emitting efficiencies of the organic electroluminescence devices according to Experimental Examples 2 and 3 are as follows.

For the organic electroluminescence device manufactured as described above, electroluminescence (EL) characteristics were measured by M7000 manufactured by McScience Inc., and based on the measurement result thereof, $T_{90}$ was measured by a lifetime measurement equipment (M6000) manufactured by McScience Inc. when the reference brightness was 6,000 cd/m².

Characteristics of the organic electroluminescence device of the present invention are as shown in the following Tables 25 to 27. For reference, Table 25 is an example in which the two host compounds in Experimental Example 2 were simultaneously deposited by using an individual supply source, Table 26 is an example in which the two light emitting compounds in Experimental Example 3 were pre-mixed, and then deposited by using one supply source, and Table 27 is an example in which the single host material in Experimental Example 2 was applied.

[Ref 1]

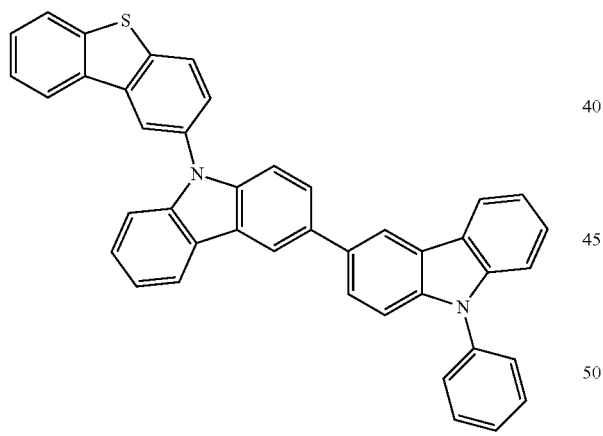

[Ref 2]

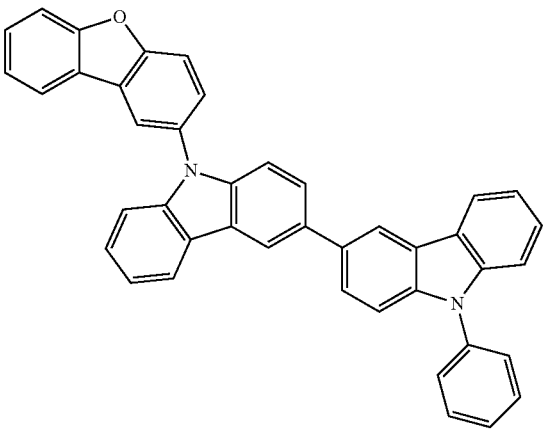

[Ref 3]

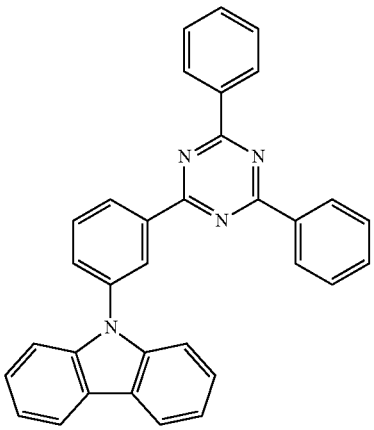

TABLE 25

|  | Light emitting layer compound | Mixture weight ratio | Driving voltage (V) | Efficiency (cd/A) | Color coordinate (x, y) | Lifetime ($T_{90}$) |
|---|---|---|---|---|---|---|
| Example 67 | 1-39:2-2 | 1:8 | 4.74 | 53.2 | (0.251, 0.714) | 201 |
| Example 68 |  | 1:5 | 4.72 | 58.2 | (0.241, 0.711) | 224 |
| Example 69 |  | 1:2 | 4.33 | 77.2 | (0.236, 0.717) | 384 |
| Example 70 |  | 1:1 | 4.42 | 76.8 | (0.247, 0.727) | 321 |
| Example 71 |  | 2:1 | 4.62 | 70.2 | (0.233, 0.714) | 280 |
| Example 72 |  | 5:1 | 4.37 | 69.3 | (0.243, 0.714) | 178 |
| Example 73 |  | 8:1 | 4.24 | 69.0 | (0.267, 0.712) | 164 |
| Example 74 | 1-39:2-3 | 1:2 | 4.37 | 73.2 | (0.241, 0.711) | 373 |
| Example 75 |  | 1:1 | 4.48 | 72.8 | (0.257, 0.729) | 319 |

TABLE 25-continued

| | Light emitting layer compound | Mixture weight ratio | Driving voltage (V) | Efficiency (cd/A) | Color coordinate (x, y) | Lifetime ($T_{90}$) |
|---|---|---|---|---|---|---|
| Example 76 | | 2:1 | 4.63 | 71.2 | (0.231, 0.714) | 271 |
| Example 77 | 1-40:2-2 | 1:2 | 4.36 | 76.2 | (0.241, 0.711) | 381 |
| Example 78 | | 1:1 | 4.49 | 74.8 | (0.247, 0.727) | 323 |
| Example 79 | | 2:1 | 4.64 | 72.1 | (0.253, 0.694) | 290 |
| Example 80 | 1-40:2-3 | 1:2 | 4.34 | 72.2 | (0.241, 0.711) | 331 |
| Example 81 | | 1:1 | 4.41 | 70.8 | (0.241, 0.714) | 291 |
| Example 82 | | 2:1 | 4.61 | 70.2 | (0.231, 0.711) | 259 |
| Example 83 | 1-67:2-2 | 1:2 | 4.34 | 77.2 | (0.246, 0.717) | 379 |
| Example 84 | | 1:1 | 4.41 | 76.7 | (0.251, 0.711) | 311 |
| Example 85 | | 2:1 | 4.66 | 73.1 | (0.241, 0.711) | 279 |
| Example 86 | 1-67:2-3 | 1:2 | 4.44 | 76.2 | (0.246, 0.697) | 340 |
| Example 87 | | 1:1 | 4.51 | 75.7 | (0.247, 0.727) | 311 |
| Example 88 | | 2:1 | 4.96 | 73.2 | (0.223, 0.714) | 262 |
| Example 89 | 1-46:2-2 | 1:2 | 4.46 | 71.2 | (0.261, 0.711) | 301 |
| Example 90 | | 1:1 | 4.59 | 70.7 | (0.241, 0.711) | 289 |
| Example 91 | | 2:1 | 4.61 | 69.1 | (0.256, 0.717) | 261 |
| Example 92 | 1-46:2-3 | 1:2 | 4.41 | 70.8 | (0.221, 0.691) | 291 |
| Example 93 | | 1:1 | 4.53 | 69.3 | (0.247, 0.727) | 269 |
| Example 94 | | 2:1 | 4.59 | 68.2 | (0.243, 0.714) | 252 |
| Example 95 | 1-41:2-2 | 1:2 | 4.46 | 70.8 | (0.267, 0.712) | 296 |
| Example 96 | | 1:1 | 4.60 | 70.4 | (0.241, 0.721) | 284 |
| Example 97 | | 2:1 | 4.61 | 68.8 | (0.252, 0.737) | 255 |
| Example 98 | 1-41:2-3 | 1:2 | 4.41 | 69.3 | (0.221, 0.691) | 285 |
| Example 99 | | 1:1 | 4.53 | 68.8 | (0.247, 0.687) | 261 |
| Example 100 | | 2:1 | 4.61 | 67.2 | (0.242, 0.714) | 247 |
| Comparative Example 8 | Ref 3:2-2 | 1:2 | 4.31 | 65.2 | (0.251, 0.711) | 210 |
| Comparative Example 9 | | 1:1 | 4.63 | 63.3 | (0.266, 0.707) | 192 |
| Comparative Example 10 | | 2:1 | 4.79 | 61.1 | (0.241, 0.691) | 182 |
| Comparative Example 11 | Ref 3:2-3 | 1:2 | 4.31 | 64.7 | (0.231, 0.721) | 199 |
| Comparative Example 12 | | 1:1 | 4.63 | 62.3 | (0.266, 0.687) | 189 |
| Comparative Example 13 | | 2:1 | 4.79 | 61.2 | (0.241, 0.711) | 172 |
| Comparative Example 14 | 1-39:Ref 1 | 1:2 | 4.33 | 70.3 | (0.246, 0.717) | 182 |
| Comparative Example 15 | | 1:1 | 4.42 | 69.6 | (0.247, 0.727) | 179 |
| Comparative Example 16 | | 2:1 | 4.62 | 68.1 | (0.253, 0.694) | 162 |
| Comparative Example 17 | 1-39:Ref 2 | 1:2 | 4.32 | 69.7 | (0.243, 0.714) | 178 |
| Comparative Example 18 | | 1:1 | 4.44 | 68.3 | (0.241, 0.711) | 174 |
| Comparative Example 19 | | 2:1 | 4.45 | 66.2 | (0.241, 0.711) | 159 |
| Comparative Example 20 | 1-40:Ref 1 | 1:2 | 4.36 | 69.7 | (0.241, 0.691) | 177 |
| Comparative Example 21 | | 1:1 | 4.49 | 69.1 | (0.257, 0.727) | 171 |
| Comparative Example 22 | | 2:1 | 4.64 | 68.3 | (0.243, 0.714) | 167 |
| Comparative Example 23 | 1-40:Ref 2 | 1:2 | 4.44 | 68.8 | (0.241, 0.714) | 166 |
| Comparative Example 24 | | 1:1 | 4.45 | 67.9 | (0.241, 0.711) | 165 |
| Comparative Example 25 | | 2:1 | 4.36 | 66.6 | (0.246, 0.697) | 161 |
| Comparative Example 26 | 1-67:Ref 1 | 1:2 | 4.46 | 69.3 | (0.266, 0.717) | 185 |
| Comparative Example 27 | | 1:1 | 4.59 | 69.2 | (0.241, 0.714) | 179 |
| Comparative Example 28 | | 2:1 | 4.61 | 68.1 | (0.241, 0.711) | 171 |
| Comparative Example 29 | 1-67:Ref 2 | 1:2 | 4.41 | 68.6 | (0.247, 0.727) | 183 |
| Comparative Example 30 | | 1:1 | 4.53 | 67.2 | (0.223, 0.694) | 175 |
| Comparative Example 31 | | 2:1 | 4.59 | 66.1 | (0.241, 0.714) | 161 |
| Comparative Example 32 | 1-46:Ref 1 | 1:2 | 4.46 | 69.3 | (0.241, 0.711) | 180 |

TABLE 25-continued

| | Light emitting layer compound | Mixture weight ratio | Driving voltage (V) | Efficiency (cd/A) | Color coordinate (x, y) | Lifetime ($T_{90}$) |
|---|---|---|---|---|---|---|
| Comparative Example 33 | | 1:1 | 4.59 | 68.2 | (0.251, 0.691) | 177 |
| Comparative Example 34 | | 2:1 | 4.61 | 67.1 | (0.246, 0.717) | 163 |
| Comparative Example 35 | 1-46:Ref 2 | 1:2 | 4.61 | 68.2 | (0.251, 0.711) | 172 |
| Comparative Example 36 | | 1:1 | 4.41 | 66.4 | (0.247, 0.727) | 168 |
| Comparative Example 37 | | 2:1 | 4.53 | 65.1 | (0.243, 0.694) | 161 |
| Comparative Example 38 | 1-41:Ref 1 | 1:2 | 4.47 | 69.1 | (0.241, 0.721) | 175 |
| Comparative Example 39 | | 1:1 | 4.44 | 67.9 | (0.251, 0.693) | 172 |
| Comparative Example 40 | | 2:1 | 4.63 | 67.0 | (0.246, 0.711) | 158 |
| Comparative Example 41 | 1-41:Ref 2 | 1:2 | 4.61 | 67.7 | (0.251, 0.721) | 167 |
| Comparative Example 42 | | 1:1 | 4.35 | 66.1 | (0.237, 0.737) | 163 |
| Comparative Example 43 | | 2:1 | 4.56 | 64.7 | (0.243, 0.699) | 155 |

TABLE 26

| | Light emitting layer compound | Mixture weight ratio | Driving voltage (V) | Efficiency (cd/A) | Color coordinate (x, y) | Lifetime ($T_{90}$) |
|---|---|---|---|---|---|---|
| Example 101 | 1-39:2-2 | 1:8 | 4.72 | 53.7 | (0.253, 0.714) | 234 |
| Example 102 | | 1:5 | 4.68 | 58.9 | (0.241, 0.691) | 252 |
| Example 103 | | 1:2 | 4.33 | 77.2 | (0.256, 0.717) | 513 |
| Example 104 | | 1:1 | 4.42 | 76.8 | (0.247, 0.727) | 451 |
| Example 105 | | 2:1 | 4.62 | 70.2 | (0.243, 0.714) | 413 |
| Example 106 | | 5:1 | 4.37 | 69.3 | (0.257, 0.737) | 286 |
| Example 107 | | 8:1 | 4.24 | 69.0 | (0.243, 0.732) | 262 |
| Example 108 | 1-39:2-3 | 1:2 | 4.37 | 73.2 | (0.241, 0.691) | 401 |
| Example 109 | | 1:1 | 4.48 | 72.8 | (0.257, 0.729) | 449 |
| Example 110 | | 2:1 | 4.63 | 71.2 | (0.241, 0.714) | 401 |
| Example 111 | 1-40:2-2 | 1:2 | 4.36 | 76.2 | (0.241, 0.711) | 507 |
| Example 112 | | 1:1 | 4.49 | 74.8 | (0.247, 0.727) | 453 |
| Example 113 | | 2:1 | 4.64 | 72.1 | (0.233, 0.714) | 423 |
| Example 114 | 1-40:2-3 | 1:2 | 4.34 | 72.2 | (0.241, 0.691) | 461 |
| Example 115 | | 1:1 | 4.41 | 70.8 | (0.241, 0.714) | 423 |
| Example 116 | | 2:1 | 4.61 | 70.2 | (0.231, 0.711) | 381 |
| Example 117 | 1-67:2-2 | 1:2 | 4.34 | 77.2 | (0.246, 0.717) | 503 |
| Example 118 | | 1:1 | 4.41 | 76.7 | (0.241, 0.694) | 440 |
| Example 119 | | 2:1 | 4.66 | 73.1 | (0.231, 0.711) | 409 |
| Example 120 | 1-67:2-3 | 1:2 | 4.44 | 76.2 | (0.246, 0.717) | 470 |
| Example 121 | | 1:1 | 4.51 | 75.7 | (0.247, 0.727) | 455 |
| Example 122 | | 2:1 | 4.96 | 73.2 | (0.253, 0.714) | 396 |
| Example 123 | 1-46:2-2 | 1:2 | 4.46 | 71.2 | (0.241, 0.691) | 430 |
| Example 124 | | 1:1 | 4.59 | 70.7 | (0.241, 0.711) | 413 |
| Example 125 | | 2:1 | 4.61 | 69.1 | (0.236, 0.717) | 396 |
| Example 126 | 1-46:2-3 | 1:2 | 4.41 | 70.8 | (0.241, 0.711) | 421 |
| Example 127 | | 1:1 | 4.53 | 69.3 | (0.257, 0.727) | 393 |
| Example 128 | | 2:1 | 4.59 | 68.2 | (0.243, 0.694) | 382 |
| Example 129 | 1-41:2-2 | 1:2 | 4.46 | 70.7 | (0.241, 0.693) | 425 |
| Example 130 | | 1:1 | 4.62 | 70.2 | (0.241, 0.721) | 408 |
| Example 131 | | 2:1 | 4.65 | 68.8 | (0.236, 0.717) | 391 |
| Example 132 | 1-14:2-3 | 1:2 | 4.41 | 70.2 | (0.241, 0.711) | 415 |
| Example 133 | | 1:1 | 4.55 | 69.0 | (0.257, 0.737) | 387 |
| Example 134 | | 2:1 | 4.60 | 67.9 | (0.243, 0.732) | 377 |
| Example 135 | 1-39:2-7 | 1:2 | 4.32 | 70.2 | (0.263, 0.704) | 425 |
| Example 136 | | 1:1 | 4.46 | 72.5 | (0.251, 0.683) | 386 |
| Example 137 | 1-39:2-9 | 1:2 | 4.42 | 65.4 | (0.271, 0.701) | 395 |
| Example 138 | | 1:1 | 4.63 | 67.2 | (0.266, 0.697) | 369 |
| Example 139 | 1-39:2-11 | 1:2 | 4.72 | 67.5 | (0.271, 0.705) | 415 |
| Example 140 | | 1:1 | 4.85 | 69.4 | (0.267, 0.682) | 387 |
| Example 141 | 1-46:2-7 | 1:2 | 4.46 | 64.2 | (0.263, 0.662) | 432 |
| Example 142 | | 1:1 | 4.69 | 65.5 | (0.253, 0.672) | 385 |
| Comparative Example 44 | Ref 3:2-2 | 1:2 | 4.31 | 65.2 | (0.241, 0.711) | 250 |

TABLE 26-continued

| | Light emitting layer compound | Mixture weight ratio | Driving voltage (V) | Efficiency (cd/A) | Color coordinate (x, y) | Lifetime ($T_{90}$) |
|---|---|---|---|---|---|---|
| Comparative Example 45 | | 1:1 | 4.63 | 63.3 | (0.256, 0.697) | 241 |
| Comparative Example 46 | | 2:1 | 4.79 | 61.1 | (0.241, 0.711) | 234 |
| Comparative Example 47 | Ref 3:2-3 | 1:2 | 4.31 | 64.7 | (0.231, 0.711) | 243 |
| Comparative Example 48 | | 1:1 | 4.63 | 62.3 | (0.246, 0.717) | 233 |
| Comparative Example 49 | | 2:1 | 4.79 | 61.2 | (0.251, 0.691) | 220 |
| Comparative Example 50 | 1-39:Ref 1 | 1:2 | 4.33 | 70.3 | (0.246, 0.717) | 249 |
| Comparative Example 51 | | 1:1 | 4.42 | 69.6 | (0.247, 0.727) | 229 |
| Comparative Example 52 | | 2:1 | 4.62 | 68.1 | (0.243, 0.694) | 221 |
| Comparative Example 53 | 1-39:Ref 2 | 1:2 | 4.32 | 69.7 | (0.233, 0.714) | 231 |
| Comparative Example 54 | | 1:1 | 4.44 | 68.3 | (0.241, 0.711) | 221 |
| Comparative Example 55 | | 2:1 | 4.45 | 66.2 | (0.241, 0.691) | 213 |
| Comparative Example 56 | 1-40:Ref 1 | 1:2 | 4.36 | 69.7 | (0.231, 0.711) | 235 |
| Comparative Example 57 | | 1:1 | 4.49 | 69.1 | (0.247, 0.727) | 220 |
| Comparative Example 58 | | 2:1 | 4.64 | 68.3 | (0.243, 0.714) | 210 |
| Comparative Example 59 | 1-40:Ref 2 | 1:2 | 4.44 | 68.8 | (0.251, 0.694) | 234 |
| Comparative Example 60 | | 1:1 | 4.45 | 67.9 | (0.241, 0.711) | 221 |
| Comparative Example 61 | | 2:1 | 4.36 | 66.6 | (0.246, 0.717) | 215 |
| Comparative Example 62 | 1-67:Ref 1 | 1:2 | 4.46 | 69.3 | (0.236, 0.697) | 229 |
| Comparative Example 63 | | 1:1 | 4.59 | 69.2 | (0.241, 0.714) | 215 |
| Comparative Example 64 | | 2:1 | 4.61 | 68.1 | (0.251, 0.711) | 210 |
| Comparative Example 65 | 1-67:Ref 2 | 1:2 | 4.41 | 68.6 | (0.247, 0.727) | 245 |
| Comparative Example 66 | | 1:1 | 4.53 | 67.2 | (0.243, 0.694) | 234 |
| Comparative Example 67 | | 2:1 | 4.59 | 66.1 | (0.241, 0.714) | 229 |
| Comparative Example 68 | 1-46:Ref 1 | 1:2 | 4.46 | 69.3 | (0.251, 0.711) | 241 |
| Comparative Example 69 | | 1:1 | 4.59 | 68.2 | (0.241, 0.691) | 235 |
| Comparative Example 70 | | 2:1 | 4.61 | 67.1 | (0.246, 0.717) | 221 |
| Comparative Example 71 | 1-46:Ref 2 | 1:2 | 4.61 | 68.2 | (0.241, 0.711) | 231 |
| Comparative Example 72 | | 1:1 | 4.41 | 66.4 | (0.237, 0.727) | 227 |
| Comparative Example 73 | | 2:1 | 4.53 | 65.1 | (0.243, 0.714) | 219 |
| Comparative Example 74 | 1-41:Ref 1 | 1:2 | 4.49 | 69.0 | (0.221, 0.721) | 236 |
| Comparative Example 75 | | 1:1 | 4.62 | 67.9 | (0.231, 0.621) | 230 |
| Comparative Example 76 | | 2:1 | 4.63 | 66.6 | (0.256, 0.727) | 216 |
| Comparative Example 77 | 1-41:Ref 2 | 1:2 | 4.64 | 67.7 | (0.251, 0.731) | 225 |
| Comparative Example 78 | | 1:1 | 4.43 | 66.0 | (0.257, 0.697) | 222 |
| Comparative Example 79 | | 2:1 | 4.55 | 64.7 | (0.243, 0.694) | 214 |

TABLE 27

| | Light emitting layer compound | Driving voltage (V) | Efficiency (cd/A) | Color coordinate (x, y) | Lifetime ($T_{90}$) |
|---|---|---|---|---|---|
| Comparative Example 80 | 2-2 | 4.75 | 51.2 | (0.254, 0.724) | 121 |
| Comparative Example 81 | 2-3 | 4.83 | 50.9 | (0.233, 0.703) | 112 |
| Comparative Example 82 | Ref 1 | 4.83 | 52.4 | (0.258, 0.727) | 95 |
| Comparative Example 83 | Ref 2 | 4.93 | 51.5 | (0.247, 0.737) | 83 |
| Comparative Example 84 | Ref 3 | 4.81 | 55.9 | (0.246, 0.727) | 104 |

The organic light emitting device of the present invention includes a light emitting layer which uses a host and a phosphorescent dopant, and the host is composed of a host compound (p-n type) in which two or more compounds are mixed, and as a result, the organic light emitting device of the present invention has better lifetime characteristics than an organic light emitting device including a host compound composed of a single compound in the related art.

In particular, the p-n type host of the present invention has an advantage in that the ratio of the host may be adjusted to increase the light emitting characteristics, and the advantage is a result which can be achieved by appropriately combining a P host having a good hole mobility and an n host having a good electron mobility.

Further, in the present invention, the light emitting host composed of plural species of compounds was deposited by pre-mixing mixtures, and then forming the host by one deposition supply source. In this case, since the deposition is not conducted several times, the uniformity and thin film characteristics of the thin film may be improved, the process procedures may be simplified, the costs may be reduced, and a device in which the efficiency and lifetime have been improved may be formed.

The invention claimed is:

1. A hetero-cyclic compound represented by the following Chemical Formula 1:

[Chemical Formula 1]

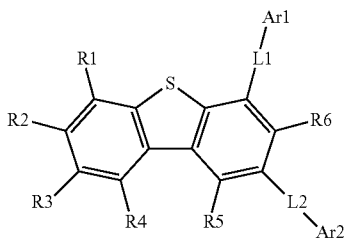

in Chemical Formula 1,

L1 and L2 are the same as or different from each other, and each independently a direct bond or a substituted or unsubstituted $C_6$ to $C_{60}$ arylene group, Ar1 is selected from the group consisting of a substituted or unsubstituted pyridine group; a substituted or unsubstituted pyrimidine group; a substituted or unsubstituted triazine group; a substituted or unsubstituted quinoline group; a substituted or unsubstituted quinazoline group; a substituted or unsubstituted phenanthroline group; and a substituted or unsubstituted benzoimidazole group, Ar2 is represented by any one of the following Chemical Formulae 3 and 4,

[Chemical Formula 3]

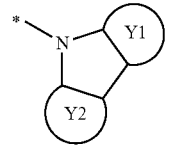

[Chemical Formula 4]

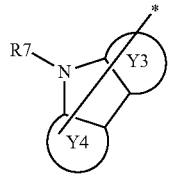

in Chemical Formulae 3 and 4,

Y1 to Y4 are the same as or different from each other, and each independently a substituted or unsubstituted $C_6$ to $C_{60}$ aromatic hydrocarbon ring; or a substituted or unsubstituted $C_2$ to $C_{60}$ aromatic hetero ring, R1 to R7 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups combine with each other to form a substituted or unsubstituted aliphatic or aromatic hydrocarbon ring, and R, R', and R" are the same as or different from each other, and are each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

2. The hetero-cyclic compound of claim 1, wherein Chemical Formula 3 is represented by any one of the following structural formulae:

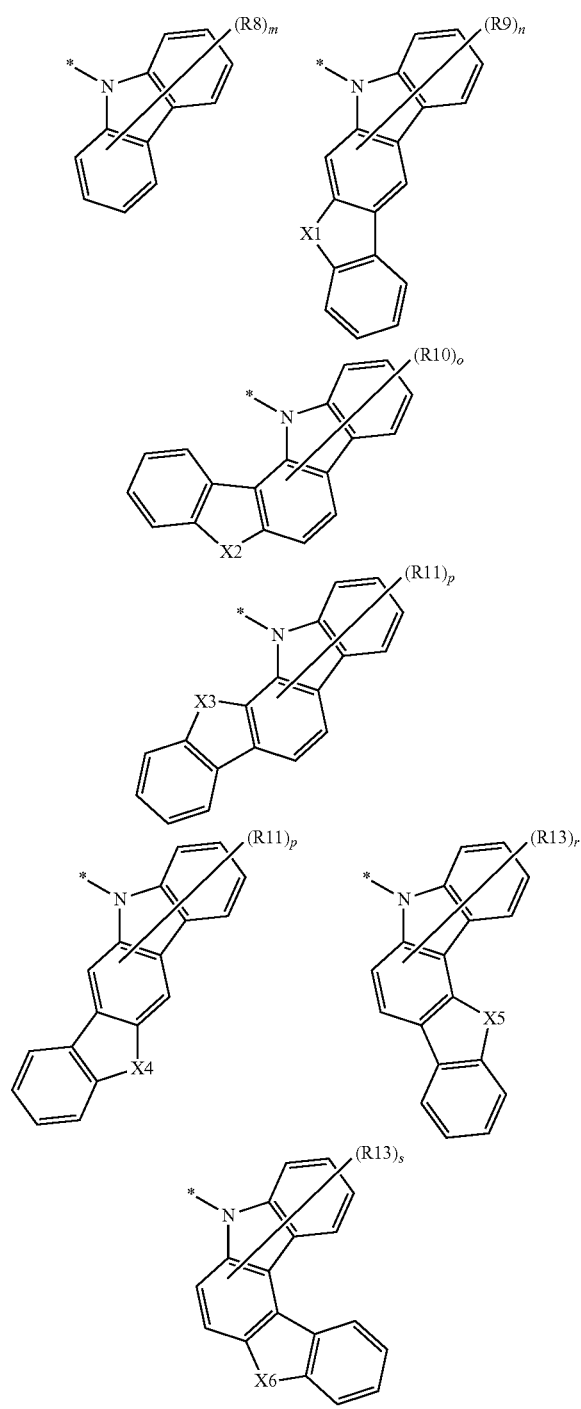

in the structural formulae, X1 to X6 are the same as or different from each other, and each independently NR, S, O, or CR'R", R8 to R14 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups combine with each other to form a substituted or unsubstituted aliphatic or aromatic hydrocarbon ring, R, R', and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, and m is an integer of 0 to 8, and n, o, p, q, r, and s are each independently an integer of 0 to 6.

3. The hetero-cyclic compound of claim 1, wherein Chemical Formula 4 is represented by any one of the following structural formulae:

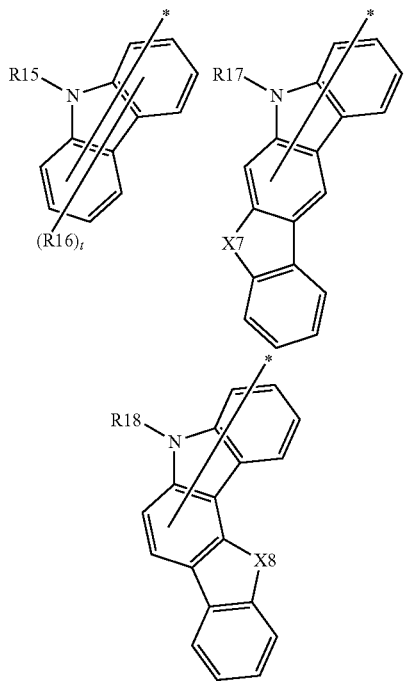

in the structural formulae, X7 and X8 are the same as or different from each other, and each independently NR, S, O, or CR'R", R15 to R18 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups combine with each other to form a substituted or unsubstituted aliphatic or aromatic hydrocarbon ring, and R, R', and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, and t is an integer of 0 to 7.

4. The hetero-cyclic compound of claim 1, wherein Chemical Formula 1 is represented by any one of the following Chemical Formulae 5 to 10:

[Chemical Formula 5]

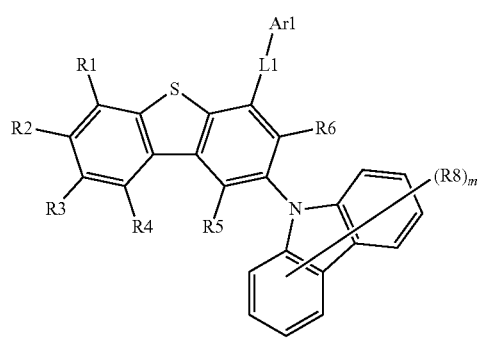

[Chemical Formula 6]

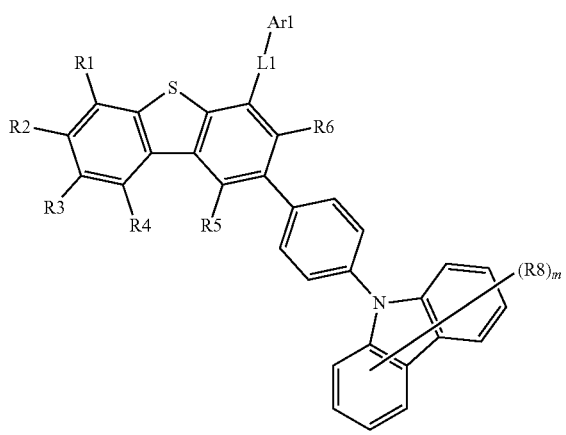

[Chemical Formula 7]

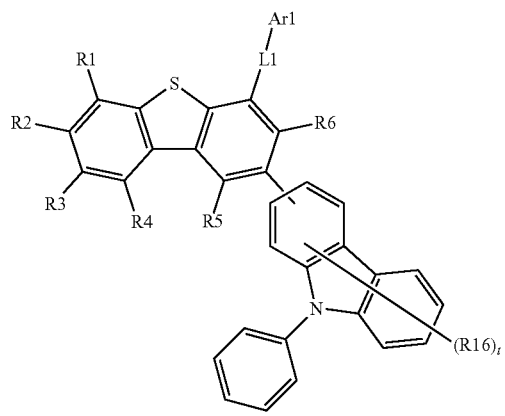

[Chemical Formula 8]

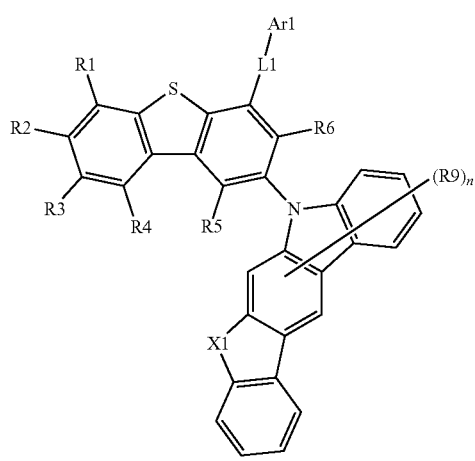

[Chemical Formula 9]

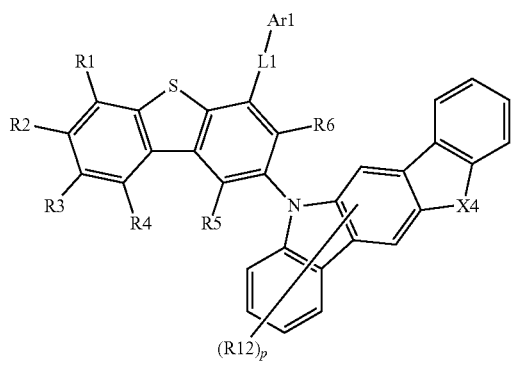

-continued

[Chemical Formula 10]

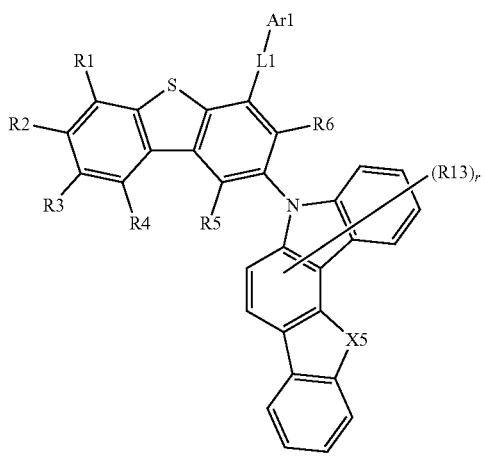

in Chemical Formulae 5 to 10,
the definitions of R1 to R6, L1, and Ar1 are the same as those in Chemical Formula 1,
X1, X4, and X5 are the same as or different from each other, and each independently NR, S, O, or CR'R",
R8, R9, R12, R13, and R16 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups combine with each other to form a substituted or unsubstituted aliphatic or aromatic hydrocarbon ring,
R, R', and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, and
m is an integer of 0 to 8, n, q, and r are each independently an integer of 0 to 6, and t is an integer of 0 to 7.

5. The hetero-cyclic compound of claim 1, wherein R1 to R6 of Chemical Formula 1 are each independently hydrogen or deuterium.

6. The hetero-cyclic compound of claim 2, wherein R8 to R14 of the structural formulae are each independently hydrogen; deuterium; a substituted or unsubstituted $C_6$ to $C_{60}$ aryl group; or a substituted or unsubstituted $C_2$ to $C_{60}$ heteroaryl group.

7. The hetero-cyclic compound of claim 3, wherein R5 to R18 of the structural formulae are each independently hydrogen; deuterium; a substituted or unsubstituted $C_6$ to $C_{60}$ aryl group; or a substituted or unsubstituted $C_2$ to $C_{60}$ heteroaryl group.

8. The organic light emitting device of claim 1, wherein Chemical Formula 1 is represented by any one of the following compounds:

1-17

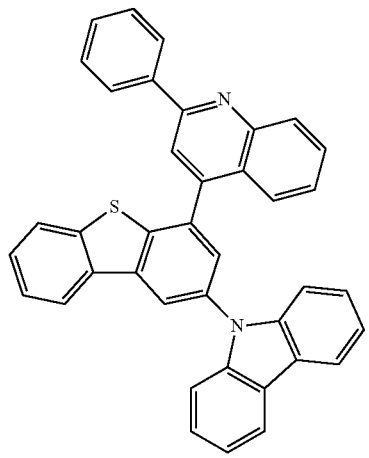

1-18

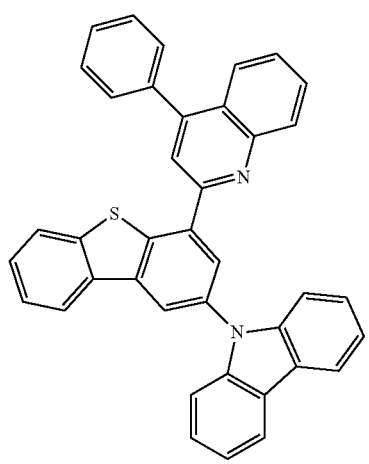

1-19

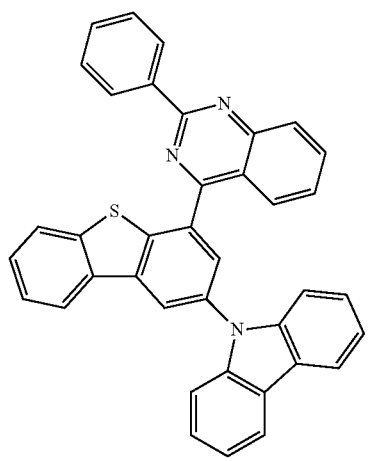

1-20
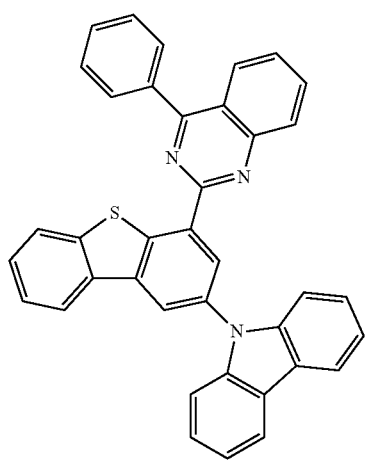
1-21
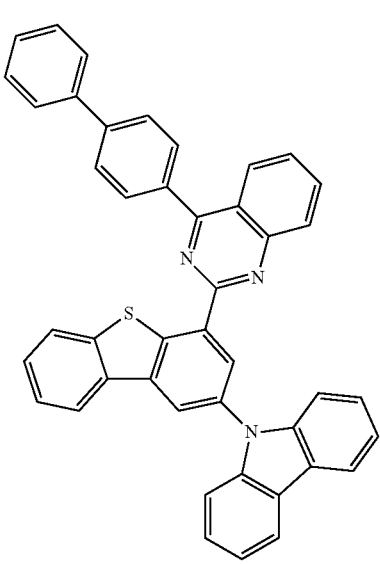
1-22
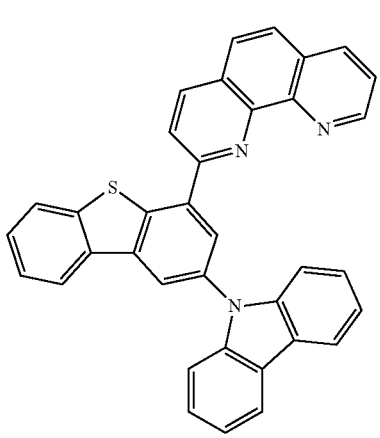
1-29
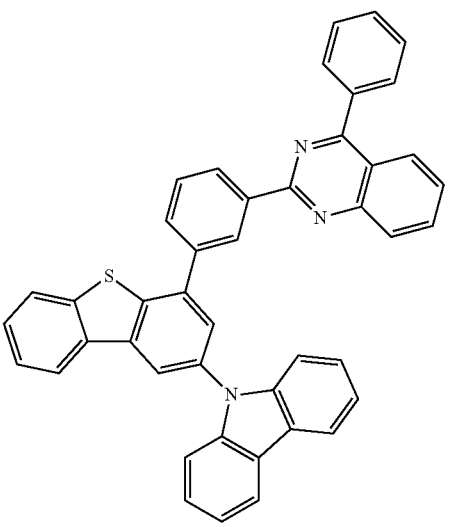
1-30
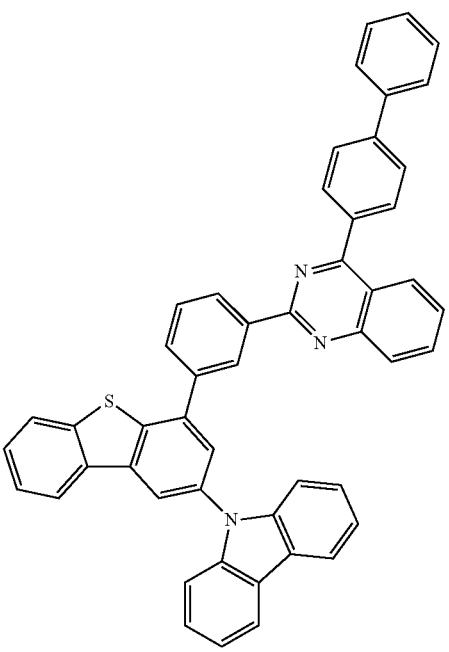

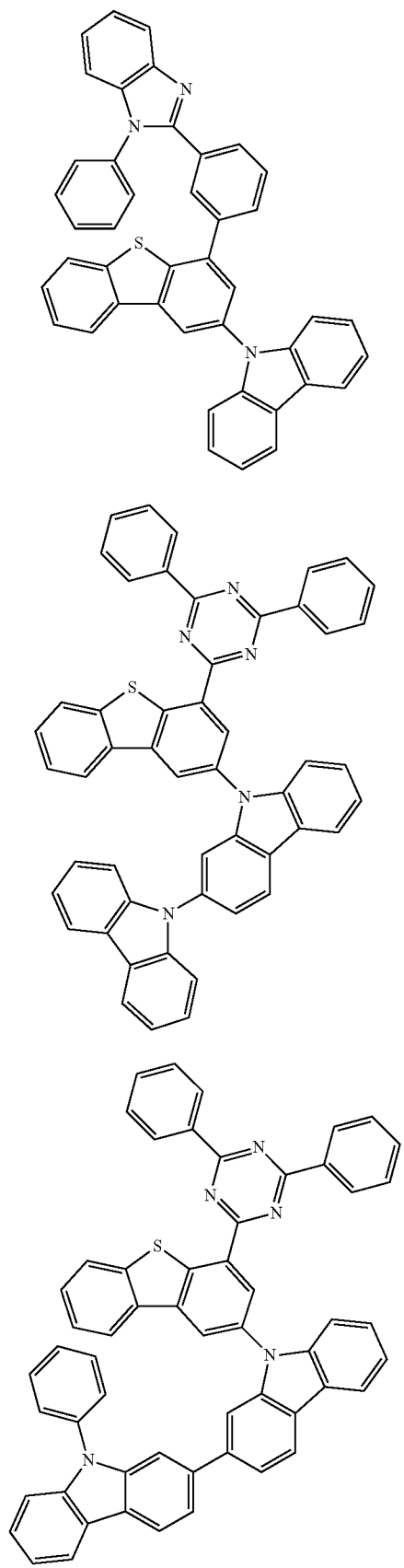
1-31
1-53
1-54
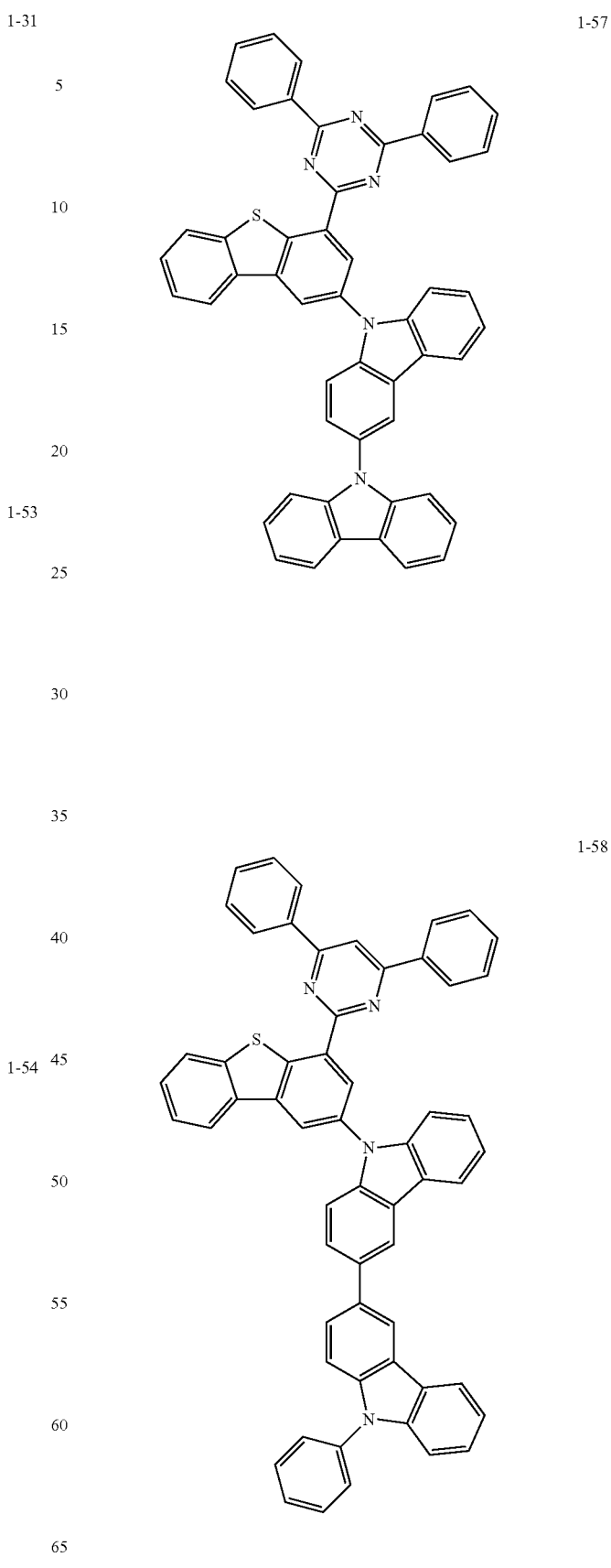
1-57
1-58

1-59
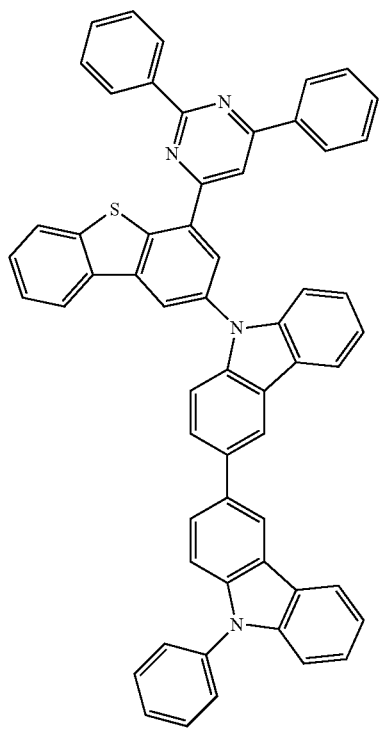
1-60
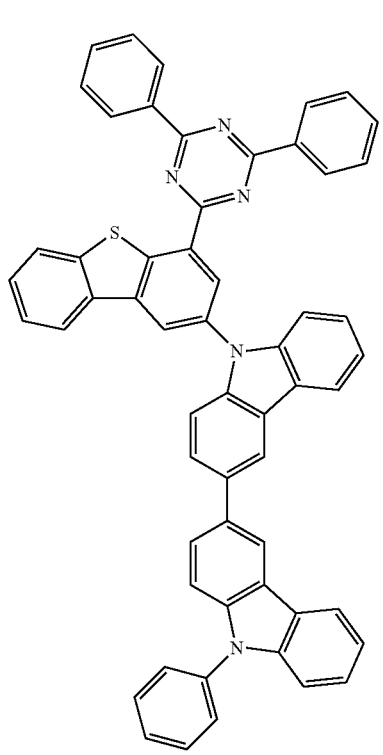
1-61
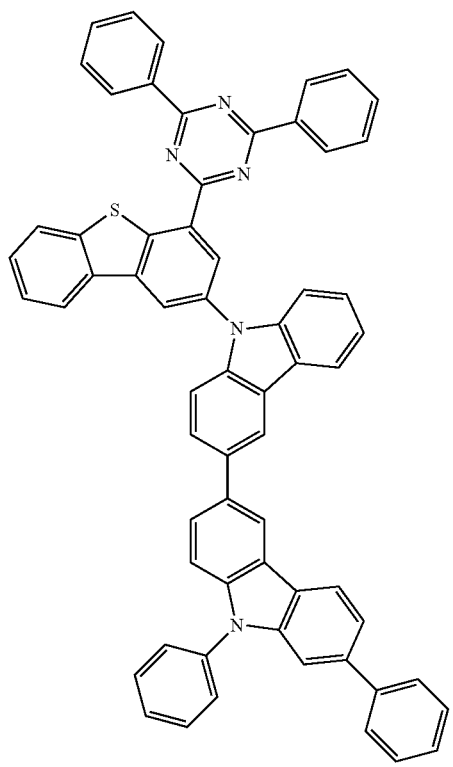
1-62
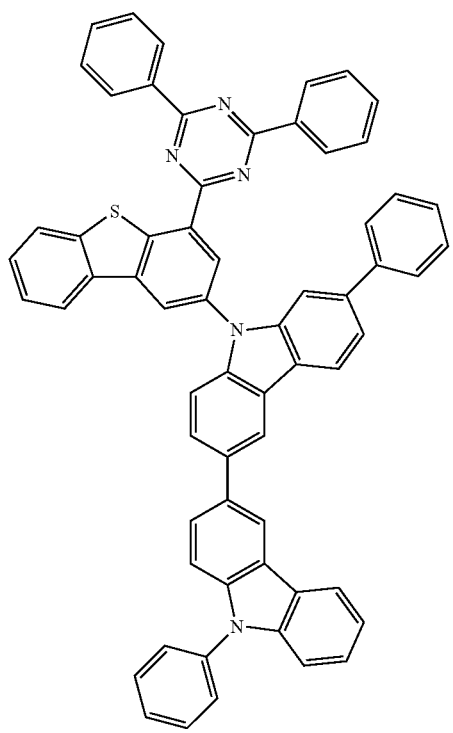

287
-continued
1-65
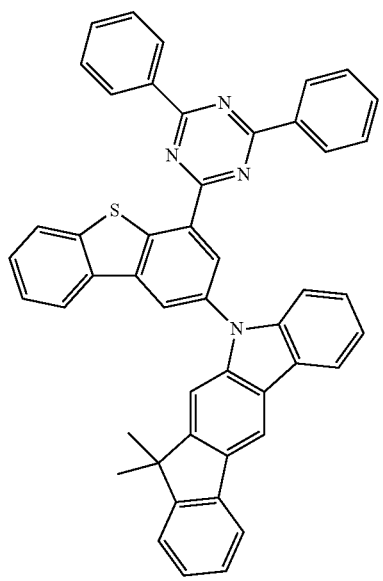
1-66
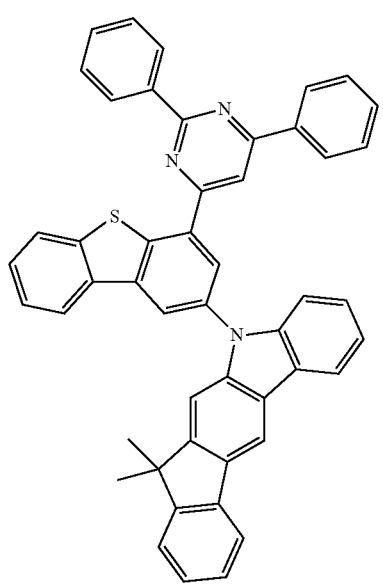
288
-continued
1-67
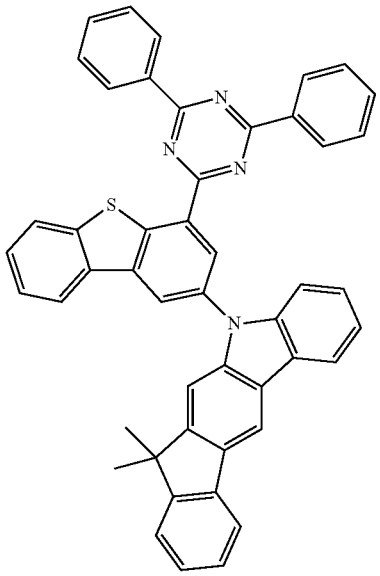
1-68
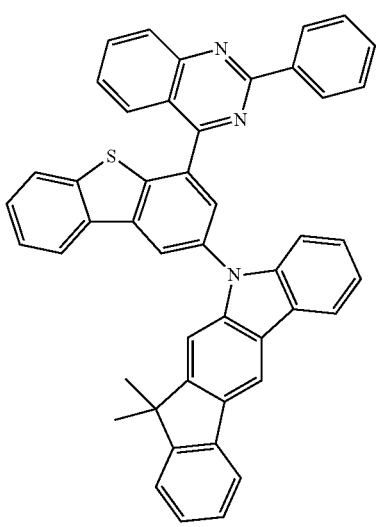

1-69
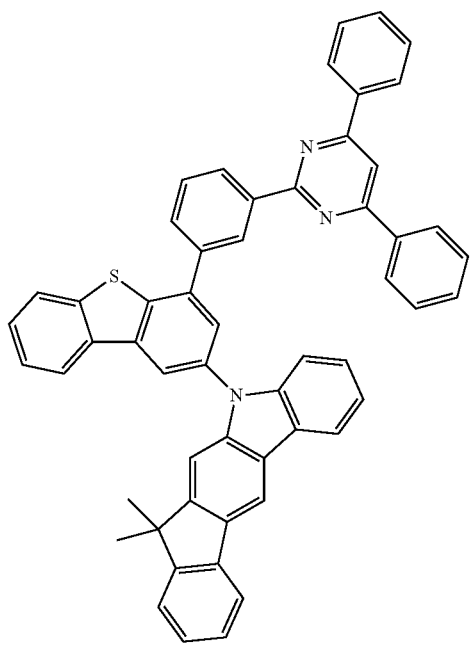
1-71
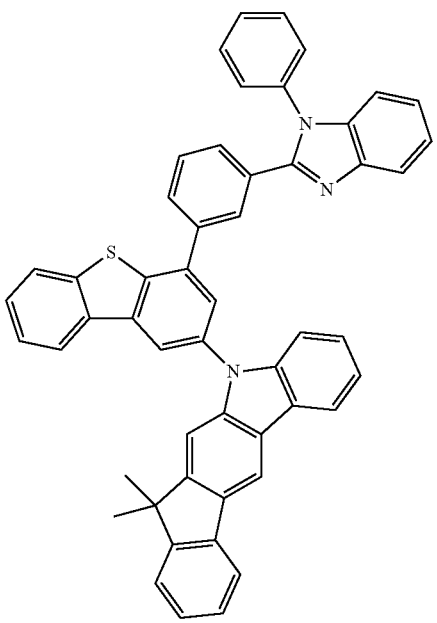
1-70
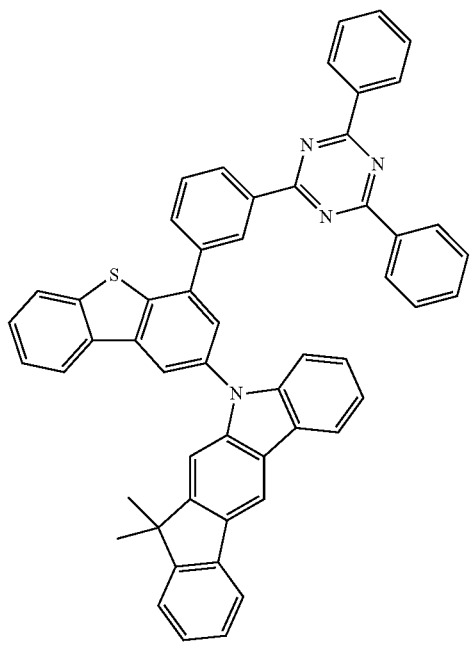
1-72
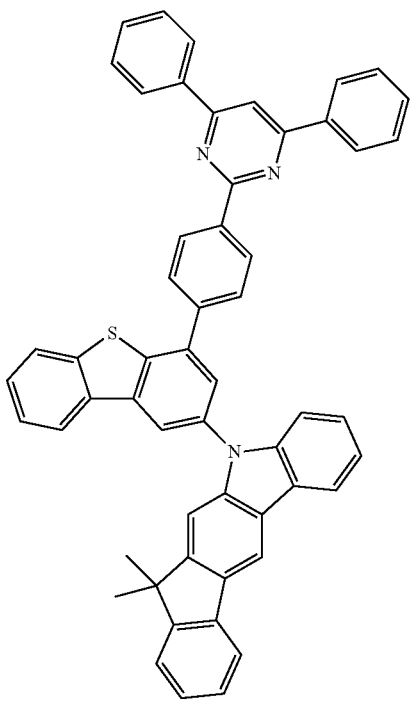

1-73
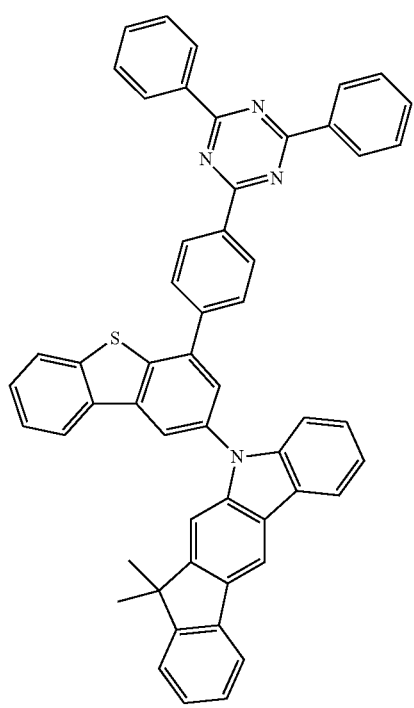
1-74
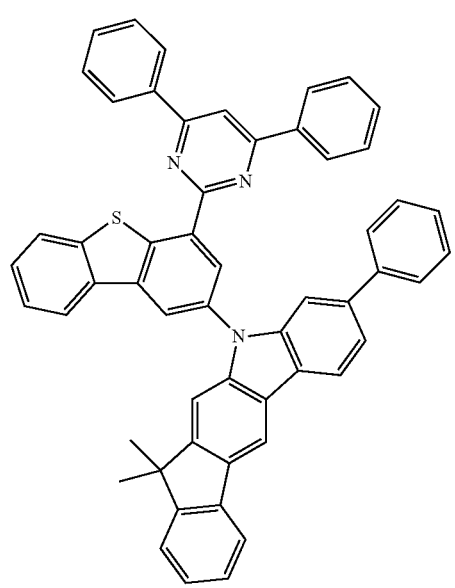
1-75
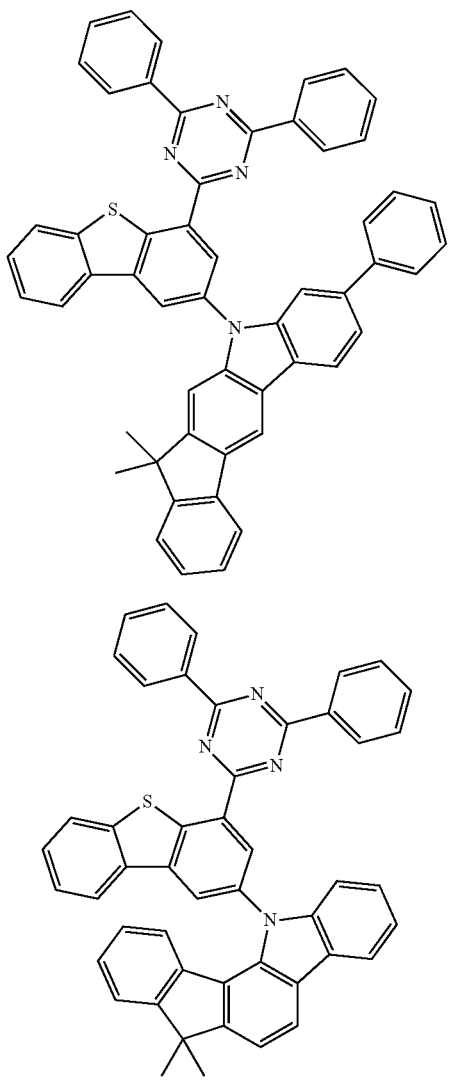
1-76
1-77
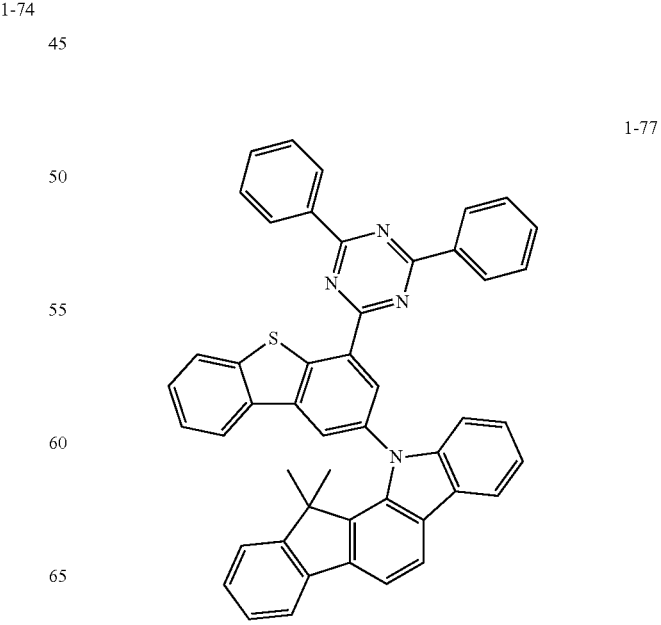

1-78
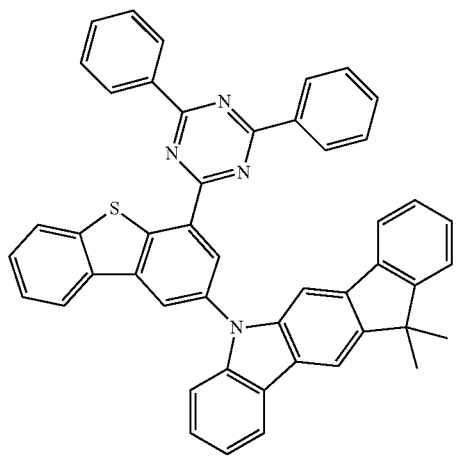
1-79
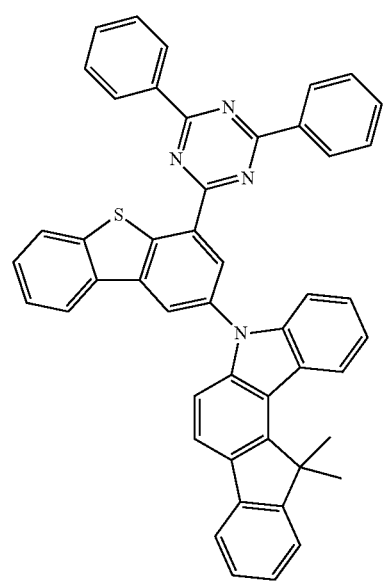
1-80
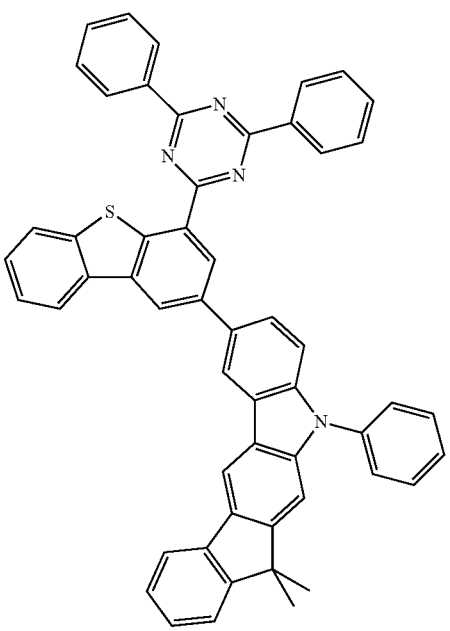
1-81
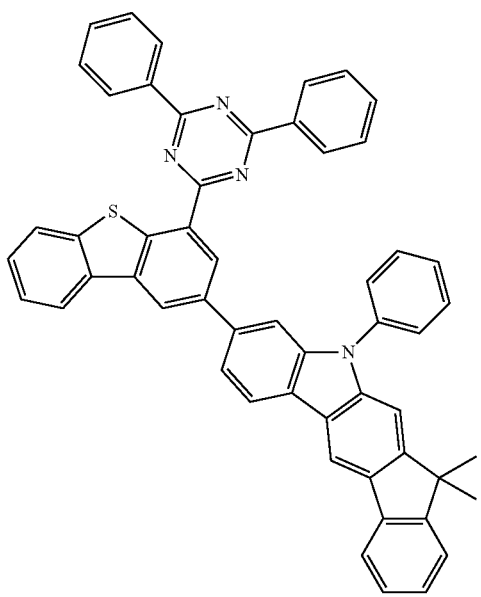
1-82
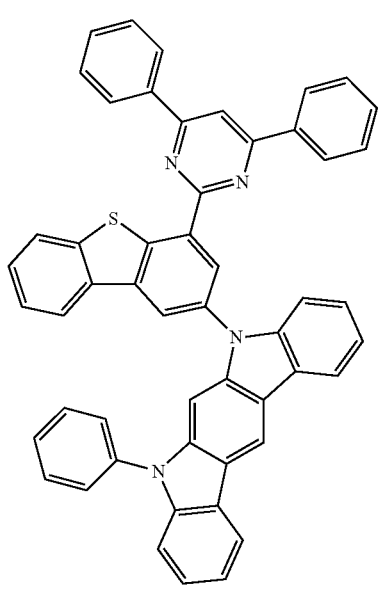

-continued
1-83
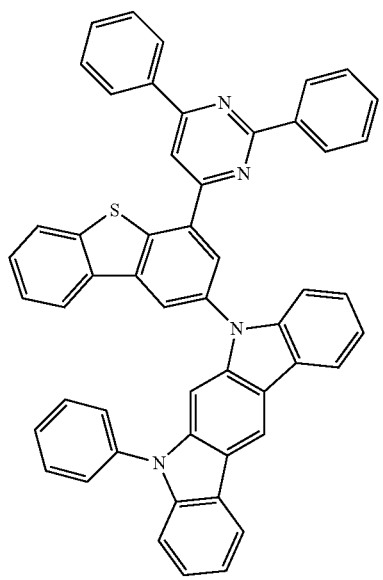
1-84
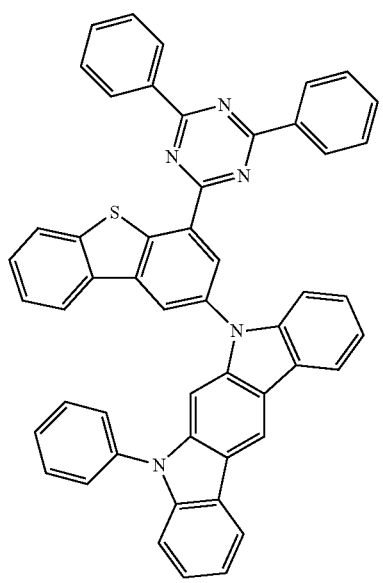
1-85
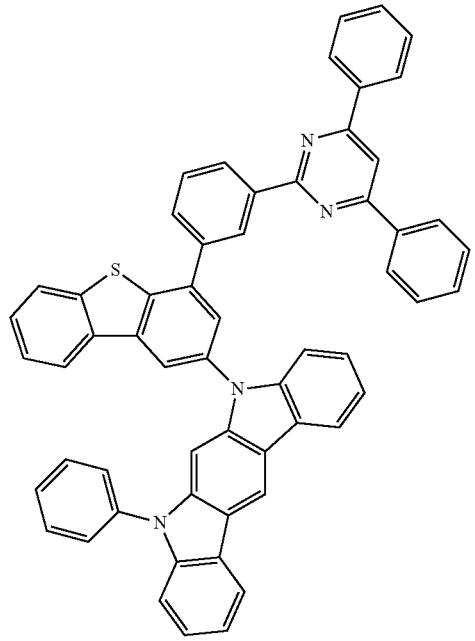
1-86
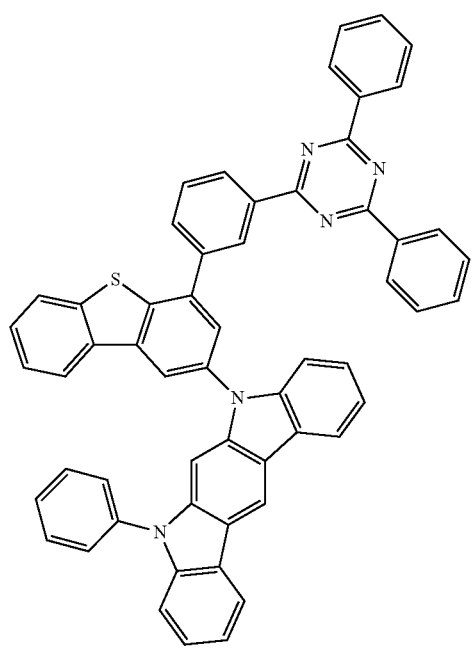

1-87
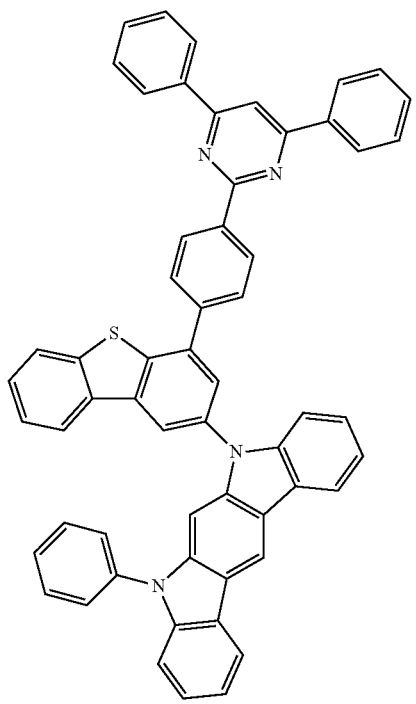
1-89
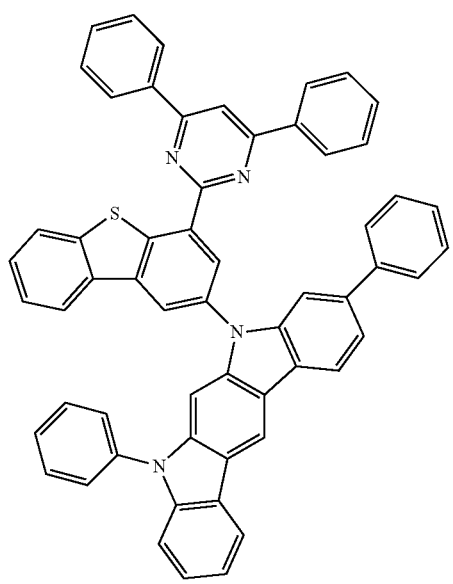
1-88
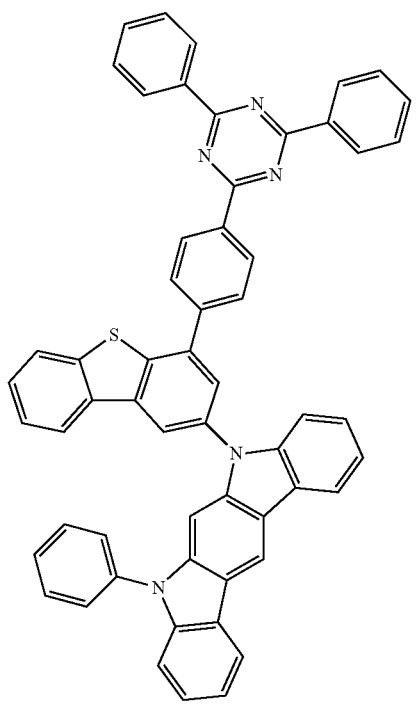
1-91
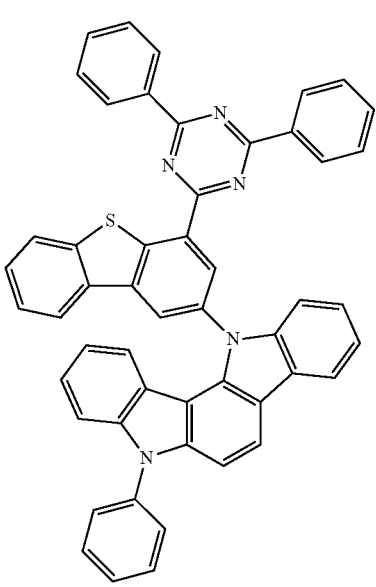

1-92
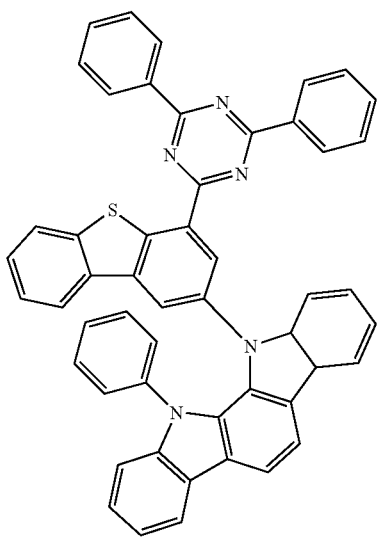
1-93
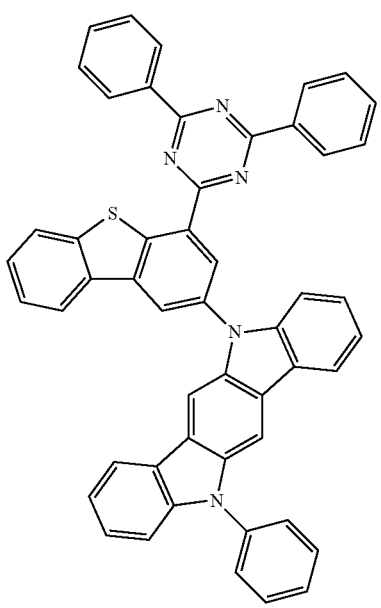
1-94
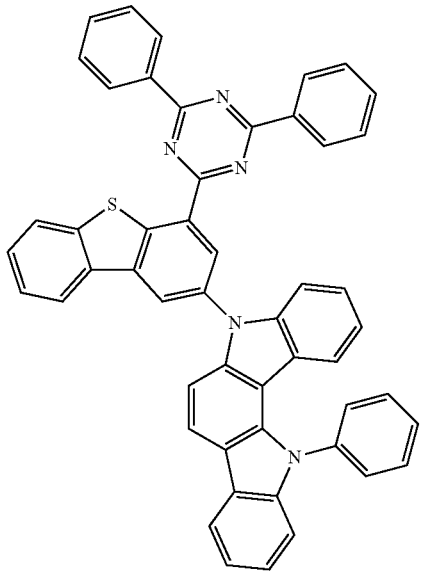
1-95
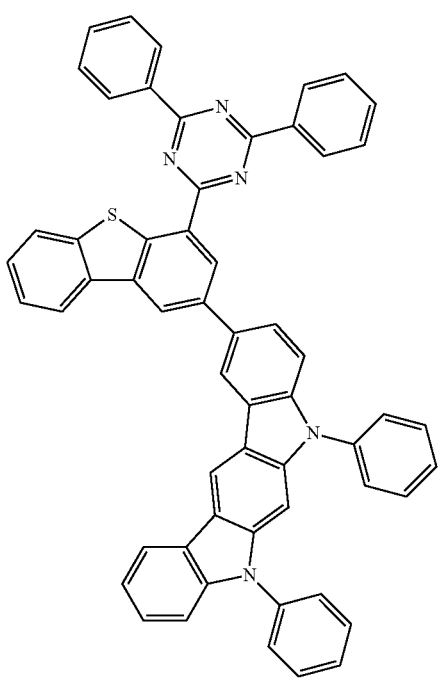

301
-continued
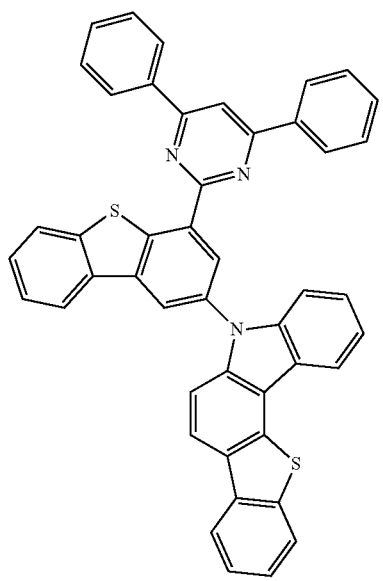
1-96
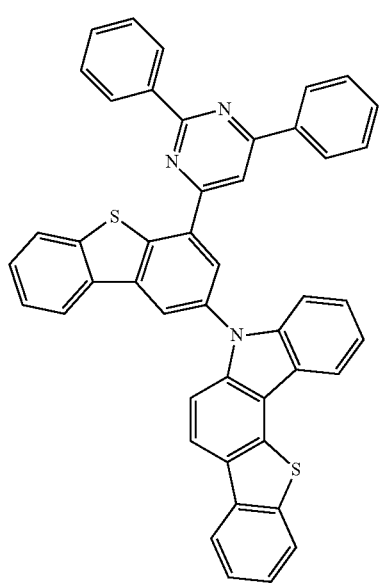
1-97
302
-continued
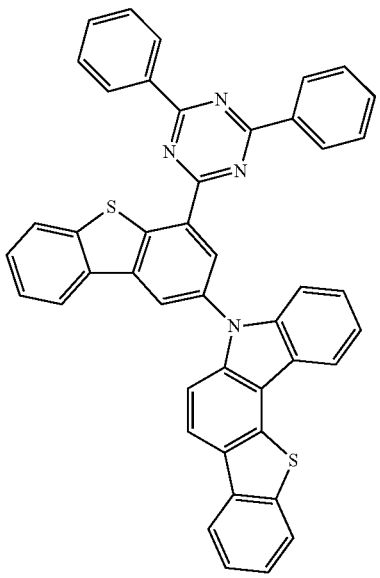
1-98
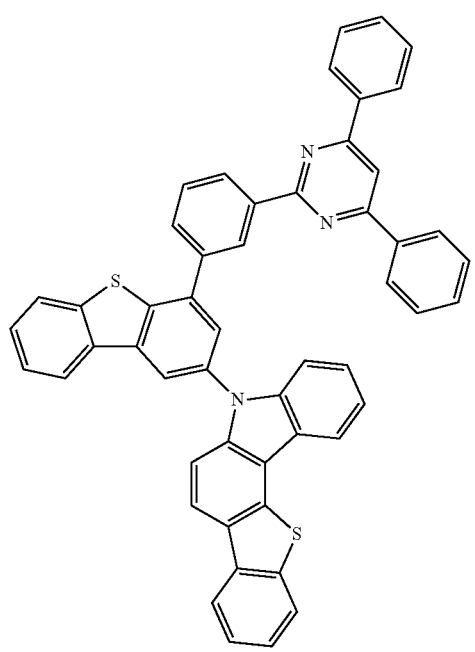
1-99

303
-continued
1-100
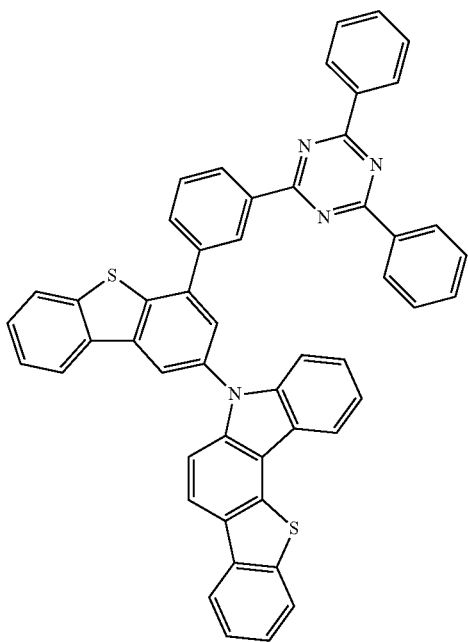
1-101
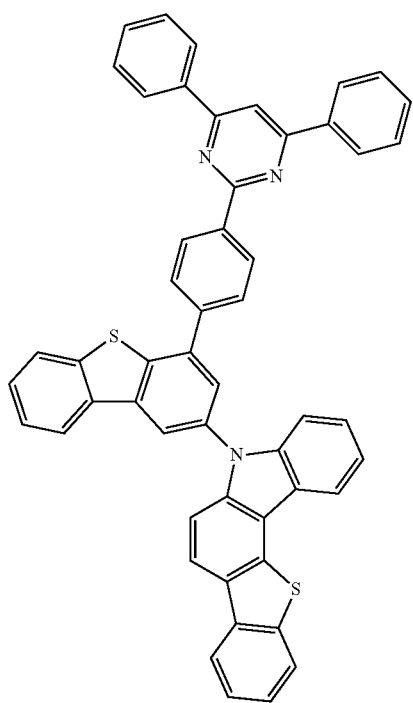
304
-continued
1-102
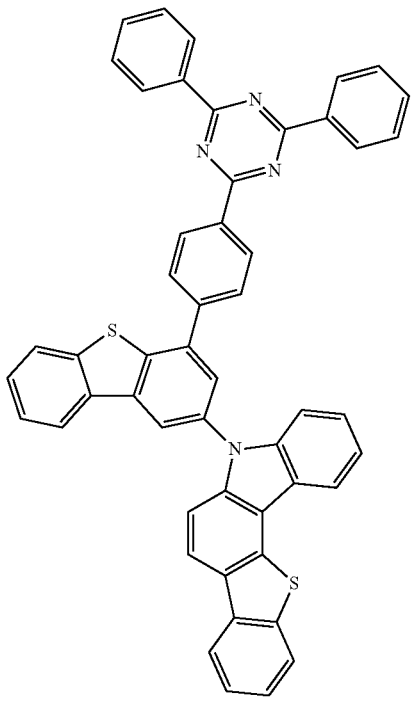
1-103
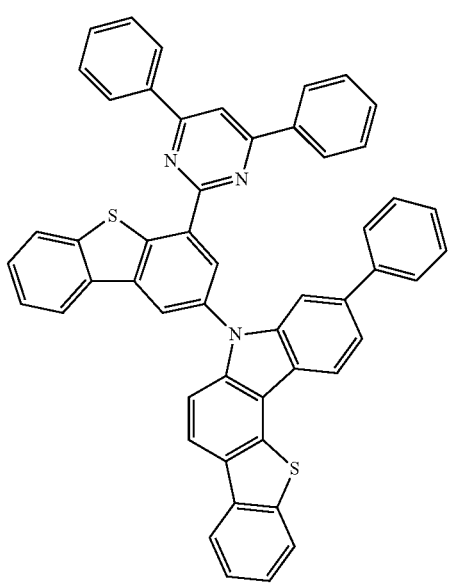

305
-continued
1-104
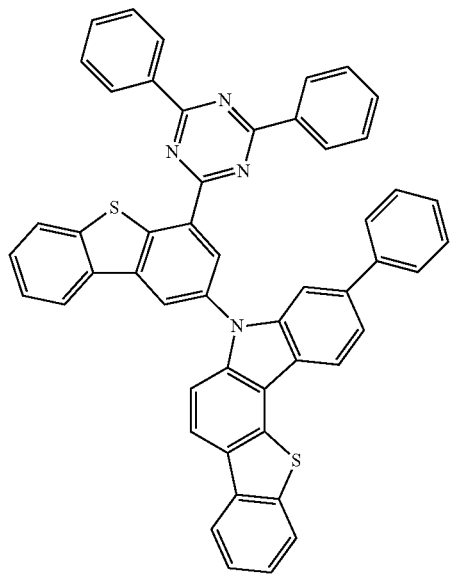
1-105
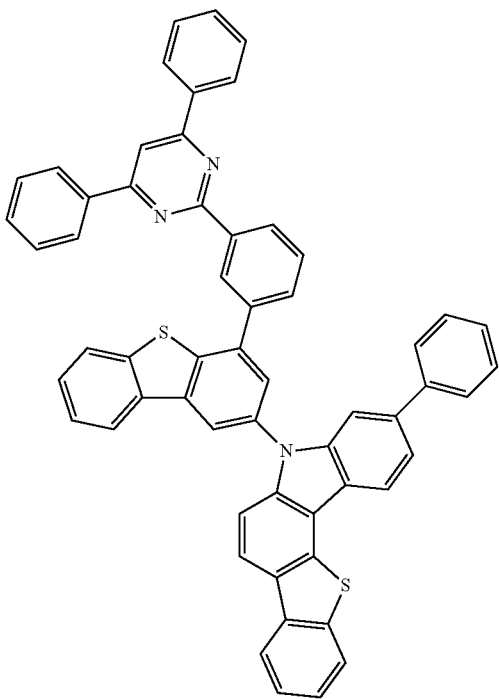
306
-continued
1-106
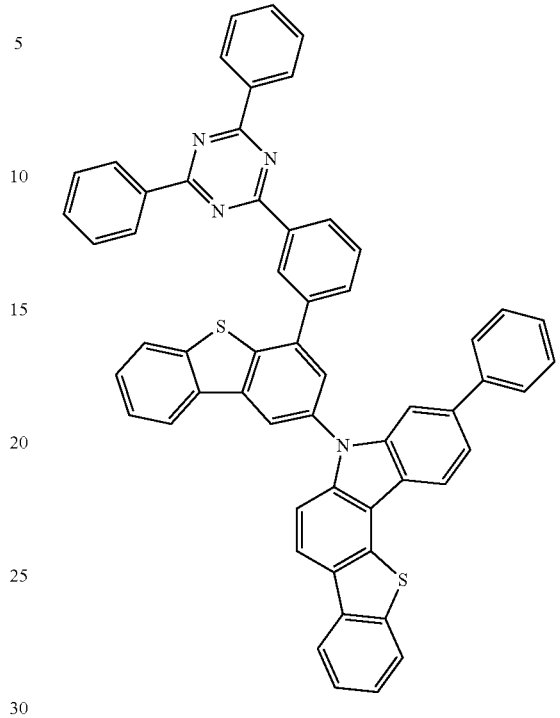
1-107
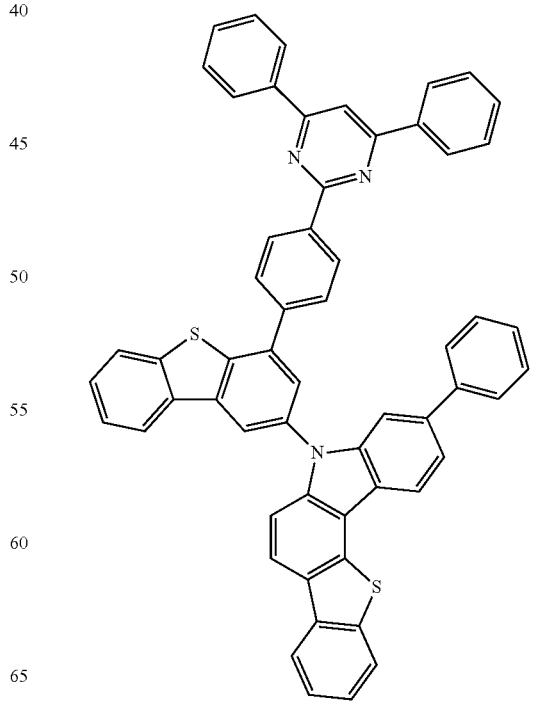

1-108
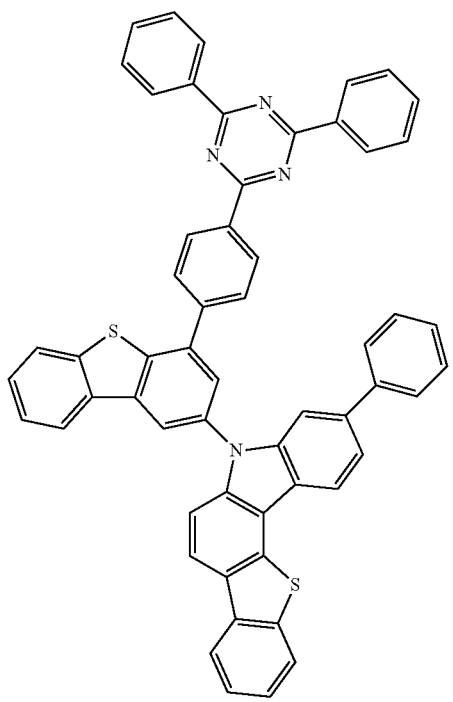
1-109
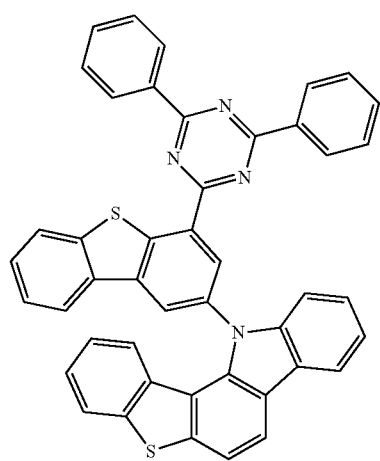
1-110
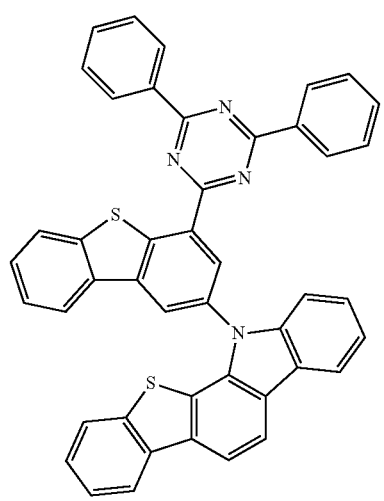
1-111
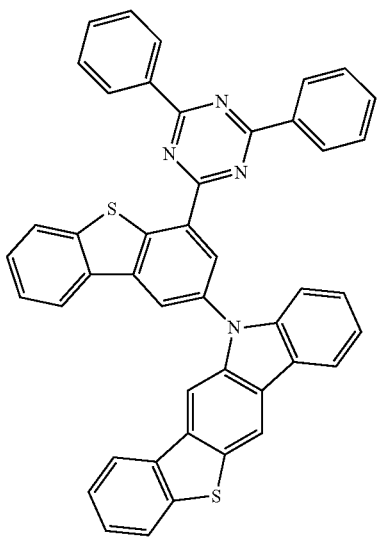
1-112
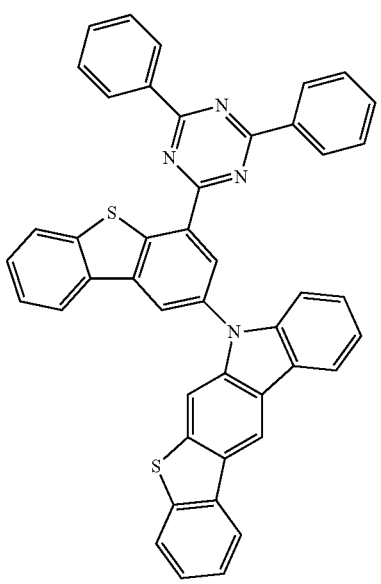
1-113
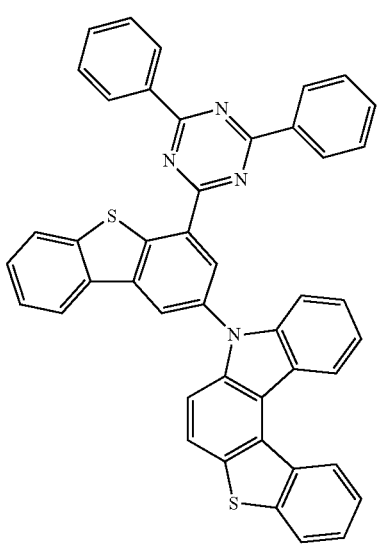

1-114
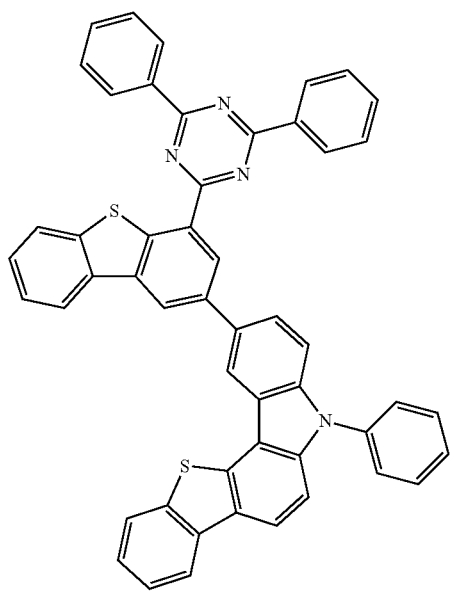
1-115
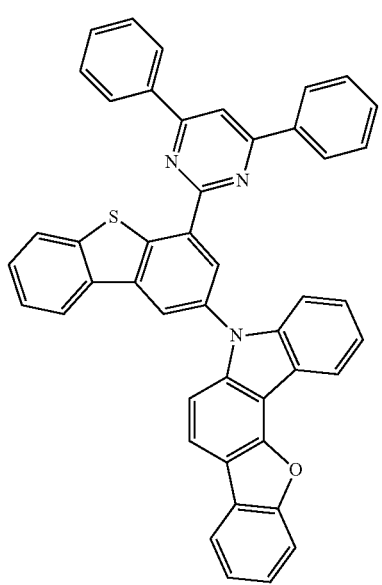
1-116
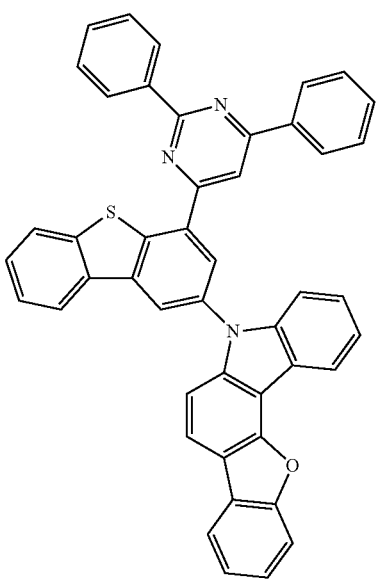
1-117
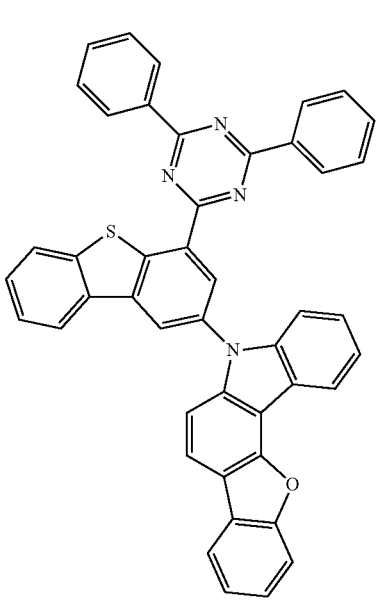

311
-continued
1-118
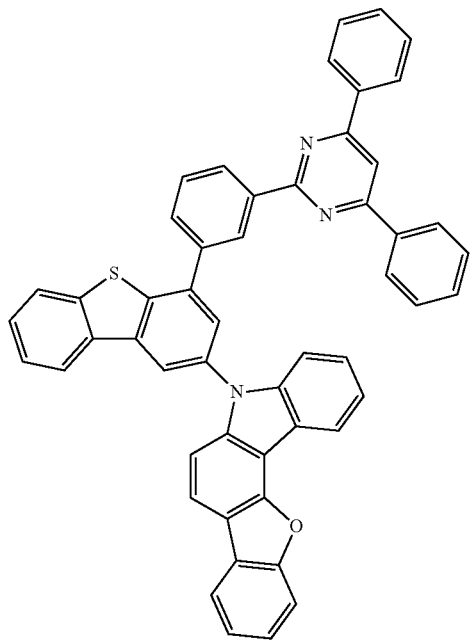
1-119
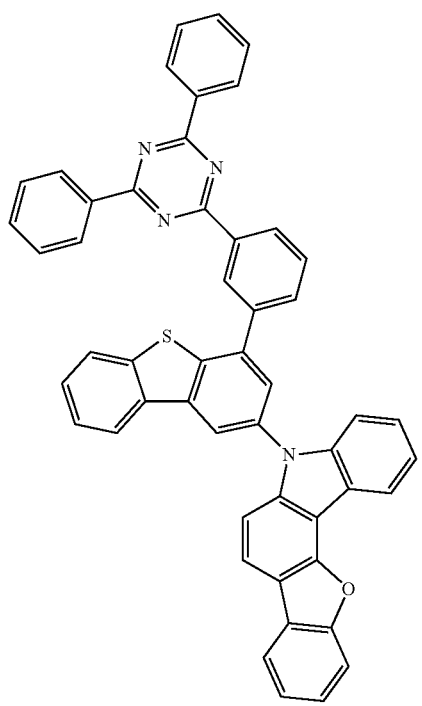
312
-continued
1-120
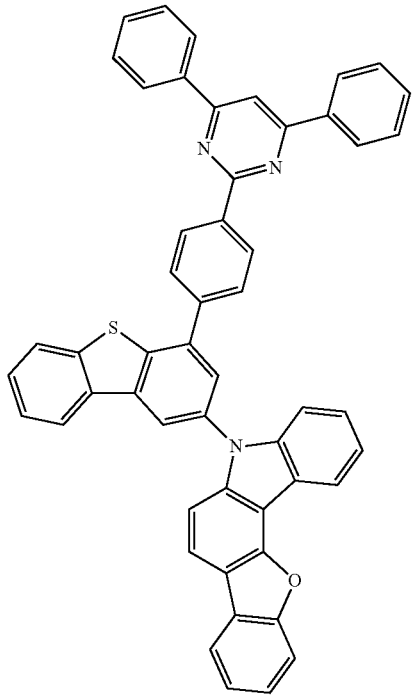
1-121
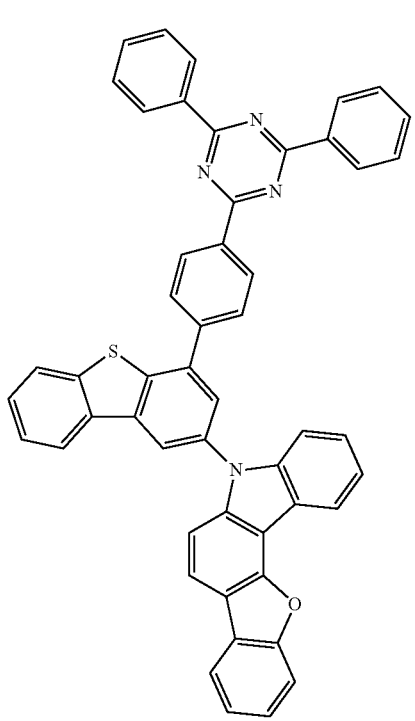

-continued
1-122
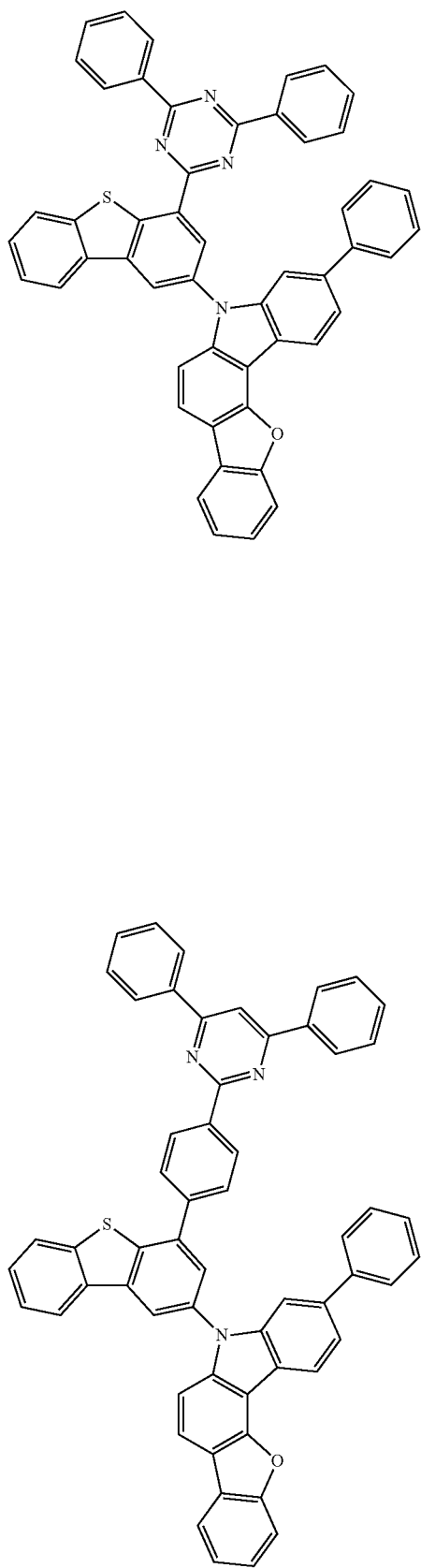
1-123
1-124
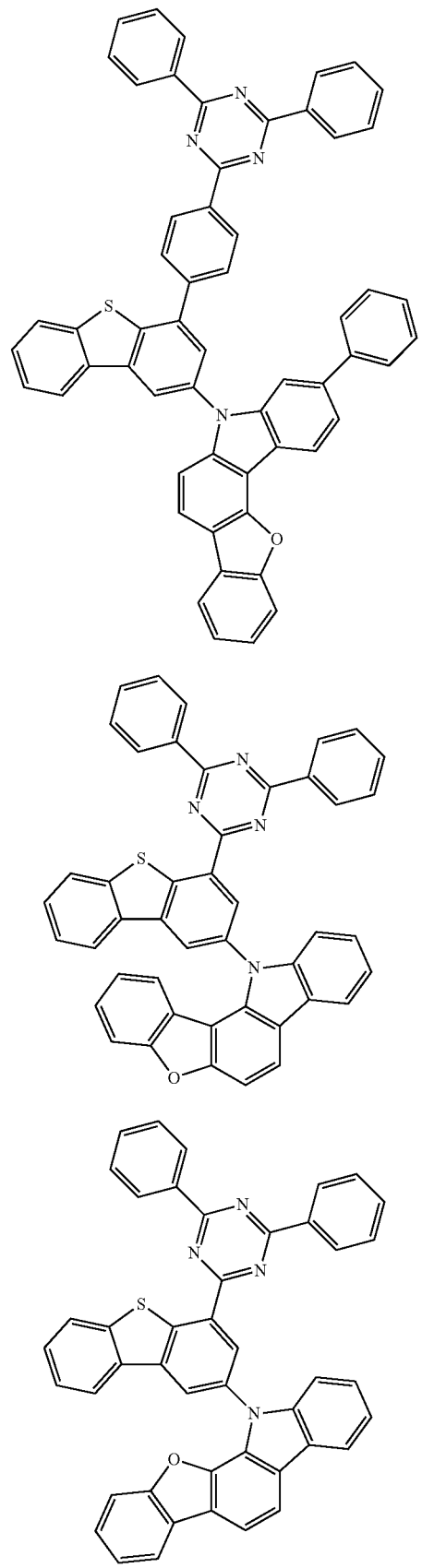
1-125
1-126

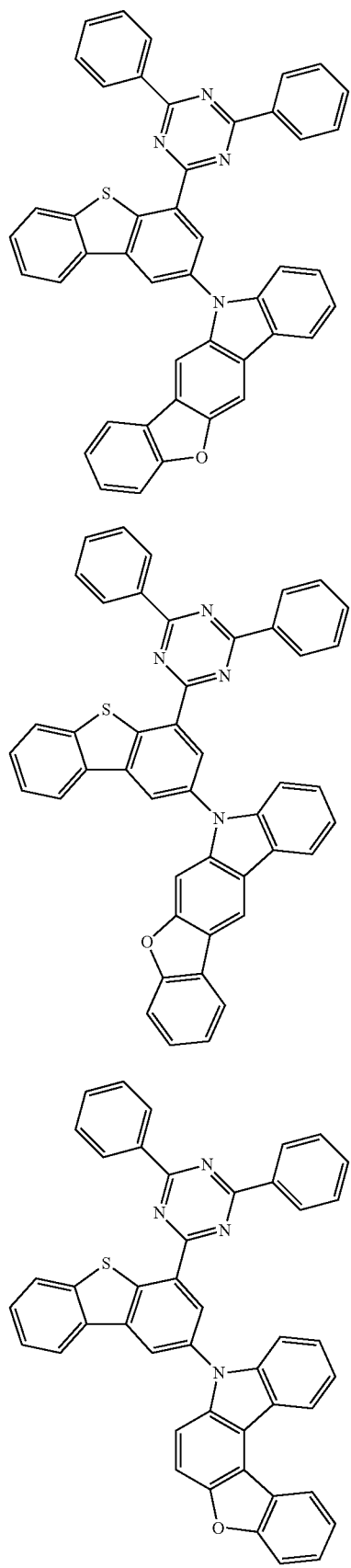
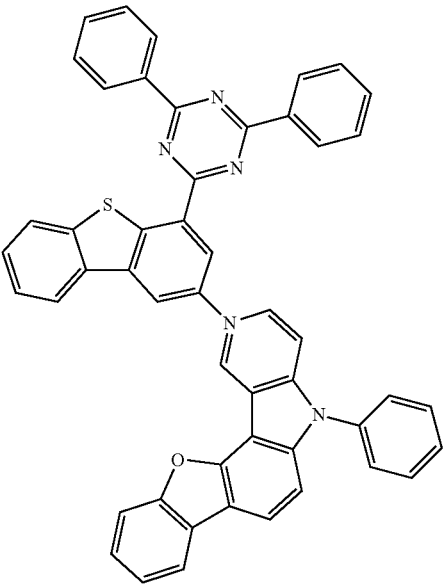
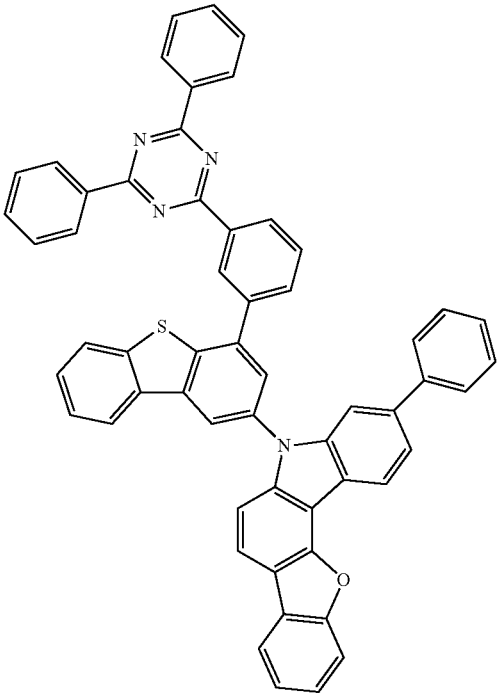

317
-continued
1-132
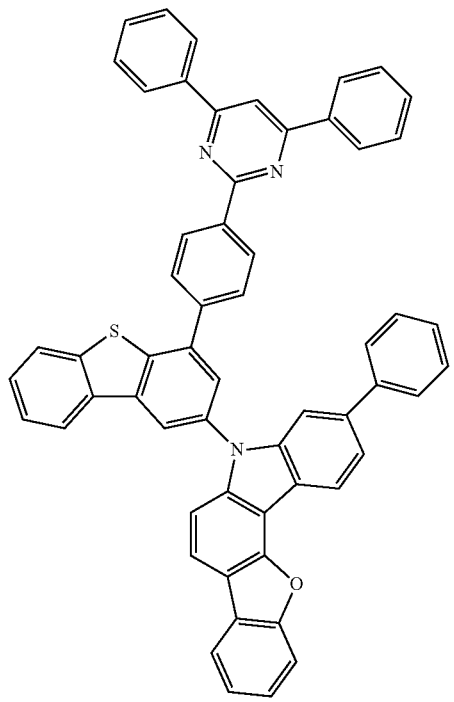
1-133
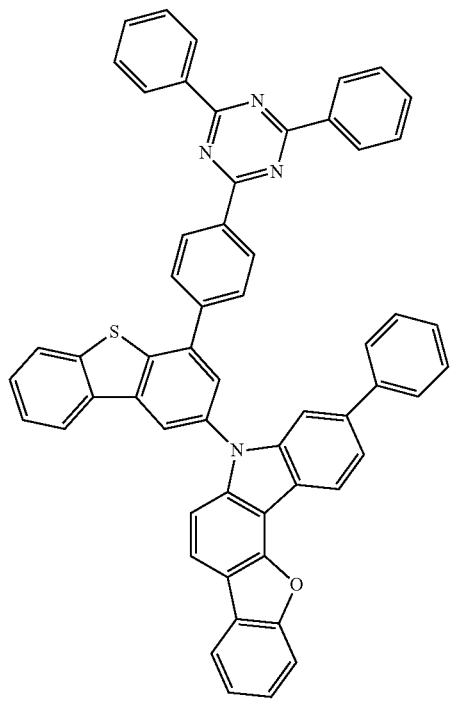
318
-continued
1-134
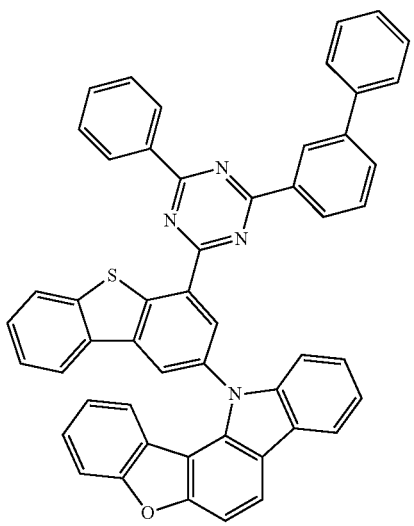
1-135
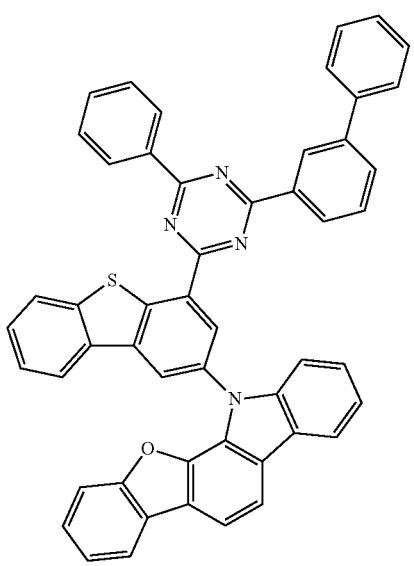

1-136
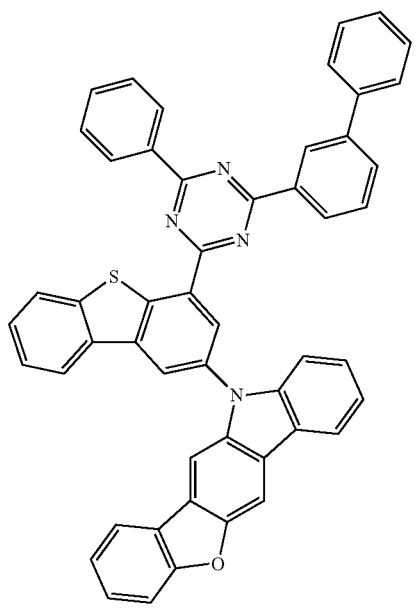
1-138
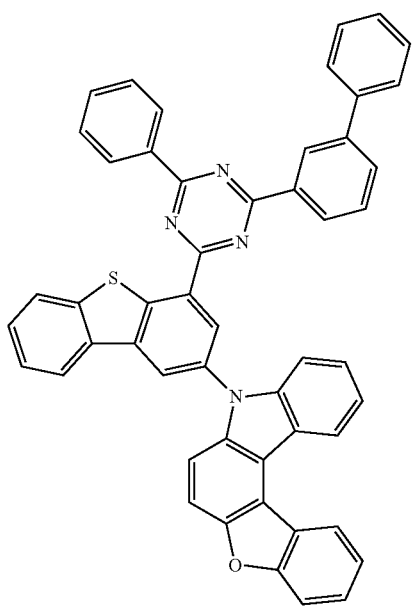
1-137
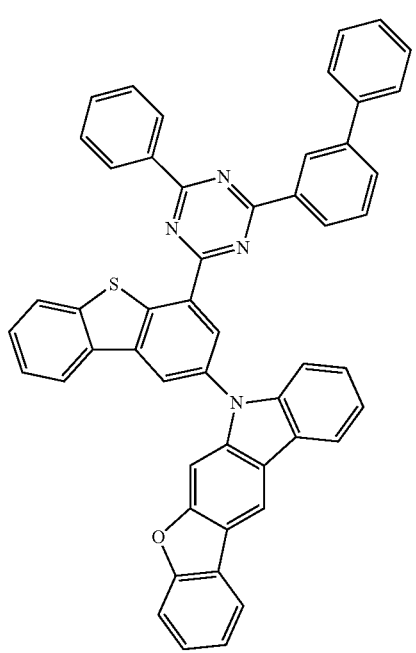
1-139
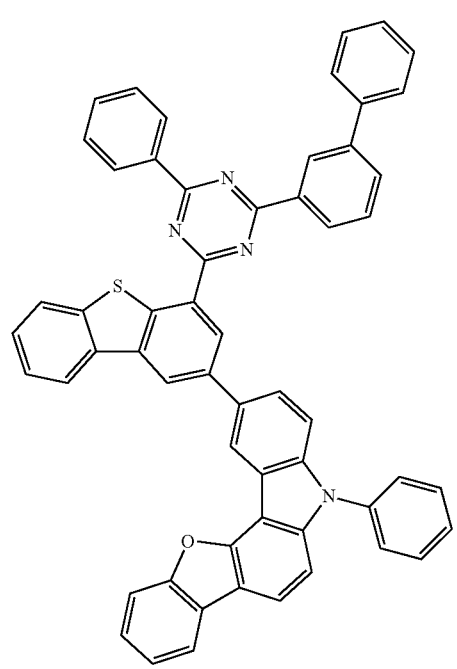

-continued
1-144
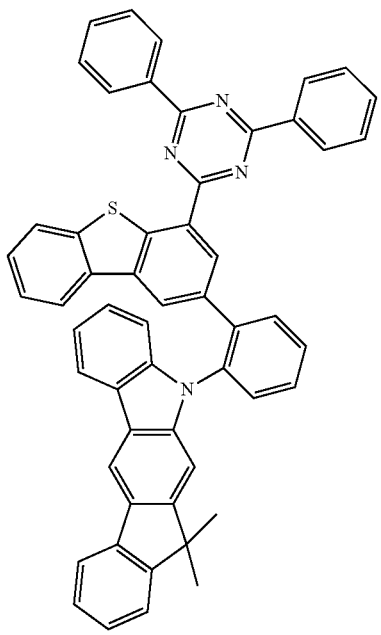
1-146
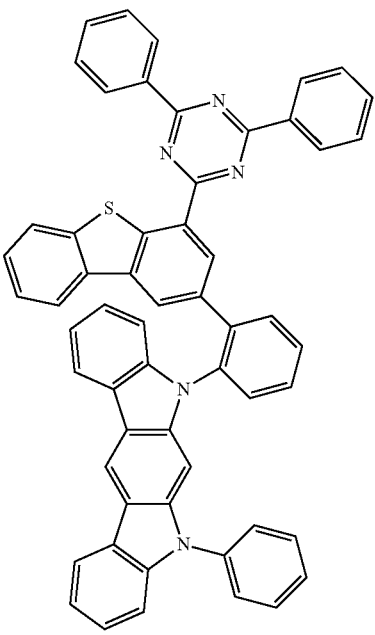
1-145
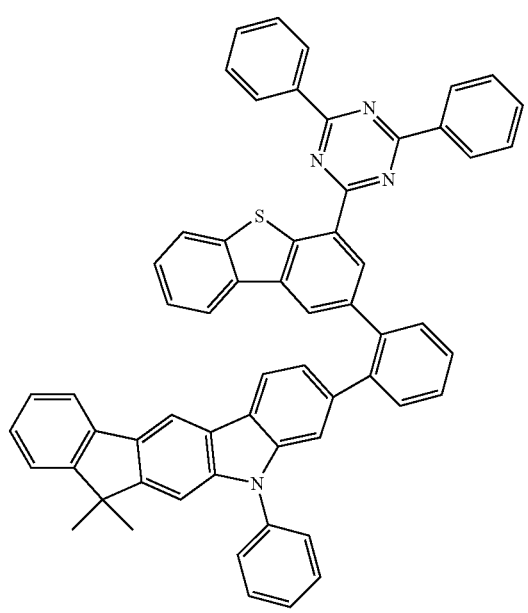
1-147
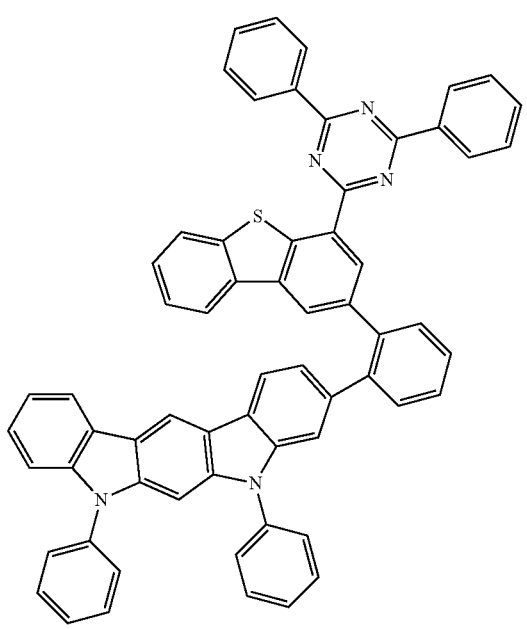

323
-continued
1-148
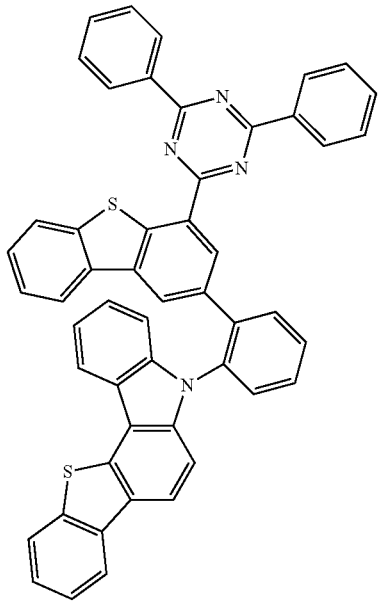
1-149
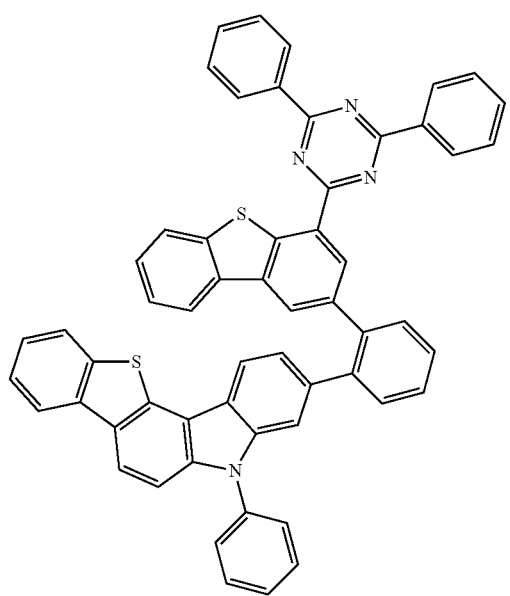
324
-continued
1-150
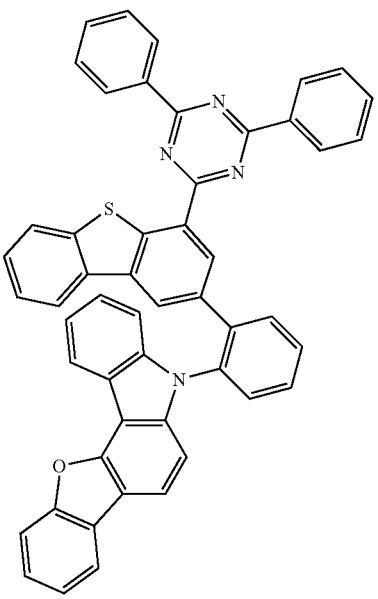
1-151
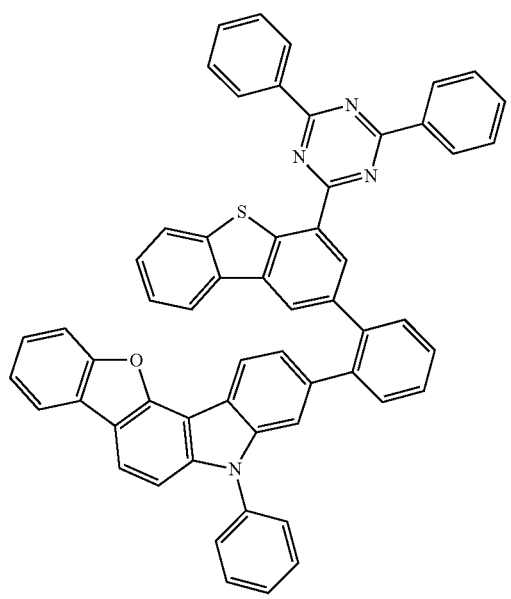

-continued
1-155
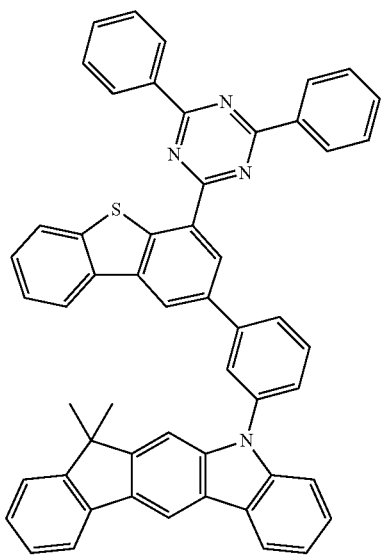
1-156
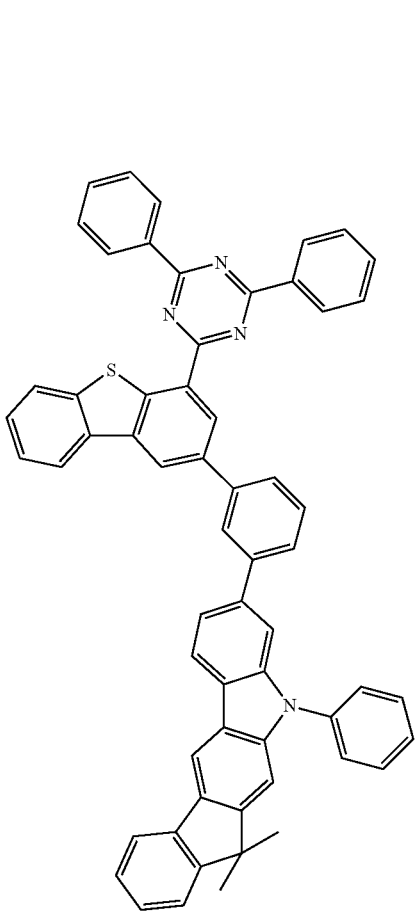
-continued
1-157
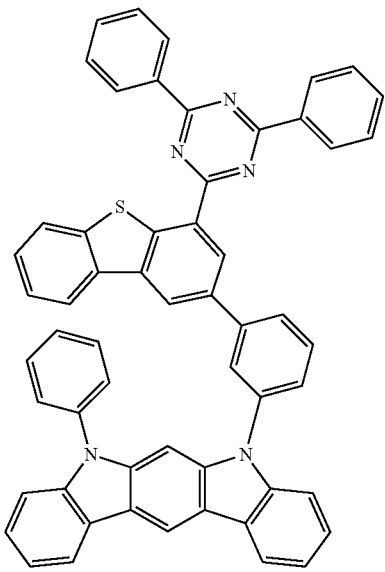
1-158
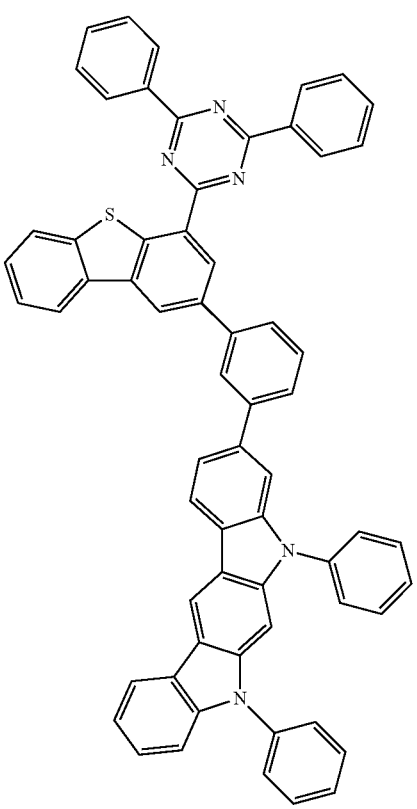

1-159
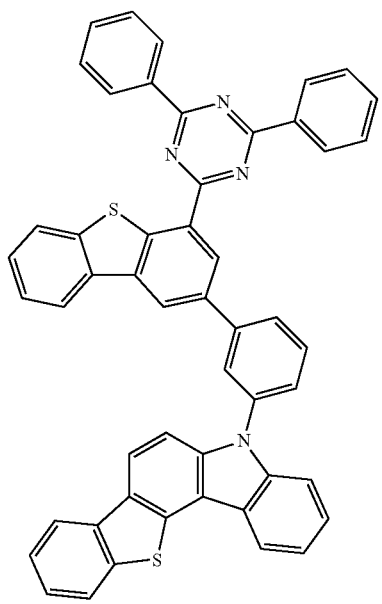
1-161
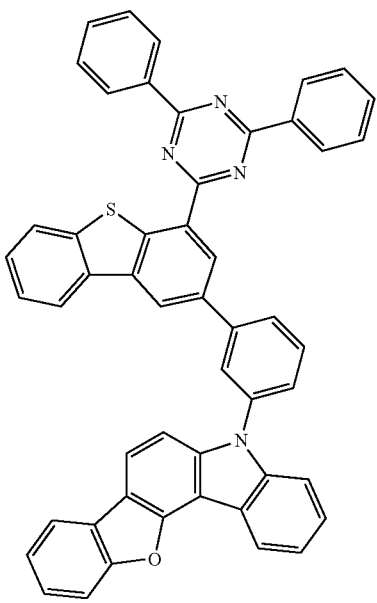
1-160
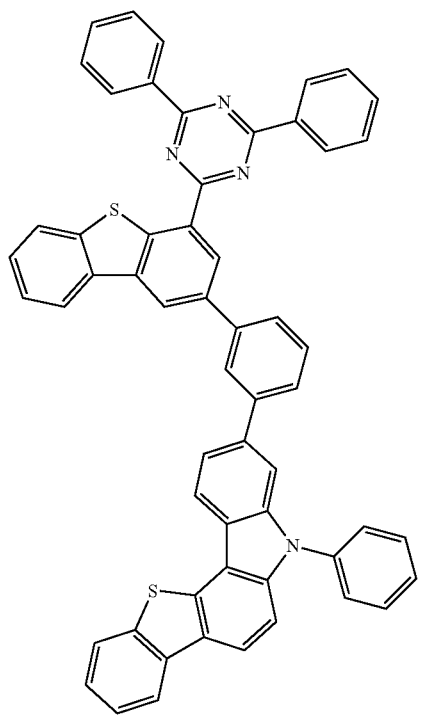
1-162
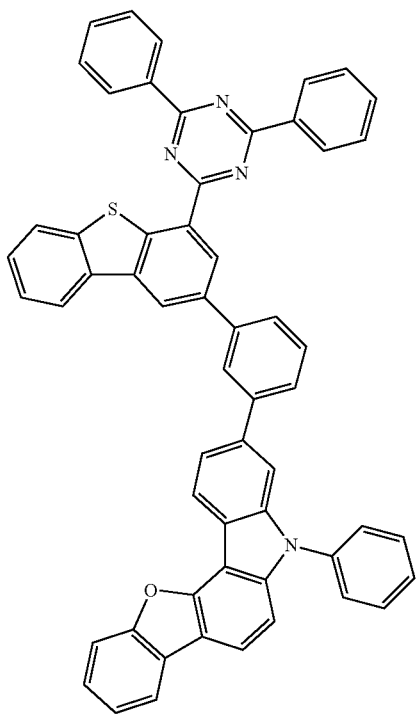

1-166
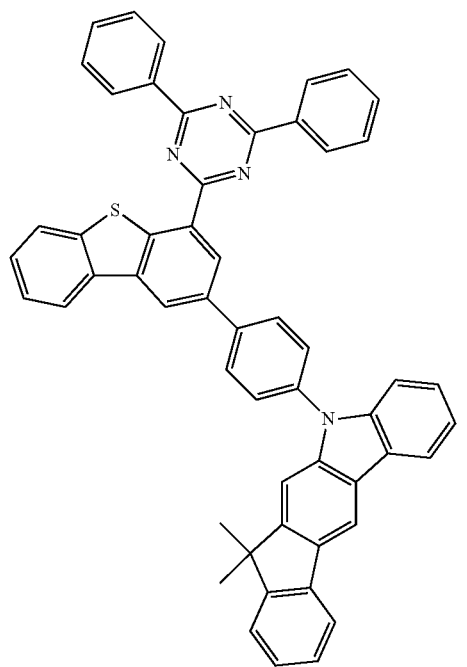
1-167
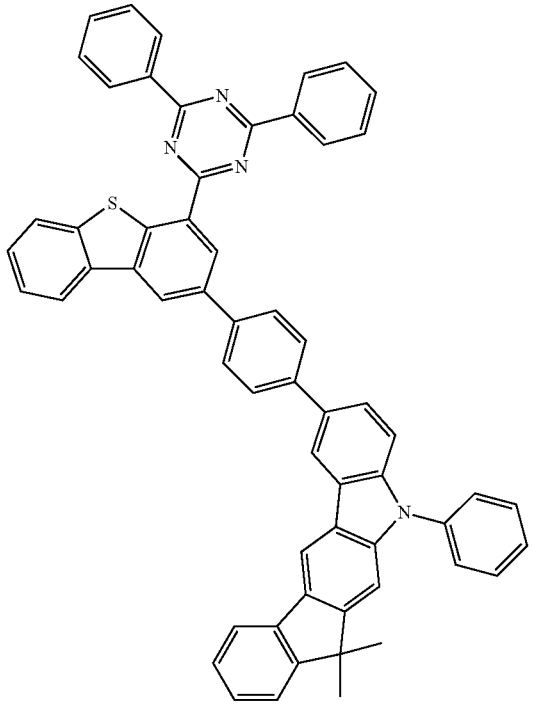
1-168
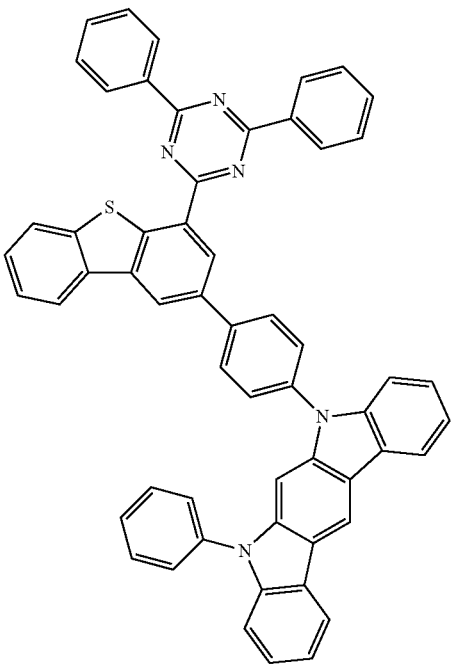
1-169
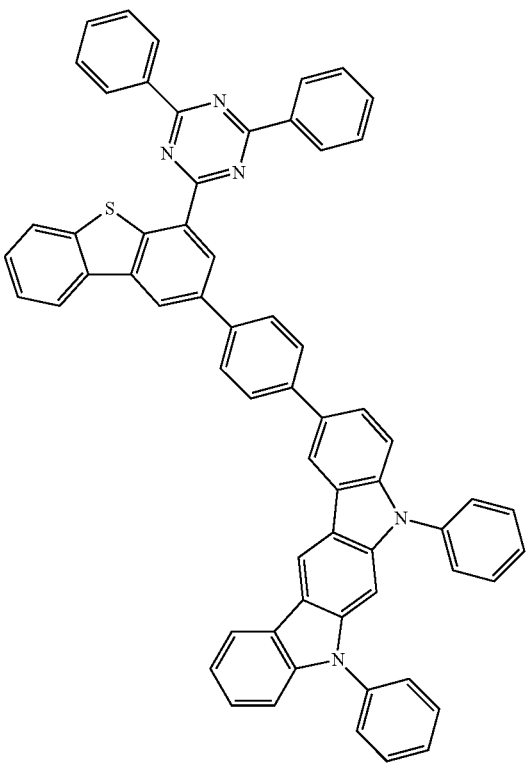

-continued
1-170
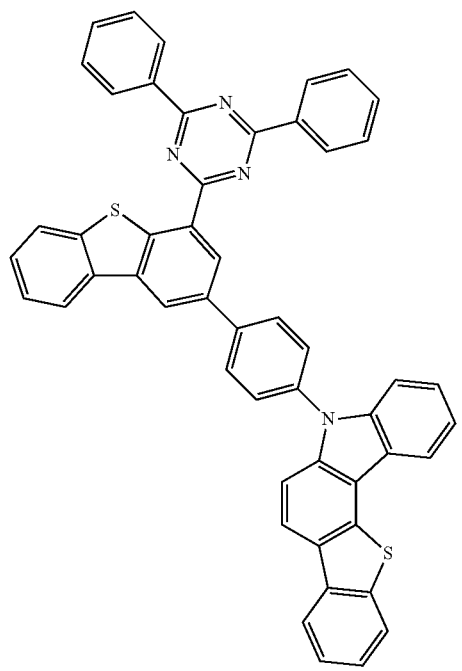
1-171
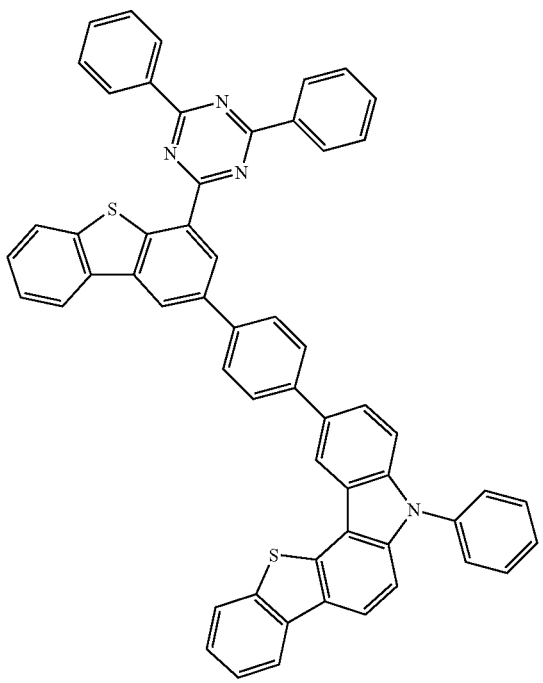
-continued
1-172
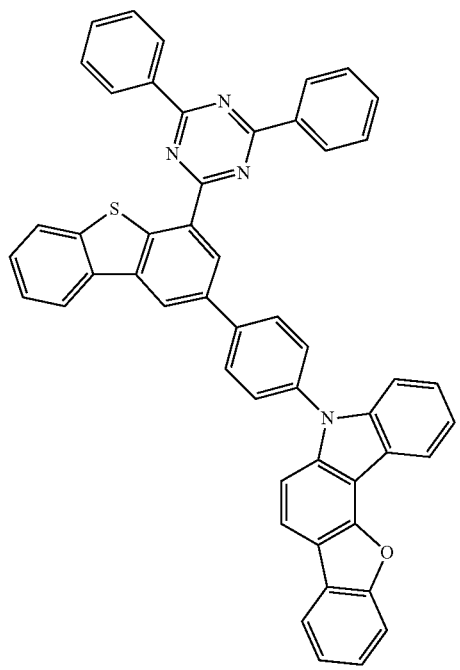
1-173
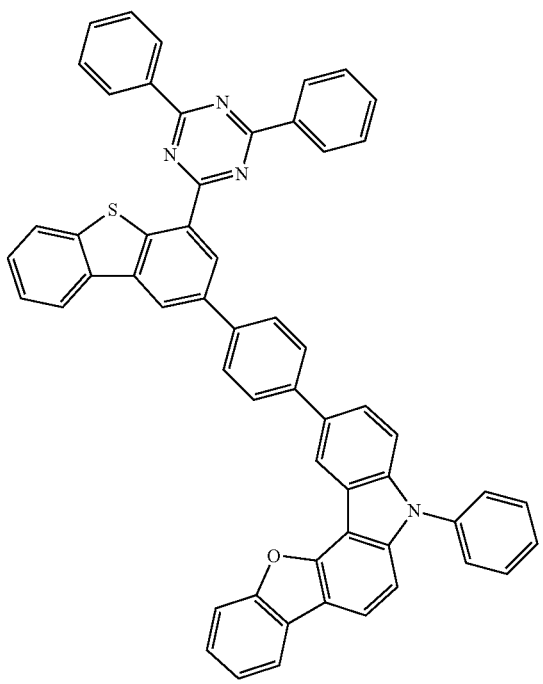

1-176
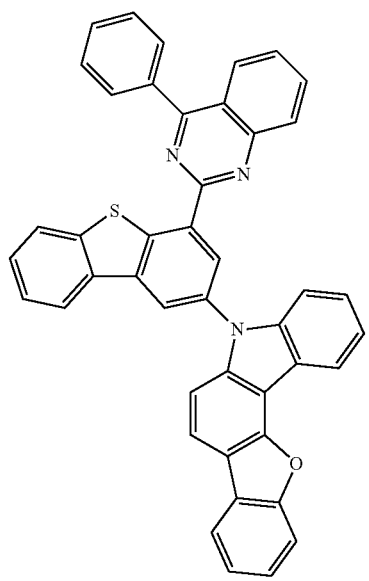
1-177
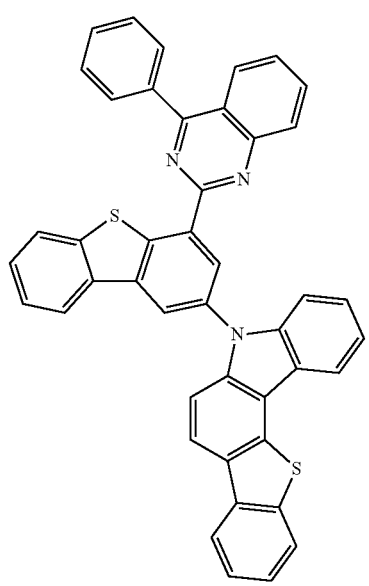
1-178
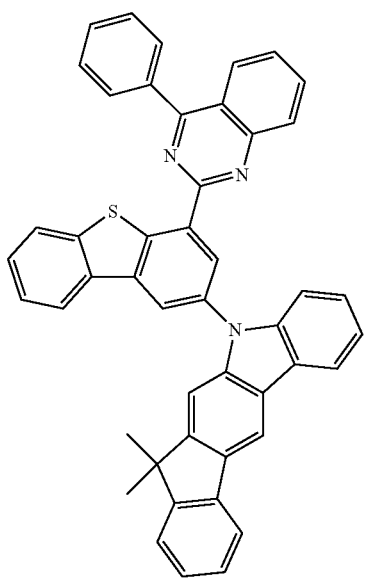
1-179
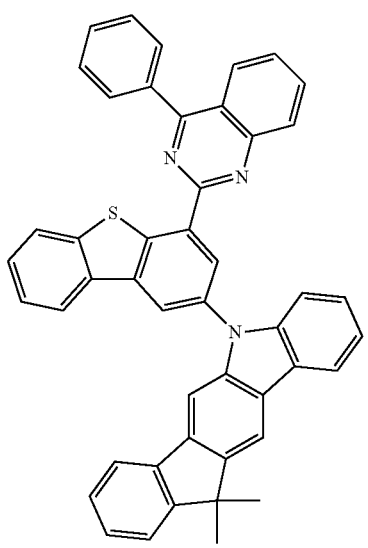
1-180
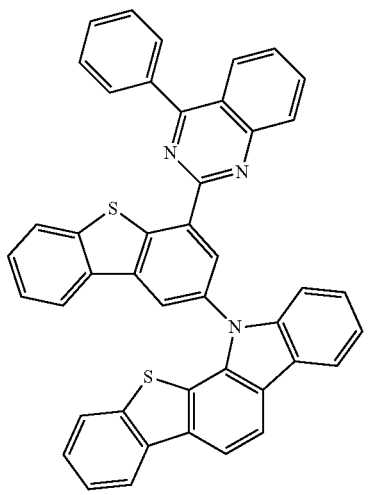

1-181

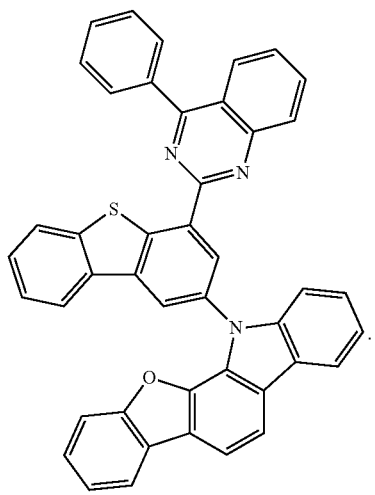

[Chemical Formula 2]

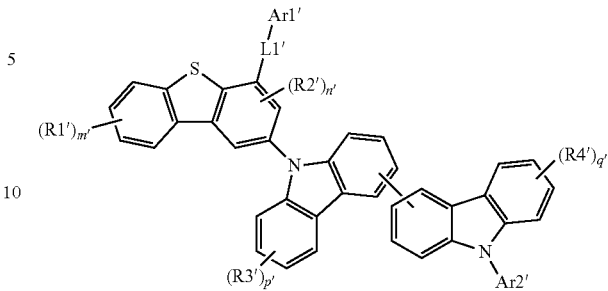

9. An organic light emitting device comprising:
a positive electrode;
a negative electrode; and
one or more organic material layers provided between the positive electrode and the negative electrode,
wherein one or more layers of the organic material layers comprise the hetero-cyclic compound of claim 1.

10. The organic light emitting device of claim 9, wherein the organic material layer comprise at least one layer of a hole blocking layer, an electron injection layer, and an electron transport layer, and at least one layer of the hole blocking layer, the electron injection layer, and the electron transport layer comprises the hetero-cyclic compound.

11. The organic light emitting device of claim 9, wherein the organic material layer comprises a light emitting layer, and the light emitting layer comprises the hetero-cyclic compound.

12. The organic light emitting device of claim 9, wherein the organic material layer comprises one or more layers of a hole injection layer, a hole transport layer, and a layer which injects and transports holes simultaneously, and one layer of the layers comprises the hetero-cyclic compound.

13. The organic light emitting device of claim 9, wherein the organic material layer comprising the hetero-cyclic compound further comprises a compound represented by the following Chemical Formula 2:

in Chemical Formula 2,
R1' to R4' are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R''; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups combine with each other to form a substituted or unsubstituted aliphatic or aromatic hydrocarbon ring,
L1' is a direct bond or a substituted or unsubstituted $C_6$ to $C_{60}$ arylene group,
Ar1' is a substituted or unsubstituted $C_6$ to $C_{60}$ aryl group; or a substituted or unsubstituted $C_2$ to $C_{60}$ heteroaryl group including at least one of S and O,
Ar2' is a substituted or unsubstituted $C_6$ to $C_{60}$ aryl group; or a substituted or unsubstituted $C_2$ to $C_{60}$ heteroaryl group,
R, R', and R'' are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, and
m', p' and q' are each independently an integer of 0 to 4, and n' is an integer of 0 to 2.

14. The organic light emitting device of claim 13, wherein Chemical Formula 2 is represented by any one of the following Chemical Formulae 11 to 22:

[Chemical Formula 11]
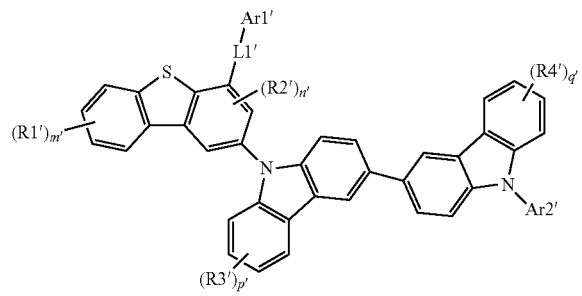
[Chemical Formula 12]
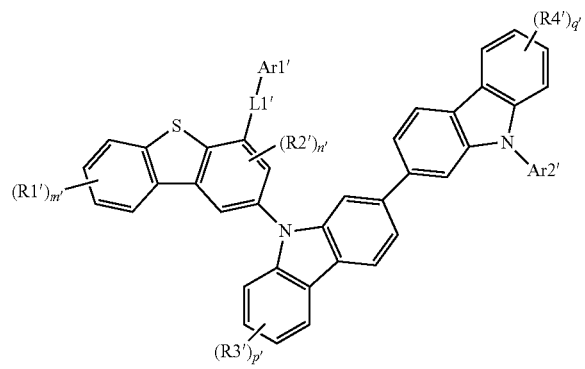
[Chemical Formula 13]
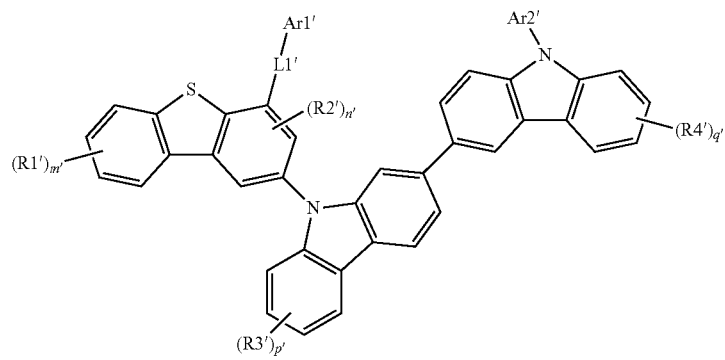
[Chemical Formula 14]
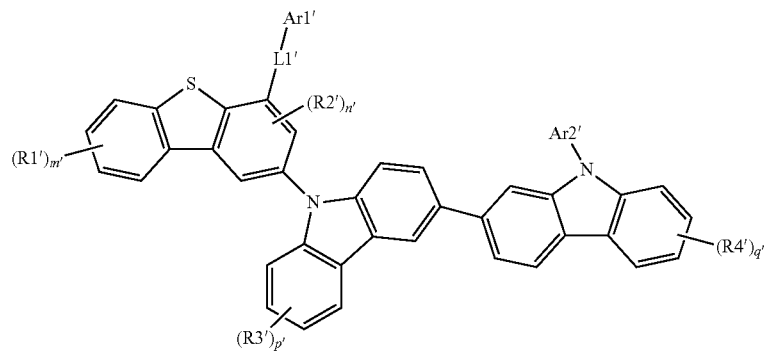
[Chemical Formula 15]
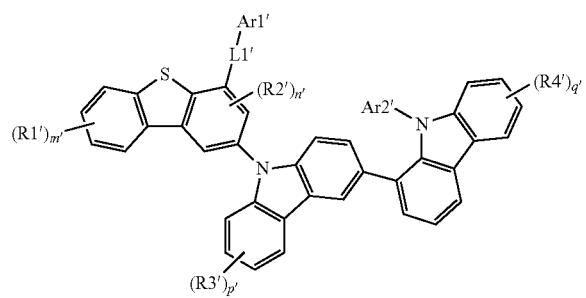
[Chemical Formula 16]
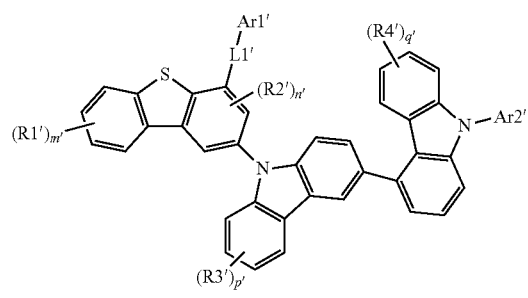

[Chemical Formula 17]
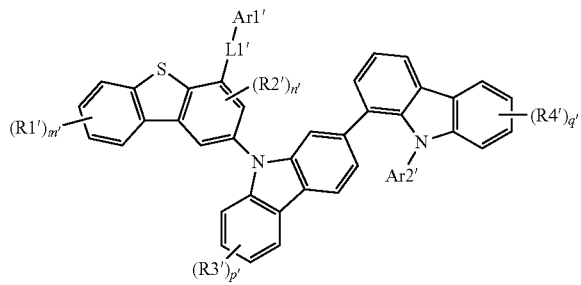
[Chemical Formula 18]
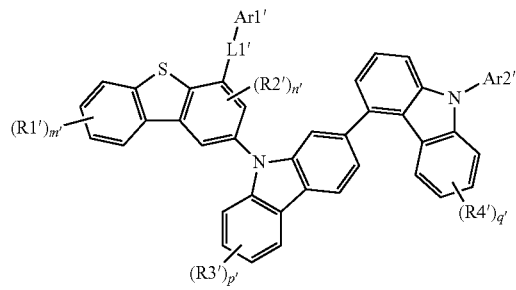
[Chemical Formula 19]
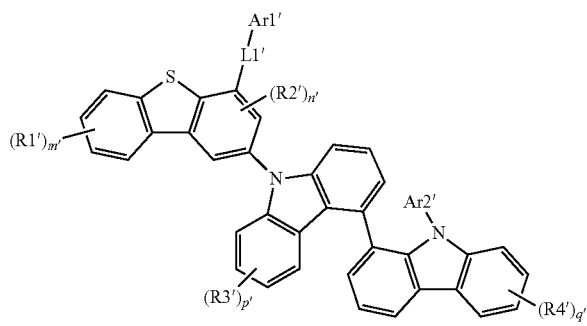
[Chemical Formula 20]
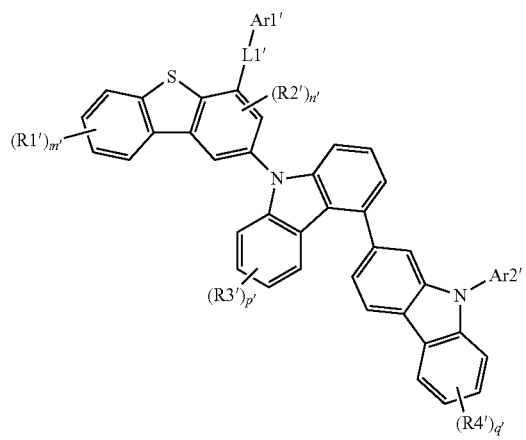
[Chemical Formula 21]
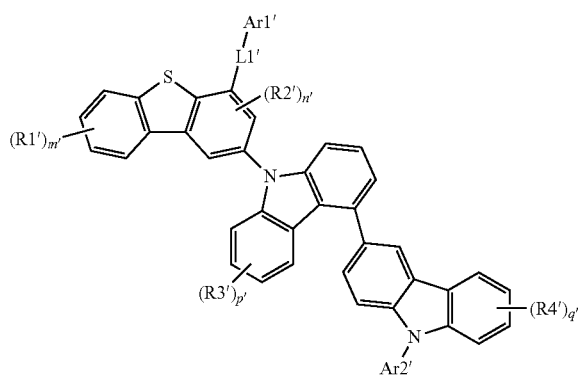
[Chemical Formula 22]
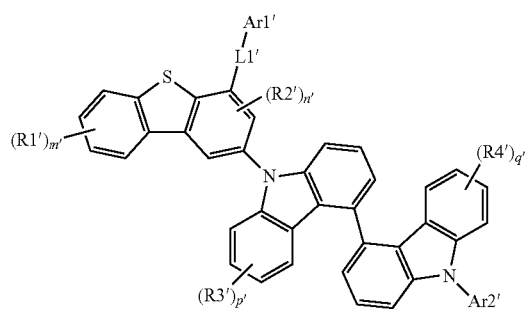
in Chemical Formulae 11 to 22, the definitions of L1, Ar1, Ar2, R1 to R4, m, n, p, and q are the same as those in Chemical Formula 2.
15. The organic light emitting device of claim 13, wherein Chemical Formula 2 is represented by any one of the following compounds:

2-1
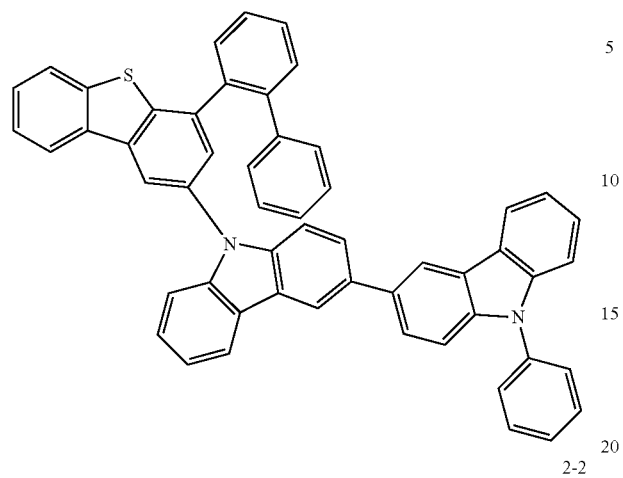
2-2
2-4
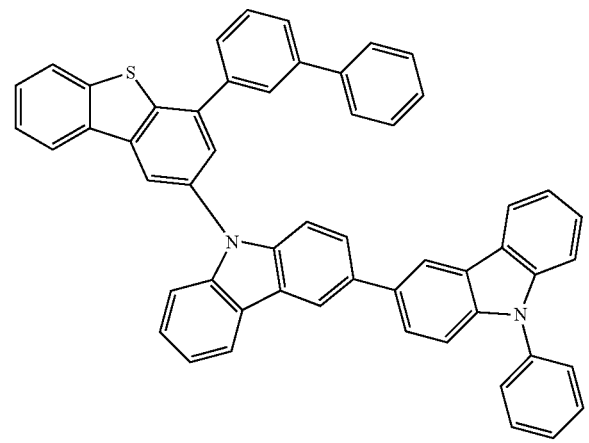
2-5
2-3
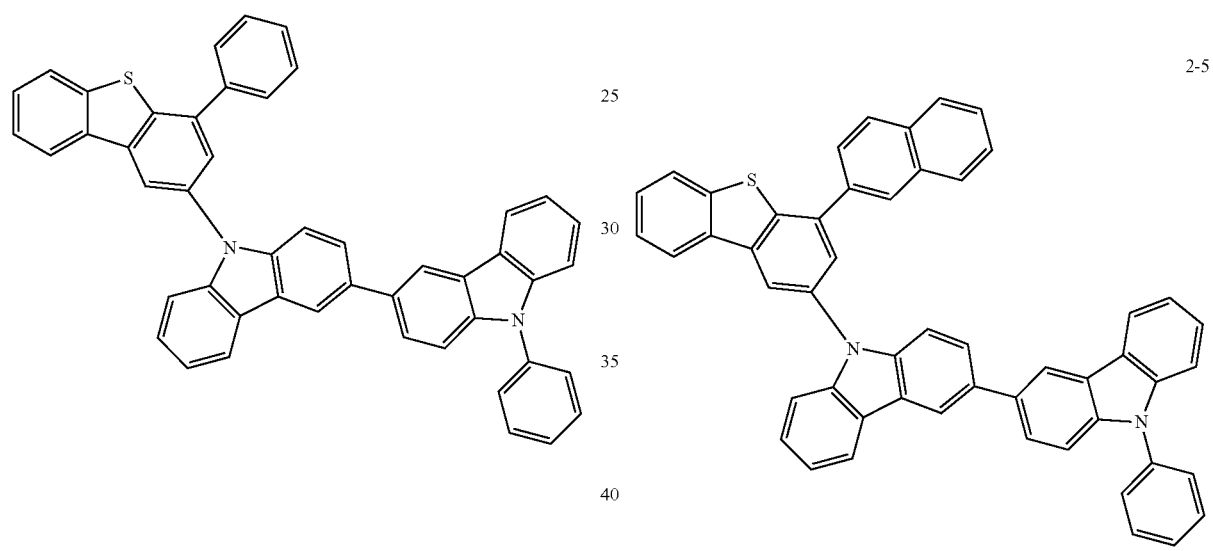
2-6
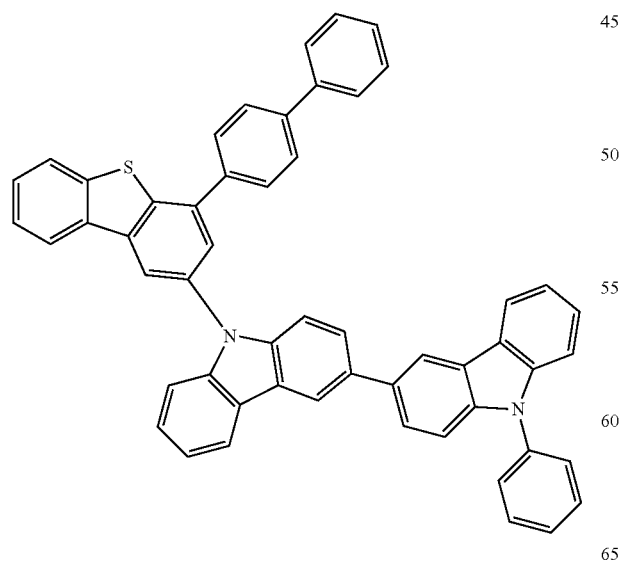
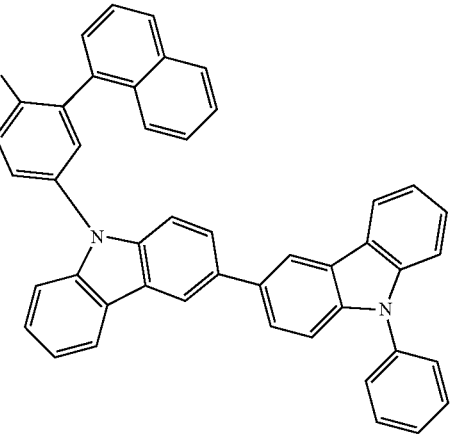

2-7
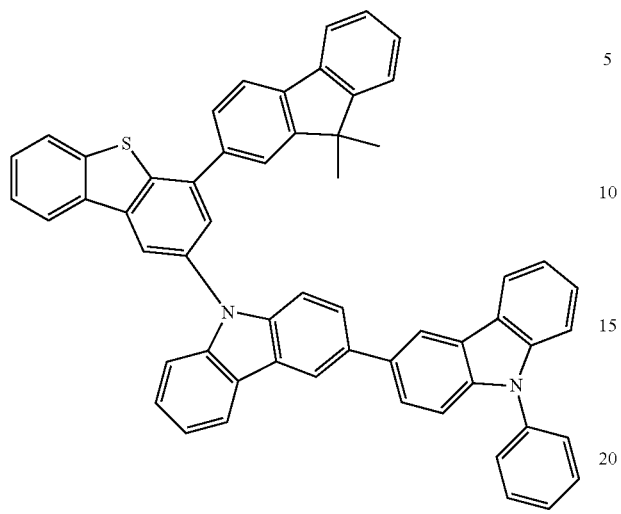
2-8
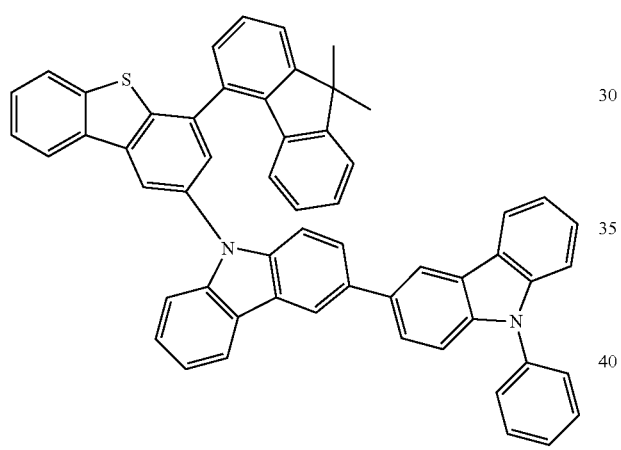
2-9
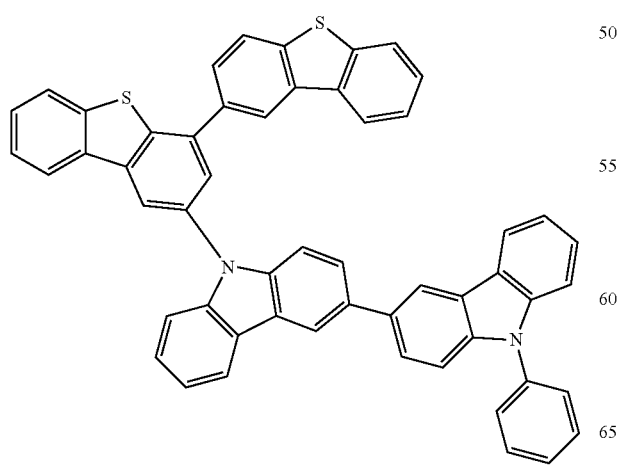
2-10
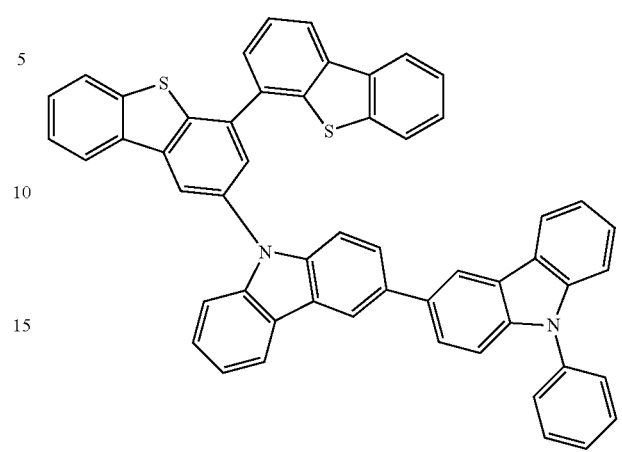
2-11
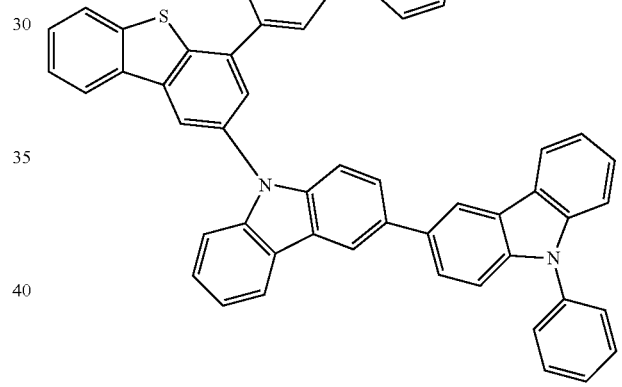
2-12
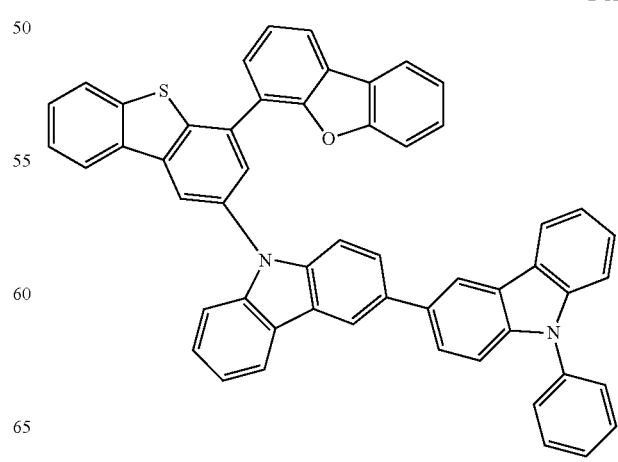

345
-continued
2-13
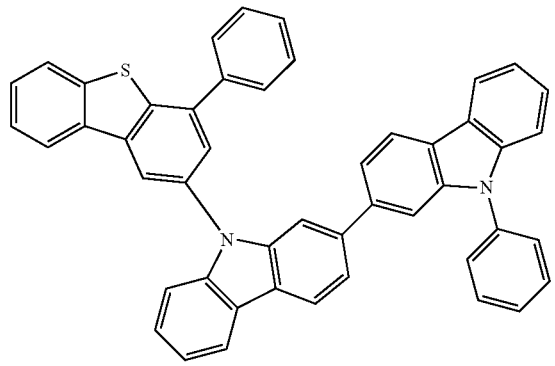
2-14
2-15
2-16
346
-continued
2-17
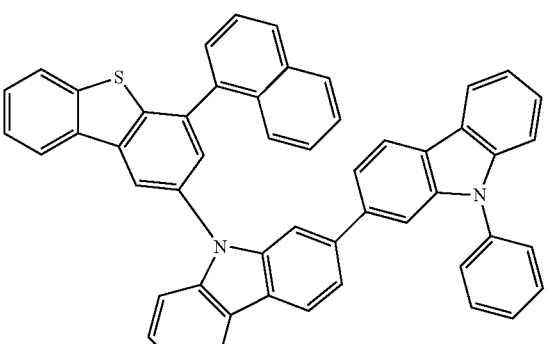
2-18
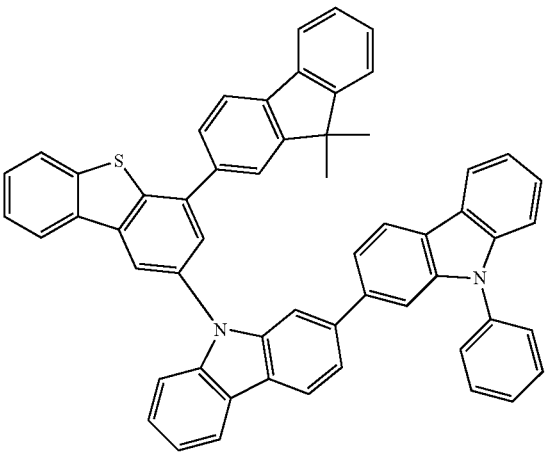
2-19
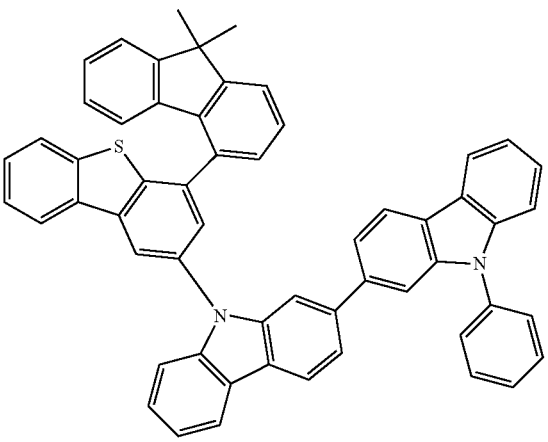

2-20
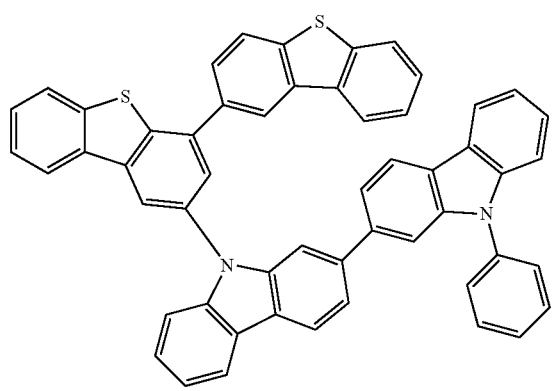
2-21
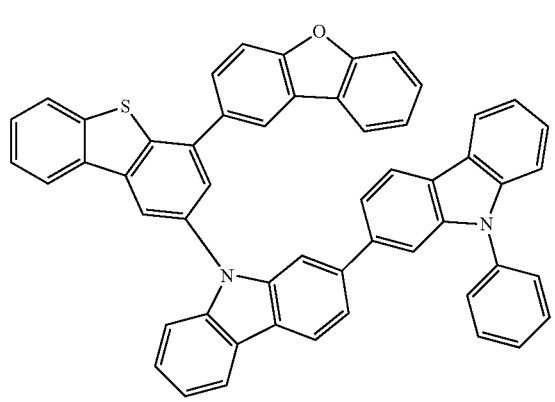
2-22
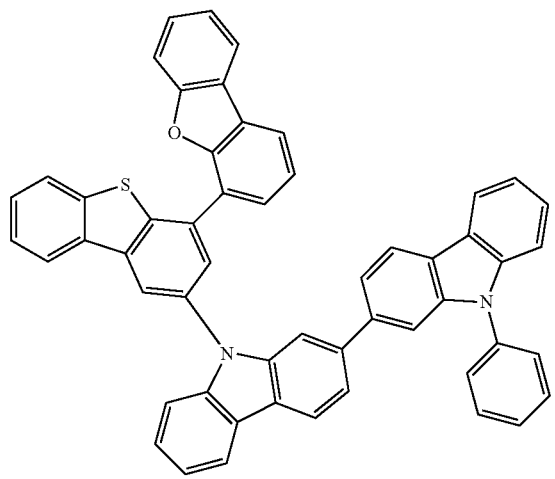
2-23
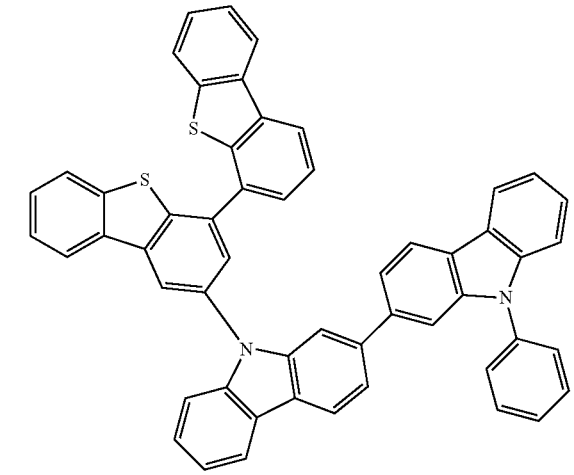
2-24
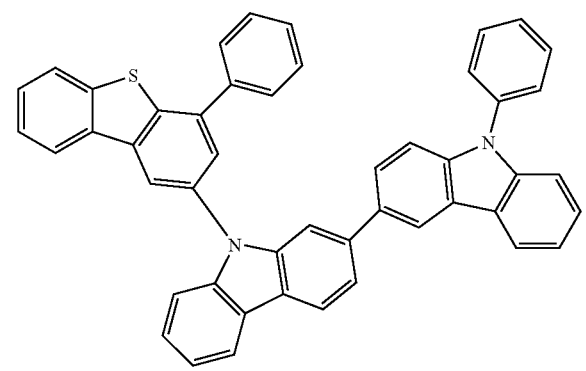
2-25
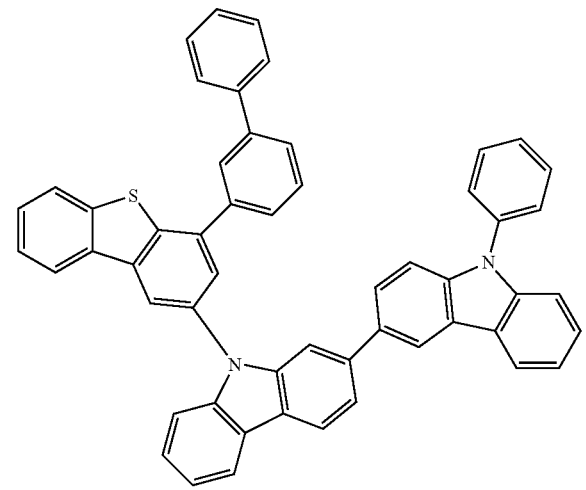

2-26
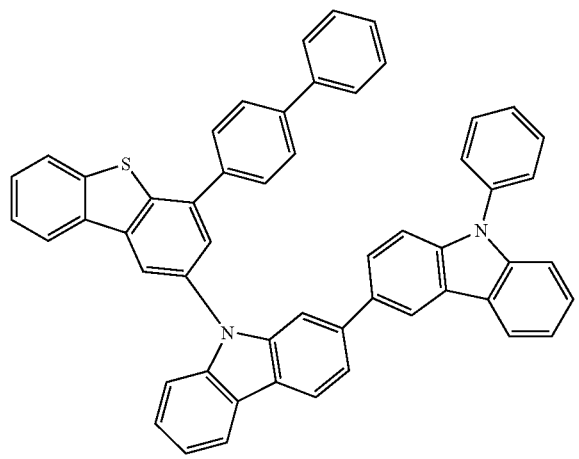
2-29
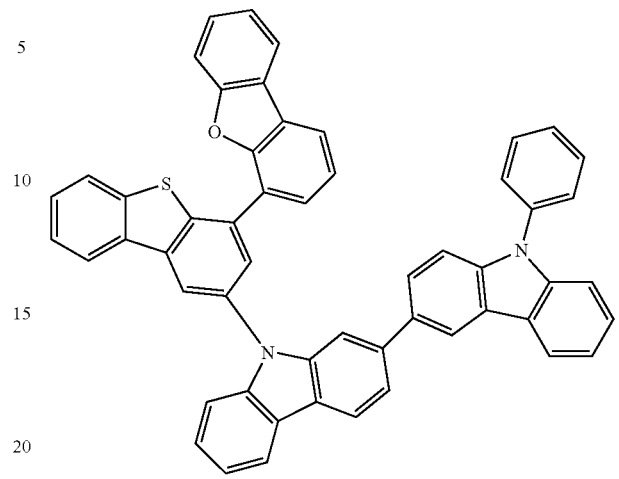
2-27
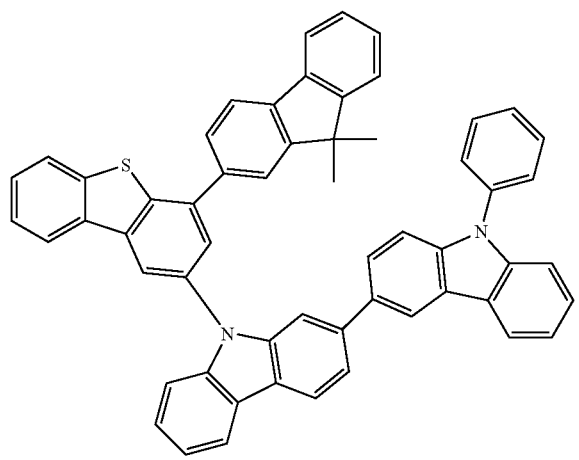
2-30
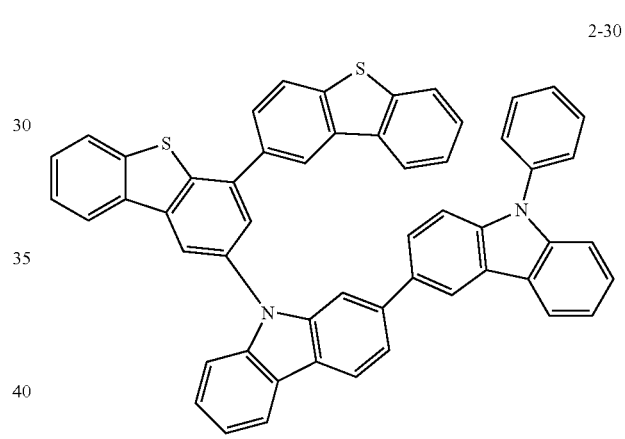
2-28
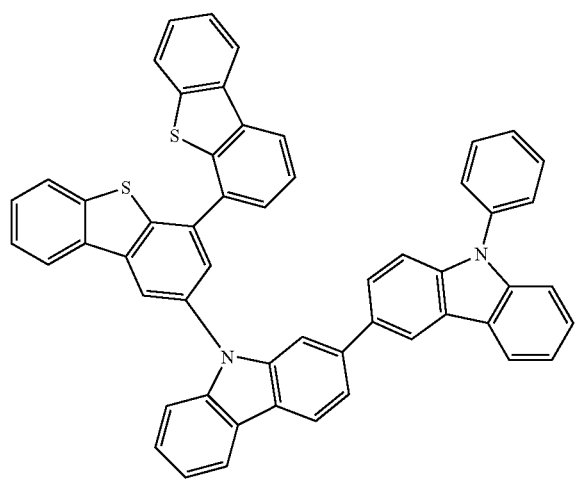
2-31
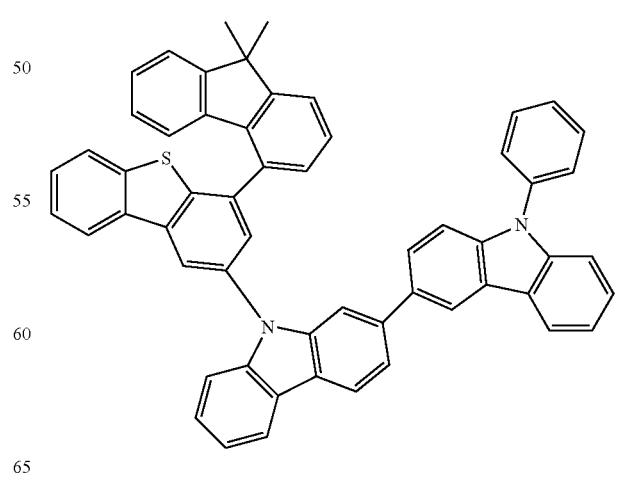

351
-continued
352
-continued
2-32
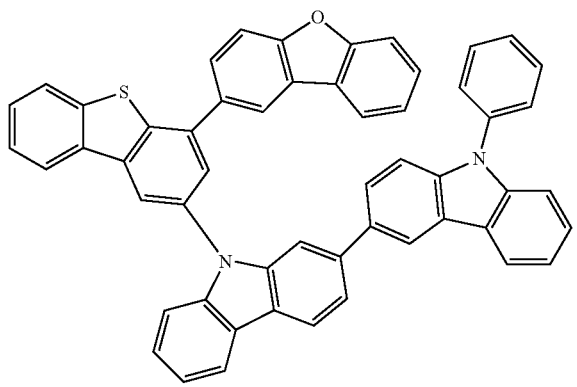
2-36
2-33
2-37
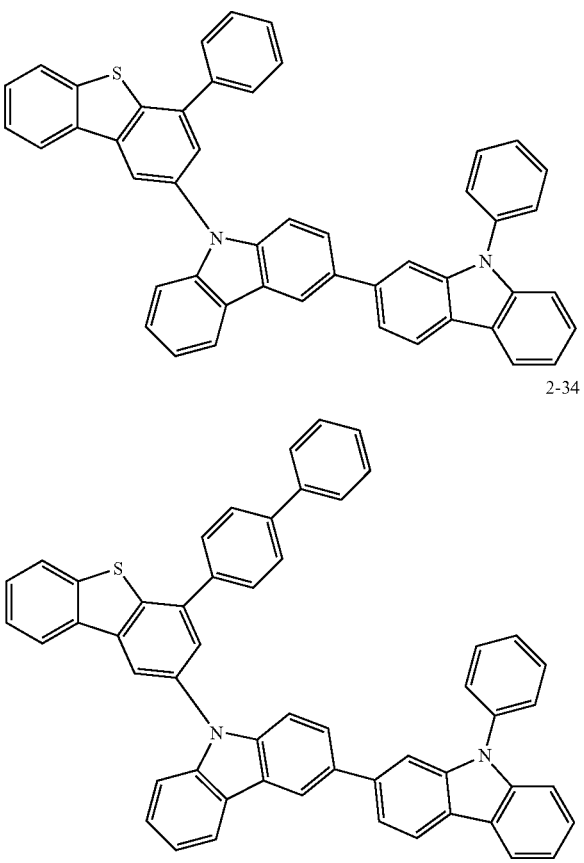
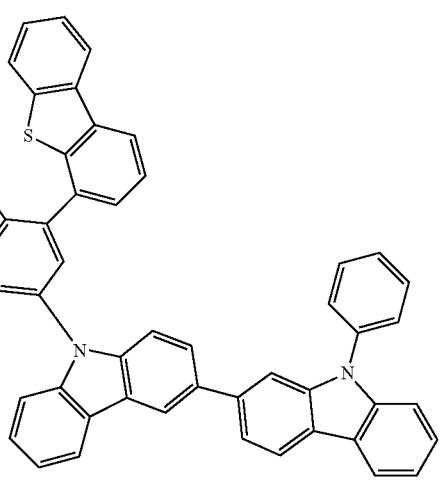
2-34
2-35
2-38
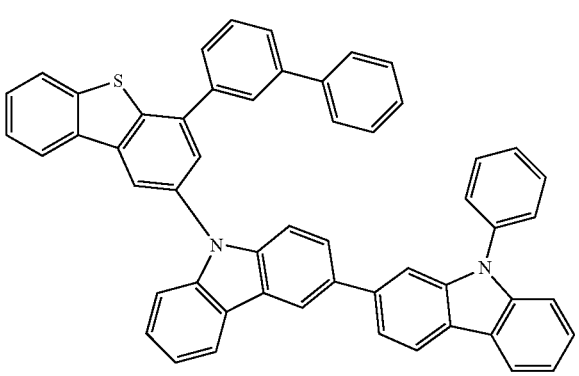

2-39
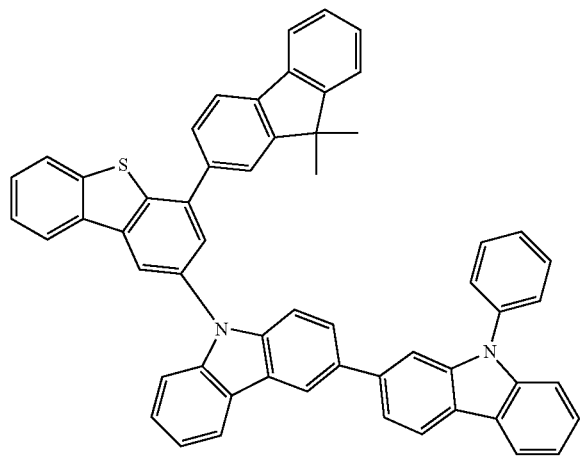
2-42
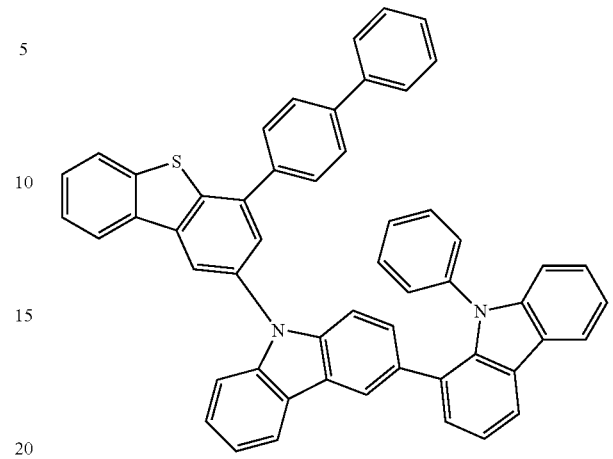
2-40
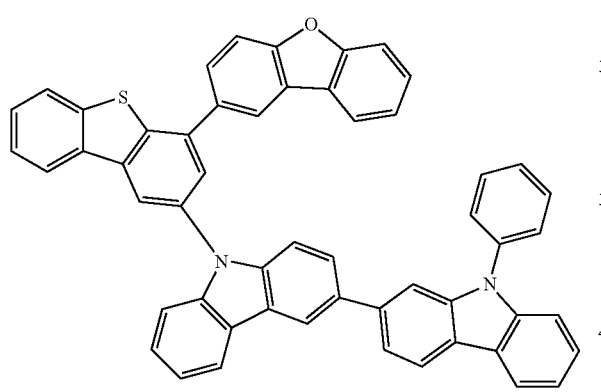
2-43
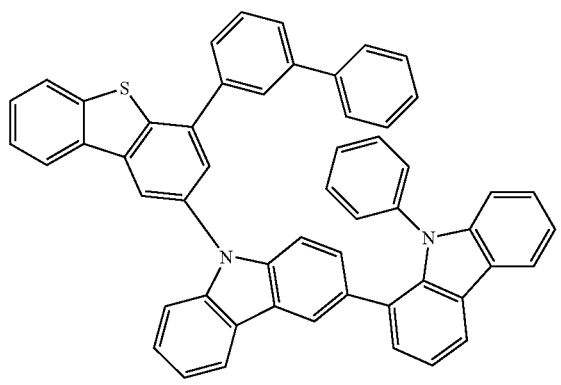
2-41
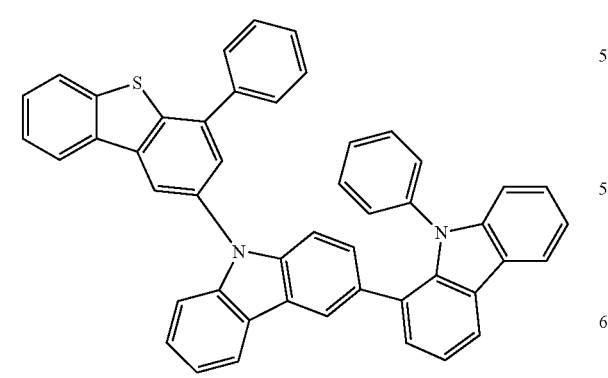
2-44
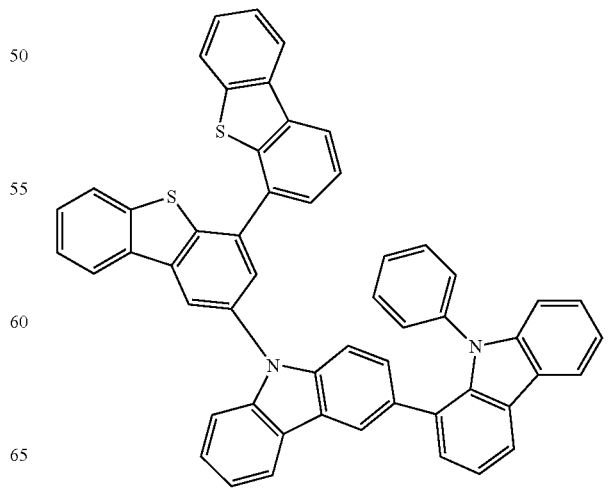

2-45
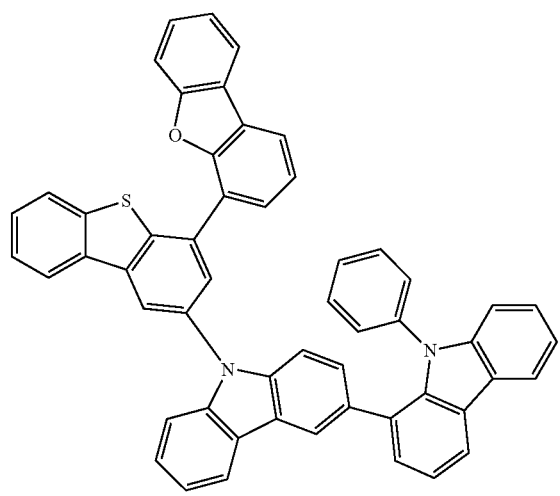
2-46
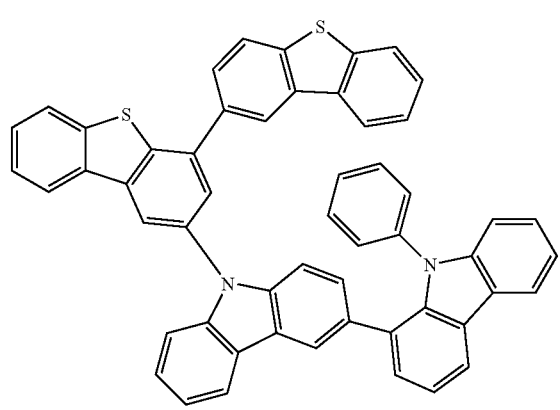
2-47
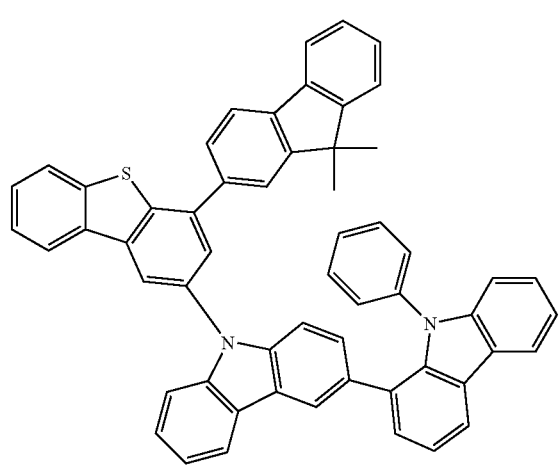
2-48
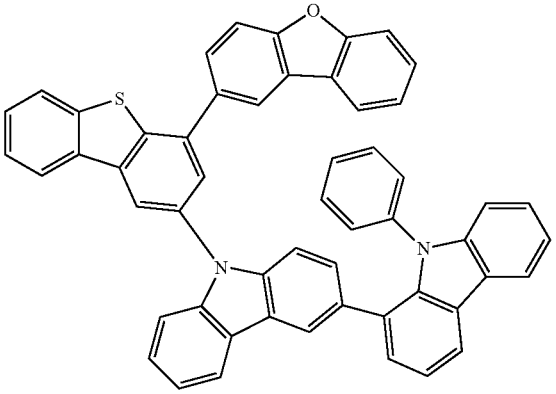
2-49
2-50
2-51
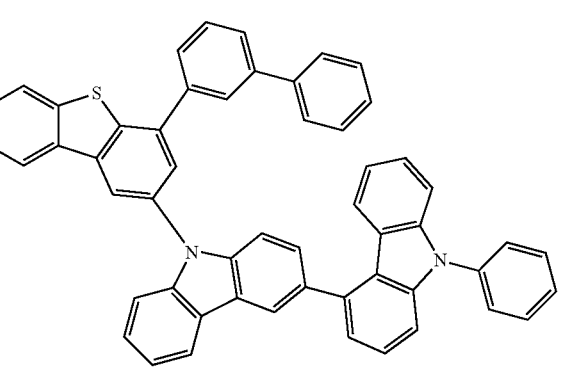

2-52
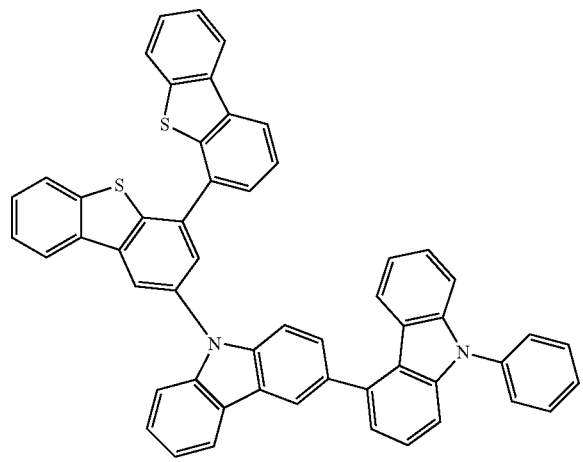
2-55
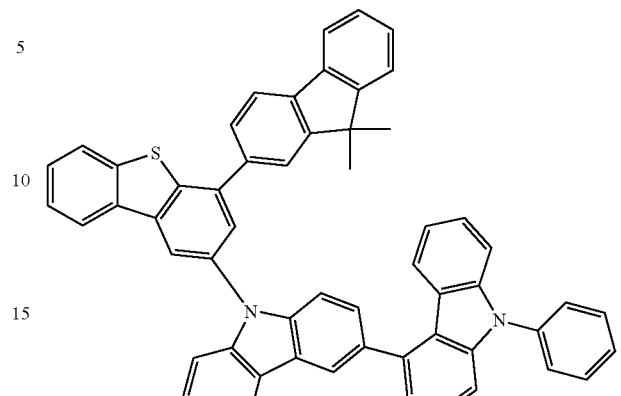
2-53
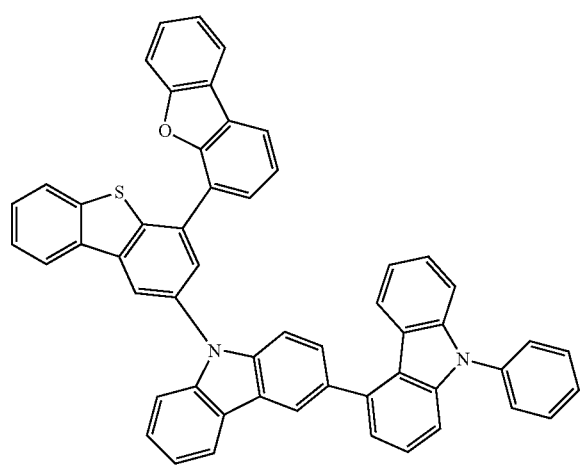
2-56
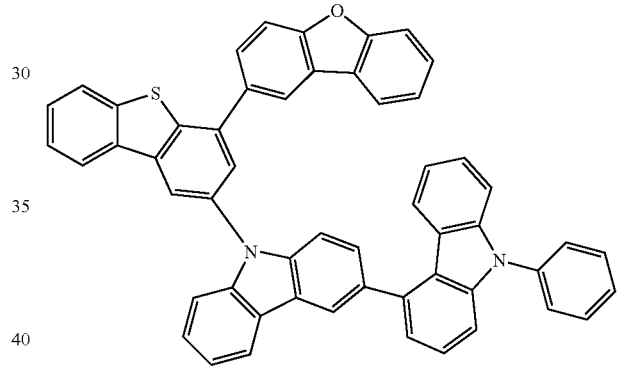
2-54
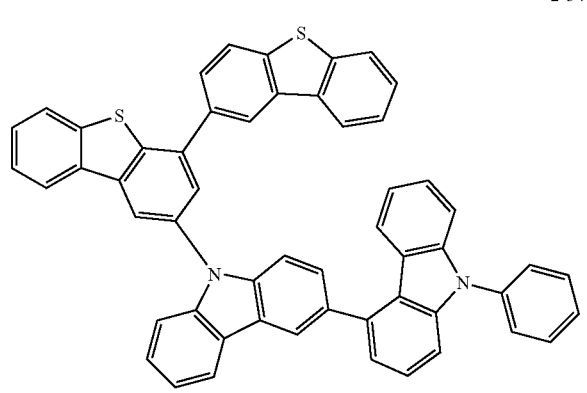
2-57
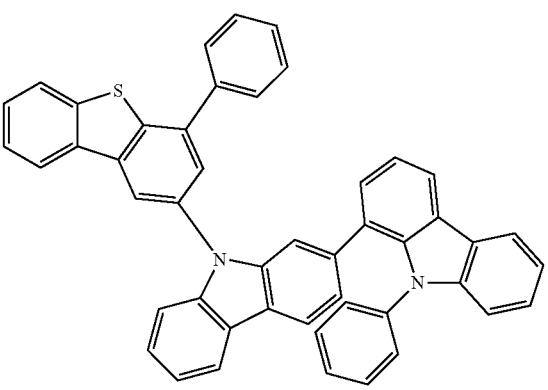

-continued
2-58
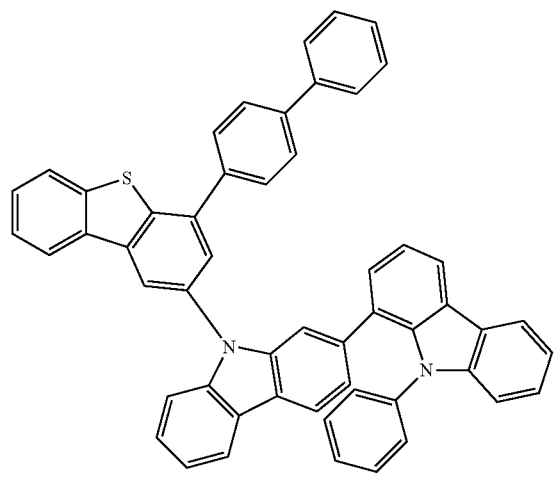
2-59
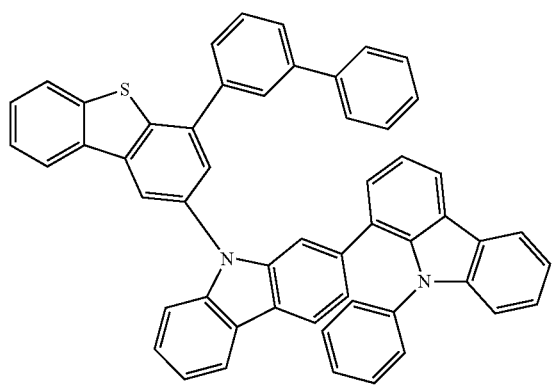
2-60
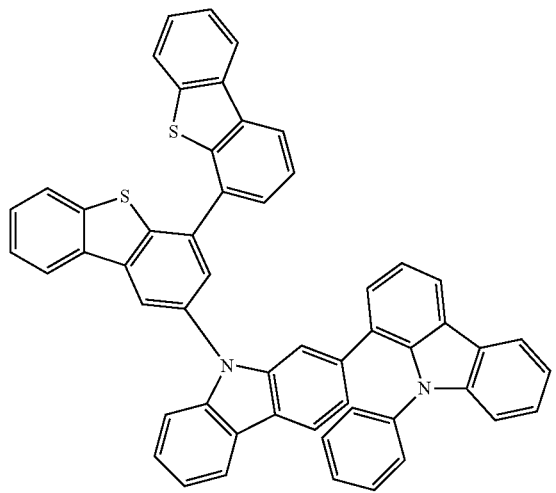
-continued
2-61
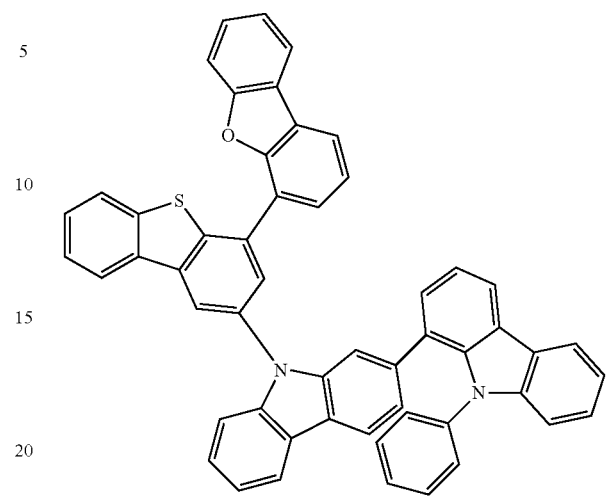
2-62
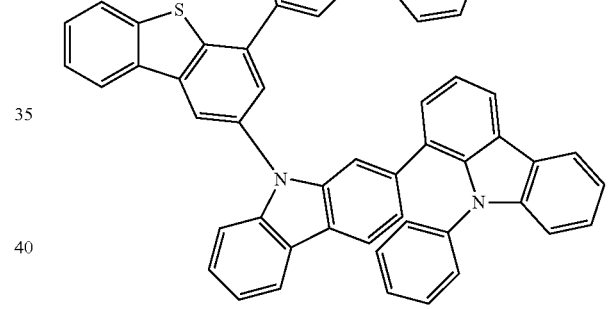
2-63
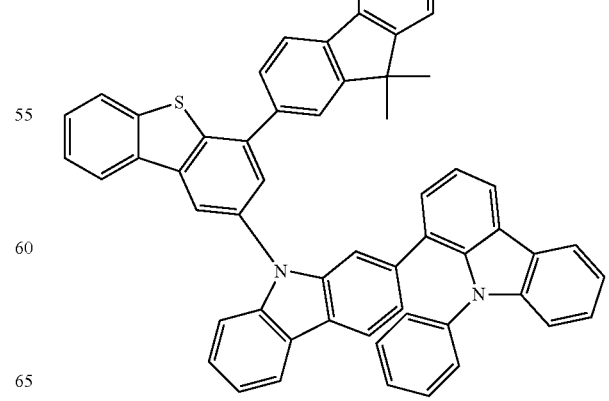

2-64
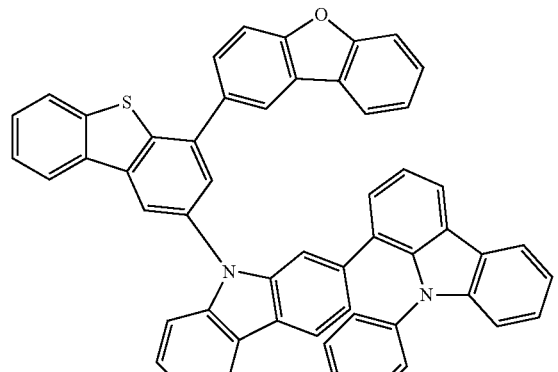
2-65
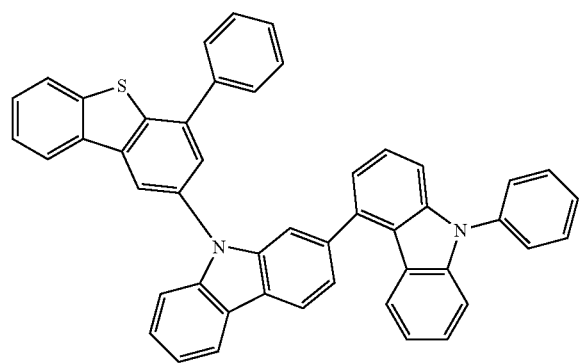
2-66
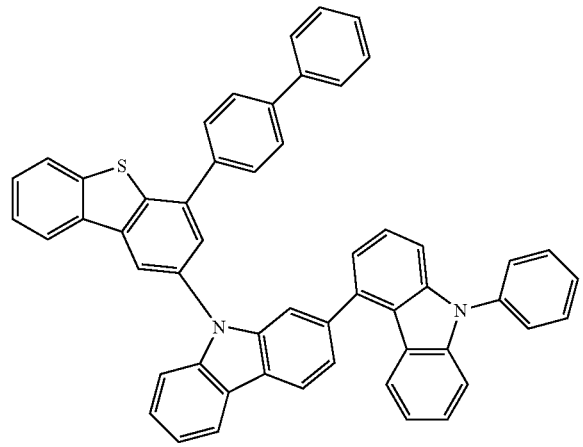
2-67
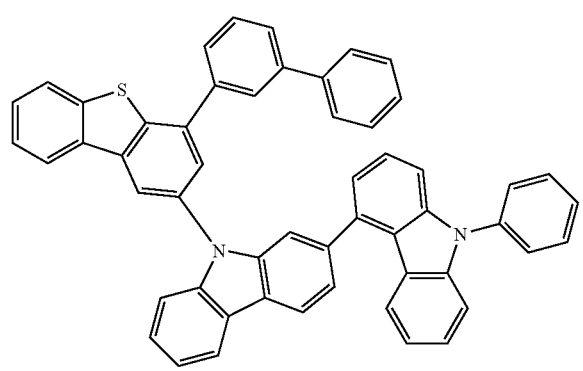
2-68
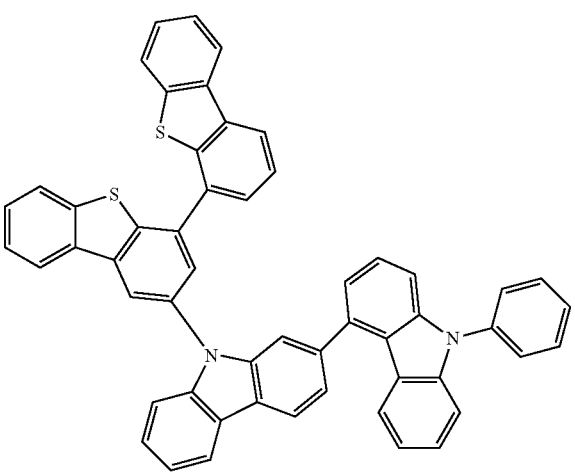
2-69
2-70
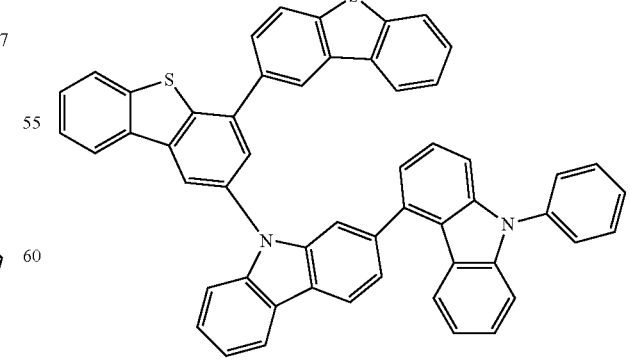

2-71
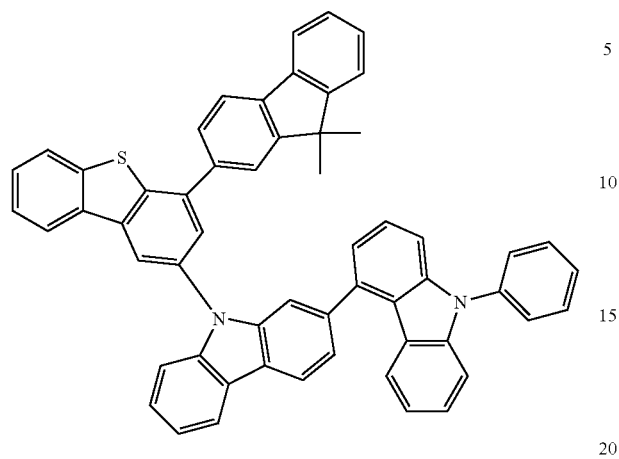
2-74
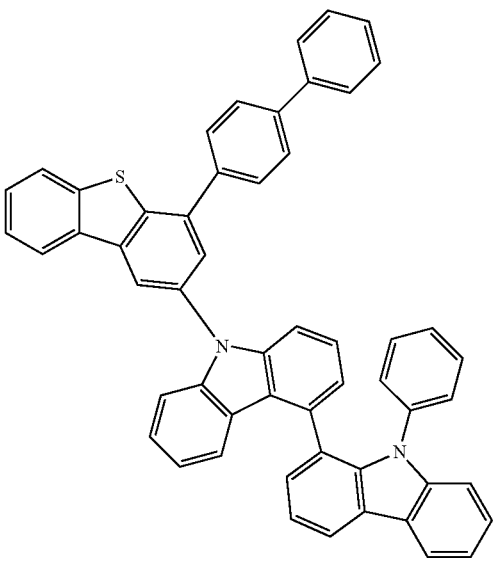
2-72
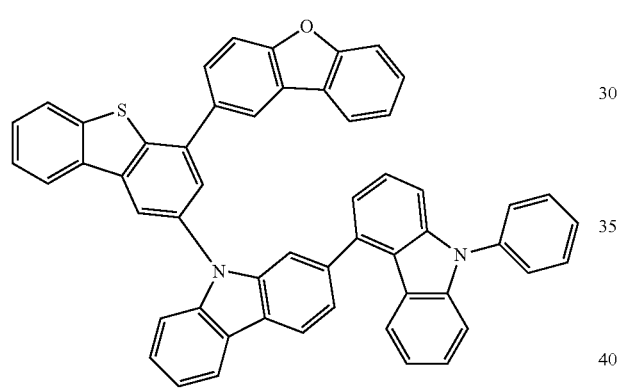
2-75
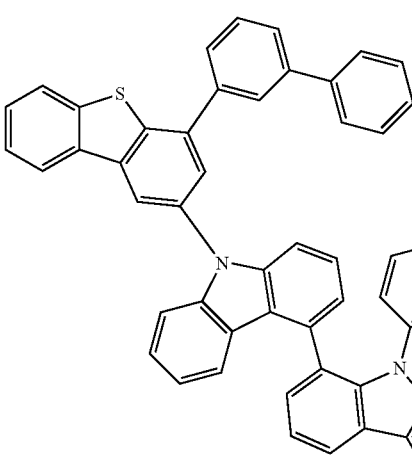
2-73
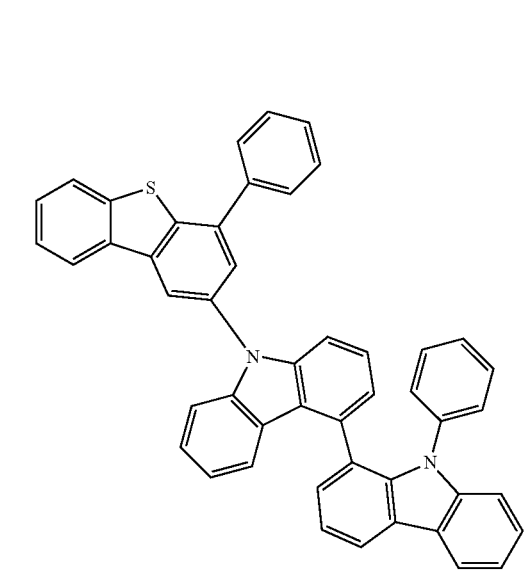
2-76
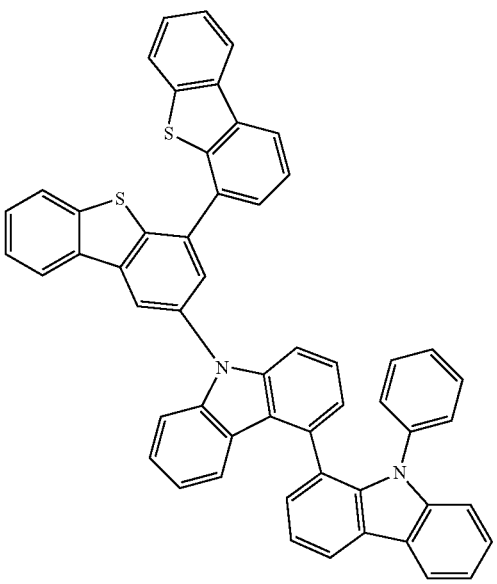

2-77
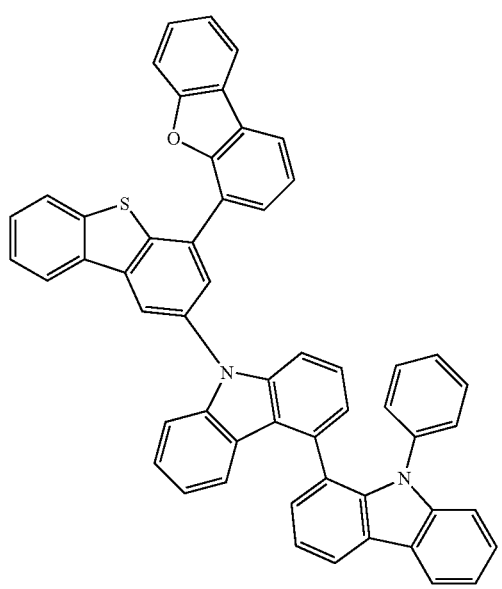
2-78
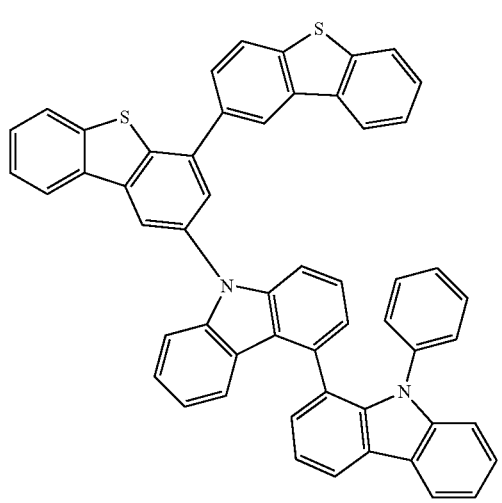
2-79
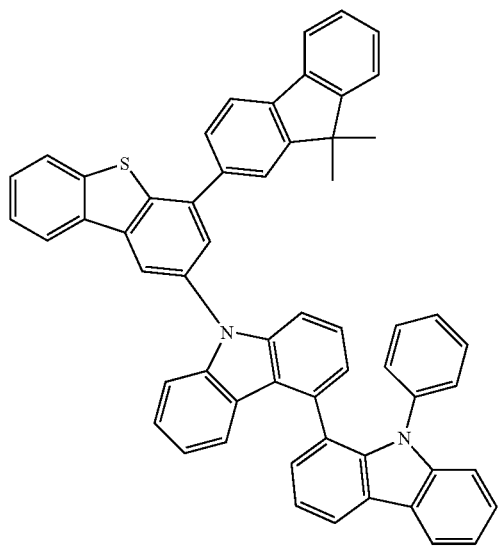
2-80
2-81
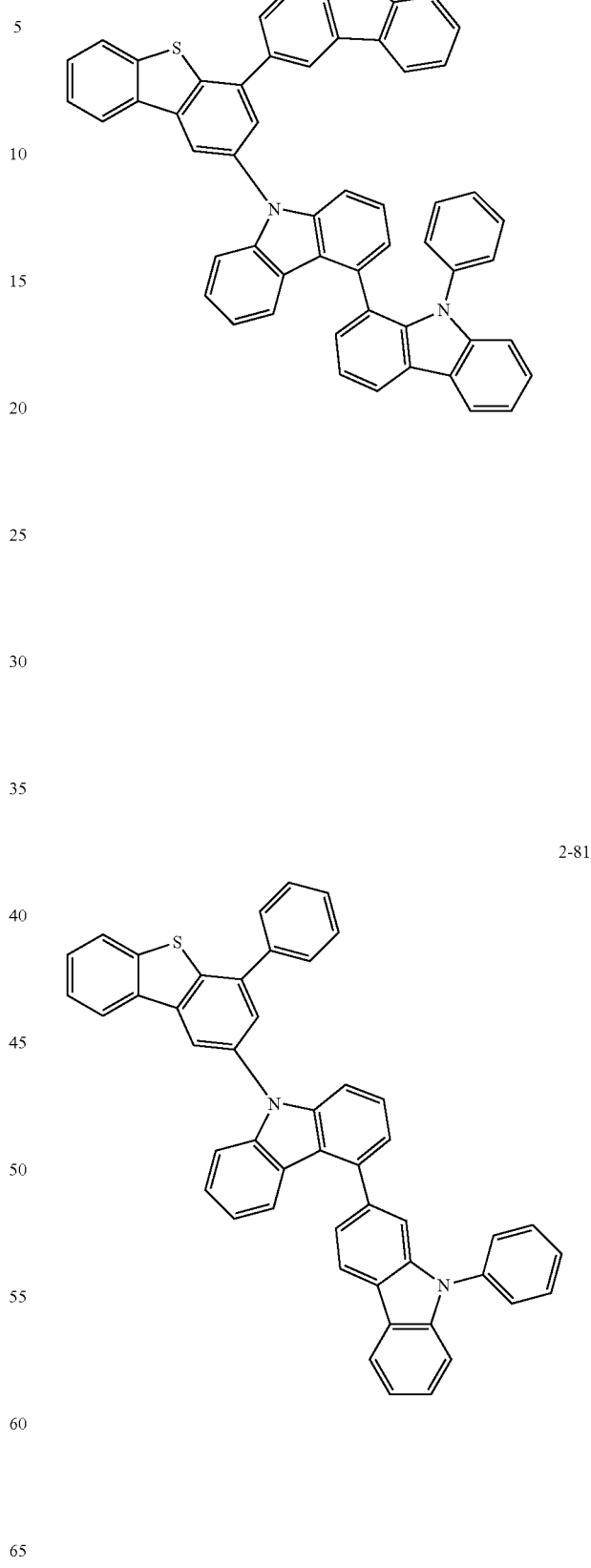

2-82
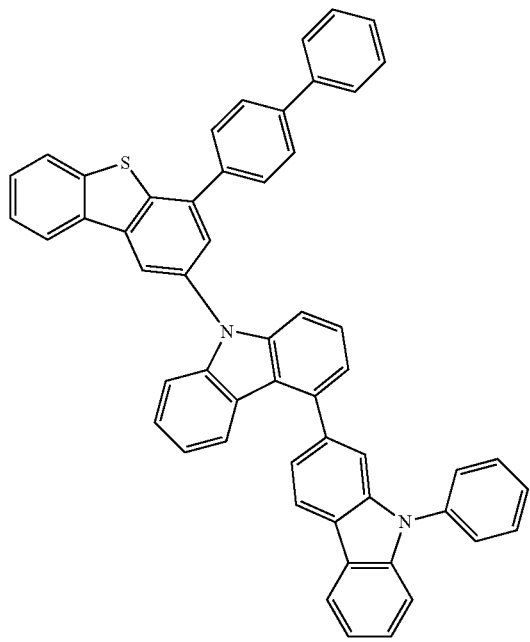
2-83
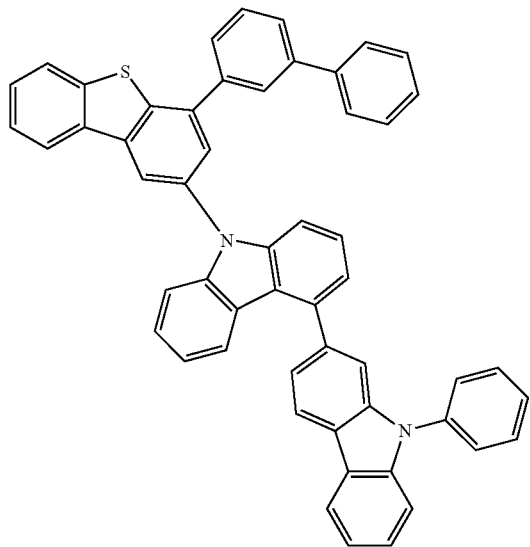
2-84
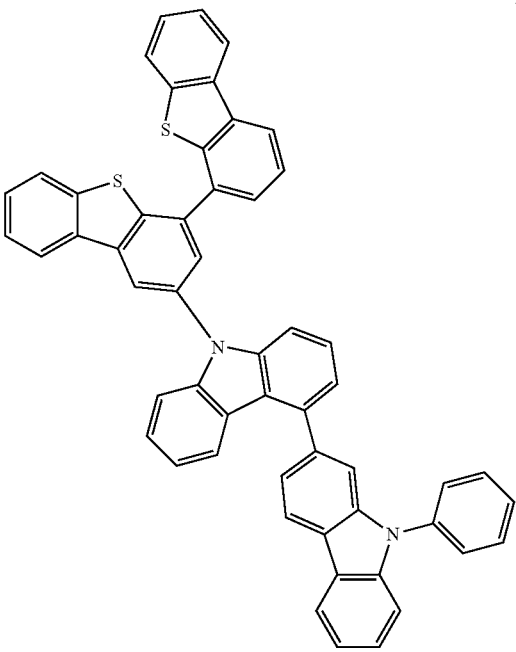
2-85
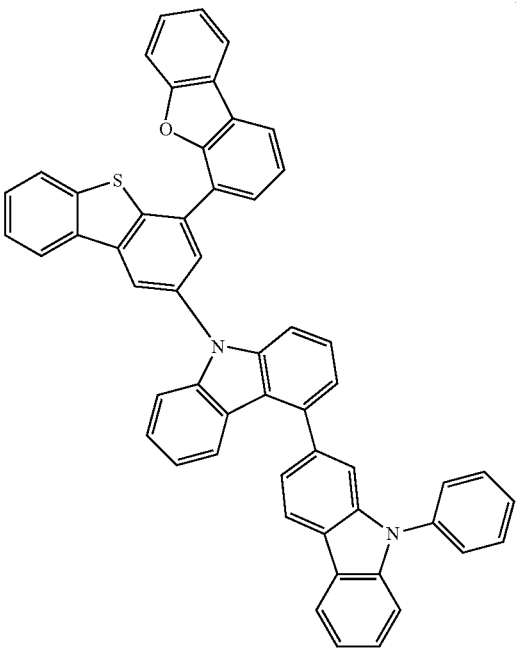

2-86
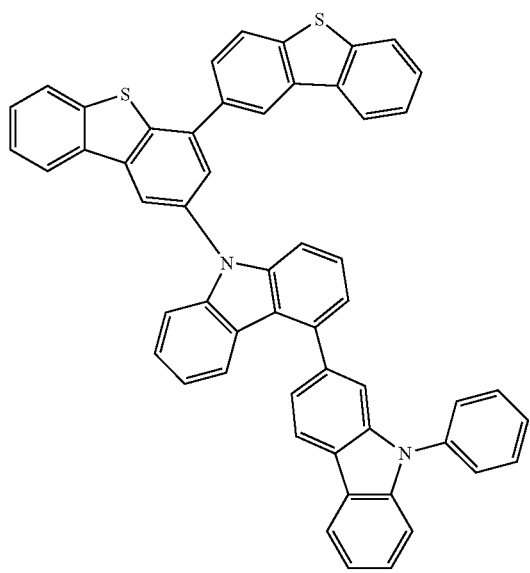
2-87
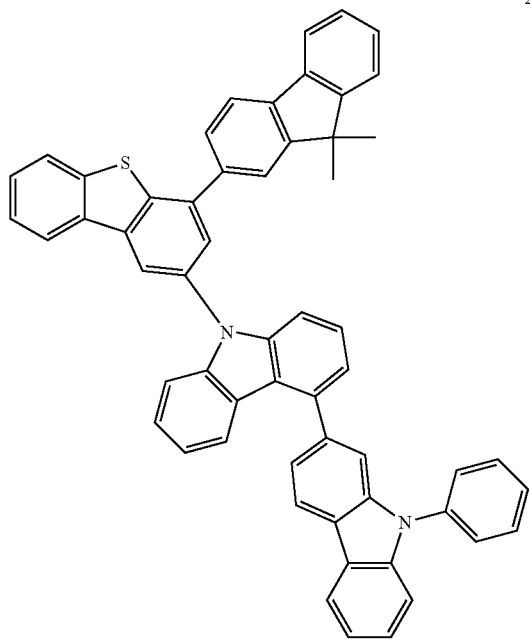
2-88
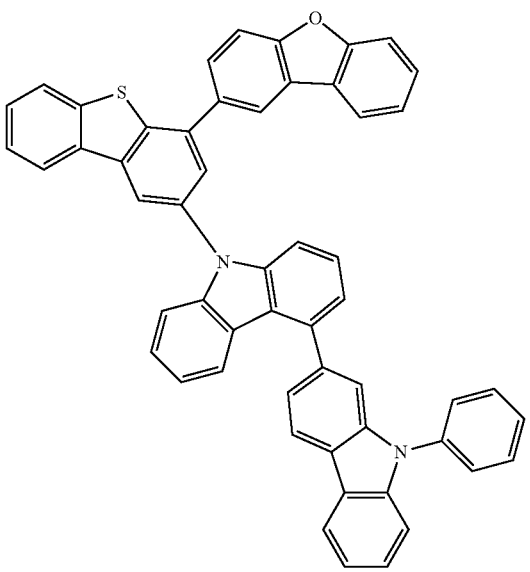
2-89
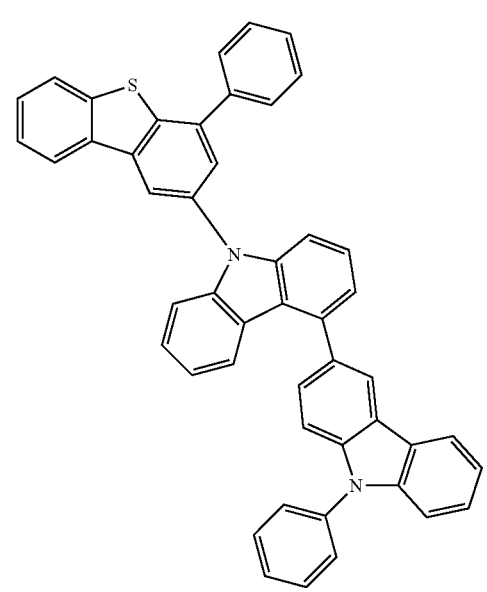

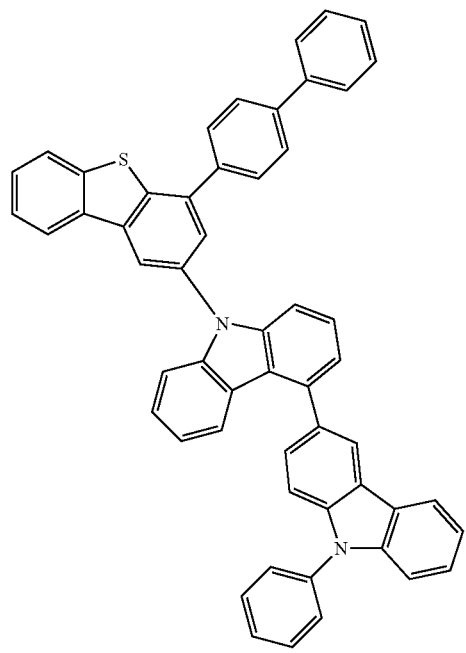
2-90
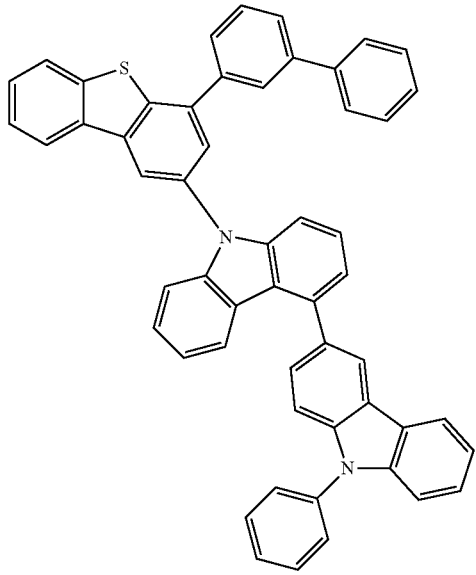
2-91
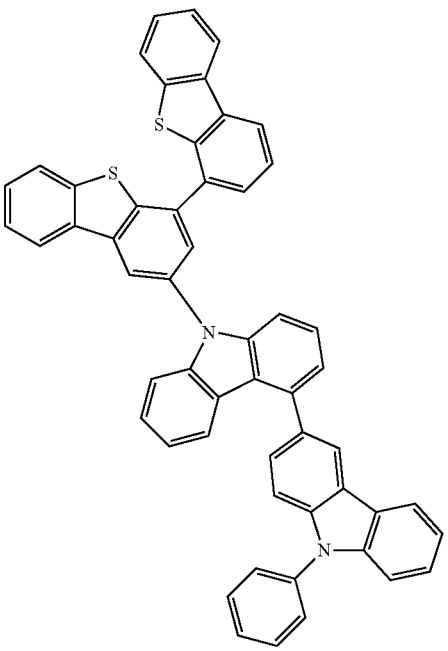
2-92
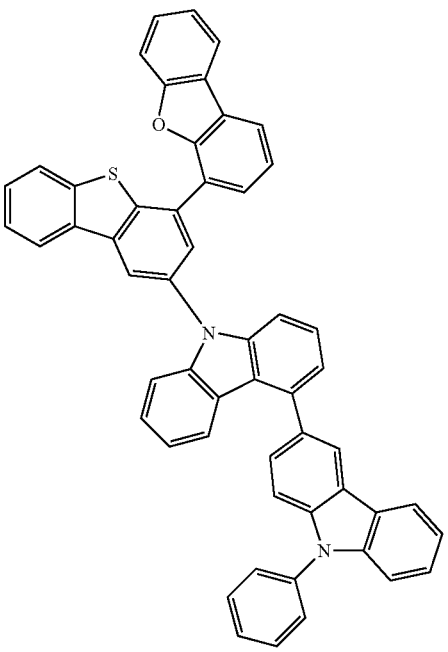
2-93

2-94
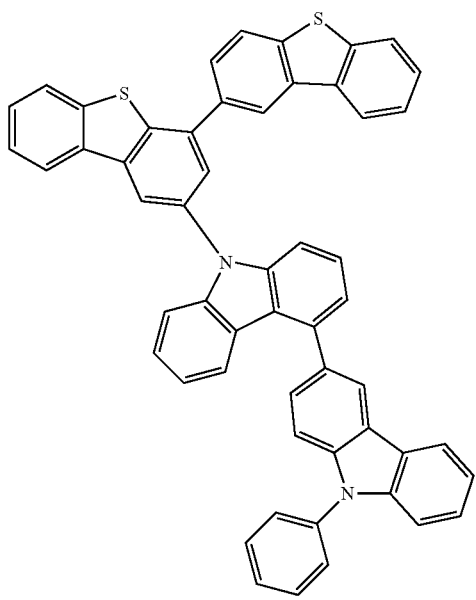
2-96
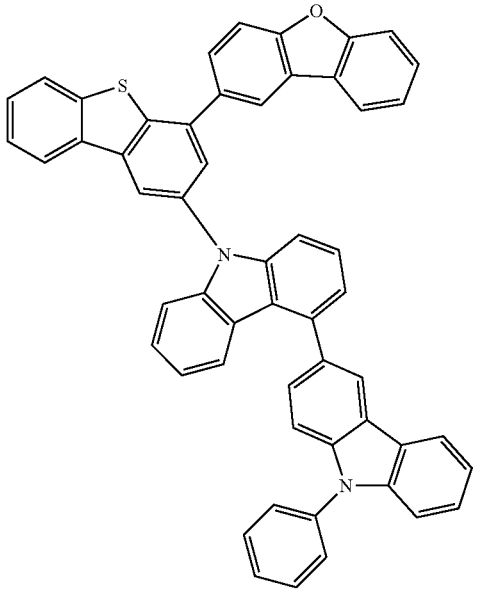
2-95
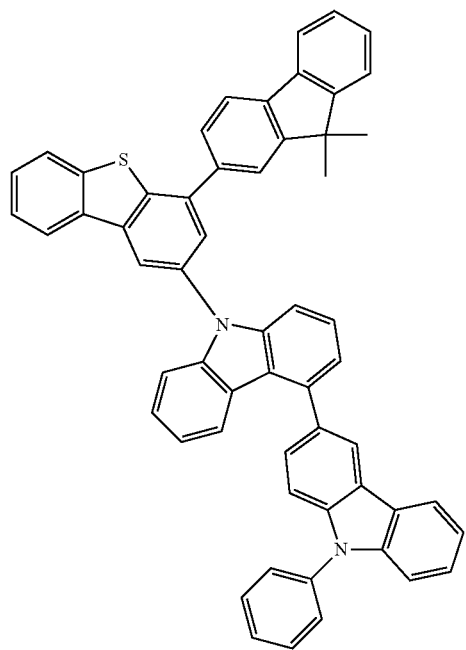
2-97
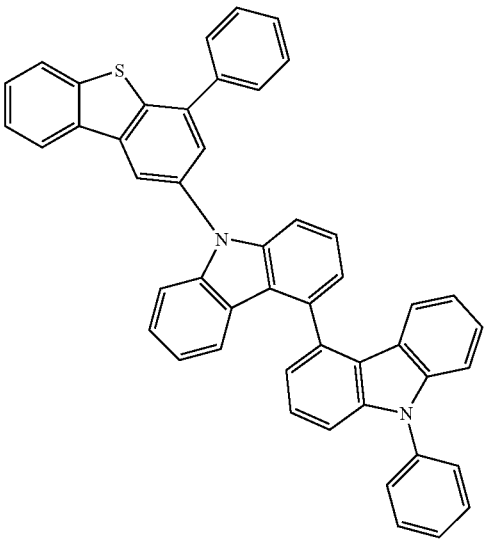

2-98
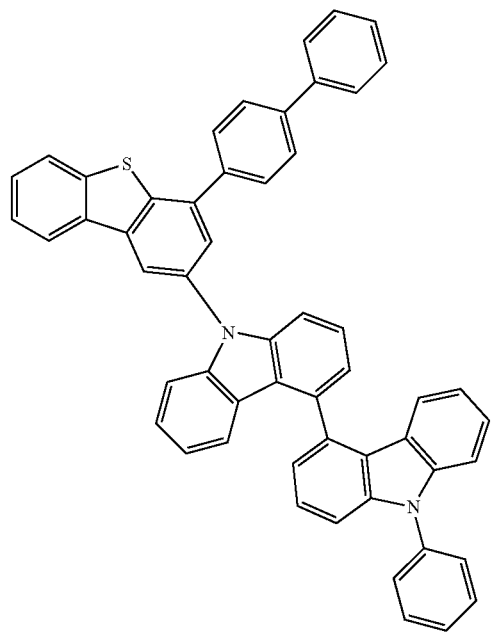
2-99
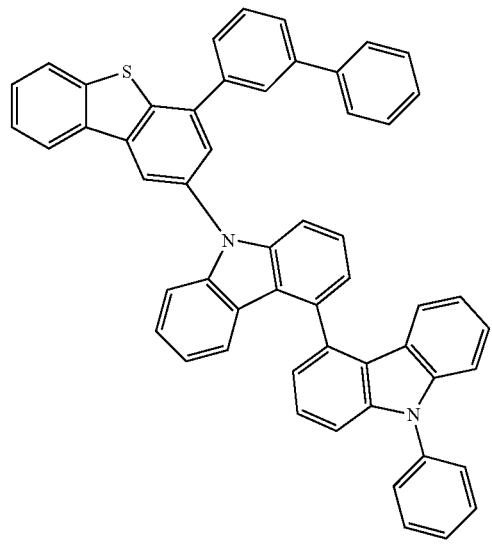
2-100
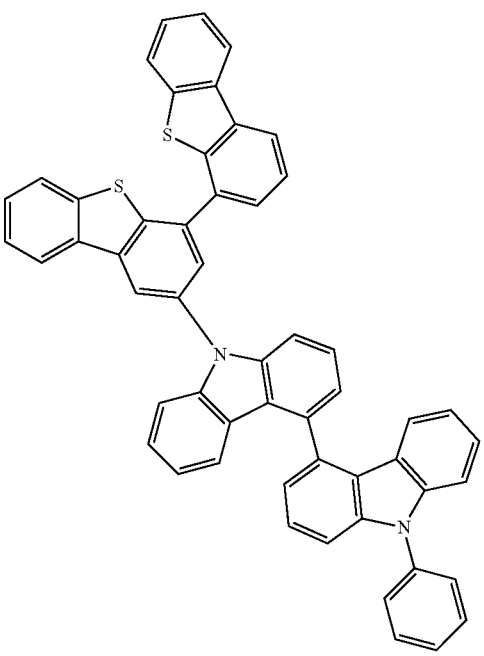
2-101
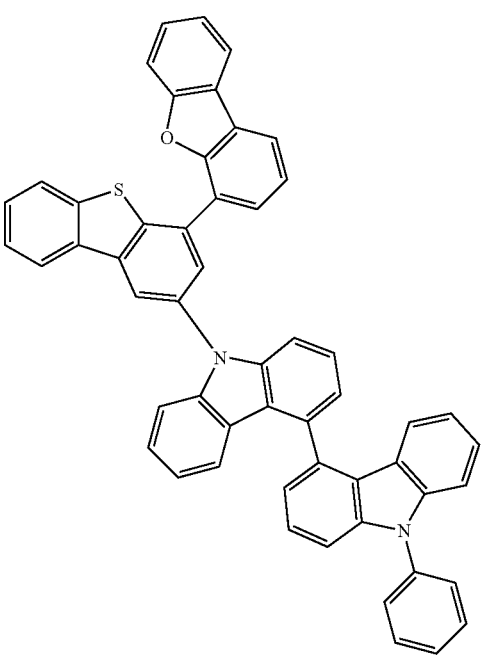

-continued

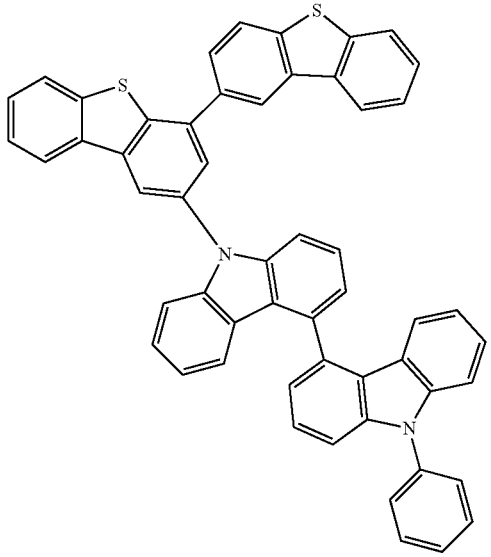
2-102

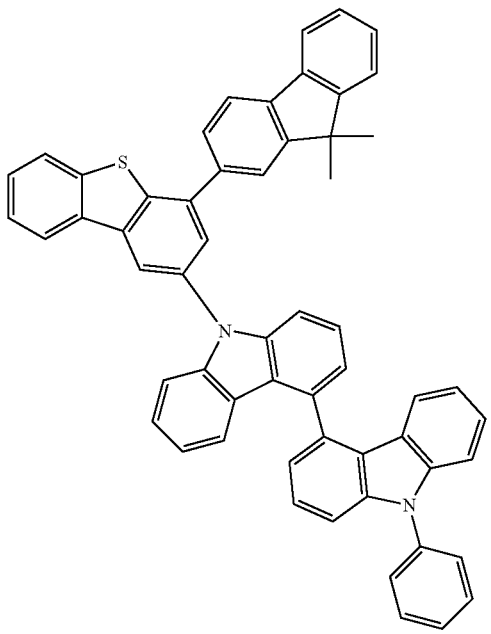
2-103

-continued

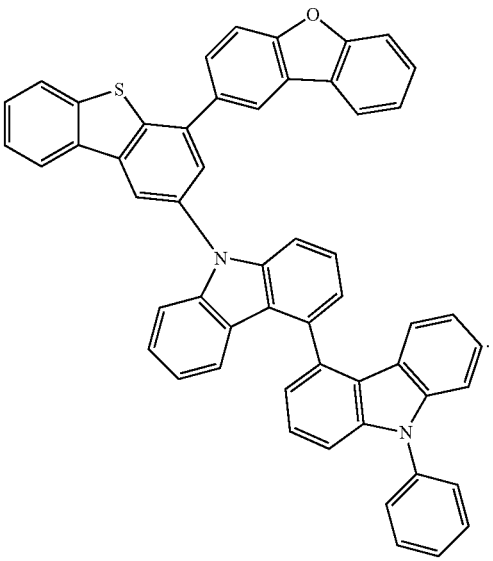
2-104

16. A composition for an organic material layer of an organic light emitting device, comprising:
both a hetero-cyclic compound represented by the following Chemical Formula 1 and a compound represented by the following Chemical Formula 2:

[Chemical Formula 1]

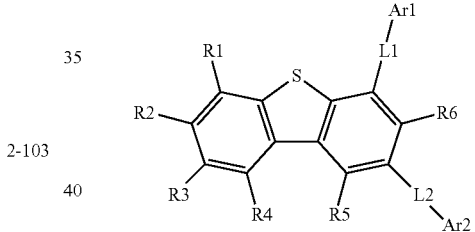

[Chemical Formula 2]

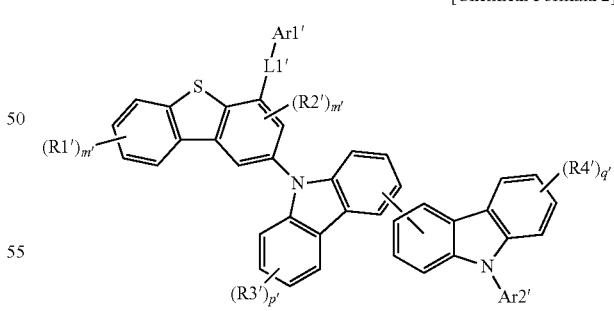

in Chemical Formulae 1 and 2,
L1 and L2 are the same as or different from each other, and each independently a direct bond or a substituted or unsubstituted $C_6$ to $C_{60}$ arylene group,
Ar1 is a substituted or unsubstituted $C_2$ to $C_{60}$ heteroaryl group comprising at least one N,
Ar2 is represented by any one of the following Chemical Formulae 3 and 4,

[Chemical Formula 3]

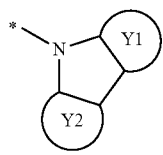

[Chemical Formula 4]

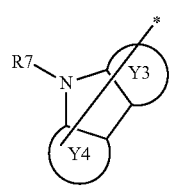

Y1 to Y4 are the same as or different from each other, and each independently a substituted or unsubstituted $C_6$ to $C_{60}$ aromatic hydrocarbon ring; or a substituted or unsubstituted $C_2$ to $C_{60}$ aromatic hetero ring, R1 to R7 and R1' to R4' are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups combine with each other to form a substituted or unsubstituted aliphatic or aromatic hydrocarbon ring, L1' is a direct bond or a substituted or unsubstituted $C_6$ to $C_{60}$ arylene group, Ar1' is a substituted or unsubstituted $C_6$ to $C_{60}$ aryl group; or a substituted or unsubstituted $C_2$ to $C_{60}$ heteroaryl group including at least one of S and O, Ar2' is a substituted or unsubstituted $C_6$ to $C_{60}$ aryl group; or a substituted or unsubstituted $C_2$ to $C_{60}$ heteroaryl group, R, R', and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, m', p' and q' are each independently an integer of 0 to 4, and n' is an integer of 0 to 2.

17. The composition for the organic material layer of the organic light emitting device of claim 16, wherein a weight ratio of the hetero-cyclic compound represented by Chemical Formula 1:the compound represented by Chemical Formula 2 in the composition is 1:10 to 10:1.

* * * * *